United States Patent
Anderson et al.

(10) Patent No.: US 12,383,611 B2
(45) Date of Patent: Aug. 12, 2025

(54) NEISSERIA MENINGITIDIS COMPOSITIONS AND METHODS THEREOF

(71) Applicant: Pfizer Inc., New York, NY (US)

(72) Inventors: Annaliesa Sybil Anderson, Upper Saddle River, NJ (US); John Lance Perez, Doylestown, PA (US); Kathrin Ute Jansen, New York, NY (US); Paul Liberator, Holmdel, NJ (US); Cuiwen Tan, Ridgewood, NJ (US); Thomas Richard Jones, Bluffton, SC (US); Johannes Frederik Beeslaar, Sandwich (GB); Judith Absalon, Bronx, NY (US); Jason Douglas Maguire, Chesapeake, VA (US); Shannon Lea Harris, Boston, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 17/764,153

(22) PCT Filed: Sep. 24, 2020

(86) PCT No.: PCT/IB2020/058928
§ 371 (c)(1),
(2) Date: Mar. 25, 2022

(87) PCT Pub. No.: WO2021/059181
PCT Pub. Date: Apr. 1, 2021

(65) Prior Publication Data
US 2022/0401544 A1   Dec. 22, 2022

Related U.S. Application Data

(60) Provisional application No. 63/040,498, filed on Jun. 17, 2020, provisional application No. 62/907,097, filed on Sep. 27, 2019.

(51) Int. Cl.
| | |
|---|---|
| A61K 39/095 | (2006.01) |
| A61K 39/00 | (2006.01) |
| A61K 47/02 | (2006.01) |
| A61K 47/64 | (2017.01) |
| A61P 31/04 | (2006.01) |
| C07K 14/22 | (2006.01) |

(52) U.S. Cl.
CPC ........... *A61K 39/095* (2013.01); *A61K 47/02* (2013.01); *A61K 47/646* (2017.08); *A61P 31/04* (2018.01); *C07K 14/22* (2013.01); *A61K 2039/545* (2013.01); *A61K 2039/55505* (2013.01); *A61K 2039/627* (2013.01); *A61K 2039/70* (2013.01)

(58) Field of Classification Search
None
See application file for complete search history.

(56) References Cited

U.S. PATENT DOCUMENTS

| | | |
|---|---|---|
| 4,057,685 A | 11/1977 | McIntire |
| 4,376,110 A | 3/1983 | David et al. |
| 4,459,286 A | 7/1984 | Hilleman et al. |
| 4,554,101 A | 11/1985 | Hopp |
| 4,650,764 A | 3/1987 | Temin et al. |
| 4,666,829 A | 5/1987 | Glenner et al. |
| 4,673,574 A | 6/1987 | Anderson |
| 4,708,871 A | 11/1987 | Geysen |
| 4,709,017 A | 11/1987 | Collier et al. |
| 4,797,368 A | 1/1989 | Carter et al. |
| 4,808,700 A | 2/1989 | Anderson et al. |
| 4,861,719 A | 8/1989 | Miller |
| 4,912,094 A | 3/1990 | Myers et al. |
| 4,925,792 A | 5/1990 | Rappuoli |
| 4,950,740 A | 8/1990 | Greenfield et al. |
| 4,980,289 A | 12/1990 | Temin et al. |
| 5,057,540 A | 10/1991 | Kensil et al. |
| 5,078,996 A | 1/1992 | Conlon, III et al. |
| 5,124,263 A | 6/1992 | Temin et al. |
| 5,139,941 A | 8/1992 | Muzyczka et al. |
| 5,254,339 A | 10/1993 | Morein |
| 5,399,346 A | 3/1995 | Anderson et al. |
| 5,439,808 A | 8/1995 | Blake et al. |
| 5,459,127 A | 10/1995 | Felgner et al. |
| 5,514,581 A | 5/1996 | Ferrari et al. |

(Continued)

FOREIGN PATENT DOCUMENTS

| | | |
|---|---|---|
| CA | 2004810 | 6/1990 |
| CA | 2012311 | 9/1990 |

(Continued)

OTHER PUBLICATIONS

Tarkka et al, "Antibody production to a meningococcal outer membrane protein cloned into live *Salmonella typhimurium* aroA vaccine strain", Micrb. Pathogen 6:327-335 (1989).

(Continued)

*Primary Examiner* — S. Devi

(74) *Attorney, Agent, or Firm* — Rebecca Wright

(57) ABSTRACT

In one aspect, the disclosure relates to a composition including a factor H binding protein (fHBP) and a *Neisseria meningitidis* non-serogroup B capsular polysaccharide, and methods of use thereof. The disclosure further relates to uses of a composition that includes fHBP, such as, for example, uses to elicit an immune response against *N. meningitidis* serogroup B strains and non-serogroup B strains. The compositions and methods described herein are directed to administration in humans, including adults, adolescents, toddlers, and infants.

13 Claims, 5 Drawing Sheets

Figure 1A:
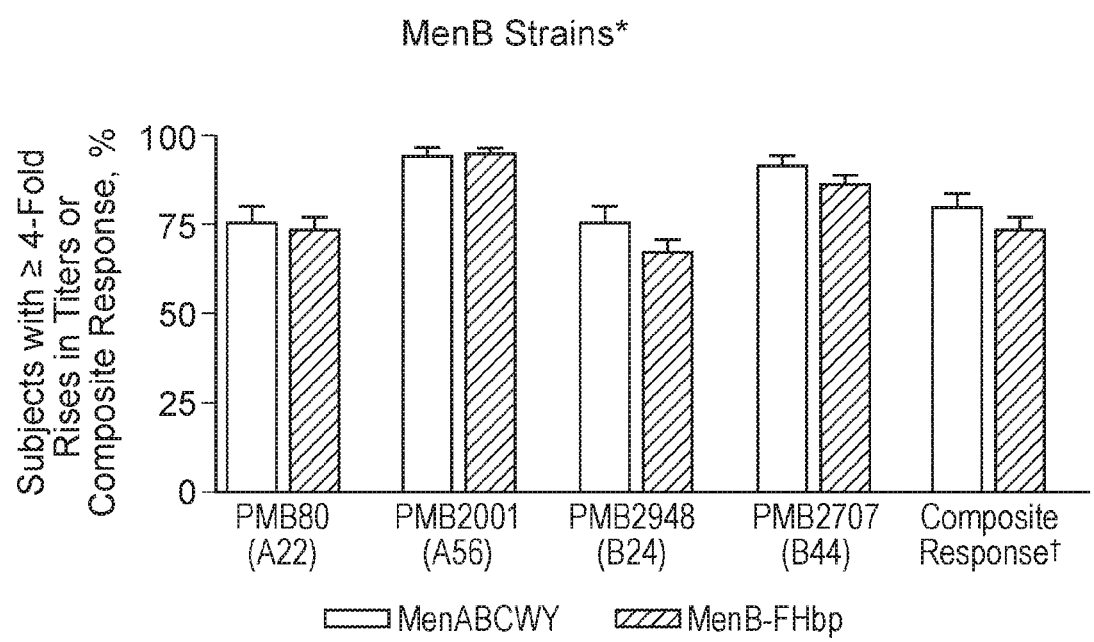

Specification includes a Sequence Listing.

(56) References Cited

U.S. PATENT DOCUMENTS

| | | |
|---|---|---|
| 5,550,213 A | 8/1996 | Anderson et al. |
| 5,565,204 A | 10/1996 | Kuo et al. |
| 5,580,859 A | 12/1996 | Felgner et al. |
| 5,583,038 A | 12/1996 | Stover |
| 5,589,466 A | 12/1996 | Felgner et al. |
| 5,597,572 A | 1/1997 | Huergo et al. |
| 5,614,382 A | 3/1997 | Metcalf |
| 5,668,004 A | 9/1997 | O'Donnell |
| 5,723,127 A | 3/1998 | Scott et al. |
| 5,739,118 A | 4/1998 | Carrano et al. |
| 5,843,711 A | 12/1998 | Collier et al. |
| 5,917,017 A | 6/1999 | Collier et al. |
| 5,955,580 A | 9/1999 | Green et al. |
| 6,113,918 A | 9/2000 | Johnson et al. |
| 6,130,085 A | 10/2000 | Hamers et al. |
| 6,149,919 A | 11/2000 | Domenighini et al. |
| 6,165,995 A | 12/2000 | Hilgers |
| 6,207,646 B1 | 3/2001 | Krieg et al. |
| 6,245,892 B1 | 6/2001 | Oaks et al. |
| 6,270,775 B1 | 8/2001 | Cleary |
| 6,281,337 B1 | 8/2001 | Cannon-Carlson et al. |
| 6,299,884 B1 | 10/2001 | Van Nest et al. |
| 6,355,253 B1 | 3/2002 | Zlotnick |
| 6,355,255 B1 | 3/2002 | Cleary et al. |
| 6,451,317 B1 | 9/2002 | Blake et al. |
| 6,455,673 B1 | 9/2002 | Collier |
| 6,610,310 B2 | 8/2003 | Hilgers |
| 6,951,653 B2 | 10/2005 | Cleary et al. |
| 7,115,730 B1 | 10/2006 | Pizza et al. |
| 7,118,757 B1 | 10/2006 | Seid et al. |
| 7,235,644 B2 | 6/2007 | Bhattacharjee et al. |
| 7,285,281 B2 | 10/2007 | Green et al. |
| 7,291,588 B2 | 11/2007 | Pizza et al. |
| 7,332,174 B2 | 2/2008 | Green et al. |
| 7,361,355 B2 | 4/2008 | Green et al. |
| 7,384,640 B1 | 6/2008 | Holmes et al. |
| 7,576,176 B1 | 8/2009 | Fraser et al. |
| 7,608,278 B2 | 10/2009 | Hoiseth et al. |
| 7,785,608 B2 | 8/2010 | Zlotnick et al. |
| 7,803,387 B2 | 9/2010 | Arico et al. |
| 7,820,789 B2 | 10/2010 | Kirkham et al. |
| 8,039,007 B2 | 10/2011 | Rappuoli et al. |
| 8,101,194 B2 | 1/2012 | Zlotnick et al. |
| 8,273,360 B2 | 9/2012 | Pizza et al. |
| 8,398,988 B2 | 3/2013 | Contorni et al. |
| 8,563,006 B2 | 10/2013 | Zlotnick et al. |
| 8,563,007 B1 | 10/2013 | Zlotnick et al. |
| 8,574,597 B2 | 11/2013 | Zlotnick |
| 8,632,995 B2 | 1/2014 | Sun et al. |
| 8,834,888 B2 | 9/2014 | Contorni |
| 8,986,710 B2 | 3/2015 | Anderson et al. |
| 9,107,873 B2 | 8/2015 | Zlotnick et al. |
| 9,132,182 B2 | 9/2015 | Zlotnick et al. |
| 9,168,293 B2 | 10/2015 | Zlotnick et al. |
| 9,249,196 B2 | 2/2016 | Fraser et al. |
| 9,249,198 B2 | 2/2016 | Fraser et al. |
| 9,266,929 B2 | 2/2016 | Fraser et al. |
| 9,267,163 B2 | 2/2016 | Arico et al. |
| 9,486,515 B2 | 11/2016 | Biemans et al. |
| 9,556,240 B2 | 1/2017 | Khandke et al. |
| 9,561,269 B2 | 2/2017 | Zlotnick et al. |
| 9,605,040 B2 | 3/2017 | von Maltzahn et al. |
| 9,623,101 B2 | 4/2017 | Zlotnick et al. |
| 9,700,071 B2 | 7/2017 | Silver et al. |
| 9,724,402 B2 | 8/2017 | Anderson et al. |
| 9,757,443 B2 | 9/2017 | Anderson et al. |
| 9,757,444 B2 | 9/2017 | Zlotnick et al. |
| 9,789,179 B2 | 10/2017 | Biemans et al. |
| 9,802,987 B2 | 10/2017 | Dilts et al. |
| 9,822,150 B2 | 11/2017 | Anderson et al. |
| 10,183,070 B2 | 1/2019 | Jansen et al. |
| 10,195,264 B2 | 2/2019 | Contorni et al. |
| 10,196,429 B2 | 2/2019 | Anderson et al. |
| 10,300,122 B2 | 5/2019 | Zlotnick et al. |
| 10,328,142 B2 | 6/2019 | Comanducci et al. |
| 10,512,681 B2 | 12/2019 | Anderson et al. |
| 10,543,267 B2 | 1/2020 | Jansen et al. |
| 10,550,159 B2 | 2/2020 | Anderson et al. |
| 10,568,953 B2 | 2/2020 | Contorni et al. |
| 10,829,521 B2 | 11/2020 | Anderson et al. |
| 10,888,611 B2 | 1/2021 | Jansen et al. |
| 10,899,802 B2 | 1/2021 | Anderson et al. |
| 11,077,180 B2 | 8/2021 | Anderson et al. |
| 11,116,829 B2 | 9/2021 | Zlotnick et al. |
| 11,730,800 B2 * | 8/2023 | Jansen ............... A61K 47/183 424/250.1 |
| 2004/0110670 A1 | 6/2004 | Arico et al. |
| 2004/0167068 A1 | 8/2004 | Zlotnick et al. |
| 2004/0249125 A1 | 12/2004 | Pizza et al. |
| 2006/0251670 A1 | 11/2006 | Comanducci et al. |
| 2006/0257413 A1 | 11/2006 | Zlotnick et al. |
| 2007/0020622 A1 | 1/2007 | Lee et al. |
| 2007/0049532 A1 | 3/2007 | Feige et al. |
| 2007/0082006 A1 | 4/2007 | Zlotnick et al. |
| 2007/0082007 A1 | 4/2007 | Zlotnick et al. |
| 2007/0148729 A1 | 6/2007 | Farley et al. |
| 2007/0253964 A1 | 11/2007 | Zlotnick et al. |
| 2008/0248065 A1 | 10/2008 | Granoff et al. |
| 2009/0016946 A1 | 1/2009 | Khandke et al. |
| 2009/0035328 A1 | 2/2009 | Granoff |
| 2009/0202593 A1 | 8/2009 | Zlotnick et al. |
| 2009/0252759 A1 | 10/2009 | Biemans et al. |
| 2011/0076299 A1 | 3/2011 | Zlotnick et al. |
| 2011/0189187 A1 | 8/2011 | Zlotnick |
| 2011/0312510 A1 | 12/2011 | Mak et al. |
| 2012/0034261 A1 | 2/2012 | Zlotnick et al. |
| 2012/0070457 A1 | 3/2012 | Daugherty et al. |
| 2012/0093852 A1 | 4/2012 | Anderson et al. |
| 2012/0107339 A1 | 5/2012 | Granoff et al. |
| 2012/0201844 A1 | 8/2012 | Zlotnick et al. |
| 2012/0294880 A1 | 11/2012 | Zlotnick et al. |
| 2012/0301496 A1 | 11/2012 | Zlotnick et al. |
| 2012/0308595 A1 | 12/2012 | Zlotnick et al. |
| 2013/0171194 A1 | 7/2013 | Khandke et al. |
| 2013/0243807 A1 | 9/2013 | Anderson et al. |
| 2013/0259889 A1 | 10/2013 | Zlotnick et al. |
| 2014/0113329 A1 | 4/2014 | Sun et al. |
| 2014/0377302 A1 | 12/2014 | Kapre et al. |
| 2015/0071959 A1 | 3/2015 | Anderson et al. |
| 2015/0216960 A1 | 8/2015 | Zlotnick et al. |
| 2015/0335724 A1 | 11/2015 | Zlotnick et al. |
| 2016/0017006 A1 | 1/2016 | Dilts et al. |
| 2016/0030543 A1 | 2/2016 | Zlotnick et al. |
| 2016/0347797 A1 | 12/2016 | Anderson et al. |
| 2017/0065714 A1 | 3/2017 | Biemans et al. |
| 2017/0173140 A1 | 6/2017 | Zlotnick et al. |
| 2017/0298102 A1 | 10/2017 | von Maltzahn et al. |
| 2018/0000923 A1 | 1/2018 | Jansen et al. |
| 2018/0022783 A1 | 1/2018 | Anderson et al. |
| 2018/0064806 A1 | 3/2018 | Biemans et al. |
| 2018/0214532 A1 | 8/2018 | Jansen et al. |
| 2018/0371030 A1 | 12/2018 | Anderson et al. |
| 2019/0127426 A1 | 5/2019 | Anderson et al. |
| 2019/0151431 A1 | 5/2019 | Zlotnick et al. |
| 2019/0231861 A1 | 8/2019 | Jansen et al. |
| 2020/0093914 A1 | 3/2020 | Anderson et al. |
| 2020/0123206 A1 | 4/2020 | Anderson et al. |
| 2020/0138933 A1 | 5/2020 | Zlotnick et al. |
| 2020/0164056 A1 | 5/2020 | Jansen et al. |
| 2021/0024589 A1 | 1/2021 | Anderson et al. |
| 2021/0085773 A1 | 3/2021 | Jansen et al. |
| 2021/0101943 A1 | 4/2021 | Anderson et al. |

FOREIGN PATENT DOCUMENTS

| | | |
|---|---|---|
| EP | 0 125 023 B1 | 11/1984 |
| EP | 0 171 496 B1 | 2/1986 |
| EP | 0 173 494 A2 | 3/1986 |
| EP | 0 184 187 A2 | 6/1986 |
| EP | 0 185 573 B1 | 6/1986 |
| EP | 0 372 501 A2 | 12/1989 |
| EP | 0 161 188 B1 | 3/1991 |
| EP | 0 467 714 A1 | 7/1991 |
| EP | 0 208 375 B1 | 11/1991 |

(56) References Cited

FOREIGN PATENT DOCUMENTS

| | | |
|---|---|---|
| EP | 0 178 220 B1 | 1/1992 |
| EP | 0 378 881 B1 | 6/1993 |
| EP | 0 427 347 B1 | 2/1995 |
| EP | 0 477 508 B1 | 7/1995 |
| EP | 0 471 177 B1 | 10/1995 |
| EP | 0 488 528 B1 | 11/1995 |
| EP | 0 453 242 B1 | 8/1996 |
| EP | 0 594 610 B1 | 9/1998 |
| EP | 1 296 713 B1 | 9/2003 |
| EP | 1 326 634 B1 | 4/2006 |
| EP | 2 351 767 A2 | 8/2011 |
| EP | 1 442 047 B1 | 3/2016 |
| JP | 1144977 A | 6/1989 |
| JP | 2011-042693 A | 3/2011 |
| JP | 2011-068676 A | 4/2011 |
| WO | 86/01533 A1 | 3/1986 |
| WO | 87/01130 A1 | 2/1987 |
| WO | 87/002671 A1 | 5/1987 |
| WO | 89/07150 A1 | 8/1989 |
| WO | 90/02806 A1 | 3/1990 |
| WO | 90/10458 A1 | 9/1990 |
| WO | 91/01146 A1 | 2/1991 |
| WO | 91/18088 A1 | 11/1991 |
| WO | 92/05263 A1 | 4/1992 |
| WO | 92/19265 A1 | 11/1992 |
| WO | 93/09239 A1 | 5/1993 |
| WO | 93/15760 A1 | 8/1993 |
| WO | 93/17712 A2 | 9/1993 |
| WO | 94/03208 A1 | 2/1994 |
| WO | 94/12649 A2 | 6/1994 |
| WO | 94/21807 A2 | 9/1994 |
| WO | 94/26914 A1 | 11/1994 |
| WO | 94/28152 A1 | 12/1994 |
| WO | 94/28938 A1 | 12/1994 |
| WO | 95/02697 A1 | 1/1995 |
| WO | 95/07358 A1 | 3/1995 |
| WO | 95/08348 A1 | 3/1995 |
| WO | 95/18863 A1 | 7/1995 |
| WO | 95/21931 A1 | 8/1995 |
| WO | 95/22617 A1 | 8/1995 |
| WO | 95/26411 A2 | 10/1995 |
| WO | 95/28494 A1 | 10/1995 |
| WO | 96/10038 A1 | 4/1996 |
| WO | 96/14086 A1 | 5/1996 |
| WO | 96/17823 A1 | 6/1996 |
| WO | 96/22378 A1 | 7/1996 |
| WO | 96/25508 A1 | 8/1996 |
| WO | 96/29094 A1 | 9/1996 |
| WO | 96/29412 A1 | 9/1996 |
| WO | 96/39036 A1 | 12/1996 |
| WO | 96/40718 A1 | 12/1996 |
| WO | 97/19182 A1 | 5/1997 |
| WO | 98/08543 A1 | 3/1998 |
| WO | 98/08874 A1 | 3/1998 |
| WO | 98/17805 A2 | 4/1998 |
| WO | 98/42721 A1 | 10/1998 |
| WO | 98/58668 A2 | 12/1998 |
| WO | 99/01157 A1 | 1/1999 |
| WO | 99/01158 A1 | 1/1999 |
| WO | 99/01175 A1 | 1/1999 |
| WO | 99/10372 A1 | 3/1999 |
| WO | 99/24578 A2 | 5/1999 |
| WO | 99/27944 A1 | 6/1999 |
| WO | 99/36544 A2 | 7/1999 |
| WO | 99/40200 A1 | 8/1999 |
| WO | 99/48525 A1 | 9/1999 |
| WO | 99/55730 A2 | 11/1999 |
| WO | 99/55872 A1 | 11/1999 |
| WO | 99/57280 A2 | 11/1999 |
| WO | 99/61053 A1 | 12/1999 |
| WO | 00/10599 A2 | 3/2000 |
| WO | 00/18434 A1 | 4/2000 |
| WO | 00/22430 A2 | 4/2000 |
| WO | 00/42192 A1 | 7/2000 |
| WO | 00/43518 A1 | 7/2000 |
| WO | 00/44890 A1 | 8/2000 |
| WO | 00/45841 A2 | 8/2000 |
| WO | 00/50075 A2 | 8/2000 |
| WO | 00/56360 A2 | 9/2000 |
| WO | 00/57906 A1 | 10/2000 |
| WO | 00/61761 A2 | 10/2000 |
| WO | 00/66741 A2 | 11/2000 |
| WO | 00/66791 A1 | 11/2000 |
| WO | 00/71574 A2 | 11/2000 |
| WO | 00/71725 A2 | 11/2000 |
| WO | 01/04316 A2 | 1/2001 |
| WO | 01/31019 A2 | 5/2001 |
| WO | 01/37863 A2 | 5/2001 |
| WO | 01/38350 A2 | 5/2001 |
| WO | 01/41800 A2 | 6/2001 |
| WO | 01/52885 A1 | 7/2001 |
| WO | 01/64920 A2 | 9/2001 |
| WO | 01/64922 A2 | 9/2001 |
| WO | 01/72337 A1 | 10/2001 |
| WO | 02/058737 A2 | 8/2002 |
| WO | 02/079243 A2 | 10/2002 |
| WO | 02/079246 A2 | 10/2002 |
| WO | 02/083710 A2 | 10/2002 |
| WO | 02/083711 A2 | 10/2002 |
| WO | 02/091998 A2 | 11/2002 |
| WO | 02/098368 A2 | 12/2002 |
| WO | 02/098369 A2 | 12/2002 |
| WO | 03/007985 A2 | 1/2003 |
| WO | 03/009869 A1 | 2/2003 |
| WO | 03/020756 A2 | 3/2003 |
| WO | 03/047619 A2 | 6/2003 |
| WO | 03/063766 A2 | 8/2003 |
| WO | 03/080678 A1 | 10/2003 |
| WO | 03/094834 A2 | 11/2003 |
| WO | 03/094960 A2 | 11/2003 |
| WO | 2004/019977 A2 | 3/2004 |
| WO | 2004/019992 A1 | 3/2004 |
| WO | 2004/032958 A1 | 4/2004 |
| WO | 2004/046177 A2 | 6/2004 |
| WO | 2004/048404 A2 | 6/2004 |
| WO | 2004/065603 A2 | 8/2004 |
| WO | 2004/067030 A2 | 8/2004 |
| WO | 2004/067033 A1 | 8/2004 |
| WO | 2004/083251 A2 | 9/2004 |
| WO | 2004/094596 A2 | 11/2004 |
| WO | 2004/103400 A2 | 12/2004 |
| WO | 2005/000345 A2 | 1/2005 |
| WO | 2005/004908 A1 | 1/2005 |
| WO | 2005/004909 A2 | 1/2005 |
| WO | 2005/020964 A1 | 3/2005 |
| WO | 2005/032583 A2 | 4/2005 |
| WO | 2005/033148 A1 | 4/2005 |
| WO | 2005/065708 A2 | 7/2005 |
| WO | 2005/090985 A1 | 9/2005 |
| WO | 2005/090986 A1 | 9/2005 |
| WO | 2005/102384 A2 | 11/2005 |
| WO | 2005/103230 A2 | 11/2005 |
| WO | 2005/105140 A2 | 11/2005 |
| WO | 2005/105141 A2 | 11/2005 |
| WO | 2005/108580 A1 | 11/2005 |
| WO | 2005/113607 A2 | 12/2005 |
| WO | 2006/000920 A2 | 1/2006 |
| WO | 2006/011060 A2 | 2/2006 |
| WO | 2006/024954 A2 | 3/2006 |
| WO | 2006/027685 A2 | 3/2006 |
| WO | 2006/046143 A2 | 5/2006 |
| WO | 2006/067632 A2 | 6/2006 |
| WO | 2006/075170 A1 | 7/2006 |
| WO | 2006/081259 A2 | 8/2006 |
| WO | 2006/096701 A2 | 9/2006 |
| WO | 2006/120576 A2 | 11/2006 |
| WO | 2007/000314 A2 | 1/2007 |
| WO | 2007/000341 A2 | 1/2007 |
| WO | 2007/000342 A2 | 1/2007 |
| WO | 2007/000343 A2 | 1/2007 |
| WO | 2007/026249 A2 | 3/2007 |
| WO | 2007/028408 A1 | 3/2007 |
| WO | 2007/060548 A2 | 5/2007 |
| WO | 2007/071786 A2 | 6/2007 |

(56) References Cited

FOREIGN PATENT DOCUMENTS

| WO | 2007/127665 A2 | 8/2007 |
|---|---|---|
| WO | 2007/111940 A2 | 10/2007 |
| WO | 2007/127668 A2 | 11/2007 |
| WO | 2007/144316 A2 | 12/2007 |
| WO | 2007/144317 A2 | 12/2007 |
| WO | 2008/001222 A2 | 1/2008 |
| WO | 2008/001224 A2 | 1/2008 |
| WO | 2008/013943 A2 | 1/2008 |
| WO | 2008/079372 A2 | 7/2008 |
| WO | 2008/084411 A2 | 7/2008 |
| WO | 2008/149238 A2 | 12/2008 |
| WO | 2009/010877 A2 | 1/2009 |
| WO | 2009/016515 A2 | 2/2009 |
| WO | 2009/050586 A1 | 4/2009 |
| WO | 2009/104097 A2 | 8/2009 |
| WO | 2009/109550 A1 | 9/2009 |
| WO | 2009/114485 A1 | 9/2009 |
| WO | 2009/143168 A2 | 11/2009 |
| WO | 2009/158142 A1 | 12/2009 |
| WO | 2010/027872 A1 | 3/2010 |
| WO | 2010/028096 A2 | 3/2010 |
| WO | 2010/028859 A1 | 3/2010 |
| WO | 2010/067202 A2 | 6/2010 |
| WO | 2010/070453 A2 | 6/2010 |
| WO | 2010/077422 A2 | 7/2010 |
| WO | 2010/109323 A1 | 9/2010 |
| WO | 2010/109324 A1 | 9/2010 |
| WO | 2010/127172 A2 | 11/2010 |
| WO | 2011/024072 A2 | 3/2011 |
| WO | 2011/039631 A2 | 4/2011 |
| WO | 2011/042516 A2 | 4/2011 |
| WO | 2011/051893 A1 | 5/2011 |
| WO | 2011/080595 A2 | 7/2011 |
| WO | 2011/110531 A2 | 9/2011 |
| WO | 2011/110634 A1 | 9/2011 |
| WO | 2011/110635 A1 | 9/2011 |
| WO | 2011/126863 A1 | 10/2011 |
| WO | 2011/161653 A1 | 12/2011 |
| WO | 2012/020326 A1 | 2/2012 |
| WO | 2012/025873 A2 | 3/2012 |
| WO | 2012/031271 A1 | 3/2012 |
| WO | 2012/032169 A1 | 3/2012 |
| WO | 2012/032489 A1 | 3/2012 |
| WO | 2012/032498 A2 | 3/2012 |
| WO | 2012/035519 A1 | 3/2012 |
| WO | 2012/117377 A1 | 9/2012 |
| WO | 2012/134975 A1 | 10/2012 |
| WO | 2013/132452 A2 | 9/2013 |
| WO | 2014/136064 A2 | 9/2014 |
| WO | 2015/033251 A2 | 3/2015 |
| WO | 2016/132294 A1 | 8/2016 |
| WO | 2016/178123 A1 | 11/2016 |
| WO | 2018/142280 A2 | 8/2018 |

OTHER PUBLICATIONS

Telford et al., "Chapter 1: Genomics and Proteomics in Vaccine Design", New Bacterial Vaccines, Kleweur Academic/Plenum Publishers, USA, pp. 1-11 (2003).

Tettelin et al, "Complete Genome Sequence of Neisseria meningitidis Serogroup B Strain MC58", Science 287:1809-1815 (2000).

Ton-That et al, "Purification and characterization of sortase, the transpeptidase that cleaves surface proteins of Staphylococcus aureus at the LPXTG motif", Proc Natl Acad Sci 96(22):12424-12429 (1999).

Tondella et al, "Distribution of Neisseria meningitidis Serogroup B Serosubtypes and Serotypes Circulating in the United States", Journal of Clinical Microbiology 38(9):3323-3328 (2000).

Uchida et al, "Diphtheria Toxin and Related Proteins: I. Isolation and Properties of Mutant Proteins Serologically Related to Diphtheria Toxin", The Journal of Biological Chemistry 248(11):3838-3844 (1973).

Uli et al., "Outer Membrane Vesicles of VA-MENGOC-BC Vaccine Against Serogroup B of Neisseria Meningitidis: Analysis of Protein Components by Two-Dimensional Gel Electrophoresis and Mass Spectrometry", Proteomics 6:3389-3399 (2006).

Ulmer et al, "Heterologous Protection Against Influenza by Injection of DNA Encoding a Viral Protein", Science 259:1745-1748 (1993).

U.S. Pat. No. 8,398,988 B2 Prosecution History (Feb. 23, 2012-Feb. 27, 2013).

VA-MENGOC-BC® Summary of Product Characteristics (Dec. 2011) along with translation into English and translation certificate dated Jul. 6, 2015.

Van Der Ende et al, "Deletion of porA by Recombination between Clusters of Repetitive Extragenic Palindromic Sequences in Neisseria meningitidis", Infection and Immunity 67(6):2928-2934 (1999).

Van Der Ende et al, "Multiple Mechanisms of Phase Variation of PorA in Neisseria meningitidis", Infection and Immunity 68(12):6685-6690 (2000).

Van Der Ley et al, "Construction of Neisseria meningitidis Strains Carrying Multiple Chromosomal Copies of the porA gene for Use in the production of a Multivalent Outer Membrane Vesicle Vaccine", Vaccine 13(4):401-407 (1995).

Vesikari et al, "Meningococcal Serogroup B Bivalent rLP2086 Vaccine Elicits Broad and Robust Serum Bactericidal Responses in Healthy Adolescents", Journal of the Pediatric Infectious Diseases Society, (Aug. 4, 2015), pp. 1-9, Electronic Publication Date: Aug. 4, 2015.

Vesikari et al, "Immunogenicity, Safety, and Tolerability of Bivalent rLP2086 Meningococcal Group B Vaccine Administered Concomitantly With Diphtheria, Tetanus, and Acellular Pertussis and Inactivated Poliomyelitis Vaccines to Healthy Adolescents", Journal of the Pediatric Infectious Diseases Society, (Jan. 23, 2016), pp. 1-8, Electronic Publication Date: Jan. 23, 2016.

Vidor, "The Nature and Consequences of Intra- and Inter-vaccine Interference." J Comp. Pathol. 137 Suppl 1:S62-S66 (2007).

Wahl et al, "Improved Radioimaging and Tumor Localization with Monoclonal F(ab')2", J Nucl Med 24:316-325 (1983).

Wang et al, "Prevalence and genetic diversity of candidate vaccine antigens among invasive Neisseria meningitidis isolates in the United States", Vaccine 29:4739-4744 (2011).

Webster's II New Riverside University Dictionary, The Riverside Publishing Company, p. 933 (1984).

Weldingh et al, "Two-Dimensional Electrophoresis for Analysis of Mycobacterium tuberculosis Culture Filtrate and Purification and Characterization of Six Novel Proteins", Infection and Immunity 66(8):3492-3500 (1998).

Welsch et al, "Protective Activity of Monoclonal Antibodies to Genome-Derived Neisserial Antigen 1870, a Neisseria meningitidis Candidate Vaccine", The Journal of Immunology 172:5606-5615 (2004).

Welsch et al, Factor H and Neisserial pathogenesis, Vaccine 26(Supp8): I40-I45 (2008).

Wiertz et al, "T-Cell Responses to Outer Membrane Proteins of Neisseria meningitidis: Comparative Study of the Opa, Opc, and Por A Proteins", Infection and Immunity 64(1) 298-304 (1996).

Williams et al, "Introduction of foreign genes into tissues of living mice by DNA-coated microprojectiles", Proc. Natl. Acad. Sci. 88:2726-2730 (1991).

Wilson et al, "Hepatocyte-directed Gene Transfer in Vivo Leads to Transient Improvement of Hypercholesterolemia in Low Density Lipoprotein Receptor-deficient Rabbits", The Journal of Biological Chemistry 267(2):963-967 (1992).

Witze et al, "Mapping Protein Post-Translational Modifications with Mass Spectrometry", Nat Methods 4(10):798-806 (2007).

Wolf et al, "Conditions Affecting Direct Gene Transfer into Rodent Muscle In Vivo", Biotechniques 11(4):474-485 (1991).

Wolff et al, "Direct Gene Transfer into Mouse Muscle in Vivo", Science 247:1465-1468 (1990).

Woods et al, "Resistance to Meningococcemia Apparently Conferred by Anti-H.8 Monoclonal Antibody Is Due to Contaminating Endotoxin and Not to Specific Immunoprotection", Infection and Immunity 55(8): 1927-1928 (1987).

(56) References Cited

OTHER PUBLICATIONS

Wu et al, "Receptor-mediated in Vitro Gene Transformation by a Soluble DNA Carrier System", The Journal of Biological Chemistry 262(10):4429-4432 (1987).
Wu et al, "Receptor-mediated Gene Delivery and Expression in Vivo", The Journal of Biological Chemistry 263 (29):14621-14624 (1988).
Wyeth Neisseria Meningitidis Serogroup B Vaccine, Vaccine and Related Biological Products Advisory Committee Pre-Meeting Background Document, URL:http://www.fda.gov/downloads/AdvisoryCommittees/CommitteesMeetingMaterials/BloodVaccinesandOtherBiologics/VaccinesandRelatedBiologicalProductsAdvisoryCommittee/UCM249479.pdf, Mar. 4, 2011.
Yakushi et al, "Lethality of the Covalent Linkage between Mislocalized Major Outer Membrane Lipoprotein and the Peptidoglycan of *Escherichia coli*", Journal of Bacteriology 179(9):2857-2862 (1997).
Yakushi et al, "A new ABC transporter mediating the detachment of lipid-modified proteins from membranes", Nature Cell Biology 2:212-218 (2000).
York, "Pfizer's Investigational Vaccine, rLP2086, for Invasive Meningococcal Serogroup B Disease", Sabin Vaccine Institute, http://www.sabin.org/sites/sabin.org/files/Laura%20J%20York.pdf, accessed Aug. 1, 2014.
Yutsudo et al, "The Gene Encoding a New Mitogenic Factor in a *Streptococcus pyogenes* Strain Is Distributed Only in Group A Streptococci", Infection and Immunity 62(9):4000-4004 (1994).
Zagursky et al, "Bioinformatics: Use in Bacterial Vaccine Delivery", BioTechniques 31(3):636-659 (2001).
Zavascki et al, "First Case Report of Neisseria lactamica Causing Cavitary Lung Disease in an Adult Organ Transplant Recipient", Journal of Clinical Microbiology 44(7):2666-2668 (2006).
Zhu et al, "Evaluation of Recombinant Lipidated P2086 Protein as a Vaccine Candidate for Group B Neisseria meningitidis in a Murine Nasal Challenge Model", Infection and Immunity 73(10):6838-6845 (2005).
Zhu et al, "Intranasal immunization of mice with recombinant lipidated P2086 protein reduces nasal colonization of group B Neisseria meningitidis", Vaccine 24:5420-5425 (2006).
Zollinger, "New and Improved Vaccines Against Meningococcal Disease", New Generation Vaccines, 2nd Ed., Myron M. Levine, et al. eds., Marcel Dekker, Inc., New York, NY pp. 469-488 (1997).
Zufferey et al, "Self-Inactivating Lentivirus Vector for Safe and Efficient In Vivo Gene Delivery", Journal of Virology 72(12):9873-9880 (1998).
Romero et al, "Current Status of Meningococcal Group B Vaccine Candidates: Capsular or Noncapsular?" Clinical Microbiology Reviews 7(4):559-575 (1994).
Rose et al, "Pyruvic Acid is Attached Through Its Central Carbon Atom to the Amino Terminus of the Recombinant DNA-derived DNA-binding Protein Ner of Bacteriophage Mu", The Journal of Biological Chemistry 267 (27):19101-19106 (1992).
Rosenqvist et al, "Human Antibody Responses to Meningococcal Outer Membrane Antigens after Three Doses of the Norwegian Group B Meningococcal Vaccine", Infection and Immunity 63(12):4642-4652 (1995).
Rosenqvist et al, "Effect of Aluminium Hydroxide and Meningococcal Serogroup C Capsular Polysaccharide on the Immunogenicity and Reactogenicity of a Group B Neisseria Meningitides Outer Membrane Vesicle Vaccine", Dev Biol Stand 92:323-333 (1998).
Rosenstein et al, "Meningococcal Vaccines", Infectious Disease Clinics of North America 15(1):155-169 (2001).
Ross et al, "Identification of Vaccine Candidate Antigens from a Genomic Analysis of Porphyromonas gingivalis", Vaccine 19:4135-4142 (2001).
Saez-Llorens et al, "Immunogenicity and Safety of Investigationals Vaccine Formulations Against Meningococcal Serogroups A, B, C, W, and Y in Healthy Adolescents", Human Vaccines and Immunotherapeutics 11(6):1507-1517 (2015).

Sahagan et al, "A Genetically Engineered Murine/Human Chimeric Antibody Retains Specificity for Human Tumor-Associated Antigen", The Journal of Immunology 137(3):1066-1074 (1986).
Salzberg et al, "Microbial gene identification using interpolated Markov models", Nucleic Acids Research 26(2):544-548 (1998).
Sambrook et al, "Analysis and Cloning of Eukaryotic Genomic DNA", Molecular Cloning: A Laboratory Manual, Second Edition, Cold Spring Harbor Laboratory Press, Cold Spring Harbor, New York, Chapter 9, pp. 9.1-9.62 (1989).
Sambrook et al, "Synthetic Oligonucleotide Probes", Molecular Cloning: A Laboratory Manual, Second Edition, Cold Spring Harbor Laboratory Press, Cold Spring Harbor, New York, Chapter 11, pp. 11.1-11.61 (1989).
Sambrook et al., Molecular Cloning: A Laboratory Manual, Third Edition, Cold Spring Harbor Laboratory Press, Cold Spring Harbor, New York (2001).
Samulski et al, "A Recombinant Plasmid from Which an Infectious Adeno-Associated Virus Genome Can Be Excised In Vitro and Its Use To Study Viral Replication", Journal of Virology 61(10):3096-3101 (1987).
Samulski et al, "Helper-Free Stocks of Recombinant Adeno-Associated Viruses: Normal Integration Does Not Require Viral Gene Expression", Journal of Virology 63(9):3822-3828 (1989).
Sanger Centre FTP files [online] URL: ftp://ftp.sanger.ac.uk/pub/pathogens/nm/, dated Jul. 23, 2008.
Sanger Centre's "Projects" website as of Dec. 10, 1997 as retrievable via http:/web.archive.org, accessed Mar. 15, 2010.
Sankaran, K, et al., "Lipid Modification of Bacterial Prolipoprotein", The Journal of Biological Chemistry, 269 (31):19701-19706 (1994).
Sankaran et al, "Modification of Bacterial Lipoproteins", Methods in Enzymology 250:683-697 (1995).
Sastalla et al, "Codon-Optimized Fluorescent Proteins Designed for Expression in Low-GC Gram-Positive Bacteria", Applied and Environmental Microbiology, 75(7):2099-2110 (2009).
Saukkonen et al., "Protective efficacy of monoclonal antibodies to class 1 and class 3 outer membrane proteins of Neisseria meningitidis B:15:P1.16 in infant rat infection model: new prospects for vaccine development", Microbial Pathogenesis 3:261-267 (1987).
Saunders et al, "A rapid and sensitive PCR strategy employed for amplification and sequencing of porA from a single colony-forming unit of Neisseria meningitidis", Gene 137:153-162 (1993).
Saunders et al, "Confirmation of Suspicious Cases of Meningococcal Meningitidis by PCR and Enzyme-Linked Immunosorbet Assay", J. Clin. Microbiol. 35(12):3215-3219 (1997).
Sedegah et al, "Protection against malaria by immunization with plasmid DNA encoding circumsporozoite protein", Proc. Natl. Acad. Sci. 91:9866-9870 (1994).
Sedegah et al, "Improving Protective Immunity Induced by DNA-Based Immunization: Priming with Antigen and GM-CSF-Encoding Plasmid DNA and Boosting witih Antigen-Expressing Recombinant Poxvirus", The Journal of Immunology 164:5905-5912 (2000).
Seib et al, "Characterization of Diverse Subvariants of the Meningococcal Factor H (fH) Binding Protein for Their Ability To Bind fH, To Mediate Serum Resistance, and To Induce Bactericidal Antibodies", Infection and Immunity 79 (2):970-981 (2011).
Sepelyak et al, "Adsorption of Pepsin by Aluminum Hydroxide I: Adsorption Mechanism", Journal of Pharmaceutical Sciences 73(11):1514-1517 (1984).
Sequence Analysis in Molecular Biology. Treasure Trove or Trivial Pursuit, Gunnar von Heijne, Academic Press (1987).
Sequence Analysis Primer, Gribskov and Devereux, eds., M Stockton Press, New York 1991.
Serruto et al, "Genome-based approaches to develop vaccines against bacterial pathogens", Vaccine 27:3245-3250 (2009).
Sheldon et al, "A phase 1, randomized, open-label, active-controlled trial to assess the safety of a meningococcal serogroup B bivalent rLP2086 vaccine in healthy adults", Human Vaccines & Immunotherapeutics 8(7):888-895 (2012).
Sierra et al, "Vaccine Against Group B Neisseria Meningitidis: Protection Trial and Mass Vaccination Results in Cuba", NIPH Annals 14(2): 195-210 (1991).

(56) References Cited

OTHER PUBLICATIONS

Smith et al, "Nucleotide sequence determination and genetic analysis of the bacteroides plasmid, pBI143," Plasmid 34(3):211-222 (1995).
Snape et al, "Immunogenicity of Two Investigational Serogroup B Meningococcal Vaccines in the First Year of Life", The Pediatric Infectious Disease Journal 29(11):e71-e79 (2010).
Snapper et al, "Bacterial Lipoproteins May Substitute for Cytokines in the Humoral Immune Response to T Cell-Independent Type II Antigens", The Journal of Immunology 155:5582-5589 (1995).
Snapper et al, "IL-3 and Granulocyte-Macrophage Colony-Stimulating Factor Strongly Induce Ig secretion by Sort-Purified Murine B Cells Activated Through the Membrane Ig, but Not the CD40, Signaling Pathway", The Journal of Immunology 154:5842-5850 (1995).
Sonnenberg et al, "Definition of Mycobacterium tuberculosis Culture Filtrate Proteins by Two-Dimensional Polyacrylamide Gel Electrophoresis, N-Terminal Amino Acid Sequencing, and Electrospray Mass Spectrometry", Infection and Immunity 65(11):4515-4524 (1997).
Sonnhammer et al, "Pfam: A Comprehensive Database of Protein Domain Families Based on Seed Alignments", PROTEINS: Structure, Function, and Genetics 28:405-420 (1997).
Stedman's Medical Dictionary, Illustrated, 24th Edition, Williams & Wilkins, Baltimore, Maryland, p. 707 (1982).
Stevens, "Streptococcal Toxic-Shock Syndrome: Spectrum of Disease, Pathogenesis, and New Concepts in Treatment", Emerging Infectious Diseases 1(3):69-78 (1995).
Stockbauer et al, "A natural variant of the cysteine protease virulence factor of group A *Streptococcus* with an arginine-glycine-aspartic acid (RGD) motif preferentially binds human integrins alphavbeta3 and alphaIIbbeta3", Proc. Natl. Acad. Sci. 96:242-247 (1999).
Stratford-Perricaudet et al, "Widespread Long-term Gene Transfer to Mouse Skeletal Muscles and Heart", J. Clin. Invest. 90:626-630 (1992).
Strauss, "Using DNA Fragments as Probes", Current Protocols in Molecular Biology, Supp. 24, 6.3.1-6.3.6 (1993).
Suhrbier, "Multi-epitope DNA vaccines", Immunology and Cell Biology 75(4):402-408 (1997).
Sun et al, "Chimeric antibody with human constant regions and mouse variable regions directed against carcinoma-associated antigen 17-1A", Proc. Natl. Acad. Sci. 84:214-218 (1987).
Supplementary Declaration by Dr. Julian Parkhill submitted in Opposition Proceedings against Novartis EP1645631 on May 10, 2010.
Supplementary Submission in Opposition Proceedings against Novartis EP 1 645 631 submitted May 25, 2010.
Sutcliff et al, "Lipoproteins of Gram-Positive Bacteria", Journal of Bacteriology 177(5):1123-1128 (1995).
Sworn Statement from Dr. Rino Rappuoli submitted in Opposition Proceedings against Novartis EP1645631 on Oct. 14, 2011.
Sworn Statement from Dr. Giovanna Campanella submitted in Opposition Proceedings against Novartis EP1409013 on Nov. 10, 2011.
Tappero et al, "Immunogenicity of 2 Serogroup B Outer-Membrane Protein Meningococcal Vaccines", JAMA 281 (16):1520-1527 (1999).
Paoletti et al, "Potency of clinical group B streptococcal conjugate vaccines", Vaccine 19(15-16):2118-2126 (2001).
Park et al, "DIVCLUS: an automatic method in the GEANFAM-MER package that finds homologous domains in single- and multi-domain proteins", Bioinformatics 14(2):144-150 (1998).
Parkhill, "Campylobacter jejuni genome sequence at the Sanger Centre", (May 8, 1998), available at: http://www.bio.net/bionet/mm/bionews/1997-May/00442.html.
Parkhill et al, "Complete DNA sequence of a serogroup A strain of Neisseria meningitidis Z2491", Nature 404:502-506 (2000).
Patel, "Outbreaks of Serogroup B Meningococcal Disease on University Campuses—2013", Medical Officer, Meningitis and Vaccine Preventable Diseases Branch, http://www.cdc.gov/vaccines/acip/meetings/downloads/slides-2014-02/04-Mening-Patel.pdf, 16 Pages, Apr. 3, 2014.
Patentees' Further Submission Under Rule 116 EPC in Opposition against Novartis EP 1 645 631 submitted Oct. 14, 2011.
Patentee's Response to Notice of Opposition by GlaxoSmithKline Biologicals S.A. against Wyeth Holdings LLC's EP 2 343 308 submitted May 2, 2016.
Patentees' Response to Opposition against Novartis EP 1 645 631 submitted May 8, 2009.
Patentees' Submissions Under Rule 116 EPC in Opposition against Novartis EP 1 645 631 submitted Sep. 13, 2011.
PCT Annex to Form PCT/ISA/206 Communication Relating to the Results of the Partial International Search, PCT/US2007/026238.
PCT International Preliminary Report on Patentability for PCT/US2007/026238 issued Jun. 24, 2009.
PCT International Search Report for PCT/US02/32369 issued Nov. 14, 2003.
PCT International Search Report for PCT/US2007/026238 issued Feb. 23, 2009.
PCT International Search Report for PCT/IB2011/053934 issued Jan. 20, 2012.
PCT International Search Report and Written Opinion for International Application No. PCT/IB2020/050988 mailed on Jul. 17, 2020.
Perrett et al, "Towards an improved serogroup B Neisseria meningitidis vaccine", Expert Opin. Biol. Ther. 5 (12):1611-1625 (2005).
Peterson et al, "Review of the Folin Phenol Protein Quantitation Method of Lowry, Rosebrough, Farr and Randall", Analytical Biochemistry 100(2):201-220 (1979).
Pettersson et al, "The meningococcal lactoferrin receptor", IPNC Abstract (1998).
Pettersson et al, "Vaccine potential of the Neisseria meningitidis Lactoferrin-binding Proteins LbpA and LbpB", Vaccine 24(17):3545-3557 (2006).
Phillips, "The challenge of gene therapy and DNA delivery", Journal of Pharmacy and Pharmacology 53:1169-1174 (2001).
Pierschbacher et al, "Influence of Stereochemistry of the Sequence Arg-Gly-Asp-Xaa on Binding Specificity in Cell Adhesion", The Journal of Biological Chemistry 262(36):17294-17298 (1987).
Pillai et al, "Outer membrane protein (OMP) based vaccine for Neisseria meningitidis serogroup B", Vaccine 23:2206-2209 (2005).
Pizza et al, "Identification of Vaccine Candidates Against Serogroup B Meningococcus by Whole-Genome Sequencing", Science 287:1816-1820 (2000).
Pizza, Preparation of Meningococcal Antigens (2005), available at: http://cordis.europa.eu/search/index.cfm?fuseaction=result.document &RS LANG=EN&RS RCN=7461241&q=.
Pizza et al, "Factor H-binding protein, a unique meningococcal vaccine antigen", Vaccine 26(Supp8):I46-I48 (2008).
Podbielski et al, "The Group A Streptococcal virR49 Gene Controls Expression of Four Structural vir Regulon Genes", Infection and Immunity 63(1):9-20 (1995).
Polakowski, "Pharmacovigilence Plan Review—Trumenba", XP055266007, Retrieved from the Internet: URL:http//www.fda.gov/downloads/BiologicsBlood/Vaccines/Vaccines/ApprovedProducts/UCM424630: pp. 1-28, Nov. 23, 2014.
Pollitt et al, "Effect of Amino Acid Substitutions at the Signal Peptide Cleavage Site of the *Escherichia coli* Major Outer Membrane Lipoprotein", The Journal of Biological Chemistry 261(4):1835-1837 (1986).
Poolman et al, "Colony variants of Neisseria meningitidis strain 2996 (B-2b:P1.2): influence of class-5 outer membrane proteins and lipopolysaccharides", J Med Microbiol 19(2):203-209 (1985).
Poolman, "Development of a meningococcal vaccine," Infectious Agents and Disease 4(1):13-28 (1995).
Poolman, "Bacterial Outer Membrane Protein Vaccines: The Meningococcal Example", Advances in Experimental Medicine & Biology 397:73-77 (1996).
Preliminary Opinion of the Opposition Division in Opposition against Novartis EP 1 645 631 dated Jun. 24, 2011.
Proft et al, "Identification and Characterization of Novel Superantigens from *Streptococcus pyogenes*", J. Exp. Med. 189(1):89-101 (1999).

(56) References Cited

OTHER PUBLICATIONS

Progress through the Sanger Institute FTP Server, submitted in Opposition Proceedings against Novartis EP1645631 on May 8, 2009.
Prome et al, "Structure of the Human Adult Hemoglobin Minor Fraction A1b bu Electrospray and Secondary Ion Mass Spectrometry. Pyruvic Acid as Amino-Terminal Blocking Group", The Journal of Biological Chemistry 266 (20):13050-13054 (1991).
Prome et al, "Characterization of new amino-terminal blocking groups in the normal human adult hemoglobin Hb A1b", Eur. Mass Spectrom. 1(2):195-201 (1995).
Prosecution history of U.S. Appl. No. 13/455,326, dated Apr. 26, 2013, downloaded from PAIR Aug. 12, 2013 (Third-party submission under 37 CFR 1.290).
PSORT analysis of 200 of the sequences disclosed in PCT/US99/09346, submitted in Opposition Proceedings against Novartis EP1645631 on May 25, 2010 Part 1.
PSORT analysis of 200 of the sequences disclosed in PCT/US99/09346, submitted in Opposition Proceedings against Novartis EP1645631 on May 25, 2010 Part 2.
PSORT analysis of Seq Id Nos. 4 and 6, and of 'Contig295' 300mer, submitted in Opposition Proceedings against Novartis EP1645631 on May 8, 2009.
PSORT prediction result for Seq Id No. 2, submitted in Opposition Proceedings against Novartis EP1645631 on May 25, 2010.
Pugsley, "The Complete General Secretory Pathway in Gram-Negative Bacteria", Microbiological Reviews 57 (1):50-108 (1993).
Quinn et al, "Immunological Relationship between the Class I Epitope of Streptococcal M Protein and Myosin", Infection and Immunity 66(9):4418-4424 (1998).
Random House Dictionary, Random House, New York, p. 546 (1984).
Reda et al, "Phylogenetic Distribution of Streptococcal Superantigen SSA Allelic Variants Provides Evidence for Horizontal Transfer of ssa within *Streptococcus pyogenes*", Infection and Immunity 64(4):1161-1165 (1996).
Reisinger et al., "Safety, Tolerability, and Immunogenicity of Gardasil Given Concomitantly with Menactra and Adacel" Pediatrics 125(6):1142-1151 (2010).
Richmond et al, "Safety, immunogenicity, and tolerability of meningococcal serogroup B bivalent recombinant lipoprotein 2086 vaccine in healthy adolescents: a randomised, single-blind, placebo-controlled, phase 2 trial", The Lancet Infectious Disease 12(8):597-607 (2012).
Richmond et al, "A bivalent Neisseria meningitidis recombinant lipidated factor H binding protein vaccine in young adults: Results of a randomised, controlled, dose-escalation phase 1 trial", Vaccine 30:6163-6174 (2012).
Rinaudo et al, "Vaccinology in the genome era", The Journal of Clinical Investigation 119(9):2515-2525 (2009).
Rodriguez et al, "The Epidemiological Impact of Antimeningococcal B Vaccination in Cuba", Mem Inst Oswaldo Cruz 94(4):433-440 (1999).
Cannon, "Conserved Lipoproteins of Pathogenic Neisseria Species Bearing the H.8 Epitope: Lipid-Modified Azurin and H.8 Outer Membrane Protein", Clinical Microbiology Reviews 2(Suppl):S1-S4 (1989).
Cantini et al, "Solution Structure of the Immunodominant Domain of Protective Antigen GNA1870 of Neisseria meningitidis", The Journal of Biological Chemistry 281(11):7220-7227 (2006).
Carillo et al, "The Multiple Sequence Alignment Problem in Biology", SIAM J. Appl. Math. 48(5):1073-1082 (1988).
Chao et al., "Endocarditis due to Neisseria sicca: Report of One Case", Acta Paed Sin 38(3):229-231 (1997).
Cheetham et al, "An HPLC Method for the Determination of Acetyl and Pyruvyl Groups in Polysaccharides, Carbohydrade Polymers", School of Chemistry, The University of New South Wales, 5 (6): 399-406 (1985).
Chen et al., "Cloning and Expression of the Streptococcal C5a Peptidase Gene in *Escherichia coli*: Linkage to the Type 12 M Protein Gene", Infection and Immunity 57(6):1740-1745 (1989).
Chen et al, "Determination of the Optimal Aligned Spacing Between the Shine—Dalgarno Sequence and the Translation Initiation Codon of *Escherichia coli* mRNAs", Nucleic Acids Research 22(23):4953-4957 (1994).
Chmouryguina et al, "Conservation of the C5a Peptidase Genes in Group A and B Streptococci", Infection and Immunity 64(7):2387-2390 (1996).
Chu et al, "Further Studies on the Immunogenicity of Haemophilus influenzae Type b and Pneumococcal Type 6A Polysaccharide-Protein Conjugates", Infection and Immunity 40(1):245-256 (1983).
Cockerill et al, "Molecular, Serological, and Clinical Features of 16 Consecutive Cases of Invasive Streptococcal Disease", Clinical Infectious Diseases 26:1448-1458 (1998).
Coleman et al, "Virus Attenuation by Genome-Scale Changes in Codon Pair Bias", Science 320:1784-1787 (2008).
Computational Molecular Biology: Sources and Methods for Sequence Analysis, Lesk A.M. et., Oxford University Press, New York, 1988.
Courtney et al, "Cloning, Sequencing, and Expression of a Fibronectin/Fibrinogen-Binding Protein from Group A Streptococci", Infection and Immunity 62(9):3937-3946 (1994).
Cserzo et al, "Prediction of transmembrane alpha-helices in prokaryotic membrane proteins: the dense alignment surface method", Protein Engineering 10(6):673-676 (1997).
Cunningham et al, "Immunological Crossreactivity Between the Class I Epitope of Streptococcal M Protein and Myosin", Adv Exp Med Biol 418:887-892 (1997).
Curiel et al, "High-Efficiency Gene Transfer Mediated by Adenovirus Coupled to DNA-Polylysine Complexes", Human Gene Therapy 3:147-154 (1992).
Curriculum Vitae of Professor Paul M. Dunman, Ph.D., submitted in Opposition Proceedings against Novartis EP 1 645 631 on Sep. 14, 2011.
Curriculum Vitae of Lakshmi Khandke, Ph.D., submitted in Opposition Proceedings against Novartis EP1409013 on Nov. 18, 2011.
DalbØge et al, "In vivo processing of N-terminal methionine in *E. coli*", FEBS Letters 266(1-2):1-3 (1990).
Dale et al, "Passive Protection of Mice Against Group A Streptococcal Pharyngeal Infection by Lipoteichoic Acid", The Journal of Infectious Diseases 169:319-323 (1994).
Dale et al, "Hyaluronate Capsule and Surface M Protein in Resistance to Opsonization of Group A Streptococci", Infection and Immunity 64(5):1495-1501 (1996).
Dale et al, "Recombinant, octavalent group A streptococcal M protein vaccine", Vaccine 14(10):944-948 (1996).
Database EMBL [Online] EBI, Kohara, Y., "Caenorhabditis elegans cDNA clone yk26f2: 5' end, single read," Database accession No. D35881 (Aug. 13, 1994).
Database Geneseq 'Online' "Neisseria gonorrheae ORF 741 protein sequence Seq Id 2534" XP002320504, Mar. 21, 2000.
Database Geneseq 'Online', "Neisseria meningitidis ORF 741 protein sequence Seq Id No. 2536", XP002320506, Mar. 21, 2000.
Database Geneseq 'Online', "N. gonorrhoeae amino acid sequence Seq Id 1586", XP002320505, Mar. 7, 2003.
Database Geneseq Online, "Neisseria meningitides ORF2086 protein-encoding gene SedID61" AAY75530, Jan. 29, 2004.
Database Geneseq Online, "Neisseria meningitides ORF2086 protein-encoding gene SedID61" AAZ54292-NT, Jan. 29, 2004.
Database Geneseq Online, "N. meningitidis NL096 fHBP protein fragment Seq Id 76", XP002703350, Database accession No. AXQ90374, Nov. 26, 2009.
Database Geneseq Online, "Neisseria meningitidis modified fHBP fusion protein SEQ:140", XP002703351, Database accession No. AZG10689, Apr. 28, 2011.
Database Geneseq Online, "Neisseria meningitidis modified fHBP NL096 SEQ:76", XP002703352, Database accession No. AZG10625, Apr. 28, 2011.
Database UniPro 'Online', "Hypothetical Protein NMB1870", XP002308111, Oct. 1, 2000.
Database UniProt 'Online', "Putative lipoprotein N meningitidis (Serotype A)", XP002320503, Oct. 1, 2000.

(56) References Cited

OTHER PUBLICATIONS

DATABASE Uniprot [Online] Jul. 5, 2004, "Factor H binding protein variant A22_001"; Flags: Fragment, retrieved from EBI; Uniprot database accession No. Q6VS35; Database entry from Oct. 28, 2014, entryversion 28, sequence version 2 updated on Sep. 23, 2008 See strains Neisseria meningitidis: CDC-1034 and L4-891.
Database Uniprot [Online] Jul. 4, 2004, "SubName: Full=Factor H binding protein variant A05_001";Flags: Fragment, retrieved from EBI; UNIPROT database accession No. Q6VS29; Database entry from Oct. 28, 2014, entry version 29, sequence version 1See strains Neisseria meningitidis M98-250732 & M98250771.
Database UniProt Online, "Subname: Full=Factor H binding protein variant A62_001; Subname: Full=Factor H binding protein variant A62_002; Flags: Fragment", XP002703353, Database accession No. COJF81, May 5, 2009.
Datasheet for MENCEVAX™, International Data Sheet version 2.1 (May 15, 2000).
Datasheet for MENOMUNE™, product information as of Feb. 2001.
Datasheet for MeNZB® vaccine product prepared Jun. 23, 2009.
De et al, "Purification and characterization of Streptococcus pneumoniae palmitoylated pneumococcal surface adhesin A expressed in Escherichia coli", Vaccine 18:1811-1821 (2000).
Deasy et al, "Challenges for Development of Meningococcal Vaccines in Infants and Children", Expert Review of Vaccines 10(3): 335-343 (2011).
Declaration by Dr. Julian Parkhill, submitted in Opposition Proceedings against Novartis EP1645631 on Jul. 23, 2008.
Declaration of Dr. Ellen Murphy, submitted in Opposition Proceedings against Novartis EP 1 645 631 on Sep. 14, 2011.
Declaration by Professor Paul Dunman, submitted in Opposition Proceedings against Novartis EP1645631 on Sep. 14, 2011.
Declaration of Emilio A. Emini, Ph.D., submitted in Opposition Proceedings against Novartis EP1645631 on Nov. 3, 2011.
Declaration of Lakshmi Khandke, Ph.D., submitted in Opposition Proceedings against Novartis EP1409013 on Dec. 21, 2011.
Definition of "epitope" from Henderson's Dictionary of Biological Terms, 11th edition, Eleanor Lawrence ed., pp. 37, 184 and cover pages (1997).
Delgado et al, "Lipoprotein NMB0928 from Neisseria meningitidis Serogroup B as a Novel Vaccine Candidate", Vaccine 25:8420-8431 (2007).
Dempsey et al, "The physical map of the chromosome of a serogroup A strain of Neisseria meningitidis shows complex rearrangements relative to the chromosomes of the two mapped strains of the closely related species N. gonorrhoeae," Journal of Bacteriology 177(22):6390-6400 (1995).
Devereux et al, "A comprehensive set of sequence analysis programs for the VAX", Nucleic Acids Research 12 (1):387-395 (1984).
Lowry et al, "Protein Measurement with the Folin Phenol Reagent", J. Biol. Chem. 193(1):265-275 (1951).
Lucidarme et al, "Characterization of fHbp, nhba (gna2132), nadA, porA, Sequence Type (ST), and Genomic Presence of IS1301 in Group B Meningococcal ST269 Clonal Complex Isolates from England and Wales", Journal of Clinical Microbiology 47(11):3577-3585 (2009).
Lucidarme et al, "Characterization of fHbp, nhba (gna2132), nadA, porA, and Sequence Type in Group B Meningococcal Case Isolates Collected in England and Wales during Jan. 2008 and Potential Coverage of an Investigational Group B Meningococcal Vaccine", Clinical and Vaccine Immunology 17(6):919-929 (2010).
Lukashin et al, "GeneMark.hmm: new solutions for gene finding", Nucleic Acids Research 26(4): 1107-1115 (1998).
Lukomski et al., "Extracellular Cysteine Protease Produced by Streptococcus pyogenes Participates in the Pathogenesis of Invasive Skin Infection and Dissemination in Mice", Infection and Immunity 67(4): 1779-1788 (1999).

Lunn et al, "Effects of Prolipoprotein Signal Peptide Mutations on Secretion of Hybrid Prolipo-beta-lactamase in Escherichia coli", The Journal of Biological Chemistry 262(17):8318-8324 (1987).
Luo et al, "The Dual Role of Lipids of the Lipoproteins in Trumenba, a Self-Adjuvanting Vaccine Against Meningococcal Meningitis B Disease"", The AAPS Journal 18(6):1562-1575 (2016)".
Machy et al, "Gene transfer from targeted liposomes to specific lymphoid cells by electroporation", Proc. Natl. Acad. Sci. 85:8027-8031 (1988).
Madore, "Characterization of immune response as an indicator of Haemophilus influenzae type b vaccine efficacy", The Pediatric Infectious Disease Journal 17(9):Supplement:S207-S210 (1998).
Malito et al, "Defining a protective epitope on factor H binding protein, a key meningococcal virulence factor and vaccine antigen", PNAS 110(9):3304-3309 (2013).
Mann, et al, "Construction of a Retrovirus Packaging Mutant and Its Use to Produce Helper-Free Defective Retrovirus", Cell 33:153-159 (1983).
Markowitz et al, "A Safe Packaging Line for Gene Transfer: Separating Viral Genes on Two Different Plasmids", Journal of Virology 62(4): 1120-1124 (1988).
Marshall et al, "A phase 2 open-label safety and immunogenicity study of a meningococcal B bivalent rLP2086 vaccine in healthy adults", Vaccine 31(12):1569-1575 (2013).
Martin et al, "Highly Conserved Neisseria meningitidis Surface Protein Confers Protection against Experimental Infection", J. Exp. Med. 185(7):1173-1183 (1997).
Mascioni et al, "Backbone and side-chain assignment of the lipidated and non-lipidated forms of the meningococcal puter membrane protein LP2086", Biomol. NMR Assign. 2009, 3:111-113, published online: Mar. 5, 2009.
Mascioni et al, "Structural Basis for the Immunogenic Properties of the Meningococcal Vaccine Candidate LP2086", Journal of Biological Chemistry 284(13):8738-8746 (2009).
Masignani et al, "Vaccination against Neisseria meningitidis Using Three Variants of the Lipoprotein GNA1870", J. Exp. Med. 197(6):789-799 (2003).
Matsuka et al, "Fibrinogen Cleavage by the Streptococcus pyogenes Extracellular Cysteine Protease and Generation of Antibodies That Inhibit Enzyme Proteolytic Activity", Infection and Immunity 67(9):4326-4333 (1999).
Mazmanian et al, "Staphylococcus aureus Sortase, an Enzyme that Anchors Surface Proteins to the Cell Wall", Science 285:760-763 (1999).
McAtee et al, "Characterization of a Helicobacter pylori vaccine candidate by proteome techniques", Journal of Chromatography B, Biomedical Sciences and Applications 714:325-333 (1998).
McAtee et al, "Identification of Potential Diagnostic and Vaccine Candidates of Helicobacter pylori by "Proteome" Technologies", Helicobacter 3(3):163-169 (1998).
McAtee et al, "Identification of Potential Diagnostic and Vaccine Candidates of Helicobacter pylori by Two- Dimensional Gel Electrophoresis, Sequence Analysis, and Serum Profiling", Clinical and Diagnostic Laboratory Immunology 5(4):537-542 (1998).
McCormick, "Human Gene Therapy: The First Round", BioTechnology 3(8):689-693 (1985).
McGuiness et al, "Class 1 outer membrane protein of Neisseria meningitidis: epitope analysis of the antigenic diversity between strains, implications for subtype definition and molecular epidemiology", Molecular Microbiology 7 (4):505-514 (1993).
McNeil et al, "Detection of LP2086 on the cell surface of Neisseria meningitidis and its accessibility in the presence of serogroup B capsular polysaccharide", Vaccine 27:3417-3421 (2009).
McNeil et al, "Role of Factor H Binding Protein in Neisseria meningitidis Virulence and Its Potential as a Vaccine Candidate to Broadly Protect against Meningococcal Disease", Microbiology and Molecular Biology Reviews 77 (2):234-252 (2013).
McNeil et al, "Predicting the Susceptibility of Meningococcal Serogroup B Isolates to Bactericidal Antibodies Elicited by Bivalent rLP2086, a Novel Prophylactic Vaccine", mBio 9(2):e00036-18 (2018).

(56) References Cited

OTHER PUBLICATIONS

Meinnel et al, "Methionine as translation start signal: A review of the enzymes of the pathway in *Escherichia coli*", Biochimie 75(12): 1061-1075 (1993).
Mejlhede et al, "Ribosomal-1 Frameshifting during Decoding of Bacillus subtilis cdd Occurs at the Sequence CGA AAG", Journal of Bacteriology 181(9):2930-2937 (1999).
Menactra prescribing information, http://www.fda.gov/downloads/BiologicsBloodVaccines/Vaccines/ApprovedProducts/UCM131170.pdf, revised Aug. 26, 2014, accessed Feb. 14, 2015.
Menactra, Australian Public Assessment Report for Groups A, C, Y and W-135 Meningococcal Polysaccharide Diphtheria Toxoid Conjugate Vaccine, https://www.tga.gov.au/file/1277/download , Aug. 31, 2011, accessed Feb. 13, 2015 (part 1 and 2).
Mencevax, New Zealand data sheet, http://www.medsafe.govt.nz/profs/datasheet/m/Mencevaxacwyinj.pdf, date of preparation Mar. 25, 2014, accessed Feb. 14, 2015.
Menveo Package insert, http://www.fda.gov/downloads/BiologicsBloodVaccines/Vaccines/ApprovedProducts/UCM201349.pdf, accessed Feb. 19, 2015, revised Aug. 2013.
"Methionyl aminopeptidase"—INTENZ database of the European Bioinformatics Institute dated Sep. 22, 2008.
Milagres et al., "Specificity of Bactericidal Antibody Response to Serogroup B Miningococcal Strains in Brazilian Children after Immunization with an Outer Membrane Vaccine", Infection and Immunity 66(10):4755-4761 (1998).
Miller et al, "Improved Retroviral Vectors for Gene Transfer and Expression", BioTechniques 7(9):980-990 (1992).
Minutes of Oral Proceedings in Opposition against Novartis EP 1 645 631 dated Mar. 5, 2012.
Mir et al, "Long-term, high level in vivo gene expression after electric pulse-mediated gene transfer into skeletal muscle", Academie des sciences 321:893-899 (1998).
Moe et al, "Sequential Immunization with Vesicles Prepared from Heterologous Neisseria meningitidis Strains Elicits Broadly Protective Serum Antibodies to Group B Strains", Infection and Immunity 70(11): 6021-6031 (2002).
Molinari et al, "The Fibronectin-Binding Protein of *Streptococcus pyogenes*, SfbI, Is Involved in the Internalization of Group A Streptococci by Epithelial Cells", Infection and Immunity 65(4):1357-1363 (1997).
Monsigny et al, "Colorimetric Determination of Neutral Sugars by a Resorcinol Sulfuric Acid Micromethod", Analytical Biochemistry 175:525-530 (1988).
Morbidity and Mortality Weekly Report (MMWR), Recommendations and Reports, Case Definitions for Infectious Conditions Under Public Health Surveillance, May 2, 1997, vol. 46, No. RR-10.
Moreno et al, "Immunity and Protection of Mice Against Neisseria meningitidis Group B by Vaccination, Using Polysaccharide Complexed with Outer Membrane Proteins: A Comparison with Purified B Polysaccharide", Infection and Immunity 47(2):527-533 (1985).
Morley et al, "Vaccine prevention of meningococcal disease, coming soon?", Vaccine 20:666-687 (2002).
Morrison et al, "Chimeric human antibody molecules: Mouse antigen-binding domains with human constant region domains", Proc. Natl. Acad. Sci. 81:6851-6855 (1984).
Mountzouros et al, "Detection of Complement-Mediated Antibody-Dependent Bactericidal Activity in a Fluorescence-Based Serum Bactericidal Assay for Group B Neisseria meningitidis", Journal of Clinical Microbiology 38 (8):2878-2884 (2000).
Moxon, "Applications of molecular microbiology to vaccinology," Lancet 350(9086):1240-1244 (1997).
Munkley et al, "Blocking of Bactericidal Killing of Neisseria meningitidis by Antibodies Directed Against Class 4 Outer Membrane Protein", Microbial Pathogenesis 11:447-452 (1991).
Murphy et al, "Sequence Diversity of the Factor H Binding Protein Vaccine Candidate in Epidemiologically Relevant Strains of Serogroup B Neisseria meningitidis" The Journal of Infectious Diseases 200:379-389 (2009).
Murphy, "HM807466: Neisseria meningitidis strain M08452 factor H binding protein variant B153 (fhbp) gene, partial cds.", URL:http://getentry.ddbj.nig.ac.jp/getentry/na/HM807466/?filetype=html, Jul. 21, 2010.
Duby et al, "Using Synthetic Oligonucleotides as Probes", Current Protocols in Molecular Biology, Supp. 2, 6.4.1-6.4.10 (1993).
Eddy, "Hidden Markov models", Current Opinion in Structural Biology 6:361-365 (1996).
Egan et al, "Relationship between tightness of binding and immunogenicity in an aluminum-containing adjuvant-adsorbed hepatitis B vaccine", Vaccine 27(24):3175-3180 (2009).
Ellen et al, "M Protein-Associated Adherence of *Streptococcus pyogenes* to Epithelial Surfaces: Prerequisite for Virulence", Infection and Immunity 5(5):826-830 (1972).
Ellis, "New Technologies for Making Vaccines", Vaccines, Plotkin et al. editors, W.B. Saunders Company, Philadelphia, Chapter 29, pp. 568-575 (1988).
Eng et al, "An Approach to Correlate Tandem Mass Spectral Data of Peptides with Amino Acid Sequences in a Protein Database", J Am Soc Mass Spectrom 5:976-989 (1994).
EP Application No. 02804818.9 Request for Further Processing submitted Jun. 5, 2012.
EP Application No. 07075161.5 Response to Communication submitted Oct. 28, 2009.
Erdile et al, "Role of Attached Lipid in Immunogenicity of Borrelia burgdorferi OspA", Infection and Immunity 61 (1):81-90 (1993).
European Patent Office, Boards of Appeal: Summons to attend oral proceedings along with a preliminary opinion Issued on Aug. 12, 2021 for Wyeth LLC's EP2613806.
Falugi et al, "Rationally designed strings of promiscuous CD4+ T cell epitopes provide help to Haemophilus Influenzae type b oligosaccharide: a model for new conjugate vaccines", Eur. J. Immunol. 31:3816-3824 (2001).
Farley et al, "Characterization, cloning and expression of different subfamilies of the ORF2086 gene from Neisseria meningitidis", Abstracts of the Thirteenth International Pathogenic Neisseria Conference, (Ed) Caugant et al., Oslo, Norway, p. 124, Sep. 1-6, 2002.
Farley et al, poster entitled "Characterization, Cloning and Expression of Different Subfamlies of the ORF 2086 gene Neisseria Meningitidis", presented at the Thirteenth International Pathogenic Neisseria Conference (the 'IPNC Oslo 2002'), hosted at the Norwegian Institute of Public Health, Oslo, Norway between Sep. 1, 2002 and Sep. 6, 2002, as evidenced by photographs and transcript thereof.
Feavers et al, "Meningococcal protein antigens and vaccines", Vaccine 275:B42-B50 (2009).
Felgner et al, "Lipofection: A highly efficient, lipid-mediated DNA-transfection procedure", Proc. Natl. Acad. Sci. 84:7413-7417 (1987).
Felgner et al, "Cationic liposome-mediated transfection", Nature 337:387-388 (1989).
Final Written Submission in Preparation of Oral Proceedings in Opposition against Novartis EP 1 645 631 submitted Sep. 14, 2011.
Findlow et al, "Multicenter, Open-Label, Randomized Phase II Controlled Trial of an Investigational Recombinant Meningococcal Serogroup B Vaccine With and Without Outer Membrane Vesicles, Administered in Infance", Clinical Infectious Diseases 51(10):1127-1137 (2010).
Fischetti et al, "Conservation of a hexapeptide sequence in the anchor region of surface proteins from Gram-positive cocci", Molecular Microbiology 4(9):1603-1605 (1990).
Fleischmann et al, "Whole-Genome Random Sequencing and Assembly of Haemophilus influenzae Rd", Science 269:496-501 (1995).
Fletcher et al, "Vaccine Potential of the Neisseria meningitidis 2086 Lipoprotein", Infection and Immunity 72 (4):2088-2100 (2004).
Fogg et al, "Constitutive Expression of Fibronectin Binding in *Streptococcus pyogenes* as a Result of Anaerobic Activation of rofA", Journal of Bacteriology 179(19):6172-6180 (1997).
Fontana et al, "A genomic approach to identify vaccine candidates against gonococcus", Abstract from the 13th International Pathogenic Neisseria Conference, Oslo Norway, Sep. 1-6, 2002, p. 248 (http://neisseria.org/ipnc/history.shtml).
Foster et al, "Surface protein adhesins of *Staphylococcus aureus*", Trends in Microbiology 6(12):484-488 (1998).

(56) References Cited

OTHER PUBLICATIONS

Frankel et al, "Characterization of diphtheria fusion proteins targeted to the human interleukin-3 receptor", Protein Engineering 13(8):579-591 (2000).
Fraser et al, "Genomic sequence of a Lyme disease spirochaete, Borrelia burgdorferi", Nature 390:580-591 (1997).
Fredriksen et al, "Production, Characterization and Control of MenB-Vaccine <<Folkehelsa>>: An Outer Membrane Vesicle Vaccine Against Group B Meningococcal Disease", NIPH Annals 14(2):67-80 (1991).
Fukasawa et al, "Neisseria meningitidis serogroup C polysaccharide and serogroup B outer membrane vesicle conjugate as a bivalent meningococcus vaccine candidate", Vaccine 17:2951-2958 (1999).
Gandhi et al, "Characteristics of a new meningococcal serogroup B vaccine, bivalent rLP2086 (MenB-FHbp: Trumenba®)", Postgraduate Medicine 128(6):548-556 (2016).
Gasparini et al, "Neisseria meningitidis B vaccines: recent advances and possible immunization policies", Expert Rev. Vaccines 13(3):345-364 (2014).
Gentz et al, "Bioassay for trans-activation using purified human immunodeficiency virus tat-encoded protein: Trans-activation requires mRNA synthesis", Proc. Natl. Acad. Sci. 86:821-824 (1989).
Geyer et al, "Immunochemical Properties of Oligosaccharide-Protein Conjugates with Klebsiella-K2 Specificity", Medical Microbiology and Immunology 165:271-288 (1979).
Geysen et al, "Use of peptide synthesis to probe viral antigens for epitopes to a resolution of a single amino acid", Proc. Natl. Acad. Sci. USA 81(13):3998-4002 (1984).
Geysen et al, "A Priori Delineation of a Peptide Which Mimics a Discontinuous Antigenic Determinant", Molecular Immunology 23(7):709-715 (1986).
Gil et al, "Proteomic Study via a Non-Gel Based Approach of Meningococcal Outer Membrane Vesicle Vaccine Obtained from Strain CU385" Human Vaccines 5(5):347-356 (2009).
Giuliani et al, "The Region Comprising Amino Acids 100 to 255 of Neisseria meningitidis Lipoprotein GNA 1870 Elicits Bactericidal Antibodies", Infection and Immunity 73(2):1151-1160 (2005).
Giuliani et al, "A universal vaccine for serogroup B meningococcus" Proc Natl Acad Sci 103(29):10834-10839 (2006).
Giuliani et al, Diagram showing the production of the GNA2091-GNA1870 fusion protein (2006).
*GlaxoSmithKline UK Ltd v Wyeth Holdings LLC* [2016] EWHC 1045 (Ch) (May 12, 2016); Case No. HP-2015-000002; 66 pages; accessed http://www.bailii.org/ew/cases/EWHC/Ch/2016/1045.html on Jul. 11, 2016.
Gold et al, "Chapter 78. Translational Initiation", *Escherichia coli* and Salmonella Typhimurium: Cellular and Molecular Biology, Ed. Neidhardt FC, vol. 2, pp. 1302-1307 (1987).
Goldschneider et al, "Human Immunity to the Meningococcus I. The Role of Humoral Antibodies", Journal of Experimental Medicine 129(6):1307-1326 (1969).
Goldschneider et al, "Human Immunity to the Meningococcus II. Development of Natural Immunity", Journal of Experimental Medicine 129(6):1327-1348 (1969).
Gomez et al, "The Bacillus subtilis lipoprotein LplA causes cell lysis when expressed in *Escherichia coli*", Microbiology 140:1839-1845 (1994).
Gotschlich et al, "Human Immunity to the Meningococcus. IV. Immunogenicity of Group A and Group C Meningococcal Polysaccharides in Human Volunteers", Journal of Experimental Medicine 129(6): 1367-1384 (1969).
Gotschlich et al, "Human Immunity to the Meningococcus. V. The Effect of Immunization with Meningococcal Group C Polysaccharide on the Carrier State", Journal of Experimental Medicine 129(6): 1385-1395 (1969).
Graham et al, "Characteristics of a Human Cell Line Transformed by DNA from Human Adenovirus Type 5", J. Gen. Virology 36:59-72 (1977).
Graham, "Covalently closed circles of human adenovirus DNA are infectious", The EMBO Journal 3(12):2917-2922 (1984).

Grandi, "Reverse Vaccinology: A Critical Analysis", Encyclopedia of Genetics, Genomics, Proteomics and Bioinformatics, pp. 1320-1330 (2005).
Green et al, "The e (P4) Outer Membrane Protein of Haemophilus influenzae: Biologic Activity of Anti-e Serum and Cloning and Sequencing of the Structural Gene", Infection and Immunity 59(9):3191-3198 (1991).
Greenspan et al, "Defining epitopes: It's not as easy as it seems", Nature Biotechnology 17:936-937 (1999).
Griffin et al, "Computer Analysis of Sequence Data", Methods in Molecular Biology, vol. 24, Part 1, Chapter 1, Humana Press, New Jersey (1994).
Griffiss et al., "Structural relationships and sialylation among meningococcal L1, L8, and L3,7 lipooligosaccharide serotypes", J. Biol. Chem. 275(13):9716-9724 (2000).
Guillen et al., "Comparison of the DNA Sequence of Nine Different Genes for the Class 1 Outer Membrane Protein from Neisseria meningitidis", Biotechnologia Applicada 10:108-113 (1993).
Gupta, "Aluminum compounds as vaccine adjuvants", Advanced Drug Delivery Reviews 32(3):155-172 (1998).
Guzman et al, "Tight Regulation, Modulation, and High-Level Expression by Vectors Containing the Arabinose PBAD Promoter", Journal of Bacteriology 177(14):4121-4130 (1995).
Hacker et al, "Pathogenicity islands of virulent bacteria: structure, function and impact on microbial evolution", Molecular Microbiology 23(6):1089-1097 (1997).
Hanski et al, "Expression of protein F, the fibronectin-binding protein of *Streptococcus pyogenes* JRS4, in heterologous streptococcal and enterococcal strains promotes their adherence to respiratory epithelial cells", Infection and Immunity 60(12):5119-5125 (1992).
Hanski et al, "Protein F, a fibronectin-binding protein, is an adhesin of the group A *streptococcus Streptococcus pyogenes*", Proc. Natl. Acad. Sci. 89:6172-6176 (1992).
Hansson et al, "Expression of Truncated and Full-Length Forms of the Lyme Disease Borrelia Outer Surface Protein A in *Escherichia coli*", Protein Expression and Purification 6:15-24 (1995).
Harris et al, "Preclinical evidence for the potential of a bivalent fHBP vaccine to prevent Neisseria meningitidis serogroup C disease", Human Vaccines 7(Supplement):68-74 (2011).
Havrix prescribing information, https://www.gsksource.com/pharma/content/dam/GlaxoSmithKline/US/en/Prescribing_Information/Havrix/pdf/HAVRIX.PDF, revised Jul. 2014, accessed Feb. 18, 2015.
Hayashi et al, "Lipoproteins in Bacteria", Journal of Bioenergetics and Biomembranes 22(3):451-471 (1990).
Hearn, et al, "Application of 1, 1'-Carbonyldiimidazole-Activated Matrices for the Purification of Proteins: III. The Use of 1,1'-Carbonyldiimidazole-Activated Agaroses in the Biospecific Affinity Chromatographic Isolation of Serum Antibodies", J. Chromatogr. 218:509-518 (1981).
Hecht et al, "NAR Breakthrough Article: Measurements of translation initiation from all 64 codons in *E. coli*", Nucleic Acids Research 45(7):3615-3626 (2017).
Hedari et al, "Meningococcal Serogroups A, C, W-135, and Y Tetanus Toxoid Conjugate Vaccine: A New Conjugate Vaccine Against Invasive Meningococcal Disease", Infect Drug Resist. 7:85-99 (2014).
Hem et al, "Chapter 9: Structure and Properties of Aluminum-Containing Adjuvants", Vaccine Design: The Subunit and Adjuvant Approach, Plenum Press, New York, pp. 249-276 (1995).
Hernandez-Sanchez et al, "lambda bar minigene-mediated inhibition of protein synthesis involves accumulation of peptidyl-tRNA and starvation for tRNA", The EMBO Journal 17(13):3758-3765 (1998).
Hornyik et al, "Cerebrospinal Fluid Shunt Infection by Neisseria sicca", Pediatr Neurosurg 21:189-191 (1994).
Houghten, "General Method for the rapid solid-phase synthesis of large Nos. of peptides: Specificity of antigen-antibody interaction at the level of individual amino acids", Proceedings of the National Academy of Sciences of USA 82:5131-5135 (1985).
Huang et al, "The streptokinase gene of group A streptococci: cloning, expression in *Escherichia coli*, and sequence analysis", Molecular Microbiology 3(2): 197-205 (1989).

(56) References Cited

OTHER PUBLICATIONS

Hung, "The Neisseria meningitidis Macrophage Infectivity Potentiator Protein Induces Cross-Strain Serum Bactericidal Activity and Is a Potential Serogroup B Vaccine Candidate", Infection and Immunity, 79(9):3784-3791 (2011).

Hynes et al, "Analysis of a Second Bacteriophage Hyaluronidase Gene from *Streptococcus pyogenes*: Evidence for a Third Hyaluronidase Involved in Extracellular Enzymatic Activity", Infection and Immunity 63(8):3015-3020 (1995).

Hynes et al, "The extracellular hyaluronidase gene (hylA) of *Streptococcus pyogenes*", FEMS Microbiology Letters 184:109-112 (2000).

Interlocutory Decision of the Opposition Division in Opposition against Novartis EP 1 645 631 dated May 21, 2012 Part 1.

Interlocutory Decision of the Opposition Division in Opposition against Novartis EP 1 645 631 dated May 21, 2012 Part 2.

Isberg et al, "Binding and internalization of microorganisms by integrin receptors", Trends in Microbiology 2(1):10-14 (1994).

Jackson et al, U.S. Appl. No. 60/098,685, filed Sep. 1, 1998.

Jiang et al, "Broad vaccine coverage predicted for a bivalent recombinant factor H binding protein based vaccine to prevent serogroup B meningococcal disease", Vaccine 28:6086-6093 (2010).

Johnson et al, "Analysis of the Human Ig Isotype Response to Lactoferrin Binding Protein A from Neisseria meningitidis", FEMS Immunology and Medical Microbiology 25(4):349-354 (1999).

Jones et al, "The Importance of the Location of Antibody Binding on the M6 Protein for Opsonization and Phagocytosis of Group A M6 Streptococci", J. Exp. Med. 167:1114-1123 (1988).

Kafri et al, "A Packaging Cell Line for Lentivirus Vectors", Journal of Virology 73(1):576-584 (1999).

Kaplitt et al, "Expression of a Functional Foreign Gene in Adult Mammalian Brain following in Vivo Transfer via a Herpes Simplex Virus Type 1 Defective Viral Vector", Molecular and Cellular Neurosciences 2:320-330 (1991).

Kihlberg et al, "Protein H, an Antiphagocytic Surface Protein in *Streptococcus pyogenes*", Infection and Immunity 67 (4):1708-1714 (1999).

Klein et al, "Distinctive properties of signal sequences from bacterial lipoproteins", Protein Engineering 2(1):15-20 (1988).

Koeberling at el, "Bactericidal Antibody Responses Elicited by a Meningococcal Outer Membrane Vesicle Vaccine with Overexpressed Factor H-binding Protein and Genetically Attenuated Endotoxin", The Journal of Infectious Diseases 198:262-270 (2008).

Koebnik, "Proposal for a peptidoglycan-associating alpha-helical motif in the C-terminal regions of some bacterial cell-surface proteins", Molecular Microbiology 16(6):1269-1270 (1995).

Kohler et al, "Continuous cultures of fused cells secreting antibody of predefined specificity", Nature 256:495-497 (1975).

Konar et al, "Importance of Inhibition of Binding of Complement Factor H for Serum Bactericidal Antibody Responses to Meningococcal Factor H-binding Protein Vaccines", The Journal of Infectious Diseases 208:627-636 (2013).

Kuipers et al, "Improved site-directed mutagenesis method using PCR", Nucleic Acids Research 19(16):4558 (1991).

Kuo et al, "Efficient Gene Transfer into Primary Murine Lymphocytes Obviating the Need for Drug Selection", Blood 82(3):845-852 (1993).

Kuo et al, "Characterization of a Recombinant Pneumolysin n and Its Use as a Protein Carrier for Pneumococcal Type 18C Conjugate Vaccines", Infection and Immunity 63(7):2706-2713 (1995).

Kyte et al, "A Simple Method for Displaying the Hydropathic Character of a Protein", J. Mol. Biol. 157:105-132 (1982).

Landt et al, "A general method for rapid site-directed mutagenesis using the polymerase chain reaction", Gene 96:125-128 (1990).

Lasalle et al, "An Adenovirus Vector for Gene Transfer into Neurons and Glia in the Brain", Science 259:988-990 (1993).

Lebkowski et al, "Adeno-Associated Virus: a Vector System for Efficient Introduction and Integration of DNA into a Variety of Mammalian Cell Types", Molecular and Cellular Biology 8(10):3988-3996 (1988).

Lee et al, "Clinical Review STN: 125549 Application Type Biologics License Application STN# 125549 CBER Received Date Division/Office DVRPA/OVRR Priority Review Yes Reviewer Name", XP055265361, Retrieved from the Internet: URL:http://www.fda.gov/downloads/BiologicsBloodVaccines/Vaccines/ApprovedProducts/UCM424626, Jun. 16, 2014.

Levrero et al., "Defective and nondefective adenovirus vectors for expressing foreign genes in vitro and in vivo", Gene 101:195-202 (1991).

Liu et al, "Chimeric mouse-human IgG1 antibody that can mediate lysis o f cancer cells", Proc. Natl. Acad. Sci. 84:3439-3443 (1987).

Liu et al, "High-throughput imaging of bacterial colonies grown on filter plates with application to serum bactericidal assays", Journal of Immunological Methods 292(1-2):187-193 (2004).

Loessner et al, "Evidence for a Holin-Like Protein Gene Fully Embedded Out of Frame in the Endolysin Gene of *Staphylococcus aureus* Bacteriophage 187", Journal of Bacteriology 181(15):4452-4460 (1999).

Nakai et al, "Expert System for Predicting Protein Localization Sites in Gram-Negative Bacteria", Proteins: Structure, Function, and Genetics 11:95-110 (1991).

Naldini et al, "Lentiviruses as gene transfer agents for delivery to non-dividing cells", Current Opinion in Biotechnology 9:457-463 (1998).

Nassif, "A Furtive Pathogen Revealed", Science 287:1767-1768 (2000).

Navarre et al, "Surface Proteins of Gram-Positive Bacteria and Mechanisms of Their Targeting to the Cell Wall Envelope", Microbiology and Molecular Biology Reviews 63(1):174-229 (1999).

NCBI GenBank No. AAF42204.1, Tettelin, H. et al., "Hypothetical protein [Neisseria meningitidis]", Feb. 25, 2000, accessed Jul. 12, 2012.

NCBI GenBank: ABL 14232.1,: "FHBP/GNA1870 variant [Neisseria meningitidis]"; Dec. 11, 2006.

NCBI GenBank: ACI46789.1; "Factor H binding protein variant A62_001, partial [Neisseria meningitidis]", Aug. 4, 2009.

NCBI GenBank : ACI46791, "Factor H binding protein variant A04_001, partial [Neisseria meningitidis]". Aug. 4, 2009.

NCBI GenBank: ACB38141.1, factor H-binding protein [Neisseria meningitidis] (Jun. 4, 2010).

NCBI GenBank: AE004969, "Neisseria gonorrhoeae FA 1090 chromosome Entire clone gono strain FA1090, complete sequence", Sep. 26, 2000.

NCBI GenBank: AGA84310.1, "factor H binding protein, partial [Neisseria meningitidis]" (Dec. 25, 2012).

NCBI GenBank: AY330365.1; "Neisseria meningitidis strain CDC1492 factor H binding protein variant A22_001 (fhbp) gene, partial cds"; Mar. 12, 2009; accessed Jun. 3, 2014.

NCBI GenBank: AY330400.1; "Neisseria meningitidis strain M982 factor H binding variant B09_001 (fhbp) gene, partial cds"; Mar. 12, 2009; accessed Jun. 3, 2014.

NCBI GenBank: AY330401.1; "Neisseria meningitidis strain 880049 factor H binding protein variant B03_001 (fhbp) gene, partial cds"; Mar. 12, 2009; accessed Jun. 3, 2014.

NCBI GenBank No. EF108319.1, O'Leary, M. M. et al., Neisseria meningitidis strain NM452 FHBP/GNA1870 variant (GNA1870) gene, complete cds, Nov. 8, 2006, accessed Sep. 5, 2012.

NCBI GenBank: FJ184103.1; "Neisseria meningitidis factor H binding protein variant A12_001 (fhbp) gene, partial cds"; Aug. 4, 2009; accessed Jun. 3, 2014.

NCBI GenBank: FJ184126.1; "Neisseria meningitidis factor H binding protein variant B02_001 (fhbp) gene, partial cds"; Aug. 4, 2009; accessed Jun. 3, 2014.

NCBI GenBank: FJ184157.1; "Neisseria meningitidis factor H binding protein variant B44_001 (fhbp) gene, partial cds"; Aug. 4, 2009; accessed Jun. 3, 2014.

NCBI GenBank: FJ184233.1, "Neisseria meningitidis factor H binding protein variant B09_004 (fhbp) gene, partial cds" (Aug. 4, 2009).

NCBI GenBank: NC_003112.2; "Neisseria meningitidis MC58 chromosome, complete genome" (Aug. 3, 2016).

(56) References Cited

OTHER PUBLICATIONS

NCBI GenBank: YP_002342062.1, "Putative Lipoprotein [Neisseria Meningitidis Z2491]", dated May 8, 2009, accessed Aug. 4, 2009.
Nielsen et al, "Identification of prokaryotic and eukaryotic signal peptides and prediction of their cleavage sites", Protein Engineering 10(1):1-6 (1997).
Nimenrix product monograph, gsk.com/media/673251/nimenrix.pdf, accessed Feb. 19, 2015, date of revision Jan. 9, 2015.
Nimenrix product monograph, http://webprod5.hc-sc.gc.ca/dpd-bdpp/item-iteme.do?pm-mp=00033642, accessed Mar. 2016. Date of revision Nov. 9, 2015.
Nizet et al, "Genetic Locus for Streptolysin S Production by Group A *Streptococcus*", Infection and Immunity 68 (7):4245-4254 (2000).
Nordstrand et al, "Allele Substitution of the Streptokinase Gene Reduces the Nephritogenic Capacity of Group A *Streptococcal* Strain NZ131", Infection and Immunity 68(3):1019-1025 (2000).
Notice of Opposition against Novartis EP 1 645 631 submitted Jul. 23, 2008.
Novartis Media Release, "New Phase II data show Novartis investigational Meningitidis B vaccine may also protect Infants six months and older", issued Oct. 9, 2008.
Novartis Media Release, "Novartis submits Bexsero®, a multicomponent meningococcal B vaccine, for regulatory review in Europe", issued Dec. 23, 2010.
Okuda et al, "Lipoprotein sorting in bacteria", Annu. Rev. Microbiol., 65:239-259 (2011).
Olmsted et al., "High-Resolution Visualization by Field Emission Scanning Electron Microscopy of Enterococcus faecalis Surface Proteins Encoded by the Pheromone-Inducible Conjugative Plasmid pCF10", Journal of Bacteriology 175(19):6229-6237 (1993).
Opponent's Further Submission in Preparation of Oral Proceedings in Opposition against Novartis EP 1 645 631 submitted Nov. 3, 2011.
Opposition documents (part 1 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 2 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 3 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 4 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 5 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 6 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 7 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 8 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 9 of 11 parts) submitted to the European Patent Office in EP2343308 dated Nov. 13, 2015 to Dec. 23, 2015, https://register.epo.org/application?No. EP10183020&Ing-en&tab=doclist, accessed Mar. 30, 2016.
Opposition documents (part 10 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 11 of 11 parts) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition papers EP2343308 May 2-9, 2016; 274 pages; accessed https://register.epo.org/application?number=EP10183020&Ing=en&tab=doclist on May 16, 2016.
Opposition papers EP2343308 Apr. 6-13, 2016; 30 pages; accessed https://register.epo.org/application?number=EP10183020&Ing=en&tab=doclist on May 16, 2016.
Opposition notice EP2343308_(Nov. 13, 2015); 21 pages; accessed https://register.epo.org/application?number=EP10183020&Ing=en&tab=doclist on Apr. 21, 2016.
Oudega et al, "A lipoprotein signal peptide plus a cysteine residue at the amino-terminal end of the periplasmic proteins beta-lactamase is sufficient for its lipid modification, processing and membrane localization in *Escherichia coli*", FEMS Microbiology Letters 108:353-360 (1993).
Oudega et al, "*Escherichia coli* SecB, SecA, and SecY Proteins Are Required for Expression and Membrane Insertion of the Bacteriocin Release Protein, a Small Lipoprotein", Journal of Bacteriology 175(5):1543-1547 (1993).
Pajon et al, "Frequency of factor H-binding protein modular groups and susceptibility to cross-reactive bactericidal activity in invasive meningococcal isolates", Vaccine 28:2122-2129 (2010).
Pannekoek et al, "Construction of recombinant neisserial Hsp60 proteins and mapping of antigenic domains", Molecular Microbiology 15(2):277-285 (1995).
Aasel et al, "Most antibodies to PorB and Rmp do not bind to viable meningococci, but bind strongly to ethanol-killed bacteria", Abstract from the 11th International Pathogenic Neisseria Conference (Nice France, Nov. 1-6, 1998), pp 37-38 (http://neisseria.org/ipnc/history.shtml).
Abdillahi and Poolman, "Whole-cell ELISA for typing Neisseria meningitidis with monoclonal antibodies", FEMS Microbiology Letters 48:367-371 (1987).
Abdillahi and Poolman, "Neisseria meningitidis group B serosubtyping using monoclonal antibodies in whole-cell Elisa", Microbial Pathogenesis 4:27-32 (1988).
Achtman, "Epidemic spread and antigenic variability of Neisseria meningitidis", Trends in Microbiology 3(5):186-192 (1995).
Adacel Prescribing information, http://www.fda.gov/downloads/biologicsbloodvaccines/vaccines/approvedproducts/ucm142764.pdf, "Revised: [XX/201X]", accessed Feb. 14, 2015.
Adams et al, "Design and synthesis of potent Quillaja saponin vaccine adjuvants", J Am Chem Soc. 132(6):1939-1945 (2010).
Alignment of the amino acid sequences of Seq Id No. 13 of EP3549601 and Seq Id No. 60 of WO 03/063766.
Alignment of the amino acid sequences of Seq Id No. 21 of EP3549601 and Seq Id No. 12 of WO 2008/079372.
Alignment of the amino acid sequences of Seq Id No. 21 of EP3549601 and fHBP subvariant 1.15 (Genbank accession No. EU541896).
Alm et al, "Genomic-sequence comparison of two unrelated isolates of the human gastric pathogen Helicobacter bylori", Nature 397:176-180 (1999).
Altschul et al, "Basic Local Alignment Search Tool", J. Mol. Biol. 215:403-410 (1990).
Altschul and Lipman, "Protein database searches for multiple alignments", Proc. Natl. Acad. Sci. 87:5509-5513 (1990).
Altschul et al, "Gapped BLAST and PSI-BLAST: a new generation of protein database search programs", Nucleic Acids Research 25(17): 3389-3402 (1997).
Ambrosch et al, "Immunogenicity and side-effects of a new tetravalent meningococcal polysaccharide vaccine", Bulletin of the World Health Organization 61(2):317-323 (1983).

(56) References Cited

OTHER PUBLICATIONS

Andersen et al, "Immune Responses to Meningococcal Outer Membrane Vesicles After Intranasal Immunisation", Twelfth International Pathogenic Neisseria Conference, Nov. 12-17, 2000, Galveston, Texas (Abstract #057).

Anderson, "Techniques for the preservation of three-dimensional structure in preparing specimens for the electron microscope", Transactions of the New York Academy of Sciences, 13:130-134 (1951).

Anderson, "Elicitation of Functional Antibodies by a Group B Neisseria meningitidis Bivalent rLP2086 Vaccine in Non-Human Primates", NHP IPNC Poster Presentation 2008.

Anderson et al, "Potential Impact of the Bivalent rLP2086 Vaccine on Neisseria meningitidis Invasive Disease and Carriage Isolates in Two Adolescent Populations"; poster presented at the 30th Annual Meeting of the European Society for Paediatric Infectious Diseases; May 8-12, 2012; Thessaloniki, Greece; http://epostersonline.s3.amazonaws.com/espid2012/espid2012.02400cf.NORMAL.pdf, May 12, 2012.

Anderson et al, "Potential impact of the bivalent rLP2806 vaccine on Neisseria meningitidis carriage and invasive serogroup B disease", Human Vaccines & Immunotherapeutics 9(3):471-479 (2013).

Assaf-Casals and Dbaibo, "Meningococcal Quadrivalent Tetanus Toxoid Conjugate Vaccine (MenACWY-TT, Nimenrix): A review of its Immunogenicity, Safety, Co-Administration, and Antibody Persistence", Human Vaccines and Immunotherapeutics 12(7):1825-1837 (2016).

Baker, "Prevention of Meningococcal Infection in the United States: Current Recommendations and Future Considerations", Journal of Adolescent Health 59(2):S29-S37 (2016).

Bambini et al, "Distribution and genetic variability of three vaccine components in a panel of strains representative of the diversity of serogroup B meningococcus", Vaccine 27:2794-2803 (2009).

Bantam Medical Dictionary, Third Edition, pp. 302-303 (2000).

Baraldo et al., "N19 Polyepitope as a Carrier for Enhanced Immunogenicity and Protective Efficacy of Meningococcal Conjugate Vaccines", Infection and Immunity 72(8):4884-4887 (2004).

Barbour and Züuckert, "New tricks of tick-borne pathogen", Nature 390:553 & 555 (1997).

Bateman et al, "The Pfam Protein Families Database", Nucleic Acids Research 28(1):263-266 (2000).

Beard et al, "Transcription Mapping of Mouse Adenovirus Type 1 Early Region 3", Virology 175:81-90 (1990).

Beernink et al, "Prevalence of Factor H-Binding Protein Variants and NadA among Meningococcal Group B Isolates from the United States: Implications for the Development of a Multicomponent Group B Vaccine", The Journal of Infectious Diseases 195:1472-1479 (2007).

Beernink and Granoff, "The modular architecture of meningococcal factor H-binding protein", Microbiology 155:2873-2883 (2009).

Bender et al, "Evidence that the Packaging Signal of Moloney Murine Leukemia Virus Extends into the gag Region", Journal of Virology 61(5):1639-1646 (1987).

Benson, "Tandem repeats finder: a program to analyze DNA sequences", Nucleic Acids Research 27(2):573-580 (1999).

Bergmann et al, "An endogenously synthesized decamer peptide efficiently primes cytotoxic T cells specific for the HIV-1 envelope glycoprotein", Eur. J. Immunol. 23(11):2777-2781 (1993).

Bergmann et al, "Flanking Residues Alter Antigenicity and Immunogenicity of Multi-Unit CTL Epitopes", The Journal of Immunology 157:3242-3249 (1996).

Bernfield et al, "Identification of a novel vaccine candidate for group B Neisseria meningitidis", Abstracts of the Thirteenth International Pathogenic Neisseria Conference, (Ed) Caugant et al. Oslo, Norway, p. 116, Sep. 1-6, 2002.

Bernstein et al, "Gene Transfer with Retrovirus Vectors", Genet. Eng. 7:235-261 (1985).

Bethell, et al, "A Novel Method of Activation of Cross-Linked Agaroses with 1,1'-Carbonyldiimidazole Which Gives a Matrix for Affinity Chromatography Devoid of Additional Charged Groups", J. Biol. Chem., 254:2572-2574 (1979).

Better et al, "*Escherichia coli* Secretion of an Active Chimeric Antibody Fragment", Science 240:1041-1043 (1988).

Beuvery et al, "Preparation and Immunochemical Characterization of Meningococcal Group C Polysaccharide-Tetanus Toxoid Conjugates as a New Generation of Vaccines", Infection and Immunity 40(1):39-45 (1983).

Beuvery et al, "Preparation and Physicochemical and Immunological Characterization of Polysaccharide-Outer Membrane Protein Complexes of Neisseria meningitidis", Infection and Immunity 40(1):369-380 (1983).

Bhattacharjee et al, "A Noncovalent Complex Vaccine Prepared with Detoxified *Escherichia coli* J5 (Rc Chemotype) Lipopolysaccharide and Neisseria meningitidis Group B Outer Membrane Protein Produces Protective Antibodies against Gram-Negative Bacteremia", The Journal of Infectious Diseases 173:1157-1163 (1996).

Biagini et al, "Expression of factor H binding protein in meningococcal strains can vary at least 15-fold and is genetically determined", Proceedings of the National Academy of Sciences 113(10):2714-2719 (2016).

Biocomputing: Informatics and Genome Projects, Smith D.W., ed., Academic Press, New York (1994).

Bjune et al, "Effect of Outer Membrane Vesicle Vaccine Against Group B Meningococcal Disease in Norway", The Lancet 338(8775):1093-1096 (1991).

Borrow et al, "Meningococcal surrogates of protection-serum bactericidal antibody activity", Vaccine 23:2222-2227 (2005).

Boslego et al, "Chapter 17: Gonorrhea Vaccines", Vaccines and Immunotherapy, SJ Cryz Jr. ed., Pergamon Press, pp. 211-223 (1991).

Boulianne et al, "Production of functional chimaeric mouse/human antibody", Nature 312:643-646 (1984).

Brown, "Hybridization Analysis of DNA Blots", Current Protocols in Molecular Biology, Supp. 21, 2.10.1-2.10.16 (1993).

Budroni et al, "Neisseria Meningitidis is Structured in Clades Associated with Restriction Modification Systems that Modulate Homologous Recombination", PNAS, Mar. 15, 2011, 108 (11): 4494-4499 and supporting information pp. 1-17 (2011).

Cabilly et al, "Generation of antibody activity from immunoglobulin polypeptide chains produced in *Escherichia coli*", Proc. Natl. Acad. Sci. 81:3273-3277 (1984).

Callahan et al, "The Importance of Surface Charge in the Optimization of Antigen-Adjuvant Interactions", Pharmaceutical Research 8(7):851-858 (1991).

Harris, S.L., et al., "The bivalent factor H binding protein meningococcal serogroup B vaccine elicits bactericidal antibodies against representative non-serogroup B meningococci", Vaccine, 2018, 36(45):6867-6874.

Zlotnick et al., "The Discovery and Development of a Novel Vaccine to Protect against Neisseria Meningitidis Serogroup B Disease", Human Vaccines & Immunotherapeutics 11(1):5-13 (2014) XP055265976.

\* cited by examiner

Local Reactions*

NEISSERIA MENINGITIDIS COMPOSITIONS AND METHODS THEREOF

CROSS REFERENCE TO RELATED APPLICATIONS

This application is a National Stage Application of International Application No. PCT/IB2020/058928, filed Sep. 24, 2020, which claims the benefit under 35 U.S.C. § 119(e) of U.S. Provisional Application Ser. No. 62/907,097, filed Sep. 27, 2019 and U.S. Provisional Application Ser. No. 63/040,498, filed Jun. 17, 2020, all of which are incorporated by reference in their entirety.

FIELD OF THE DISCLOSURE

The present disclosure relates to *Neisseria meningitidis* compositions and methods thereof.

BACKGROUND OF THE DISCLOSURE

*Neisseria meningitidis* is a Gram-negative encapsulated bacterium that can cause sepsis, meningitis, and death. *N. meningitidis* can be classified into at least 12 serogroups (including serogroups A, B, C, 29E, H, I, K, L, W-135 (mostly now referred to as W), X, Y and Z) based on chemically and antigenically distinctive polysaccharide capsules. Strains with five of the serogroups (A, B, C, Y, and W135) are responsible for the majority of disease.

Meningococcal meningitis is a devastating disease that can kill children and young adults within hours despite the availability of antibiotics. There is a need for improved immunogenic compositions against meningococcal serogroups A, B, C, Y, and W135 and/or X.

Currently, a cross-protective vaccine or composition effective against a wide range of MnB and meningococcal serogroups A, C, Y, and W and/or X isolates is not yet commercially available. Accordingly, a cross-protective vaccine or composition effective against diverse MnB and meningococcal serogroups A, C, Y, and W and/or X isolates is needed.

It is a further object of the disclosure to provide improved schedules for administering a meningococcal vaccine. Under the current recommendation scheme, there are four to five vaccinations given against meningococcal serogroups A, C, W, Y and B, given at different ages. There is an unmet need for efficient vaccinations that may to simplify immunization schedules and improve vaccination coverage to achieve further reductions in invasive meningococcal disease (IMD).

SUMMARY OF THE DISCLOSURE

To meet these and other needs, the present disclosure relates to *Neisseria meningitidis* compositions and methods thereof.

The inventors discovered a method of inducing an immune response in a human, including administering to the human a composition comprising a) a polypeptide derived from a *Neisseria meningitidis* factor H binding protein (fHBP); (b) a *Neisseria meningitidis* serogroup A capsular saccharide conjugate; (c) a *Neisseria meningitidis* serogroup C capsular saccharide conjugate; (d) a *Neisseria meningitidis* serogroup W capsular saccharide conjugate; and (e) a *Neisseria meningitidis* serogroup Y capsular saccharide conjugate, wherein the composition induces an immune response to at least one of *N. meningitidis* serogroups A, C, W-135 and Y capsular polysaccharides and *N. meningitidis* serogroup B, wherein the immune response includes a titer of serum bactericidal antibodies that is higher than a titer of serum bactericidal antibodies induced by a respective licensed vaccine against the serogroup.

The inventors surprisingly discovered a method of inducing an immune response in a human, including administering to the human a composition comprising a) a first polypeptide derived from a *Neisseria meningitidis* factor H binding protein (fHBP); (b) a second polypeptide derived from a *Neisseria meningitidis* factor H binding protein (fHBP); (c) a *Neisseria meningitidis* serogroup A capsular saccharide conjugate; (d) a *Neisseria meningitidis* serogroup C capsular saccharide conjugate; (e) a *Neisseria meningitidis* serogroup W capsular saccharide conjugate; and (f) a *Neisseria meningitidis* serogroup Y capsular saccharide conjugate, wherein the composition induces an immune response to at least one of *N. meningitidis* serogroups A, C, W-135 and Y capsular polysaccharides and *N. meningitidis* serogroup B, wherein the immune response includes a titer of serum bactericidal antibodies that is higher than a titer of serum bactericidal antibodies induced by a respective licensed vaccine against the serogroup.

In some embodiments, the polypeptide includes an amino acid sequence having at least 70% identity to any one amino acid sequence selected from SEQ ID NO: 1 to SEQ ID NO: 62.

In a preferred embodiment, the composition includes (a) a first polypeptide including the amino acid sequence set forth in SEQ ID NO: 1; (b) a second polypeptide including the amino acid sequence set forth in SEQ ID NO: 2; (c) a *Neisseria meningitidis* serogroup A capsular saccharide conjugated to an adipic acid dihydrazide (ADH) linker by 1-cyano-4-dimethylamino pyridinium tetrafluoroborate, wherein the linker is conjugated to tetanus toxoid by carbodiimide chemistry; (d) a *Neisseria meningitidis* serogroup C capsular saccharide conjugated to an ADH linker by 1-cyano-4-dimethylamino pyridinium tetrafluoroborate, wherein the linker is conjugated to tetanus toxoid by carbodiimide chemistry; (e) a *Neisseria meningitidis* serogroup W capsular saccharide directly conjugated to tetanus toxoid by 1-cyano-4-dimethylamino pyridinium tetrafluoroborate, in the absence of a linker; and (f) a *Neisseria meningitidis* serogroup Y capsular saccharide directly conjugated to tetanus toxoid by 1-cyano-4-dimethylamino pyridinium tetrafluoroborate, in the absence of a linker.

In some embodiments, the composition elicits an immune response to any one of *N. meningitidis* serogroups A, C, W-135 and Y, wherein said serum bactericidal antibody response is higher than that elicited by a licensed *N. meningitidis* serogroups A, C, W-135 and Y meningococcal capsular polysaccharide vaccine.

In some embodiments, the composition elicits an immune response to *N. meningitidis* serogroup A, wherein said serum bactericidal antibody response is higher than that elicited by a licensed *N. meningitidis* serogroups A, C, W-135 and Y meningococcal capsular polysaccharide vaccine.

In some embodiments, the composition elicits an immune response to *N. meningitidis* serogroup C, wherein said serum bactericidal antibody response is higher than that elicited by a licensed *N. meningitidis* serogroups A, C, W-135 and Y meningococcal capsular polysaccharide vaccine.

In some embodiments, the composition elicits an immune response to *N. meningitidis* serogroup W, wherein said serum bactericidal antibody response is higher than that elicited by a licensed *N. meningitidis* serogroups A, C, W-135 and Y meningococcal capsular polysaccharide vaccine.

In some embodiments, the composition elicits an immune response to *N. meningitidis* serogroup Y, wherein said serum bactericidal antibody response is higher than that elicited by a licensed *N. meningitidis* serogroups A, C, W-135 and Y meningococcal capsular polysaccharide vaccine.

In some embodiments, the composition elicits an immune response to each of the *N. meningitidis* serogroups A, C, W-135 and Y, wherein said serum bactericidal antibody response is higher than that elicited by a licensed *N. meningitidis* serogroups A, C, W-135 and Y meningococcal capsular polysaccharide vaccine.

In some embodiments, the composition elicits an immune response to *N. meningitidis* serogroup B, wherein said serum bactericidal antibody response is higher than that elicited by a licensed meningococcal serogroup B factor H binding vaccine.

In some embodiments, the composition elicits an immune response to each of the *N. meningitidis* serogroups A, C, W-135 and Y, wherein said serum bactericidal antibody response to each of the *N. meningitidis* serogroups A, C, W-135 and Y capsular polysaccharides is higher than that elicited by a licensed *N. meningitidis* serogroups A, C, W-135 and Y meningococcal capsular polysaccharide vaccine; and the composition elicits an immune response to *N. meningitidis* serogroup B, wherein said serum bactericidal antibody response is higher than that elicited by a licensed meningococcal serogroup B factor H binding vaccine; wherein the licensed *N. meningitidis* serogroups A, C, W-135 and Y meningococcal capsular polysaccharide vaccine and the licensed meningococcal serogroup B factor H binding vaccine are administered sequentially and are not in a combined dose.

In some embodiments, the composition includes an adjuvant. In some embodiments, the composition includes an aluminum adjuvant. In some embodiments, the composition includes aluminum hydroxide. In some embodiments, the composition includes aluminum phosphate. In some embodiments, the composition includes including aluminum.

In some embodiments, at least 90% of the first polypeptide is bound to aluminum in the composition. In some embodiments, at least 90% of the second polypeptide is bound to aluminum in the composition.

In some embodiments, the composition is formulated as a sterile liquid. In some embodiments, the composition includes a pharmaceutically acceptable preservative. In some embodiments, the composition includes polysorbate-80. In some embodiments, the composition includes Tris-HCl; sodium chloride; sucrose; histidine; polysorbate 80; and aluminum phosphate.

In some embodiments, the composition includes about 120 µg/ml of the first polypeptide; about 120 µg/ml of the second polypeptide; about 0.5 mg/ml aluminum as aluminum phosphate; about 0.02 mg polysorbate-80; about 10 mM histidine; and about 150 mM sodium chloride.

In some embodiments, the composition includes about 60 µg of the first polypeptide; about 60 µg of the second polypeptide; about 5 µg of the MenA capsular saccharide conjugated to about 7.5 µg TT; about 5 µg of the MenC capsular saccharide conjugated to about 7.5 µg TT; about 5 µg of the MenW capsular saccharide conjugated to about 3.75 µg TT; about 5 µg of the MenY capsular saccharide conjugated to about 3.25 µg TT; about 97 µg Tris-HCl, pH 6.8±0.3; 4.69-4.71 mg of sodium chloride; about 28 mg of sucrose; about 0.78 mg of L-Histidine; about 0.02 mg polysorbate-80; about 0.25 mg aluminum; and further including 0.5 mL water, per dose.

In some embodiments, the immune response includes a serum bactericidal antibody. In some embodiments, the composition is capable of eliciting a booster immune response to at least one of the *N. meningitidis* serogroups A, C, W-135 and Y. In some embodiments, the composition is capable of eliciting a booster immune response to *N. meningitidis* serogroup B.

In some embodiments, the immune response is elicited in a human up to 25 years old. In some embodiments, the immune response is elicited in a human aged at least 2 months to 25 years old. In some embodiments, the immune response is elicited in a human 10 to 25 years old. In some embodiments, the immune response is elicited in a human 10 to 26 years old. In some embodiments, the immune response is elicited in a human aged 12 to <18 Months or 18 to <24 Months. In some embodiments, the immune response is elicited in a human aged 18 to <24 Months. In some embodiments, the immune response is elicited in a human aged 24 Months to <10 Years.

In some embodiments, the immune response is elicited in a human that is seronegative against *N. meningitidis* serogroups A, C, W-135 and Y. In some embodiments, the immune response is elicited in a human that is seropositive against *N. meningitidis* serogroups A, C, W-135 and Y.

In some embodiments, the composition is administered to the human in at least two doses, wherein the second dose is about 6 months after the first dose. In some embodiments, the human is at least 10 years of age and at most 17 years of age. In some embodiments, a third dose of the composition is administered to the human, wherein the human is at least 16 years of age.

In some embodiments, the composition is administered to the human in at most two doses, wherein the second dose is about 6 months after the first dose.

In some embodiments, the composition elicits an immune response against A22. In some embodiments, the composition elicits an immune response against A56. In some embodiments, the composition elicits an immune response against B24. In some embodiments, the composition elicits an immune response against B44.

In some embodiments, the composition includes about 60 µg of the first polypeptide; about 60 µg of the second polypeptide; about 5 µg of the MenA capsular saccharide conjugated to about 7.5 µg TT; about 5 µg of the MenC capsular saccharide conjugated to about 7.5 µg TT; about 5 µg of the MenW capsular saccharide conjugated to about 3.75 µg TT; about 5 µg of the MenY capsular saccharide conjugated to about 3.25 µg TT; about 97 µg Tris-HCl, pH 6.8±0.3; 4.69-4.71 mg of sodium chloride; about 28 mg of sucrose; about 0.78 mg of L-Histidine; about 0.02 mg polysorbate-80; about 0.25 mg aluminum; and further including 0.5 mL water, per dose.

A composition including (a) a first polypeptide derived from a *Neisseria meningitidis* factor H binding protein (fHBP); (b) a second polypeptide derived from a *Neisseria meningitidis* factor H binding protein (fHBP); (c) a *Neisseria meningitidis* serogroup A capsular saccharide conjugate; (d) a *Neisseria meningitidis* serogroup C capsular saccharide conjugate; (e) a *Neisseria meningitidis* serogroup W capsular saccharide conjugate; and (f) a *Neisseria meningitidis* serogroup Y capsular saccharide conjugate; wherein the composition elicits an immune response to at least one of *N. meningitidis* serogroups A, C, W-135 and Y, wherein said serum bactericidal antibody response is higher than that elicited by a licensed vaccine against the *N. meningitidis* serogroup.

In some embodiments, the polypeptide includes an amino acid sequence having at least 70% identity to any one amino acid sequence selected from SEQ ID NO: 1 to SEQ ID NO: 62.

A composition including (a) a first polypeptide derived from a *Neisseria meningitidis* factor H binding protein (fHBP); (b) a second polypeptide derived from a *Neisseria meningitidis* factor H binding protein (fHBP); (c) a *Neisseria meningitidis* serogroup A capsular saccharide conjugated to an adipic acid dihydrazide (ADH) linker by 1-cyano-4-dimethylamino pyridinium tetrafluoroborate, wherein the linker is conjugated to tetanus toxoid by carbodiimide chemistry; (d) a *Neisseria meningitidis* serogroup C capsular saccharide conjugated to an ADH linker by 1-cyano-4-dimethylamino pyridinium tetrafluoroborate, wherein the linker is conjugated to tetanus toxoid by carbodiimide chemistry; (e) a *Neisseria meningitidis* serogroup W capsular saccharide directly conjugated to tetanus toxoid by 1-cyano-4-dimethylamino pyridinium tetrafluoroborate, in the absence of a linker; and (f) a *Neisseria meningitidis* serogroup Y capsular saccharide directly conjugated to tetanus toxoid by 1-cyano-4-dimethylamino pyridinium tetrafluoroborate, in the absence of a linker; wherein the composition elicits an immune response to at least one of the *N. meningitidis* serogroups A, C, W-135 and Y, wherein said serum bactericidal antibody response is higher than that elicited by a licensed *N. meningitidis* serogroups A, C, W-135 and Y meningococcal capsular polysaccharide vaccine.

A method for inducing an immune response against a *Neisseria meningitidis* serogroup B subfamily A strain and against a *Neisseria meningitidis* serogroup B subfamily B strain in human, including administering to the human an effective amount of the composition.

A method for inducing an immune response against a *Neisseria meningitidis* serogroup A, a *Neisseria meningitidis* serogroup C, a *Neisseria meningitidis* serogroup W, and/or a *Neisseria meningitidis* serogroup Y strain in a human, including administering to the human an effective amount of the composition.

A method for inducing an immune response against a *Neisseria meningitidis* serogroup A, *Neisseria meningitidis* serogroup B, a *Neisseria meningitidis* serogroup C, a *Neisseria meningitidis* serogroup W, and/or a *Neisseria meningitidis* serogroup Y strain in a human, including administering to the human an effective amount of the composition.

A method for inducing an immune response against a *Neisseria meningitidis* serogroup A, *Neisseria meningitidis* serogroup B, a *Neisseria meningitidis* serogroup C, a *Neisseria meningitidis* serogroup W, a *Neisseria meningitidis* serogroup Y strain, and/or a *Neisseria meningitidis* serogroup X strain in a human, including administering to the human an effective amount of the composition.

In some embodiments, the patient has not previously received a multivalent meningococcal capsular saccharide-carrier protein conjugate vaccine prior to the first administration of the composition.

In some embodiments, the patient previously received a multivalent meningococcal capsular saccharide-carrier protein conjugate vaccine prior to the first administration of the composition.

BRIEF DESCRIPTION OF THE DRAWINGS

FIG. 1A-B—Immune Responses as Measured in hSBA to (FIG. 1A) MenB Test Strains at 1 Month After Dose 2 and (FIG. 1B) MenA, MenC, MenW, and MenY Test Strains at 1 Month After Doses 1 and 2. Error bars represent 95% Cis. MenB strains note FHbp variants in parentheses. *MenA-BCWY, n=418-4432; MenB-FHbp, n=814-850. †Composite response=hSBA titer ≥LLOQ for all 4 MenB test strains. ‡MenABCWY, n=227-262; MenACWY-CRM, n=446-506. §MenABCWY, n=187-257; MenACWY-CRM, n=370-495. hSBA=serum bactericidal activity with human complement; MenA=meningococcal serogroup A; LLOQ=lower limit of quantitation; m-month; MenABCWY=pentavalent serogroups A, B, C, W, Y vaccine; MenACWY-CRM=MENVEO®, meningococcal (groups A, C, Y, and W-135) oligosaccharide CRM197 conjugate vaccine (quadrivalent meningococcal CRM vaccine); MenB=meningococcal serogroup B; MenB-FHbp=TRUMENBA®, meningococcal group B bivalent recombinant lipoprotein 2086 (bivalent rLP2086).

vaccine; MenC=meningococcal serogroup C; MenW=meningococcal serogroup W; MenY=meningococcal serogroup Y; PD=postdose.

FIG. 2A-B. (FIG. 2A) Local Reactions and (FIG. 2B) Systemic Events Reported Within 7 Days After Any Dose. MenABCWY, n=542; MenB-FHbp+MenACWY-CRM, n=1050. *At the MenABCWY/MenB-FHbp injection site. MenABCWY=pentavalent serogroups A, B, C, W, Y vaccine; MenACWY-CRM=MENVEO®, meningococcal (groups A, C, Y, and W-135) oligosaccharide CRM197 conjugate vaccine (quadrivalent meningococcal CRM vaccine); MenB-FHbp=TRUMENBA®, meningococcal group B bivalent recombinant lipoprotein 2086 (bivalent rLP2086).

FIG. 3. Estimated cases averted over 10 years under various vaccine administration strategies compared to a hypothetical no vaccination scenario.

SEQUENCE IDENTIFIERS

SEQ ID NO: 1 sets forth the amino acid sequence for a recombinant *N. meningitidis*, serogroup B, 2086 variant A05 polypeptide antigen.

SEQ ID NO: 2 sets forth the amino acid sequence for a recombinant *N. meningitidis*, serogroup B, 2086 variant B01 polypeptide antigen.

SEQ ID NO: 3 sets forth the amino acid residues at positions 1~4 of SEQ ID NO: 1 and SEQ ID NO: 2.

SEQ ID NO: 4 sets forth the amino acid sequence of the N-terminus of a recombinant Neisserial Subfamily A LP2086 polypeptide (rLP2086) (A05) polypeptide.

SEQ ID NO: 5 sets forth the amino acid sequence of the N-terminus of Neisserial Subfamily A LP2086 M98250771 polypeptide (A05) polypeptide.

SEQ ID NO: 6 sets forth the amino acid sequence for *N. meningitidis*, serogroup B, 2086 variant B153.

SEQ ID NO: 7 sets forth the amino acid sequence for *N. meningitidis*, serogroup B, 2086 variant A04.

SEQ ID NO: 8 sets forth the amino acid sequence for *N. meningitidis*, serogroup B, 2086 variant A05

SEQ ID NO: 9 sets forth the amino acid sequence for *N. meningitidis*, serogroup B, 2086 variant A12.

SEQ ID NO: 10 sets forth the amino acid sequence for *N. meningitidis*, serogroup B, 2086 variant A22.

SEQ ID NO: 11 sets forth the amino acid sequence for *N. meningitidis*, serogroup B, 2086 variant B02.

SEQ ID NO: 12 sets forth the amino acid sequence for *N. meningitidis*, serogroup B, 2086 variant B03.

SEQ ID NO: 13 sets forth the amino acid sequence for *N. meningitidis*, serogroup B, 2086 variant B09.

SEQ ID NO: 14 sets forth the amino acid sequence for *N. meningitidis*, serogroup B, 2086 variant B22.

SEQ ID NO: 15 sets forth the amino acid sequence for *N. meningitidis*, serogroup B, 2086 variant B24.

SEQ ID NO: 16 sets forth the amino acid sequence for *N. meningitidis*, serogroup B, 2086 variant B44.

SEQ ID NO: 17 sets forth the amino acid sequence for *N. meningitidis*, serogroup B, 2086 variant B16.

SEQ ID NO: 18 sets forth the amino acid sequence for *N. meningitidis*, serogroup B, 2086 variant A07.

SEQ ID NO: 19 sets forth the amino acid sequence for *N. meningitidis*, serogroup B, 2086 variant A19.

SEQ ID NO: 20 sets forth the amino acid sequence for *N. meningitidis*, serogroup B, 2086 variant A06.

SEQ ID NO: 21 sets forth the amino acid sequence for *N. meningitidis*, serogroup B, 2086 variant A15.

SEQ ID NO: 22 sets forth the amino acid sequence for *N. meningitidis*, serogroup B, 2086 variant A29.

SEQ ID NO: 23 sets forth the amino acid sequence for *N. meningitidis*, serogroup B, 2086 variant B15.

SEQ ID NO: 24 sets forth the amino acid sequence of the N-terminus of a recombinant Neisserial Subfamily B LP2086 polypeptide (rLP2086) (B01) polypeptide.

SEQ ID NO: 25 sets forth the amino acid sequence of the N-terminus of Neisserial Subfamily B LP2086 CDC-1573 polypeptide (B01) polypeptide.

SEQ ID NO: 26 sets forth the amino acid sequence for *N. meningitidis* serogroup A strain expressing factor H binding protein (fHBP) B16.

SEQ ID NO: 27 sets forth the amino acid sequence for a *N. meningitidis* serogroup C strain expressing fHBP A10. SEQ ID NO: 27 also sets forth the amino acid sequence for a *N. meningitidis* serogroup W strain expressing fHBP A10.

SEQ ID NO: 28 sets forth the amino acid sequence for a *N. meningitidis* serogroup W strain expressing fHBP A19.

SEQ ID NO: 29 sets forth the amino acid sequence for a *N. meningitidis* serogroup Y strain expressing fHBP B47.

SEQ ID NO: 30 sets forth the amino acid sequence for a *N. meningitidis* serogroup X strain expressing fHBP B49.

SEQ ID NO: 31 sets forth the amino acid sequence for a *N. meningitidis*, serogroup B, 2086 variant B16.

SEQ ID NO: 32 sets forth the amino acid sequence for a *N. meningitidis*, serogroup B, 2086 variant A07.

SEQ ID NO: 33 sets forth the amino acid sequence for a *N. meningitidis*, serogroup B, 2086 variant A19.

SEQ ID NO: 34 sets forth the amino acid sequence for a *N. meningitidis*, serogroup B, 2086 variant A06.

SEQ ID NO: 35 sets forth the amino acid sequence for a *N. meningitidis*, serogroup B, 2086 variant A15.

SEQ ID NO: 36 sets forth the amino acid sequence for a *N. meningitidis*, serogroup B, 2086 variant A29.

SEQ ID NO: 37 sets forth the amino acid sequence for a *N. meningitidis*, serogroup B, 2086 variant B15.

SEQ ID NO: 38 sets forth the amino acid sequence for a *N. meningitidis* serogroup A strain expressing factor H binding protein (fHBP) B16.

SEQ ID NO: 39 sets forth the amino acid sequence for a *N. meningitidis* serogroup C strain expressing fHBP A10. SEQ ID NO: 39 also sets forth the amino acid sequence for a *N. meningitidis* serogroup W strain expressing fHBP A10.

SEQ ID NO: 40 sets forth the amino acid sequence for a *N. meningitidis* serogroup W strain expressing fHBP A19.

SEQ ID NO: 41 sets forth the amino acid sequence for a *N. meningitidis* serogroup Y strain expressing fHBP B47.

SEQ ID NO: 42 sets forth the amino acid sequence for a *N. meningitidis* serogroup X strain expressing fHBP B49.

SEQ ID NO: 43 sets forth the amino acid sequence for a *N. meningitidis*, serogroup B, 2086 variant B44.

SEQ ID NO: 44 sets forth the amino acid sequence for a *N. meningitidis*, serogroup B, 2086 variant B09.

SEQ ID NO: 45 sets forth the amino acid sequence for a *N. meningitidis*, serogroup B, 2086 variant B09.

SEQ ID NO: 46 sets forth the amino acid sequence for a *N. meningitidis*, serogroup B, 2086 variant A05.

SEQ ID NO: 47 sets forth the amino acid sequence for a *N. meningitidis*, serogroup B, 2086 variant B01.

SEQ ID NO: 48 sets forth the amino acid sequence for a *N. meningitidis*, serogroup B, 2086 variant B01, which includes an N-terminal Cys at amino acid position 1.

SEQ ID NO: 49 sets forth the amino acid sequence for a *N. meningitidis*, serogroup B, 2086 variant B15, which includes an N-terminal Cys at amino acid position 1.

SEQ ID NO: 50 sets forth the amino acid sequence for a *N. meningitidis*, serogroup B, 2086 variant B16, which includes an N-terminal Cys at amino acid position 1.

SEQ ID NO: 51 sets forth the amino acid sequence for a *N. meningitidis*, serogroup B, 2086 variant B22.

SEQ ID NO: 52 sets forth the amino acid sequence for a *N. meningitidis*, serogroup B, 2086 variant A22.

SEQ ID NO: 53 sets forth the amino acid sequence for a *N. meningitidis*, serogroup B, 2086 variant A12.

SEQ ID NO: 54 sets forth the amino acid sequence for a *N. meningitidis*, serogroup B, 2086 variant A22.

SEQ ID NO: 55 sets forth the amino acid sequence for a *N. meningitidis* serogroup B, 2086 variant A62, which includes an N-terminal Cys at amino acid position 1.

SEQ ID NO: 56 sets forth the amino acid sequence for a *N. meningitidis*, serogroup B, 2086 variant A62.

SEQ ID NO: 57 sets forth the amino acid sequence for a *N. meningitidis*, serogroup B, 2086 variant A29, which includes an N-terminal Cys at amino acid position 1.

SEQ ID NO: 58 sets forth the amino acid sequence for a *N. meningitidis*, serogroup B, 2086 variant B22.

SEQ ID NO: 59 sets forth the amino acid sequence for a *N. meningitidis*, serogroup B, 2086 variant A05.

SEQ ID NO: 60 sets forth the amino acid sequence for a *N. meningitidis*, serogroup B, 2086 variant A05.

SEQ ID NO: 61 sets forth the amino acid sequence for a *N. meningitidis*, serogroup B, 2086 variant B24.

SEQ ID NO: 62 sets forth the amino acid sequence for a *N. meningitidis*, serogroup B, 2086 variant B24.

SEQ ID NO: 63 sets forth the amino acid sequence for a *N. meningitidis*, serogroup B, 2086 variant A02 SEQ ID NO: 64 sets forth the amino acid sequence for a *N. meningitidis*, serogroup B, 2086 variant A28.

SEQ ID NO: 65 sets forth the amino acid sequence for a *N. meningitidis*, serogroup B, 2086 variant A42.

SEQ ID NO: 66 sets forth the amino acid sequence for a *N. meningitidis*, serogroup B, 2086 variant A63.

SEQ ID NO: 67 sets forth the amino acid sequence for a *N. meningitidis*, serogroup B, 2086 variant A76.

SEQ ID NO: 68 sets forth the amino acid sequence for a *N. meningitidis*, serogroup B, 2086 variant B05.

SEQ ID NO: 69 sets forth the amino acid sequence for a *N. meningitidis*, serogroup B, 2086 variant B07.

SEQ ID NO: 70 sets forth the amino acid sequence for a *N. meningitidis*, serogroup B, 2086 variant B08.

SEQ ID NO: 71 sets forth the amino acid sequence for a *N. meningitidis*, serogroup B, 2086 variant B13.

SEQ ID NO: 72 sets forth the amino acid sequence for a *N. meningitidis*, serogroup B, 2086 variant B52.

SEQ ID NO: 73 sets forth the amino acid sequence for a *N. meningitidis*, serogroup B, 2086 variant B107.

SEQ ID NO: 74 sets forth the amino acid sequence for a *N. meningitidis*, serogroup B, 2086 variant A56.

DETAILED DESCRIPTION

The inventors discovered that a composition including at least one factor H binding protein (fHBP) and *N. meningitidis* serogroup A, C, W, and Y capsular saccharide conjugates is stable and immunogenic. The inventors further discovered that the composition induces an immune response in humans against at least 2, 3, 4, or 5 of *N. meningitidis* serogroups A, C, W, Y, and B. Surprisingly, the immune response elicited is higher than an immune response elicited by licensed vaccines against *N. meningitidis*.

In one aspect, the composition includes at least one polypeptide derived from a *N. meningitidis* factor H binding protein and at least one meningococcal capsular saccharide conjugated to a carrier protein.

Protein Derived from Factor H Binding Protein (FHBP).

In one embodiment, the composition includes any fHBP, such as, for example, any one of the following polypeptides: B24, B16, B44, A22, B03, B09, A12, A19, A05, A07, A06, A15, A29, B01, A62, B15, and any combination thereof. Preferably, the composition includes a combination of A05 and B01 polypeptides. In another preferred embodiment, the composition includes a combination of B24 and A05 polypeptides. In another embodiment, the composition includes a combination of A05, A12, B09, and B44 polypeptides. In one embodiment, the composition includes a lipidated fHBP. In one embodiment, the composition does not include a non-lipidated fHBP.

In another embodiment, the composition includes a non-lipidated fHBP, such as any one of the non-lipidated fHBP described in International Patent Publication No. WO2012/032489, US Patent Publication No. US20120093852, International Patent Publication No. WO2013/132452, and US Patent Publication No. US20160030543, which are each incorporated herein by reference in their entirety. In one embodiment, the composition includes at least one non-lipidated fHBP and at least one lipidated fHBP.

In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the amino acid sequence set forth in any one of SEQ ID NO: 1, SEQ ID NO: 2, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62.

In a preferred embodiment, the composition includes (a) a first polypeptide including the amino acid sequence set forth in SEQ ID NO: 1; (b) a second polypeptide including the amino acid sequence set forth in SEQ ID NO: 2; (c) a *Neisseria meningitidis* serogroup A capsular saccharide conjugated to an adipic acid dihydrazide (ADH) linker by 1-cyano-4-dimethylamino pyridinium tetrafluoroborate, wherein the linker is conjugated to tetanus toxoid by carbodiimide chemistry; (d) a *N. meningitidis* serogroup C capsular saccharide conjugated to an ADH linker by 1-cyano-4-dimethylamino pyridinium tetrafluoroborate, wherein the linker is conjugated to tetanus toxoid by carbodiimide chemistry; (e) a *N. meningitidis* serogroup W capsular saccharide directly conjugated to tetanus toxoid by 1-cyano-4-dimethylamino pyridinium tetrafluoroborate, in the absence of a linker; and (f) a *N. meningitidis* serogroup Y capsular saccharide directly conjugated to tetanus toxoid by 1-cyano-4-dimethylamino pyridinium tetrafluoroborate, in the absence of a linker.

First Polypeptide; MNB RLP2086 Subfamily A (A05) Protein

In one embodiment, the composition includes a first polypeptide having the amino acid sequence set forth in SEQ ID NO: 1. The polypeptide is a modified factor H binding protein (fHBP) from *N. meningitidis* strain M98250771. A description of fHBP is disclosed in WO2012032489 and US patent publication US 2012/0093852, which are each incorporated by reference in their entirety. The polypeptide is N-terminally lipidated with three predominant fatty acids C16:0, C16:1, and C18:1 covalently linked at three positions of the polypeptide. The first polypeptide includes a total of 258 amino acids.

The representative primary structure of the MnB rLP2086 A05 protein is presented in FIG. 4 of U.S. Pat. No. 10,183,070. The primary structure of the protein is illustrated in FIG. 4 of U.S. Pat. No. 10,183,070 using a single letter notation for all amino acids except for the N-terminal cysteine and glyceryl moieties (illustrated using full chemical formula). This structure includes the primary structure of the protein sequence in which the N-terminal cysteine residue is lipidated. The amino group of the N-terminal cysteine residue at the protein N-terminus is attached to a fatty acid (R1) forming an amide linkage and the cysteinyl sulfhydryl group is attached to a glycerol moiety containing two ester-bound fatty acids (R2). The structure of R1 is deduced to be hexadecanoic acid (016:0) and the structures of R2 vary depending on the MnB rLP2086 isoforms.

The first polypeptide includes two modifications introduced in the N-terminal region of the polypeptide, as compared to the corresponding wild-type sequence from *N. meningitidis* strain M98250771. A glycine in the second position is added as a consequence of introducing a cloning site. A second modification includes the deletion of four amino acids. Accordingly, in one embodiment, the first polypeptide includes a C-G-S-S sequence (SEQ ID NO: 3) at the N-terminus. See SEQ ID NO: 1, first four amino acid residues.

The N-terminal differences between the first polypeptide sequence and the wild-type Neisserial sequence is shown below. Accordingly, in one embodiment, the first polypeptide includes at least the first 2, 3, 4, 5, 6, 7, 8, 9, 10, 11, 12, 13, or more amino acid residues of the amino acid sequence set forth in SEQ ID NO: 1. Preferably, the first polypeptide includes at least the first 4, more preferably at least the first 6, and most preferably, at least the first 8 amino acid residues of SEQ ID NO: 1.

| Comparison of Predicted N-Terminal Sequences of Recombinant and Neisserial Subfamily A LP2086 Polypeptide | |
|---|---|
| rLP2086 M98250771 | CGSS-----GGGGVAAD (SEQ ID NO: 4) |
| Neisserial LP2086 M98250771 | C-SSGS-GSGGGGVAAD (SEQ ID NO: 5) |

>A05 (SEQ ID NO: 1)
CGSSGGGGVAADIGTGLADALTAPLDHKDKGLKSLTLEDSISQNGTLTLS
AQGAEKTFKVGDKDNSLNTGKLKNDKISRFDPVQKIEVDGQTITLASGEF
QIYKQDHSAVVALQIEKINNPDKIDSLINQRSFLVSGLGGEHTAFNQLPS
GKAEYHGKAFSSDDAGGKLTYTIDFAAKQGHGKIEHLKTPEQNVELASAE
LKADEKSHAVILGDTRYGSEEKGTYHLALFGDRAQEIAGSATVKIREKVH
EIGIAGKQ

In one embodiment, the first polypeptide includes the amino acid sequence set forth in SEQ ID NO: 1. In one embodiment, the first polypeptide has a total of 258 amino acids. In one embodiment, the first polypeptide does not include an amino acid sequence having less than 100% sequence identity to SEQ ID NO: 1. In another embodiment, the first polypeptide consists of the amino acid sequence set forth in SEQ ID NO: 1. In another embodiment, the first polypeptide includes the amino acid sequence KDN. See for example, amino acid residues 73-75 of SEQ ID NO: 1. In another embodiment, the first polypeptide includes the amino acid sequence set forth in SEQ ID NO: 3 at the N-terminus of the polypeptide. In another embodiment, the first polypeptide includes the amino acid sequence set forth in SEQ ID NO: 4 at the N-terminus of the polypeptide.

In a preferred embodiment, the first polypeptide is readily expressed in a recombinant host cell using standard techniques known in the art. In another preferred embodiment, the first polypeptide includes a bactericidal epitope on the N- and/or C-domain of SEQ ID NO: 1. In one embodiment, the first polypeptide includes at least the first 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 1. Preferably, the first polypeptide includes at least the first 2, more preferably at least the first 4, and most preferably, at least the first 8 amino acid residues of SEQ ID NO: 1.

In another embodiment, the first polypeptide includes at least the last 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 1.

In one embodiment, the composition includes about 30 µg/ml of a first polypeptide including the amino acid sequence set forth in SEQ ID NO: 1. In one preferred embodiment, the composition includes about 60 µg of a first polypeptide including the amino acid sequence set forth in SEQ ID NO: 1. In one preferred embodiment, the composition includes about 60 µg of a first polypeptide including the amino acid sequence set forth in SEQ ID NO: 1, wherein the composition preferably has a total volume of 0.5 ml. In another embodiment, the composition includes about 120 µg/ml of a first polypeptide including the amino acid sequence set forth in SEQ ID NO: 1.

Second Polypeptide; MNB RLP2086 Subfamily B (B01) Protein

In one embodiment, the composition includes a second polypeptide having the amino acid sequence set forth in SEQ ID NO: 2. The polypeptide is a factor H binding protein (fHBP) from *N. meningitidis* strain CDC1573. A description of fHBP is disclosed in WO2012032489 and US patent publication US 2012/0093852, which are each incorporated by reference in their entirety. The polypeptide is N-terminally lipidated with three predominant fatty acids C16:0, C16:1, and C18:1 covalently linked at three positions of the polypeptide. The second polypeptide includes a total of 261 amino acids.

The representative primary structure of the MnB rLP2086 B01 protein is presented in FIG. 5 of U.S. Pat. No. 10,183,070. The primary structure of the protein is illustrated in FIG. 5 of U.S. Pat. No. 10,183,070 using a single letter notation for all amino acids except for the N-terminal cysteine and glyceryl moieties (illustrated using full chemical formula). This structure includes the primary structure of the protein sequence in which the N-terminal cysteine residue is lipidated. The amino group of the N-terminal cysteine residue at the protein N-terminus is attached to a fatty acid (R1) forming an amide linkage and the cysteinyl sulfhydryl group is attached to a glycerol moiety containing two-ester bound fatty acids (R2). The structure of R1 is deduced to be hexadecanoic acid (C16:0) and the structures of R2 vary depending on the rLP2086 isoforms.

The second polypeptide includes one modification introduced in the N-terminal region for the rLP2086 subfamily B protein, as compared to the corresponding wild-type sequence from *N. meningitidis* strain CDC-1573. A glycine in the second position is a consequence of introducing a cloning site.

The N-terminal differences from the original Neisserial sequences are shown below.

| Comparison of Predicted N-Terminal Sequences of Recombinant and Neisserial Subfamily B LP2086 Protein | | |
|---|---|---|
| rLP2086 CDC-1573 | CGSSGGGGSGGGGVTAD | (SEQ ID NO: 24) |
| Neisserial LP2086 CDC-1573 | C-SSGGGGSGGGGVTAD | (SEQ ID NO: 25) |

In one embodiment, the second polypeptide includes a C-G-S-S sequence (SEQ ID NO: 3) at the N-terminus. See the first four amino acid residues of SEQ ID NO: 2.

>B01
(SEQ ID NO: 2)
CGSSGGGGSGGGGVTADIGTGLADALTAPLDHKDKGLKSLTLEDSISQNG

TLTLSAQGAEKTYGNGDSLNTGKLKNDKVSRFDFIRQIEVDGQLITLESG

EFQVYKQSHSALTALQTEQEQDPEHSEKMVAKRRFRIGDIAGEHTSFDKL

PKDVMATYRGTAFGSDDAGGKLTYTIDFAAKQGHGKIEHLKSPELNVDLA

VAYIKPDEKHHAVISGSVLYNQDEKGSYSLGIFGEKAQEVAGSAEVETAN

GIHHIGLAAKQ

In one embodiment, the second polypeptide includes the amino acid sequence set forth in SEQ ID NO: 2. In one embodiment, the second polypeptide has a total of 261 amino acids. In one embodiment, the second polypeptide consists of the amino acid sequence set forth in SEQ ID NO: 2. In another embodiment, the second polypeptide does not further include a polypeptide having less than 100% sequence identity to SEQ ID NO: 2. In a preferred embodiment, the first polypeptide and the second polypeptide includes a C-G-S-S(SEQ ID NO: 3) sequence at the N-terminus of the respective polypeptide.

In a preferred embodiment, the second polypeptide is readily expressed in a recombinant host cell using standard techniques known in the art. In another preferred embodiment, the second polypeptide includes a bactericidal epitope on the N- and/or C-domain of SEQ ID NO: 2. In one embodiment, the second polypeptide includes at least the first 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 2. Preferably, the second polypeptide includes at least the first 2, more preferably at least the first 4, and most preferably, at least the first 8 amino acid residues of SEQ ID NO: 2.

In another embodiment, the second polypeptide includes at least the last 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 2.

In one embodiment, the composition includes about 30 µg/ml of a first polypeptide including the amino acid sequence set forth in SEQ ID NO: 2. In one preferred embodiment, the composition includes about 60 µg of a first polypeptide including the amino acid sequence set forth in SEQ ID NO: 2. In one preferred embodiment, the composition includes about 60 µg of a second polypeptide including the amino acid sequence set forth in SEQ ID NO: 2, wherein the composition preferably has a total volume of 0.5 ml. In another embodiment, the composition includes 120 µg/ml of a second polypeptide including the amino acid sequence set forth in SEQ ID NO: 2.

Meningococcal Serogroups A, C, W, and Y (MENACWY) Capsular Saccharides

The term "saccharide" throughout this specification may indicate polysaccharide or oligosaccharide and includes both. Polysaccharides are isolated from bacteria or isolated from bacteria and sized to some degree by known methods and optionally by microfluidisation. Polysaccharides can be sized in order to reduce viscosity in polysaccharide samples and/or to improve filterability for conjugated products. Oligosaccharides have a low number of repeat units (typically 5-30 repeat units) and are typically hydrolysed polysaccharides.

Each N. meningitidis capsular saccharide may be conjugated to a carrier protein independently selected from the group consisting of TT, DT, CRM197, fragment C of TT and protein D. Although one or more N. meningitidis capsular saccharide may be conjugated to different carrier proteins from the others, in one embodiment they are all conjugated to the same carrier protein. For instance they may all be conjugated to the same carrier protein selected from the group consisting of TT, DT, CRM197, fragment C of TT and protein D. In this context CRM197 and DT may be considered to be the same carrier protein as they differ by only one amino acid. In a preferred embodiment all the N. meningitidis capsular saccharides present are conjugated to TT.

If the protein carrier is the same for 2 or more saccharides in the composition, the saccharide could be conjugated to the same molecule of the protein carrier (carrier molecules having 2 more different saccharides conjugated to it) [see for instance WO 04/083251; for example, a single carrier protein might be conjugated to MenA and MenC; MenA and MenW; MenA and MenY; MenC and MenW; MenC and MenY; Men W and MenY; MenA, MenC and MenW; MenA, MenC and MenY; MenA, MenW and MenY; MenC, MenW and MenY; MenA, MenC, MenW and MenY. Alternatively the saccharides may each be separately conjugated to different molecules of the protein carrier (each molecule of protein carrier only having one type of saccharide conjugated to it).

In one embodiment, at least 2 different saccharide conjugates are conjugated separately to the same type of carrier protein, wherein one or more saccharide(s) is/are conjugated to the carrier protein via a first type of chemical group on the protein carrier, and one or more saccharide(s) is/are conjugated to the carrier protein via a second (different) type of chemical group on the protein carrier.

In one embodiment the 2 conjugates involve the same saccharide linked to the same carrier, but by different conjugation chemistries. In an alternative embodiment 2 different saccharides are conjugated to different groups on the protein carrier.

By "conjugated separately to the same type of carrier protein" it is meant that the saccharides are conjugated to the same carrier individually (for example, MenA is conjugated to tetanus toxoid through an amine group on the tetanus toxoid and MenC is conjugated to tetanus toxoid through a carboxylic acid group on a different molecule of tetanus toxoid.)

The capsular saccharide(s) may be conjugated to the same carrier protein independently selected from the group consisting of TT, DT, CRM197, fragment C of TT and protein D. A more complete list of protein carriers that may be used in the conjugates of the disclosure is presented below. In this context CRM197 and DT may be considered to be the same carrier protein as they differ by only one amino acid. In an embodiment all the capsular saccharides present are conjugated to TT.

The saccharides may include any one of: N. meningitidis serogroup A capsular saccharide (MenA), N. meningitidis serogroup C capsular saccharide (MenC), N. meningitidis serogroup Y capsular saccharide (MenY), and N. meningitidis serogroup W capsular saccharide (MenW), or any combination thereof.

The first and second chemical groups present on the protein carrier are different from each other and are ideally natural chemical groups that may be readily used for conjugation purposes. They may be selected independently from the group consisting of: carboxyl groups, amino groups, sulphydryl groups, Hydroxyl groups, Imidazolyl groups, Guanidyl groups, and Indolyl groups. In one embodiment the first chemical group is carboxyl and the second is amino, or vice versa. These groups are explained in greater detail below.

In a specific embodiment the immunogenic composition comprises at least 2 different N. meningitidis capsular saccharides, wherein one or more is/are selected from a first group consisting of MenA and MenC which is/are conjugated to the carrier protein via the first type of chemical group on the protein carrier (for instance carboxyl), and one or more different saccharides is/are selected from a second group consisting of MenC, MenY and MenW which is/are conjugated to the carrier protein via the second type of chemical group on the protein carrier (for instance amino).

In a further embodiment the immunogenic composition of the disclosure comprises MenA conjugated via the first type of chemical group (for instance carboxyl), and MenC conjugated via the second type of chemical group (for instance amino).

In another embodiment the immunogenic composition comprises MenC conjugated via the first type of chemical group (for instance carboxyl), and MenY conjugated via the second type of chemical group (for instance amino).

In another embodiment the immunogenic composition comprises MenA conjugated via the first type of chemical group (for instance carboxyl), and MenC, MenY and MenW conjugated via the second type of chemical group (for instance amino).

In another embodiment the immunogenic composition comprises MenA and MenC conjugated via the first type of chemical group (for instance carboxyl), and MenY and MenW conjugated via the second type of chemical group (for instance amino).

The saccharides of the disclosure included in pharmaceutical (immunogenic) compositions of the disclosure are conjugated to a carrier protein such as tetanus toxoid (TT), tetanus toxoid fragment C, non-toxic mutants of tetanus toxin [note all such variants of TT are considered to be the same type of carrier protein for the purposes of this disclosure], diphtheria toxoid (DT), CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. Nos. 5,917,017 or 6,455,673; or fragment disclosed in U.S. Pat. No. 5,843,711] (note all such variants of DT are considered to be the same type of carrier protein for the purposes of this disclosure), pneumococcal pneumolysin (Kuo et al (1995) Infect Immun 63; 2706-13), OMPC (meningococcal outer membrane protein—usually extracted from N. meningitidis serogroup B—EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of C. difficile (WO 00/61761) or Protein D (EP594610 and WO 00/56360).

In an embodiment, the immunogenic composition of the disclosure uses the same type of carrier protein (independently) in at least two, three, four or each of the saccharides contained therein.

In an embodiment, the immunogenic composition of the disclosure comprises a N. meningitidis saccharide conjugated to a carrier protein selected from the group consisting of TT, DT, CRM197, fragment C of TT and protein D.

The immunogenic composition of the disclosure optionally comprises at least one meningococcal saccharide (for example MenA; MenC; MenW; MenY; MenA and MenC; MenA and MenW; MenA and MenY; MenC and Men W; Men C and MenY; Men W and MenY; MenA, MenC and MenW; MenA, MenC and MenY; MenA, MenW and MenY; MenC, MenW and MenY or MenA, MenC, MenW and MenY) conjugate having a ratio of Men saccharide to carrier protein of between 1:5 and 5:1, between 1:2 and 5:1, between 1:0.5 and 1:2.5 or between 1:1.25 and 1:2.5 (w/w). In one preferred embodiment, the composition includes MenA, MenC, MenW and MenY each conjugated to tetanus toxoid at ratios (toxoid to polysaccharide) of about 3, about 3, about 1.5 and about 1.3, respectively.

The ratio of saccharide to carrier protein (w/w) in a conjugate may be determined using the sterilized conjugate. The amount of protein is determined using a Lowry assay (for example Lowry et al (1951) J. Biol. Chem. 193, 265-275 or Peterson et al Analytical Biochemistry 100, 201-220 (1979)) and the amount of saccharide is determined using ICP-OES (inductively coupled plasma-optical emission spectroscopy) for MenA, DMAP assay for MenC and Resorcinol assay for MenW and MenY (Monsigny et al (1988) Anal. Biochem. 175, 525-530).

In an embodiment, the immunogenic composition of the disclosure comprises N. meningitidis saccharide conjugate(s) wherein the N. meningitidis saccharide(s) is conjugated to the carrier protein via a linker, for instance a bifunctional linker. The linker is optionally heterobifunctional or homobifunctional, having for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH. Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. Nos. 4,673,574, 4,808,700), hexane diamine and 6-aminocaproic acid (U.S. Pat. No. 4,459,286).

The saccharide conjugates present in the immunogenic compositions of the disclosure may be prepared by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a holoacetylated carrier protein (for example using iodoacetimide or N-succinimidyl bromoacetatebromoacetate). Optionally, the cyanate ester (optionally made by CDAP chemistry) is coupled with hexane diamine or ADH and the amino-derivatised saccharide is conjugated to the carrier protein using carbodiimide (e.g. EDAC or EDC) chemistry via a carboxyl group on the protein carrier. Such conjugates are described in PCT published application WO 93/15760 Uniformed Services University and WO 95/08348 and WO 96/29094.

Other suitable techniques use carbiinides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (Bethell et al J. Biol. Chem.

1979, 254; 2572-4, Hearn et al J. Chromatogr. 1981, 218; 509-18) followed by reaction of with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-O-161-188, EP-208375 and EP-O-477508.

A further method involves the coupling of a cyanogen bromide (or CDAP) activated saccharide derivatised with adipic acid hydrazide (ADH) to the protein carrier by Carbodiimide condensation (Chu C. et al Infect. Immunity, 1983 245 256), for example using EDAC.

In an embodiment, a hydroxyl group (optionally an activated hydroxyl group for example a hydroxyl group activated by a cyanate ester) on a saccharide is linked to an amino or carboxylic group on a protein either directly or indirectly (through a linker). Where a linker is present, a hydroxyl group on a saccharide is optionally linked to an amino group on a linker, for example by using CDAP conjugation. A further amino group in the linker for example ADH may be conjugated to a carboxylic acid group on a protein, for example by using carbodiimide chemistry, for example by using EDAC. In an embodiment, N. meningitidis capsular saccharide(s) (or saccharide in general) is conjugated to the linker first before the linker is conjugated to the carrier protein. Alternatively the linker may be conjugated to the carrier before conjugation to the saccharide.

In general the following types of chemical groups on a protein carrier can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.

Direct Coupling Approaches:
Saccharide-OH+CNBr or CDAP→cyanate ester+NH2-Prot→conjugate
Saccharide-aldehyde+NH2-Prot→Schiff base+NaCNBH3→conjugate
Saccharide-COOH+NH2-Prot+EDAC→conjugate
Saccharide-NH2+COOH-Prot+EDAC→conjugate
Indirect Coupling Via Spacer (Linker) Approaches:
Saccharide-OH+CNBr or CDAP→cyanate ester+NH2-NH2→saccharide-NH2+COOH-Prot+EDAC→conjugate
Saccharide-OH+CNBr or CDAP→cyanate ester+NH2-SH→saccharide-SH+SH-Prot (native Protein with an exposed cysteine or obtained after modification of amino groups of the protein by SPDP for instance)→saccharide-S—S-Prot
Saccharide-OH+CNBr or CDAP→cyanate ester+NH2-SH→saccharide-SH+maleimide-Prot (modification of amino groups)→conjugate
Saccharide-COOH+EDAC+NH2-NH2→saccharide-NH2+EDAC+COOH-Prot→conjugate
Saccharide-COOH+EDAC+NH2-SH→saccharide-SH+SH-Prot (native Protein with an exposed cysteine or obtained after modification of amino groups of the protein by SPDP for instance)→saccharide-S—S-Prot
Saccharide-COOH+EDAC+NH2-SH→saccharide-SH+maleimide-Prot (modification of amino groups)→conjugate
Saccharide-Aldehyde+NH2-NH2→saccharide-NH2+EDAC+COOH-Prot→conjugate
Note: instead of EDAC above, any suitable carbodiimide may be used.

In summary, the types of protein carrier chemical group that may be generally used for coupling with a saccharide are amino groups (for instance on lysine residues), COOH groups (for instance on aspartic and glutamic acid residues) and SH groups (if accessible) (for instance on cysteine residues).

In an embodiment, at least one of the N. meningitidis capsular saccharides (or saccharide in general) is directly conjugated to a carrier protein; optionally Men W and/or MenY and/or MenC saccharide(s) is directly conjugated to a carrier protein. For example MenW; MenY; MenC; MenW and MenY; MenW and MenC; MenY and MenC; or MenW, MenY and MenC are directly linked to the carrier protein. Optionally, at least one of the N. meningitidis capsular saccharides is directly conjugated by CDAP. For example MenW; MenY; MenC; MenW and MenY; MenW and MenC; MenY and MenC; or MenW, MenY and MenC are directly linked to the carrier protein by CDAP (see WO 95/08348 and WO 96/29094). In an embodiment, all N. meningitidis capsular saccharides are conjugated to tetanus toxoid.

In an embodiment, the ratio of Men W and/or Y saccharide to carrier protein is between 1:0.5 and 1:2 (w/w) and/or the ratio of MenC saccharide to carrier protein is between 1:0.5 and 1:4 or 1:0.5 and 1:1.5 (w/w), especially where these saccharides are directly linked to the protein, optionally using CDAP.

In an embodiment, at least one of the N. meningitidis capsular saccharide(s) (or saccharide in general) is conjugated to the carrier protein via a linker, for instance a bifunctional linker. The linker is optionally heterobifunctional or homobifunctional, having for example a reactive amine group and a reactive carboxylic acid group, 2 reactive amine groups or 2 reactive carboxylic acid groups. The linker has for example between 4 and 20, 4 and 12, 5 and 10 carbon atoms. A possible linker is ADH.

In an embodiment, MenA; MenC; or MenA and MenC is conjugated to a carrier protein (for example tetanus toxoid) via a linker.

In an embodiment, at least one *N. meningitidis* saccharide is conjugated to a carrier protein via a linker using CDAP and EDAC. For example, MenA; MenC; or MenA and MenC are conjugated to a protein via a linker (for example those with two hydrazino groups at its ends such as ADH) using CDAP and EDAC as described above. For example, CDAP is used to conjugate the saccharide to a linker and EDAC is used to conjugate the linker to a protein. Optionally the conjugation via a linker results in a ratio of saccharide to carrier protein of between 1:0.5 and 1:6; 1:1 and 1:5 or 1:2 and 1:4, for MenA; MenC; or MenA and MenC.

In an embodiment, the MenA capsular saccharide, where present is at least partially O-acetylated such that at least 50%, 60%, 70%, 80%, 90%, 95% or 98% of the repeat units are O-acetylated at at least one position. O-acetylation is for example present at least at the O-3 position of at least 50%, 60%, 70%, 80%, 90%, 95% or 98% of the repeat units.

In an embodiment, the MenC capsular saccharide, where present is at least partially O-acetylated such that at least 30%, 40%, 50%, 60%, 70%, 80%, 90%, 95% or 98% of ($\alpha 2 \rightarrow 9$)-linked NeuNAc repeat units are O-acetylated at at least one or two positions. O-acetylation is for example present at the O-7 and/or O-8 position of at least 30%. 40%, 50%, 60%, 70%, 80%, 90%, 95% or 98% of the repeat units.

In an embodiment, the MenW capsular saccharide, where present is at least partially O-acetylated such that at least 30%, 40%, 50%, 60%, 70%, 80%, 90%, 95% or 98% of the repeat units are O-acetylated at at least one or two positions. O-acetylation is for example present at the O-7 and/or O-9 position of at least 30%. 40%, 50%, 60%, 70%, 80%, 90%, 95% or 98% of the repeat units.

In an embodiment, the MenY capsular saccharide, where present is at least partially O-acetylated such that at least 20%, 30%, 40%, 50%, 60%, 70%, 80%, 90%, 95% or 98% of the repeat units are O-acetylated at at least one or two positions. O-acetylation is present at the 7 and/or 9 position of at least 20%, 30%, 40%, 50%, 60%, 70%, 80%, 90%, 95% or 98% of the repeat units.

The percentage of O-acetylation refers to the percentage of the repeat units containing O-acetylation. This may be measured in the saccharide prior to conjugate and/or after conjugation.

In one embodiment of the disclosure the immunogenic composition, saccharide present, or each *N. meningitidis* capsular saccharide present, is conjugated to TT. In a further embodiment each *N. meningitidis* capsular saccharide is separately conjugated to a separate carrier protein. In a further embodiment each *N. meningitidis* capsular saccharide conjugate has a saccharide:carrier ratio of 1:5-5:1 or 1:1-1:4 (w/w). In a further embodiment at least one, two or three *N. meningitidis* capsular saccharide conjugate(s) is directly conjugated to a carrier protein. In a further embodiment Men W and/or MenY, MenW and/or MenC, MenY and/or MenC, or MenW and MenC and MenY are directly conjugated to a carrier protein. In a further embodiment at least one, two or three *N. meningitidis* saccharide conjugate(s) is directly conjugated by CDAP chemistry. In a further embodiment the ratio of Men W and/or Y saccharide to carrier protein is between 1:0.5 and 1:2 (w/w). In a further embodiment the ratio of MenC saccharide to carrier protein is between 1:0.5 and 1:2 (w/w). In a further embodiment at least one, two or three *N. meningitidis* capsular saccharide(s) are conjugated to the carrier protein via a linker (which may be bifunctional such as having two reactive amino groups (such as ADH) or two reactive carboxyl groups, or a reactive amino group at one end and a reactive carboxyl group at the other). The linker can have between 4 and 12 carbon atoms.

In a further embodiment the or each *N. meningitidis* capsular saccharide(s) conjugated via a linker are conjugated to the linker with CDAP chemistry. In a further embodiment the carrier protein is conjugated to the linker using carbodiimide chemistry, for example using EDAC. In a further embodiment the or each *N. meningitidis* capsular saccharide is conjugated to the linker before the carrier protein is conjugated to the linker. In a further embodiment MenA is conjugated to a carrier protein via a linker (the ratio of MenA saccharide to carrier protein may be between 1:2 and 1:5 (w/w)). In a further embodiment MenC is conjugated to a carrier protein via a linker (the ratio of MenC saccharide to carrier protein may be between 1:2 and 1:5 (w/w)).

By using native or slightly sized polysaccharide conjugates, one or more of the following advantages may be realised: 1) a conjugate having high immungenicity which is filterable through a 0.2 micron filter; 2) immune memory may be enhanced (as in example three); 3) the alteration of the ratio of polysaccharide to protein in the conjugate such that the ratio of polysaccharide to protein (w/w) in the conjugate may be increased (this can result in a reduction of the carrier suppression effect); 4) immunogenic conjugates prone to hydrolysis (such as MenA conjugates) may be stabilised by the use of larger polysaccharides for conjugation. The use of larger polysaccharides can result in more cross-linking with the conjugate carrier and may lessen the liberation of free saccharide from the conjugate. The conjugate vaccines described in the prior art tend to depolymerise the polysaccharides prior to conjugation in order to improve conjugation. Meningococcal (or saccharide) conjugate vaccines retaining a larger size of saccharide can provide a good immune response against meningococcal disease.

The immunogenic composition of the disclosure may thus comprise one or more saccharide conjugates wherein the average size of each saccharide before conjugation is above 50 kDa, 75 kDa, 100 kDa, 110 kDa, 120 kDa or 130 kDa. In one embodiment the conjugate post conjugation should be readily filterable through a 0.2 micron filter such that a yield of more than 50, 60, 70, 80, 90 or 95% is obtained post filtration compared with the pre filtration sample.

In particular, the immunogenic composition of the disclosure comprises *N. meningitidis* capsular saccharides from at least one, two, three or four of serogroups A, C, W and Y conjugated to a carrier protein, wherein the average size (weight-average molecular weight; Mw) of at least one, two, three or four or each *N. meningitidis* saccharide is above 50 kDa, 60 kDa, 75 kDa, 100 kDa, 110 kDa, 120 kDa or 130 kDa.

In a preferred embodiment, the average Mw of the $MenA_{AH}$-TT conjugate is at least 250 kDa, 260 kDa, 270 kDa, 280 kDa, or 290 kDa, most preferably about 300 kDa, and at most 350 kDa or 330 kDa. In a preferred embodiment, the average Mw of the $MenC_{AH}$-TT conjugate is at least 150 kDa, 160 kDa, 170 kDa, 180 kDa, or 190 kDa, most preferably about 200 kDa, and at most 250 kDa or 230 kDa. In a preferred embodiment, the average Mw of the MenW-TT conjugate is at least 240, 250 kDa, 260 kDa, or 270 kDa, most preferably about 280 kDa, and at most 330 kDa or 310 kDa. In a preferred embodiment, the average Mw of the MenY-TT conjugate is at least 220 kDa, 230 kDa, 240 kDa, or 250 kDa, most preferably about 270 kDa, and at most 320 kDa or 300 kDa.

The immunogenic composition may comprise *N. meningitidis* capsular saccharides from at least one, two, three or four of serogroups A, C, W and Y conjugated to a carrier protein, wherein at least one, two, three or four or each *N.*

*meningitidis* saccharide is either a native saccharide or is sized by a factor up to ×2, ×3, ×4, ×5, ×6, ×7, ×8, ×9 or ×10 relative to the weight average molecular weight of the native polysaccharide.

For the purposes of the disclosure, "native polysaccharide" refers to a saccharide that has not been subjected to a process, the purpose of which is to reduce the size of the saccharide. A polysaccharide can become slightly reduced in size during normal purification procedures. Such a saccharide is still native. Only if the polysaccharide has been subjected to sizing techniques would the polysaccharide not be considered native.

For the purposes of the disclosure, "sized by a factor up to ×2" means that the saccharide is subject to a process intended to reduce the size of the saccharide but to retain a size more than half the size of the native polysaccharide. ×3, ×4 etc. are to be interpreted in the same way i.e. the saccharide is subject to a process intended to reduce the size of the polysaccharide but to retain a size more than a third, a quarter etc. the size of the native polysaccharide.

In an aspect of the disclosure, the immunogenic composition comprises *N. meningitidis* capsular saccharides from at least one, two, three or four of serogroups A, C, W and Y conjugated to a carrier protein, wherein at least one, two, three or four or each *N. meningitidis* saccharide is native polysaccharide.

In an aspect of the disclosure, the immunogenic composition comprises *N. meningitidis* capsular saccharides from at least one, two, three or four of serogroups A, C, W and Y conjugated to a carrier protein, wherein at least one, two, three or four or each *N. meningitidis* saccharide is sized by a factor up to ×1.5, ×2, ×3, ×4, ×5, ×6, ×7, ×8, ×9 or ×10.

The immunogenic compositions of the disclosure optionally comprise conjugates of: *N. meningitidis* serogroup C capsular saccharide (MenC), serogroup A capsular saccharide (MenA), serogroup W135 capsular saccharide (MenW), serogroup Y capsular saccharide (MenY), serogroup C and Y capsular saccharides (MenCY), serogroup C and A capsular saccharides (MenAC), serogroup C and W capsular saccharides (MenCW), serogroup A and Y capsular saccharide (MenAY), serogroup A and W capsular saccharides (MenAW), serogroup W and Y capsular saccharides (Men WY), serogroup A, C and W capsular saccharide (MenACW), serogroup A, C and Y capsular saccharides (MenACY); serogroup A, W135 and Y capsular saccharides (MenAWY), serogroup C, W135 and Y capsular saccharides (MenCWY); or serogroup A, C, W135 and Y capsular saccharides (MenACWY). This is the definition of "one, two, three or four", or "at least one of" of serogroups A, C, W and Y, or of each *N. meningitidis* saccharide where mentioned herein.

In an embodiment, the average size of at least one, two, three, four or each *N. meningitidis* saccharide is between 50 KDa and 1500 kDa, 50 kDa and 500 kDa, 50 kDa and 300 KDa, 101 kDa and 1500 kDa, 101 kDa and 500 kDa, 101 kDa and 300 kDa as determined by MALLS.

In an embodiment, the MenA saccharide, where present, has a molecular weight of 50-500 kDa, 50-100 kDa, 100-500 kDa, 55-90 KDa, 60-70 kDa or 70-80 kDa or 60-80 kDa.

In an embodiment, the MenC saccharide, where present, has a molecular weight of 100-200 kDa, 50-100 kDa, 100-150 kDa, 101-130 kDa, 150-210 kDa or 180-210 kDa.

In an embodiment the MenY saccharide, where present, has a molecular weight of 60-190 kDa, 70-180 kDa, 80-170 kDa, 90-160 kDa, 100-150 kDa or 110-140 kDa, 50-100 kDa, 100-140 kDa, 140-170 kDa or 150-160 kDa.

In an embodiment the MenW saccharide, where present, has a molecular weight of 60-190 kDa, 70-180 kDa, 80-170 kDa, 90-160 kDa, 100-150 kDa, 110-140 kDa, 50-100 kDa or 120-140 kDa.

The molecular weight or average molecular weight of a saccharide herein refers to the weight-average molecular weight (Mw) of the saccharide measured prior to conjugation and is measured by MALLS.

The MALLS technique is well known in the art and is typically carried out as described in example 2. For MALLS analysis of meningococcal saccharides, two columns (TSKG6000 and 5000PWxl) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm).

In an embodiment the *N. meningitidis* saccharides are native polysaccharides or native polysaccharides which have reduced in size during a normal extraction process.

In an embodiment, the *N. meningitidis* saccharides are sized by mechanical cleavage, for instance by microfluidisation or sonication. Microfluidisation and sonication have the advantage of decreasing the size of the larger native polysaccharides sufficiently to provide a filterable conjugate (fro example through a 0.2 micron filter). Sizing is by a factor of no more than ×20, ×10, ×8, ×6, ×5, ×4, ×3, ×2 or ×1.5.

In an embodiment, the immunogenic composition comprises *N. meningitidis* conjugates that are made from a mixture of native polysaccharides and saccharides that are sized by a factor of no more than ×20. For example, saccharides from MenC and/or MenA are native. For example, saccharides from MenY and/or MenW are sized by a factor of no more than ×20, ×10, ×8, ×6, ×5, ×4, ×3 or ×2. For example, an immunogenic composition contains a conjugate made from MenY and/or MenW and/or MenC and/or MenA which is sized by a factor of no more then ×10 and/or is microfluidised. For example, an immunogenic composition contains a conjugate made from native MenA and/or MenC and/or MenW and/or MenY. For example, an immunogenic composition comprises a conjugate made from native MenC. For example, an immunogenic composition comprises a conjugate made from native MenC and MenA which is sized by a factor of no more then ×10 and/or is microfluidised. For example, an immunogenic composition comprises a conjugate made from native MenC and MenY which is sized by a factor of no more then ×10 and/or is microfluidised.

In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0, 1.0-1.5, 1.0-1.2, 1.5-2.5, 1.7-2.2 or 1.5-2.0. All polydispersity measurements are by MALLS.

Saccharides are optionally sized up to 1.5, 2, 4, 6, 8, 10, 12, 14, 16, 18 or 20 times from the size of the polysaccharide isolated from bacteria.

In one embodiment each *N. meningitidis* saccharide is either a native polysaccharide or is sized by a factor of no more than ×10. In a further embodiment each *N. meningitidis* capsular saccharide is a native polysaccharide. In a further embodiment at least one, two, three or four *N. meningitidis* capsular saccharide(s) is sized by microfluidization. In a further embodiment each *N. meningitidis* capsular saccharide is sized by a factor of no more than ×10. In a further embodiment the *N. meningitidis* conjugates are made from a mixture of native polysaccharides and saccharides that are sized by a factor of no more than ×10. In a further embodiment the capsular saccharide from serogroup Y is sized by a factor of no more than ×10. In a further embodiment capsular saccharides from serogroups A and C are native polysaccharides and saccharides from serogroups W135 and Y are sized by a factor of no more than ×10. In a further embodiment the average size of each *N. meningitidis* capular saccharide is between 50 kDa and 300 KDa or 50 kDa and 200 kDa. In a further embodiment the immunogenic composition comprises a MenA capsular saccharide having an average size of above 50 kDa, 75 kDa, 100 kDa or an average size of between 50-100 kDa or 55-90 KDa or 60-80 kDa. In a further embodiment the immunogenic composition comprises a MenC capsular saccharide having an average size of above 50 kDa, 75 kDa, 100 kDa or between 100-200 kDa, 100-150 kDa, 80-120 kDa, 90-110 kDa, 150-200 kDa, 120-240 kDa, 140-220 kDa, 160-200 kDa or 190-200 kDa. In a further embodiment the immunogenic composition comprises a MenY capsular saccharide, having an average size of above 50 kDa, 75 kDa, 100 kDa or between 60-190 kDa or 70-180 kDa or 80-170 kDa or 90-160 kDa or 100-150 kDa, 110-145 kDa or 120-140 kDa. In a further embodiment the immunogenic composition comprises a MenW capsular saccharide having an average size of above 50 kDa, 75 kDa, 100 kDa or between 60-190 kDa or 70-180 kDa or 80-170 kDa or 90-160 kDa or 100-150 kDa, 140-180 kDa, 150-170 kDa or 110-140 kDa.

In an embodiment of the disclosure, the saccharide dose of each of the at least two, three, four or each of the *N. meningitidis* saccharide conjugates is optionally the same, or approximately the same.

In an embodiment, the immunogenic composition of the disclosure is adjusted to or buffered at, or adjusted to between pH 7.0 and 8.0, pH 7.2 and 7.6 or around or exactly pH 7.4.

The immunogenic composition or vaccines of the disclosure are optionally lyophilised in the presence of a stabilising agent for example a polyol such as sucrose or trehalose.

For the *N. meningitidis* saccharide combinations discussed above, it may be advantageous not to use any aluminium salt adjuvant or any adjuvant at all.

The active agent can be present in varying concentrations in the pharmaceutical composition or vaccine of the disclosure. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is optionally one which will provide a single therapeutically effective dosage. For bioactive substances, the minimum concentration is an amount necessary for bioactivity upon reconstitution and the maximum concentration is at the point at which a homogeneous suspension cannot be maintained.

In another embodiment, the composition includes a conjugate of a *Neisseria meningitidis* serogroup X capsular polysaccharide and a carrier molecule. The structure of the group X capsular polysaccharide consists of N-acetylglucosamine-4-phosphate residues held together by al-4 phosphodiester bonds without O-acetyl groups. The carrier molecule may be a diphtheria or tetanus toxoid, CRM 197 or protein D. In a preferred embodiment, as exemplified in the Examples, the composition does not include a conjugate of a *N. meningitidis* serogroup X capsular polysaccharide.

Further descriptions of exemplary compositions are described below.

Composition and Vaccine

In some embodiments, the composition includes a lyophilized MenACWY-TT composition that is reconstituted with a liquid MnB bivalent rLP2086 composition. The lyophilized MenACWY-TT composition and the liquid MnB bivalent rLP2086 composition are preferably compatible and stable following reconstitution for at least 24 hours at room temperature.

In preferred embodiments, the composition elicits a bactericidal antibody against *N. meningitidis* serogroup B and *N. meningitidis* serogroups other than B. For example, in some embodiments, the MnB bivalent rLP2086 composition elicits a bactericidal antibody against at least *N. meningitidis* serogroups A, C, W, Y, and X.

Furthermore, the inventors discovered that the composition elicited a geometric mean titer against *N. meningitidis* serogroups A, C, W, and Y that is consistent with the geometric mean titer observed for a licensed vaccine against *N. meningitidis* serogroups A, C, W, and Y.

In some embodiments, the composition elicits a geometric mean titer against *N. meningitidis* serogroups A, C, W, and Y that is higher than the geometric mean titer observed for a licensed vaccine against *N. meningitidis* serogroups A, C, W, and Y.

Moreover, the inventors discovered that the composition elicited a geometric mean titer against *N. meningitidis* serogroup B that is consistent with a geometric mean titer observed for a licensed vaccine against *N. meningitidis* serogroup B.

In some embodiments, the composition elicits a geometric mean titer against *N. meningitidis* serogroup B that is higher than the geometric mean titer observed for a licensed vaccine against *N. meningitidis* serogroup B.

In some embodiments, the composition including fHBP elicits an effective immune response in humans aged at least 12 months. The composition also elicits an immune response against a *N. meningitidis* serogroup X strain. In some embodiments, the composition includes at least one factor H binding polypeptide (fHBP) and at least one *N. meningitidis* capsular saccharide conjugate. In a preferred embodiment, the composition is stable and elicited an immune response against strains that express fHBP variants that are homologous to the fHBP variant in the multi-component composition and an immune response against strains that express fHBP variants that are heterologous to the fHBP variant in the multi-component composition.

In some embodiments, the liquid MnB bivalent rLP2086 composition can readily reconstitute a lyophilized MenACWY-TT composition and the combined composition is compatible and stable.

In one aspect, the disclosure relates to a composition against *Neisseria meningitidis*. The composition includes (a) a first lipidated polypeptide including the amino acid sequence set forth in SEQ ID NO: 1; (b) a second lipidated polypeptide including the amino acid sequence set forth in SEQ ID NO: 2; (c) a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate); (d) a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate); (e) a *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); (f) a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate).

In another aspect, the disclosure relates to a composition that includes a combination of a MnB bivalent rLP2086 composition and a MenACWY-TT composition. The MnB bivalent rLP2086 composition refers to a composition that includes a single *N. meningitidis* polypeptide component that induces an effective broadly protective immune response against multiple strains of *N. meningitidis* serogroup B. Specifically, in one embodiment, the MnB bivalent rLP2086 composition includes a MnB rLP2086 subfamily A protein (SEQ ID NO: 1) and MnB rLP2086 subfamily B protein (SEQ ID NO: 2). In one embodiment, the composition does not include a fusion protein. In one embodiment, the composition does not include a chimeric protein. In one embodiment, the composition does not include a hybrid protein. In one embodiment, the composition does not further include a peptide fragment. In another embodiment, the composition does not further include a Neisserial polypeptide that is not fHBP. For example, in one embodiment, the composition does not include a PorA protein. In another embodiment, the composition does not include a NadA protein. In another embodiment, the composition does not further include a Neisserial heparin binding antigen (NHBA). In another embodiment, the composition does not further include a Neisserial outer membrane vesicle (OMV). In a preferred embodiment, the composition does not further include antigens, other than the first polypeptide and the second polypeptide. In a preferred embodiment, the MnB bivalent rLP2086 composition further includes polysorbate-80. In one embodiment, the MnB bivalent rLP2086 composition further includes histidine buffer. In one embodiment, the MnB bivalent rLP2086 composition further includes sodium chloride. In one embodiment, the MnB bivalent rLP2086 composition further includes aluminum phosphate. In one embodiment, the MnB bivalent rLP2086 composition further includes polysorbate-80, histidine buffer, sodium chloride, and aluminum phosphate. Preferably, the MnB bivalent rLP2086 composition is a liquid formulation, wherein the polypeptides are formulated as 120 mcg/mL/subfamily in 10 mM histidine buffer, pH 6.0, 150 mM sodium chloride (NaCl) with 0.5 mg/mL aluminum phosphate (AlPO$_4$), and further includes 0.018 mg polysorbate-80 in a 0.5 mL dose.

The MenACWY-TT composition refers to a composition that includes purified capsular polysaccharides of *Neisseria meningitidis* Serogroup A, C, W-135 and Y, each independently conjugated to TT at ratios (TT to polysaccharide) of ~3, ~3, ~1.5 and ~1.3, respectively. Specifically, the composition includes (c) a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate); (d) a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate); (e) a *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); (f) a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate). Preferably, the MenACWY-TT composition is presented as a lyophilized powder.

MenA$_{AH}$-TT, MenC$_{AH}$-TT, MenW-TT, and MenY-TT conjugates are prepared through the following steps: manufacture of the polysaccharide drug substance intermediate, manufacture of the TT drug substance intermediate, microfluidization of the polysaccharide, derivatization of the polysaccharide (for the MenA$_{AH}$-TT and MenC$_{AH}$-TT processes only), additional purification of the TT, and conjugation of the individual polysaccharides to TT.

Regarding the MenA$_{AH}$-TT conjugate, the MenA polysaccharide is first microfluidized to reduce molecular size and viscosity, then activated via cyanylation with 1-cyano-4-dimethylamino-pyridinium tetrafluoroborate (CDAP). Activated MenA is derivatized with adipic acid dihydrazide (ADH) to form the MenA$_{AH}$. MenA$_{AH}$ and Tetanus Toxoid (TT) are coupled through carbodiimide-mediated condensation (1-ethyl-3-(3-dimethylaminopropyl)carbodiimide (EDAC) coupling technology) to form MenA$_{AH}$-Tetanus Toxoid Conjugate (MenA$_{AH}$-TT).

Regarding the MenC$_{AH}$-TT conjugate, the MenC polysaccharide is first microfluidized to reduce molecular size and viscosity, then activated via cyanylation with CDAP. Activated MenC is derivatized with adipic acid dihydrazide (ADH) to form the MenC$_{AH}$. MenC$_{AH}$ and TT are coupled through carbodiimide-mediated condensation EDAC coupling technology) to form MenC$_{AH}$-Tetanus Toxoid (MenC$_{AH}$-TT).

Regarding the MenW-TT conjugate, MenW polysaccharide is first microfluidized to reduce molecular size and viscosity, then activated via cyanylation with CDAP. Activated MenW is directly coupled to TT to form MenW-Tetanus Toxoid (MenW-TT).

Regarding the MenY-TT conjugate, MenY polysaccharide is first microfluidized to reduce molecular size and viscosity, then activated via cyanylation with CDAP. Activated MenY is directly coupled to TT to form MenY-Tetanus Toxoid (MenY-TT).

In another aspect, the polypeptide antigens are derived from at most two *N. meningitidis* serogroup B strains induces an effective broadly protective immune response against multiple strains of *N. meningitidis* serogroup B. Accordingly, in one embodiment, the composition does not further include a polypeptide that is not derived from *N. meningitidis* serogroup B fHBP subfamily A M98250771 strain and/or *N. meningitidis* serogroup B fHBP subfamily B CDC1573 strain.

In one embodiment, the composition does not further include a polypeptide having less than 100% sequence identity to SEQ ID NO: 1. In another embodiment, the composition does not further include a polypeptide having less than 100% sequence identity to SEQ ID NO: 2. For example, the composition does not further include a polypeptide having less than 100% sequence identity to the full length of SEQ ID NO: 1 and/or SEQ ID NO: 2.

In one embodiment, the composition further includes polysorbate-80, aluminum, histidine, and sodium chloride. In one embodiment, the composition includes about 60 µg of a first lipidated polypeptide including the amino acid sequence set forth in SEQ ID NO: 1, about 60 µg of a second lipidated polypeptide including the amino acid sequence set forth in SEQ ID NO: 2, 2.8 molar ratio of polysorbate-80 to each polypeptide, 0.5 mg aluminum/ml as aluminum phosphate, 10 mM histidine, and 150 mM sodium chloride, wherein the composition preferably has a total volume of about 0.5 ml.

In another aspect, the composition includes about 120 µg/ml of a first lipidated polypeptide including the amino acid sequence set forth in SEQ ID NO: 1, about 120 µg/ml of a second lipidated polypeptide including the amino acid sequence set forth in SEQ ID NO: 2, 2.8 molar ratio of polysorbate-80 to each polypeptide, 0.5 mg aluminum/ml as aluminum phosphate, 10 mM histidine, and 150 mM sodium chloride.

In a further aspect, the composition includes a) 60 µg of a first lipidated polypeptide including the amino acid sequence set forth in SEQ ID NO: 1; b) 60 µg of a second lipidated polypeptide including the amino acid sequence set forth in SEQ ID NO: 2; c) 18 µg polysorbate-80; d) 250 µg aluminum; e) 780 µg histidine, and; f) 4380 µg sodium chloride.

In an exemplary embodiment, the composition includes about 60 µg of a first lipidated polypeptide consisting of the amino acid sequence set forth in SEQ ID NO: 1, about 60 µg of a second lipidated polypeptide consisting of the amino acid sequence set forth in SEQ ID NO: 2, 2.8 molar ratio of polysorbate-80 to first lipidated polypeptide and to second lipidated polypeptide, 0.5 mg/ml aluminum phosphate, 10 mM histidine, and 150 mM sodium chloride, wherein the composition has a total volume of about 0.5 ml. In the exemplary embodiment, the composition is a sterile isotonic buffered liquid suspension. In the exemplary embodiment, the composition has a pH 6.0. In the exemplary embodiment, the first polypeptide and the second polypeptide are adsorbed to aluminum.

In one embodiment, the composition includes a MenA$_{AH}$-TT conjugate having a mean TT/polysaccharide ratio 3; a MenC$_{AH}$-TT conjugate having a mean TT/polysaccharide ratio 3; a MenW-TT conjugate having a mean TT/polysaccharide ratio 1.5; and a MenY-TT conjugate having a mean TT/polysaccharide ratio 1.3. In a preferred embodiment, the composition includes a MenA$_{AH}$-TT conjugate having 5 mcg MenA polysaccharide and ~15 mcg TT; a MenC$_{AH}$-TT conjugate having 5 mcg MenC polysaccharide and ~15 mcg TT; a MenW-TT conjugate having 5 mcg MenW polysaccharide and ~7.5 mcg TT; and a MenY-TT conjugate having 5 mcg MenY polysaccharide and ~6.5 mcg TT. The composition may further include Tris-HCl, sucrose, and sodium chloride.

In another embodiment, the composition includes a MenA$_{AH}$-TT conjugate; MenC$_{AH}$-TT conjugate; MenW-TT conjugate; and MenY-TT conjugate, which includes MenA polysaccharide; MenC polysaccharide; MenW polysaccharide; and MenY polysaccharide and TT carrier protein. The composition may further include sucrose and Trometanol. For example, in one embodiment, the composition includes 10 µg/mL MenA polysaccharide; 10 µg/mL MenC polysaccharide; 10 µg/mL MenW polysaccharide; and 10 µg/mL MenY polysaccharide; 88 µg/mL TT carrier protein; 164 mM sucrose; and 1.6 mM Trometanol.

In one embodiment, the composition has a total volume of about 0.5 ml. In one embodiment, a first dose of the composition has a total volume of about 0.5 ml. A "first dose" refers to the dose of the composition that is administered on Day 0. A "second dose" or "third dose" refers to the dose of the composition that is administered subsequently to the first dose, which may or may not be the same amount as the first dose.

In one aspect, the disclosure relates to a liquid immunogenic composition resulting from the lyophilized MenACWY-TT composition having been reconstituted with the liquid MnB bivalent rLP2086 composition. Reconstitution refers to restoring a dry lyophilized composition to a liquid form by the addition of a liquid diluent. In one preferred embodiment, the liquid MnB bivalent rLP2086 composition is not concomitantly administered, is not coadministered with, and is not simultaneously administered with the lyophilized MenACWY-TT composition, wherein the lyophilized MenACWY-TT composition has been reconstituted with a liquid composition that is not the liquid MnB bivalent rLP2086 composition. For example, in one preferred embodiment, the lyophilized MenACWY-TT composition is not reconstituted with an aqueous diluent consisting of sodium chloride and water and is not subsequently concomitantly administered, is not coadministered with, and is not simultaneously administered with the liquid MnB bivalent rLP2086 composition.

Rather, in a preferred embodiment, the lyophilized MenACWY-TT composition is administered with the MnB bivalent rLP2086 composition in one, i.e., a single, administration to the human. The resulting single administration (e.g., the MenABCWY composition) may result from the MnB bivalent rLP2086 composition, from a first container, being mixed with the lyophilized MenACWY-TT composition, from a second container. Alternatively, single administration of the MenABCWY composition may result from one (single) container that includes the MnB bivalent rLP2086 composition and the lyophilized MenACWY-TT composition. Delivery devices for vaccine or immunogenic compositions are known in the art. In one embodiment, the MenABCWY composition is administered concomitantly with any one of ibuprofen, paracetamol, and amoxicillin.

The composition is immunogenic after administration of a first dose to a human. In one embodiment, the first dose is about 0.5 ml in total volume.

The composition induces a bactericidal titer of serum immunoglobulin that is at least greater than 1-fold higher, preferably at least 2-fold higher, in the human after receiving the first dose than a bactericidal titer of serum immunoglobulin in the human prior to receiving the first dose, when measured under identical conditions in a serum bactericidal assay using human complement (hSBA).

The bactericidal titer or bactericidal immune response is against *N. meningitidis* serogroup B. In a preferred embodiment, the bactericidal titer or bactericidal immune response is against a *N. meningitidis* serogroup B fHBP subfamily A strain and against a *N. meningitidis* serogroup B fHBP subfamily B strain. Most preferably, the bactericidal titer or bactericidal immune response is at least against *N. meningitidis* serogroup B, fHBP subfamily B, B01 strain.

In one embodiment, the composition induces a bactericidal titer of serum immunoglobulin that is at least greater than 1-fold, such as, for example, at least 1.01-fold, 1.1-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, or 16-fold higher in the human after receiving a dose of the composition than a bactericidal titer of serum immunoglobulin in the human prior to receiving said dose, when measured under identical conditions in a serum bactericidal assay using human complement.

In one embodiment, the composition is an immunogenic composition. In one embodiment, the composition is an immunogenic composition for a human. In another embodiment, the composition is a vaccine. A "vaccine" refers to a composition that includes an antigen, which contains at least one epitope that induces an immune response that is specific for that antigen. The vaccine may be administered directly into the subject by subcutaneous, oral, oronasal, or intranasal routes of administration. Preferably, the vaccine is administered intramuscularly. In one embodiment, the composition is a human vaccine. In one embodiment, the composition is an immunogenic composition against *N. meningitidis*.

In one embodiment, the composition is a liquid composition. In a preferred embodiment, the composition is a liquid suspension composition. In another preferred embodiment, the composition is not lyophilized.

Stability

The terms "stable" and "stability" refer the ability of an antigen to remain immunogenic over a period of time. Stability may be measured in potency over time. The terms "stable" and "stability" further refer to the physical, chemical, and conformational stability of the immunogenic composition. Instability of a protein composition may be caused by chemical degradation or aggregation of the protein molecules to form higher order polymers, by dissociation of the heterodimers into monomers, deglycosylation, modification of glycosylation, or any other structural modification that reduces at least one biological activity of the protein composition included in the present disclosure. Stability may be assessed by methods well-known in the art, including measurement of a sample's light scattering, apparent attenuation of light (absorbance, or optical density), size (e.g. by size exclusion chromatography), in vitro or in vivo biological activity and/or properties by differential scanning calorimetry (DSC). Other methods for assessing stability are known in the art and can also be used according to the present disclosure.

In some embodiments, an antigen in a stable formulation of the disclosure may maintain at least 50%, 60%, 70%, 75%, 80%, 85%, 90%, 95%, 96%, 97%, 98%, 99% or 100% potency, as compared to a reference standard, for at least 1 month, 2 months, 3 months, 4 months, 5 months, 6 months, 9 months, 12 months, 18 months, 24 months, 30 months, 36 months, 42 months, 48 months, 54 months, or 60 months. In some embodiments, an antigen in a stable formulation of the disclosure may maintain at least 50% potency, as compared to a reference standard, for at least 1 year, 2 years, 3 years, 4 years or 5 years. The terms "stable" and "stability" also refer to the ability of an antigen to maintain epitopes or immunoreactivity over a period of time. For example, an antigen in a stable formulation of the disclosure may maintain at least 50%, 60%, 70%, 75%, 80%, 85%, 90%, 95%, 96%, 97%, 98%, 99% or 100% of its epitopes or immunoreactivity, as compared to a reference standard, for at least 1 month, 2 months, 3 months, 4 months, 5 months, 6 months, 9 months, 12 months, 18 months, 24 months, 30 months, 36 months, 42 months, 48 months, 54 months, or 60 months. In some embodiments, stability is measured with respect to an environmental condition. Non-limiting examples of environmental conditions include light, temperature, freeze/thaw cycles, agitation, and pH. One of skill in the art would be able to determine the presence of antigenic epitopes or immunoreactivity using the methods disclosed herein or other methods known in the art. In some embodiments, the stability of an antigen is measured from the date of its formulation. In some embodiments, the stability of an antigen is measured from the date of a change in its storage conditions. Non-limiting examples of changes in storage conditions include changing from frozen to refrigerated, changing from frozen to room temperature, changing from refrigerated to room temperature, changing from refrigerated to frozen, changing from room temperature to frozen, changing from room temperature to refrigerated, changing from light to dark, or introduction of agitation.

In one embodiment, the terms "stable" and "stability" includes the ability of an antigen to be bound to aluminum. For example, a stable formulation of the disclosure includes at least 50%, 60%, 70%, 75%, 80%, 85%, 90%, 95%, 96%, 97%, 98%, 99% or 100% of a protein that is bound to aluminum (e.g., aluminum phosphate) in the formulation, as compared to a reference standard, for at least 1 hour, 6 hours, 12 hours, 18 hours, 24 hours, 1 month, 2 months, 3 months, 4 months, 5 months, 6 months, 9 months, 12 months, 18 months, 24 months, 30 months, 36 months, 42 months, 48 months, 54 months, or 60 months. See, for example Example 13. In a preferred embodiment, at least 90%, more preferably at least 95%, and most preferably at least 99% of the total Subfamily A rLP2086 polypeptide (e.g., a polypeptide that includes the amino acid sequence set forth in SEQ ID NO: 1) is bound to aluminum in the composition. In a preferred embodiment, at least 90%, more preferably at least 95%, and most preferably at least 99% of the total Subfamily B rLP2086 polypeptide (e.g., a polypeptide that includes the amino acid sequence set forth in SEQ ID NO: 2) is bound to aluminum in the composition.

Determination of Aluminum Binding. A composition comprising aluminum and at least one protein antigen was centrifuged such that the aluminum was pelleted. Centrifugation of aluminum absorbed proteins is known in the art. See e.g., Egan et al., Vaccine, Vol. 27(24): 3175-3180 (2009). Aluminum-bound protein was also pelleted, while non-aluminum-bound protein remained in the supernatant. Total protein in the supernatant and pellet were determined by Lowry Assay. The percentage bound protein was calculated by dividing the total protein in the supernatant by the total protein added to the composition and multiplying by 100%. Similarly, the percentage unbound protein was calculated by dividing the total protein in the supernatant by the total protein added to the composition and multiplying by 100%. For compositions comprising both Subfamily A and Subfamily B antigens, the individual Subfamily A and B protein concentrations in the supernatant were determined by ion-exchange chromatography. The separation and elution of Subfamily A and B proteins was carried out using a strong anion column and a high salt concentration eluent. Both Subfamily A and B proteins were detected and quantified using a fluorescence detector set at Excitation=280 run and Emission=310 run. Subfamily A and Subfamily B proteins elute at distinct retention times and were quantified using a standard curve generated against a rLP2086 protein reference material. The percentage unbound protein was calculated by dividing the total protein in the supernatant by the total protein added to the composition and multiplying by 100%. The percentage bound protein was calculated by subtracting the percentage unbound protein from 100%.

Polysorbate-80

Polysorbate 80 (PS-80) is a non-ionic surfactant. Accelerated stability studies using an in vitro monoclonal antibody based potency assay demonstrated instability of the subfamily B protein at higher molar ratios of PS-80 to MnB rLP2086 protein in the final formulation. Further experiments with varying ratios of PS-80 have demonstrated that the optimal molar ratio of PS-80 to MnB rLP2086 protein is approximately 2.8±1.4 to retain potency.

The concentration of PS-80 in the composition is dependent on a molar ratio of PS-80 to the polypeptide. In one embodiment, the composition includes a 2.8±1.4 molar ratio of PS-80 to the first polypeptide and to the second polypeptide. In one embodiment, the composition includes a 2.8±1.1 molar ratio of PS-80 to the first polypeptide and to the second polypeptide. In one embodiment, the composition includes at least 1.9, 2.0, 2.1, 2.2, 2.3, 2.4, 2.5, 2.6, 2.7, 2.8, 2.9, 3.0, 3.1, 3.2, or 3.3 molar ratio of PS-80 to polypeptide. In one embodiment, the composition includes at most 4.0, 3.9, 3.8, 3.7, 3.6, 3.5, 3.4, 3.3, 3.2, 3.1, 3.0, or 2.9 molar ratio of PS-80 to polypeptide. Any minimum value may be combined with any maximum value described herein to define a range. Preferably, the composition includes a 2.8 molar ratio of PS-80 to polypeptide.

The PS-80 to polypeptide molar ratio is determined by calculation from the measured concentration of PS-80 and the measured total polypeptide concentration, in which both values are expressed in moles. For example, PS-80 to Protein molar ratio is determined by calculation of the measured concentration of PS-80 (e.g., by reverse phase high pressure liquid chromatography (RP-HPLC)) to the measured total protein concentration (e.g., by ion exchange-high pressure liquid chromatography (IEX-HPLC)) in the final drug substance, where both values are expressed in moles.

A RP-HPLC is used to quantitate the concentration of Polysorbate 80 in vaccine formulations. The concentration of detergent is determined by saponification of the fatty acid moiety; Polysorbate 80 is converted to free oleic acid by alkaline hydrolysis at 40° C. The sample is separated by RP-HPLC using a C18 column and quantitated using a UV detector at a wavelength of 200 nm.

The first and the second polypeptides are resolved by anion-exchange HPLC. rLP2086 (fHBP) Subfamily A and B proteins elute at distinct retention times and are quantitated using a standard curve generated against the respective rLP2086 protein reference material.

The term "molar ratio" and a description of an immunogenic composition including a fHBP and PS-80 is further disclosed in WO2012025873 and US patent publication US 2013/0171194, which are each incorporated by reference in their entirety.

The term "molar ratio" as used herein refers to the ratio of the number of moles of two different elements in a composition. In some embodiments, the molar ratio is the ratio of moles of detergent to moles of polypeptide. In some embodiments, the molar ratio is the ratio of moles of PS-80 to moles of protein. In one embodiment, based on the protein and Polysorbate 80 concentrations, the Molar Ratio may be calculated using the following equation:

$$\text{Molar Ratio} = \frac{\% \, PS-80}{\text{mg/ml protein}} \times 216$$

In one embodiment, the composition includes a molar ratio of PS-80 to MnB rLP2086 protein between 1.4 to 4.2 to retain potency. In one embodiment, the composition includes at least 1.2, 1.3, 1.4, 1.5, 1.6, 1.7, 1.8, 1.9, 2.0, 2.1, 2.2, 2.3, 2.4, 2.5, 2.6, 2.7, or 2.8. In one embodiment, the composition includes at most 4.2, 4.1, 4.0, 3.9, 3.8, 3.7, 3.7, 3.6, 3.5, 3.4, 3.3, 3.2, 3.1, 3.0, 2.9, or 2.8. Any minimum value may be combined with any maximum value described herein to define a range.

In one embodiment, the composition includes about 0.0015, 0.0017, 0.0019, 0.0021, 0.0023, 0.0025, 0.0027, 0.0029, 0.0031, 0.0033, 0.0035, 0.0037, 0.0039, 0.0041, 0.0043, 0.0045, 0.0047, 0.0049, 0.0051 mg/mL PS-80. Preferably, the composition includes about 0.0035 mg/mL PS-80.

In another embodiment, the composition includes at least 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, or 25 µg PS-80. In another embodiment, the composition includes at most 30 µg, 29 µg, 28 µg, 27 µg, 26 µg, 25 µg, 24 µg, 23 µg, 22 µg, 21 µg, 20 µg, 19 µg, or 18 µg PS-80. Any minimum value may be combined with any maximum value described herein to define a range. In a preferred embodiment, the composition includes at least 10 µg and at most 20 µg PS-80. In a most preferred embodiment, the composition includes about 18 µg PS-80.

In another embodiment, the composition includes a PS-80 concentration ranging from 0.0005% to 1%. For example, the PS-80 concentration in the composition may be at least 0.0005%, 0.005%, 0.01%, 0.02%, 0.03%, 0.04%, 0.05%, 0.06%, 0.07%, 0.08%, 0.09%, 0.10%, 0.2%, 0.3%, 0.4%, 0.5%, 0.6%, 0.7%, 0.8%, 0.9%, 1%, or 1.1% PS-80. In one embodiment, the PS-80 concentration in the composition may be at most 2.0%, 1.9%, 1.8%, 1.7%, 1.6%, 1.5%, 1.4%, 1.3%, 1.2%, 1.1%, 1.0%, 0.9%, 0.8%, or 0.7% PS-80. In a preferred embodiment, the composition includes about 0.07% PS-80. Any minimum value may be combined with any maximum value described herein to define a range.

In some embodiments, a composition that includes a combination of the first composition and the second composition may have a different molar ratio of polysorbate-80 in relation to the MnB rLP2086 polypeptides, as compared to the molar ratio of polysorbate-80 in relation to the MnB rLP2086 polypeptides in the first composition. In some embodiments, additional surfactant for the combined composition is not necessary to maintain solubility and stability of the MnB rLP2086 polypeptides in the combined composition. Accordingly, in one embodiment, the kit does not comprise greater than 0.02 mg polysorbate-80.

Aluminum

The composition includes aluminum as aluminum phosphate. $AlPO_4$ is added as a stabilizer to provide enhanced manufacturability and stability. The process for producing an aluminum phosphate is described in US patent publication US 2009/0016946, which is incorporated by reference in its entirety. In one embodiment, the composition does not further include a multivalent cation, other than aluminum. In one embodiment, the composition does not further include $Al(OH)_3$ or $Al(SO_4)_3$.

In one embodiment, the composition includes at least 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, or 250 µg aluminum. In one embodiment, the composition includes at most 500 µg, 490 µg, 480 µg, 470 µg, 460 µg, 450 µg, 440 µg, 430 µg, 420 µg, 410 µg, 400 µg, 390 µg, 380 µg, 370 µg, 360 µg, 350 µg, 340 µg, 330 µg, 320 µg, 310 µg, 300 µg, 290 µg, 280 µg, 270 µg, 260 µg, or 250 µg aluminum. Any minimum value may be combined with any maximum value described herein to define a range. In a most preferred embodiment, the composition includes 250 µg aluminum.

In one embodiment, the composition includes at least 0.005 mg/ml, 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.10 mg/ml, 0.2 mg/ml, 0.3 mg/ml, 0.4 mg/ml, or 0.5 mg/ml aluminum phosphate. In one embodiment, the composition includes at most 2.0 mg/ml, 1.9 mg/ml, 1.8 mg/ml, 1.7 mg/ml, 1.6 mg/ml, 1.5 mg/ml, 1.4 mg/ml, 1.3 mg/ml, 1.2 mg/ml, 1.1 mg/ml, 1.0 mg/ml, 0.9 mg/ml, 0.8 mg/ml, or 0.7 mg/ml PS-80. In a preferred embodiment, the composition includes about 0.07 mg/ml PS-80. Any minimum value may be combined with any maximum value described herein to define a range. In a preferred embodiment, the composition includes 0.5 mg/ml aluminum phosphate. In a most preferred embodiment, the composition includes 0.5 mg aluminum/ml as aluminum phosphate ($AlPO_4$). This concentration maintains binding (at least 90% binding or better) of the subfamily A and B proteins to aluminum.

In some embodiments, the combination of the first composition and the second composition changes the percentage of MnB rLP2086 polypeptides bound to the aluminum, when compared to the percentage of MnB rLP2086 polypeptides bound to the aluminum in the first composition. In some embodiments, the combination of the first and second compositions maintains binding of at least 90% of the total MnB rLP2086 polypeptides to the aluminum. Accordingly, in one embodiment, the percentage of total MnB rLP2086 polypeptides to the aluminum in the combined composition is at least 80%, 81%, 82%, 83%, 84%, 85%, 86%, 87%, 88%, 89%, 90%, 91%, 92%, 93%, 94%, 95%, 96%, 97%, 98%, 99%, or 100%. Preferably, the percentage of total MnB rLP2086 polypeptides to the aluminum in the combined composition is at least 90%, more preferably at least 95%, and most preferably at least 100%.

In another embodiment, the concentration of polypeptides bound to the aluminum in the immunogenic composition is not decreased after 24 hours, as compared to the concentration of polypeptides bound to the aluminum in the liquid composition prior to reconstituting the lyophilized composition. In another embodiment, the concentration of MenA$_{AH}$-TT conjugate in the immunogenic composition is not decreased after 24 hours, as compared to the concentration of the MenA$_{AH}$-TT conjugate in the lyophilized composition. In one embodiment, the concentration is decreased by at most 1%, 2%, 3%, 4%, 5%, 6%, 7%, 8%, 9%, 10%, 11%, 12%, 13%, 14%, 15%, 16%, 17%, 18%, 19%, or 20% after 24 hours, as compared to the respective concentration in the liquid composition prior to reconstitution.

In another embodiment, the concentration of MenC$_{AH}$-TT conjugate in the immunogenic composition is not decreased after 24 hours, as compared to the concentration of the MenC$_{AH}$-TT conjugate in the lyophilized composition. In another embodiment, the concentration of MenW-TT conjugate in the immunogenic composition is not decreased after 24 hours, as compared to the concentration of the MenW-TT conjugate in the lyophilized composition. In another embodiment, the concentration of MenY-TT conjugate in the immunogenic composition is not decreased after 24 hours, as compared to the concentration of the MenY-TT conjugate in the lyophilized composition. In one embodiment, the concentration is decreased by at most 1%, 2%, 3%, 4%, 5%, 6%, 7%, 8%, 9%, 10%, 11%, 12%, 13%, 14%, 15%, 16%, 17%, 18%, 19%, or 20% after 24 hours, as compared to the respective concentration in the lyophilized composition prior to reconstitution.

Excipients

In one embodiment, the composition includes histidine. In one embodiment, the composition includes at least 650 µg, 660 µg, 670 µg, 680 µg, 690 µg, 700 µg, 710 µg, 720 µg, 730 µg, 740 µg, 750 µg, 760 µg, 770 µg, 780 µg, 790 µg, 800 µg, 810 µg, 820 µg, 830 µg, 840 µg, or 850 µg of histidine. In one embodiment, the composition includes at most 1560 µg, 1500 µg, 1400 µg, 1300 µg, 1200 µg, 1100 µg, 1000 µg, 950 µg, 900 µg, 890 µg, 880 µg, 870 µg, 860 µg, 850 µg, 840 µg, 830 µg, 820 µg, 810 µg, 800 µg, 790 µg, or 780 µg of histidine. Any minimum value may be combined with any maximum value described herein to define a range. Preferably, the composition includes 780 µg histidine.

In one embodiment, the composition includes a tris, phosphate, or succinate buffer. In a preferred embodiment, the composition does not include tris buffer. In a preferred, the composition does not include phosphate buffer. In one preferred embodiment, the composition does not include succinate buffer. In a preferred embodiment, the composition includes histidine buffer.

In one embodiment, the composition includes sodium chloride. Sodium chloride concentration in MenABCWY composition may vary between 160.5-161.1 mM.

In one embodiment, the pH of the composition is between 5.5 and 7.5. In a preferred embodiment, the pH of the composition is between 5.8 and 7.0, most preferably pH 5.8 to pH 6.0. In one embodiment, the pH of the composition is at most 6.1. In one embodiment, the pH of the composition is 5.8.

Kits

A further aspect of the disclosure is a kit for administering a dose of a composition for eliciting bactericidal antibodies against *Neisseria meningitidis* in a mammal.

In one aspect, the kit includes a first composition including a first polypeptide as described above and a second polypeptide as described above. In a preferred embodiment, the first polypeptide comprises the amino acid sequence set forth in SEQ ID NO: 1. In another preferred embodiment, the second polypeptide comprises the amino acid sequence set forth in SEQ ID NO: 2. The kit further includes a second composition including a MenA$_{AH}$-TT conjugate, a MenC$_{AH}$-TT conjugate, a MenW-TT conjugate, and a MenY-TT conjugate. In one embodiment, the kit includes at least two containers, wherein a first container includes the first composition, a second container includes the second composition.

In one embodiment, the kit includes a liquid first composition and a lyophilized second composition. Preferably, the kit includes a liquid MnB bivalent rLP2086 composition and a lyophilized MenACWY-TT composition.

In some embodiments, the composition includes a combination of the first composition and the second composition changes the molar ratio of polysorbate-80 in relation to the MnB rLP2086 polypeptides in the first composition. In some embodiments, additional surfactant for the combined composition is not necessary to maintain solubility and stability of the MnB rLP2086 polypeptides in the combined composition. Accordingly, in one embodiment, the kit does not comprise greater than 0.02 mg polysorbate-80.

In one embodiment of the disclosure, the kit does not further comprise any one of the following commercial immunogenic compositions: MENACTRA®, MENVEO®, ADACEL®, HAVRIX®, GARDASIL®, REPEVAX, or any combination thereof. For example, the kit preferably does not further include a meningococcal A, C, Y and W-135 polysaccharide conjugate (MCV4) composition, wherein the carrier protein is diphtheria toxoid. In one embodiment, the kit does not further include a meningococcal A, C, Y and W-135 polysaccharide conjugate (MCV4) composition, wherein the carrier protein is $CRM_{197}$. In one embodiment, the kit does not further comprise NIMENRIX vaccine, wherein NIMENRIX comprises a diluent consisting of sodium chloride and water.

Bactericidal Activity

Disease incidence of MnB is approximately 1 in 100,000, meaning that extremely large numbers of subjects (400,000 to over 6 million) would be required to support a statistically significant assessment of efficacy. Thus, a serum bactericidal assay using human complement (hSBA), which is a surrogate of protection and vaccine efficacy, is used to assess immunogenicity in clinical trials.

Pfizer has built an extensive MnB strain collection (N=at least 1263) comprising IMD-causing isolates from Years 2000 to 2006. The MnB isolates were systematically collected from the US Centers for Disease Control and Prevention (CDC) and health and reference laboratories from European countries.

In one embodiment, immune response induced by administering the composition to a human is determined using a serum bactericidal assay using human complement (hSBA) against four *N. meningitidis* serogroup B (MnB) strains. The MnB strains used in the hSBA were selected from the strain pool. The strain pool represented a collection of systematically collected clinically relevant *N. meningitidis* strains.

The high proportion of hSBA response to all test strains, especially strains expressing lipoprotein 2086 variants with sequences heterologous to both the first polypeptide and the second polypeptide suggests that the composition is a broadly protective vaccine are sufficient to confer high seroprotection against *N. meningitidis* strains expressing rLP2086 (FHBP) from at least serogroup B, including additional serogroups, such as serogroup X.

Subfamily A Strains

In one embodiment, the hSBA strain is an *N. meningitidis* strain that expresses LP2086 (fHBP) subfamily A protein. In one embodiment, the hSBA strain is an LP2086 (fHBP) subfamily A strain that expresses a lipoprotein 2086 variant that is heterologous to a *N. meningitidis* strain expressing A05. For example, in one embodiment, the hSBA strain is an LP2086 (fHBP) subfamily A strain that expresses a lipoprotein 2086 variant that is heterologous to strain M98250771.

In one embodiment, the hSBA strain is a *N. meningitidis* strain expressing fHBP A10. In one embodiment, the hSBA strain is a *N. meningitidis* strain expressing LP2086 (fHBP) A22. In one embodiment, the hSBA strain is a *N. meningitidis* strain expressing LP2086 (fHBP) A56. In a further embodiment, the hSBA strains are LP2086 (fHBP) A22 and LP2086 (fHBP) A56 strains. In another embodiment, the hSBA strain is a *N. meningitidis* strain expressing LP2086 A04. In one embodiment, the hSBA strain is a *N. meningitidis* strain expressing LP2086 A05. In one embodiment, the hSBA strain is a *N. meningitidis* strain expressing LP2086 A12. In one embodiment, the hSBA strain is a *N. meningitidis* strain expressing LP2086 A22. In one embodiment, the hSBA strain is a *N. meningitidis* strain expressing LP2086 A12. In one embodiment, the hSBA strain is a *N. meningitidis* strain expressing LP2086 A04. In one embodiment, the hSBA strain is a *N. meningitidis* strain expressing LP2086 A19. In one embodiment, the hSBA strain is a *N. meningitidis* strain expressing LP2086 A07. In a further embodiment, the hSBA strain includes any one of an A22-, A12-, A19-, A05-, and A07-expressing strain. In one embodiment, the hSBA strains include any one of an A06-, A15-, and A29-expressing strain.

In one embodiment, the immune response is bactericidal against a *N. meningitidis* serogroup B fHPB subfamily A strain that is heterologous to a *N. meningitidis* strain expressing A05. In one embodiment, the immune response is against *N. meningitidis* serogroup B A22 strain. In one embodiment, the immune response is against *N. meningitidis* serogroup B A56 strain. In one embodiment, the immune response is against *N. meningitidis* serogroup B A06 strain. In one embodiment, the immune response is against *N. meningitidis* serogroup B A15 strain. In one embodiment, the immune response is against *N. meningitidis* serogroup B A29 strain. In one embodiment, the immune response is against *N. meningitidis* serogroup B A62 strain. In one embodiment, the immune response is bactericidal against a *N. meningitidis* serogroup B subfamily A strain that is heterologous to *N. meningitidis* strain M98250771.

In one embodiment, the immune response is bactericidal against a *N. meningitidis* serogroup B subfamily A strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to the first polypeptide. In another embodiment, the immune response is bactericidal against a *N. meningitidis* serogroup B subfamily A strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by *N. meningitidis* strain M98250771. In a preferred embodiment, the immune response is bactericidal against a *N. meningitidis* serogroup B subfamily A strain that expresses a factor H binding protein including an amino acid sequence that has at least 80%, more preferably at least 84%, identity to a factor H binding protein expressed by *N. meningitidis* strain M98250771.

In another embodiment, the immune response is bactericidal against a *N. meningitidis* serogroup B subfamily A strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to the first polypeptide. In another embodiment, the immune response is bactericidal against a *N. meningitidis* serogroup B subfamily A strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by *N. meningitidis* strain M98250771. In a preferred embodiment, the immune response is bactericidal against a *N. meningitidis* serogroup B subfamily A strain that expresses a factor H binding protein including an amino acid sequence that has at most 85%, more preferably at most 99%, identity to a factor H binding protein expressed by *N. meningitidis* strain M98250771. Any minimum value may be combined with any maximum value described herein to define a range.

In one embodiment, the immune response elicited by the composition is bactericidal not only against a *N. meningitidis* serogroup B fHPB subfamily A strain but also a *N. meningitidis* strain expressing an fHBP subfamily A polypeptide, wherein the serogroup is not serogroup B. For example, in one preferred embodiment, the immune response elicited by the composition is bactericidal against a *N. meningitidis* serogroup B subfamily A strain and against a *N. meningitidis* serogroup C strain that expresses an fHBP subfamily A polypeptide heterologous to fHBP A05. For example, in one embodiment, the immune response is against a *N. meningitidis* serogroup C strain expressing fHBP A10. In another embodiment, the immune response is against a *N. meningitidis* serogroup W strain expressing fHBP A19. In one embodiment, the immune response is bactericidal against a *N. meningitidis* strain that expresses an fHBP subfamily A polypeptide, wherein the strain is heterologous to *N. meningitidis* strain M98250771.

Subfamily B Strains

In one embodiment, the hSBA strain is an LP2086 (fHBP) subfamily B strain. In one embodiment, the hSBA strain is an LP2086 (fHBP) subfamily B strain that expresses a lipoprotein 2086 variant that is heterologous to a *N. meningitidis* strain expressing B01. For example, in one embodiment, the hSBA strain is an LP2086 (fHBP) subfamily B strain that expresses a lipoprotein 2086 variant that is heterologous to strain CDC1127. In a preferred embodiment, the hSBA strain is an LP2086 (fHBP) subfamily B strain that expresses a lipoprotein 2086 variant that is heterologous to strain CDC1573.

In one embodiment, the immune response is bactericidal against a *N. meningitidis* serogroup B fHPB subfamily B strain that is heterologous to a *N. meningitidis* strain expressing B01. In one embodiment, the immune response is against *N. meningitidis* serogroup B B24 strain. In one embodiment, the immune response is against *N. meningitidis* serogroup B B44 strain. In one embodiment, the immune response is against *N. meningitidis* serogroup B B16 strain. In one embodiment, the immune response is against *N. meningitidis* serogroup B B03 strain. In one embodiment, the immune response is against *N. meningitidis* serogroup B B09 strain. In one embodiment, the immune response is against *N. meningitidis* serogroup B B15 strain. In one embodiment, the immune response is against *N. meningitidis* serogroup B B153 strain. In one embodiment, the immune response is bactericidal against a *N. meningitidis* serogroup B subfamily B strain that is heterologous to *N. meningitidis* strain CDC1573.

In one embodiment, the immune response is bactericidal against a *N. meningitidis* serogroup B subfamily B strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to the second polypeptide. In another embodiment, the immune response is bactericidal against a *N. meningitidis* serogroup B subfamily B strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by *N. meningitidis* strain CDC1573. In a preferred embodiment, the immune response is bactericidal against a *N. meningitidis* serogroup B subfamily B strain that expresses a factor H binding protein including an amino acid sequence that has at least 80% identity, more preferably at least 87% identity, to a factor H binding protein expressed by *N. meningitidis* strain CDC1573. In another preferred embodiment, the immune response is bactericidal against a *N. meningitidis* serogroup B subfamily B strain that expresses a factor H binding protein including an amino acid sequence that has 100% identity to a factor H binding protein expressed by *N. meningitidis* strain CDC1573.

In another embodiment, the immune response is bactericidal against a *N. meningitidis* serogroup B subfamily B strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to the second polypeptide. In another embodiment, the immune response is bactericidal against a *N. meningitidis* serogroup B subfamily B strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by *N. meningitidis* strain CDC1573. In a preferred embodiment, the immune response is bactericidal against a *N. meningitidis* serogroup B subfamily B strain that expresses a factor H binding protein including an amino acid sequence that has at most 88% identity, more preferably at least 99% identity, to a factor H binding protein expressed by *N. meningitidis* strain CDC1573. Any minimum value may be combined with any maximum value described herein to define a range.

In one embodiment, the hSBA strain is an LP2086 (fHBP) B24 strain. In another embodiment, the hSBA strains is an LP2086 (fHBP) B44 strain. In a further embodiment, the hSBA strains includes LP2086 (fHBP) B24 and LP2086 (fHBP) B44 strains. In one embodiment, the hSBA strains includes LP2086 (fHBP) A22, LP2086 (fHBP) A56, LP2086 (fHBP) B24, and LP2086 (fHBP) B44 strains. In one embodiment, the hSBA strain includes B15. In one embodiment, the hSBA strain includes B153. In another embodiment, the hSBA strain is an LP2086 B16 strain. In one embodiment, the hSBA strain is an LP2086 B03 strain. In one embodiment, the hSBA strain is an LP2086 B09 strain. In a further embodiment, the hSBA strains include B24, B16, B44, B03, and B09, or any combination thereof. In another embodiment, the hSBA strains include B24, B16, B44, A22, B03, B09, A12, A19, A05, and A07, or any combination thereof. In another embodiment, the hSBA strains include A06, A07, A12, A15, A19, A29, B03, B09, B15, and B16, or any combination thereof.

In one embodiment, the method induces an immune response against a *N. meningitidis* serogroup B fHPB subfamily A strain and against a *N. meningitidis* serogroup B fHPB subfamily B strain. Preferably, the immune response is bactericidal against a *N. meningitidis* serogroup B fHPB subfamily A strain and against a *N. meningitidis* serogroup B fHPB subfamily B strain.

In one embodiment, the immune response elicited by the composition is bactericidal not only against a *N. meningitidis* serogroup B fHPB subfamily B strain but also a *N. meningitidis* strain expressing an fHBP subfamily B polypeptide, wherein the serogroup is not serogroup B. For example, in one preferred embodiment, the immune response elicited by the composition is bactericidal against a *N. meningitidis* serogroup B subfamily B strain and against a *N. meningitidis* serogroup Y strain that expresses an fHBP subfamily B polypeptide heterologous to fHBP B01. For example, in one embodiment, the immune response is against a *N. meningitidis* serogroup A strain expressing fHBP B16. In another embodiment, the immune response is against a *N. meningitidis* serogroup Y strain expressing fHBP B47. In another embodiment, the immune response is against a *N. meningitidis* serogroup X strain expressing fHBP B49. In one embodiment, the immune response is bactericidal against a *N. meningitidis* strain that expresses an fHBP subfamily B polypeptide, wherein the strain is heterologous to *N. meningitidis* serogroup B strain CDC1573.

In one aspect, the invention relates to uses of a composition including a first lipidated polypeptide variant of a *Neisseria meningitidis* serogroup B factor H binding protein (fHBP) and a second lipidated polypeptide variant of a *Neisseria meningitidis* serogroup B fHBP. In one embodiment, the composition induces a bactericidal immune response against at least one *N. meningitidis* serogroup B strain expressing a polypeptide selected from the group consisting of B A02, A28, A42, A63, A76, B05, B07, B08, B13, B52 and B107. For example, in one aspect, the invention relates to uses of a composition including a first lipidated polypeptide including the amino acid sequence set forth in SEQ ID NO: 1 and a second lipidated polypeptide including the amino acid sequence set forth in SEQ ID NO: 2.

In one embodiment, the hSBA strain is a *N. meningitidis* strain expressing fHBP B05. In one embodiment, the hSBA strain is a *N. meningitidis* strain expressing LP2086 (fHBP) B07. In one embodiment, the hSBA strain is a *N. meningitidis* strain expressing LP2086 (fHBP) B08. In another embodiment, the hSBA strain is a *N. meningitidis* strain expressing LP2086 B13. In one embodiment, the hSBA strain is a *N. meningitidis* strain expressing LP2086 B52. In one embodiment, the hSBA strain is a *N. meningitidis* strain expressing LP2086 B107. In a further embodiment, the hSBA strain includes any one strain selected from the group consisting of B05, B07, B08, B13, B52 and B107. In a further embodiment, the hSBA strain includes any one strain selected from the group consisting of B05, B07, B08, B13, B52, B107, B01, B24, B44, B16, B03, B09, B15, and B153.

In one embodiment, the immune response is bactericidal against a *N. meningitidis* serogroup B subfamily B strain that is heterologous to a *N. meningitidis* strain expressing B01. In one embodiment, the immune response is against *N. meningitidis* serogroup B B05 strain. In one embodiment, the immune response is against *N. meningitidis* serogroup B B07 strain. In one embodiment, the immune response is against *N. meningitidis* serogroup B B08 strain. In one embodiment, the immune response is against *N. meningitidis* serogroup B B13 strain. In one embodiment, the immune response is against *N. meningitidis* serogroup B B52 strain. In one embodiment, the immune response is against *N. meningitidis* serogroup B B107 strain. In one embodiment, the immune response is against *N. meningitidis* serogroup B B24 strain. In one embodiment, the immune response is against *N. meningitidis* serogroup B B44 strain. In one embodiment, the immune response is against *N. meningitidis* serogroup B B16 strain. In one embodiment, the immune response is against *N. meningitidis* serogroup B B03 strain. In one embodiment, the immune response is against *N. meningitidis* serogroup B B09 strain. In one embodiment, the immune response is against *N. meningitidis* serogroup B B15 strain. In one embodiment, the immune response is against *N. meningitidis* serogroup B B153 strain. In one embodiment, the immune response is bactericidal against a *N. meningitidis* serogroup B subfamily B strain that is heterologous to *N. meningitidis* strain CDC1573.

In one embodiment, the immune response is against a *N. meningitidis* serogroup B strain selected from the group consisting of A02, A28, A42, A63, and A76. In one embodiment, the immune response is against a *N. meningitidis* serogroup B strain selected from the group consisting of B05, B07, B08, B13, B52, B107, B01, B24, B44, B16, B03, B09, B15, and B153, and any combination thereof.

In one embodiment, the hSBA strains include B05, B07, B08, B13, B52 and B107, and any combination thereof. In a further embodiment, the hSBA strains include B05, B07, B08, B13, B52 and B107, B24, B16, B44, B03, and B09, and any combination thereof. In one embodiment, the hSBA strains include A02, A28, A42, A63, A76, B05, B07, B08, B13, B52 and B107, and any combination thereof. In another embodiment, the hSBA strains further include A06, A07, A12, A15, A19, A29, B03, B09, B15, and B16, or any combination thereof. In another embodiment, the hSBA strains include A02, A28, A42, A63, A76, B05, B07, B08, B13, B52 and B107, A06, A07, A12, A15, A19, A29, B03, B09, B15, and B16, and any combination thereof.

In one embodiment, the method induces an immune response against a *N. meningitidis* serogroup B subfamily A strain and against a *N. meningitidis* serogroup B subfamily B strain. Preferably, the immune response is bactericidal against a *N. meningitidis* serogroup B subfamily A strain and against a *N. meningitidis* serogroup B subfamily B strain. In one embodiment, the method induces an immune response against a *N. meningitidis* serogroup B strain selected from the group consisting of A02, A28, A42, A63, A76, B05, B07, B08, B13, B52 and B107, and any combination thereof. In one embodiment, the method induces an immune response against a *N. meningitidis* serogroup B strain selected from the group consisting of A02, A28, A42, A63, A76, B05, B07, B08, B13, B52 and B107, A06, A07, A12, A15, A19, A29, B03, B09, B15, and B16, and any combination thereof.

Titers

In one embodiment, the composition induces an increase in bactericidal titer in the human, as compared to the bactericidal titer in the human prior to administration of a dose of the composition, when measured under identical conditions in an hSBA. In one embodiment, the increase in bactericidal titer is compared to the bactericidal titer in the human before administration of the first dose of the composition, as compared to the bactericidal titer in the human prior to administration of the first dose of the composition, when measured under identical conditions in an hSBA. In one embodiment, the increase in titer is observed after a second dose of the composition, as compared to the bactericidal titer in the human prior to administration of the second dose of the composition, when measured under identical conditions in an hSBA. In another embodiment, the increase in bactericidal titer is observed after a third dose of the composition, as compared to the bactericidal titer in the human prior to administration of the third dose of the composition, when measured under identical conditions in an hSBA.

In one embodiment, the composition induces a bactericidal titer in the human after administration of a dose, wherein the bactericidal titer is at least greater than 1-fold higher than the bactericidal titer in the human prior to administration of the dose, when measured under identical conditions in an hSBA. For example, the bactericidal titer may be at least 1.01-fold, 1.1-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, or 16-fold higher in the human after receiving a dose of the composition, as compared to the bactericidal titer in the human prior to administration of the dose, when measured under identical conditions in an hSBA.

In one embodiment, a "responder" refers to a human, wherein the composition induces a bactericidal titer in the human after administration of a dose, wherein the bactericidal titer is at least greater than 1-fold higher than the bactericidal titer in the human prior to administration of the dose. In a preferred embodiment, the responder achieves at least a 4-fold rise in hSBA titer, as compared to a bactericidal titer in the human prior to administration of the dose. Such a responder may be referred to as having a protective titer. In some embodiments, a protective titer is one that is greater than 1:4.

In one embodiment, the hSBA titer is the reciprocal of the highest dilution of a serum sample that produces a measurable effect. For example, in one embodiment, the hSBA titer is the reciprocal of the highest 2-fold dilution of a test serum that results in at least a 50% reduction of MnB bacteria (50% bacterial survival) compared to the T30 CFU value (i.e., the number of bacteria surviving after incubation in assay wells containing all assay components except test serum; 100% bacterial survival).

In one embodiment, the composition induces a bactericidal titer in the human after receiving the first dose that is at least 2-fold higher than the bactericidal titer in the human prior to receiving the first dose (e.g., higher than the bactericidal titer in the human in the absence of the first dose), when measured under identical conditions in the hSBA. In one embodiment, the composition induces a bactericidal titer in the human that is at least 4-fold higher than the bactericidal titer in the human prior to receiving the first dose, when measured under identical conditions in a human serum bactericidal assay that utilizes human complement (hSBA). In one embodiment, the composition induces a bactericidal titer in the human that is at least 8-fold higher than the bactericidal titer in the human prior to receiving the first dose, when measured under identical conditions in a human serum bactericidal assay that utilizes human complement (hSBA).

In a preferred embodiment, the human serum complement is derived from a human having low intrinsic bactericidal activity for a given hSBA test strain. Low intrinsic bactericidal activity refers to, for example, a bactericidal titer that is at least less than a 1:4 dilution against the given hSBA test strain. In one embodiment, the human complement is derived from a human having an hSBA titer that is at least less than 1:4, such as a 1:2 dilution, against the given hSBA test strain, wherein the composition was not administered to the human.

A human may exhibit an hSBA titer of less than 1:4 prior to administration of a composition, such as the bivalent rLP2086 composition, or a human may exhibit an hSBA titer of 1:4 prior to administration of the composition. Accordingly, in preferred embodiments and examples, administration of at least one dose of the composition to the human results in an hSBA titer that is at least 4-fold greater than the titer in the human prior to the administration. In some embodiments, administration of at least one dose of the composition to the human results in an hSBA titer that is at least greater than 1:4, such as, for example, an hSBA titer of ≥1:8, an hSBA titer of ≥16, and an hSBA titer of ≥1:32. The respective Examples described herein include assessments of the proportion of human subjects having an hSBA titer ≥1:8 and/or ≥1:16, wherein the bivalent rLP2086 composition was administered to the human. In some embodiments, a 4-fold rise in titer in the human after administration of the composition as compared to before administration of the composition show that protection is associated with the composition. In some embodiments, such preferred assessments of hSBA titers greater than 1:4 show that the protection, i.e., the bactericidal immune response induced in the human, is associated with the composition.

In one embodiment, the human has an hSBA titer equal to or greater than the hSBA's lower limit of quantitation (LLOQ) after administration of the first dose of the composition. In another embodiment, the human has an hSBA titer equal to or greater than the hSBA's LLOQ after administration of the second dose of the composition. In another embodiment, the human has an hSBA titer equal to or greater than the hSBA's LLOQ after administration of the third dose of the composition.

Methods and Administration

In one aspect, the disclosure relates to a method of inducing an immune response against *N. meningitidis* in a human. In another aspect, the disclosure relates to a method of vaccinating a human.

In some embodiments, the method includes administering to the human the composition, wherein the composition induces an immune response to each of *N. meningitidis* serogroups A, C, W-135 and Y capsular polysaccharides, wherein the immune response includes a titer of serum bactericidal antibodies, and wherein the titer is higher than that induced by a licensed vaccine against *N. meningitidis* serogroups A, C, W-135 and Y meningococcal capsular polysaccharides. In some embodiments, the licensed vaccine against *N. meningitidis* serogroups A, C, W-135 and Y meningococcal capsular polysaccharides is MENVEO.

In some embodiments, the method includes administering to the human the composition, wherein the composition induces an immune response to *N. meningitidis* serogroup B, wherein the immune response includes a titer of serum bactericidal antibodies that is higher than a titer of serum bactericidal antibodies induced by a licensed vaccine against *N. meningitidis* serogroup B. In some embodiments, the licensed vaccine vaccine against *N. meningitidis* serogroup B is TRUMENBA.

In some embodiments, the method includes administering to the human the composition, wherein the composition induces an immune response to each of *N. meningitidis* serogroups A, C, W-135 and Y capsular polysaccharide and *N. meningitidis* serogroup B, wherein the immune response includes a titer of serum bactericidal antibodies to each of *N. meningitidis* serogroups A, C, W-135 and Y capsular polysaccharide that is higher than a titer of serum bactericidal antibodies induced by a licensed vaccine against *N. meningitidis* serogroups A, C, W-135 and Y capsular polysaccharide, and wherein the immune response includes a titer of serum bactericidal antibodies to *N. meningitidis* serogroup B that is higher than a titer of serum bactericidal antibodies induced by a licensed vaccine against *N. meningitidis* serogroup B. In some embodiments, the licensed vaccine against *N. meningitidis* serogroups A, C, W-135 and Y meningococcal capsular polysaccharides is MENVEO. In some embodiments, the licensed vaccine vaccine against *N. meningitidis* serogroup B is TRUMENBA.

The disclosure relates to a method for eliciting an immune response in a human of any age. In some embodiments, the human is aged at least 4 weeks, 5 weeks, 6 weeks, 7 weeks, 8 weeks, 9 weeks, 10 weeks, 11 weeks, or 12 weeks old. For example, in a preferred embodiment, the human is aged at least 6 weeks. As is known in the art, a Meningococcal Group A, C, W-135, and Y Conjugate Vaccine, such as NIMENRIX®, is suitable for infants as early as six weeks of age, and can be administered to any human aged six weeks and above. In some embodiments, the human is aged at least 6 months, 7 months, 8 months, 9 months, 10 months, 11 months, or 12 months. For example, in a preferred embodiment, the human is aged at least 12 months. In one embodiment, the human is aged between 12 and 18 months. In another aspect, the disclosure relates to a method for eliciting an immune response in a patient aged at least 18 months. In one embodiment, the human is aged between 18 and 24 months. In yet another aspect, the disclosure relates to a method for eliciting an immune response in a patient aged at least 24 months. In one embodiment, the human is aged between 24 months and 10 years. In another aspect, the disclosure relates to a method for eliciting an immune response in a patient aged 10 years and above.

In some embodiments, the human is aged between 10 years and 25 years. In some embodiments, the human is aged between 10 to 26 years old. In some embodiments, the human is aged between 12 to <18 Months. In some embodiments, the human is aged between 18 to <24 Months. In some embodiments, the human is aged between 18 to <24 Months. In some embodiments, the human is aged between ≥24 Months to <10 Years.

In some embodiments, the human is at least 16 years old. In such embodiments, the method includes administering one dose to the human, preferably at most one dose to the human aged at least 16 years old. In some embodiments, the human is at most 17 years of age.

In some embodiments, the human is aged between 10 to 12 years old. In such embodiments, the method includes administering at least one dose to the human. In a preferred embodiment, a second dose is administered to the human about 6 months after the first dose. In a preferred embodiment, the method includes administering a first dose and a second dose of the composition to the human aged between 10 to 12 years old, and a third dose of the composition is administered to the human at least four years after the first dose.

In some embodiments, the method includes administering at least two doses to the human. In a preferred embodiment, the two doses are at least about 6 months apart. In a preferred embodiment, the method includes administering a first dose and a second dose of the composition to the human aged between 10 to 12 years old, and a third dose of the composition is administered to the human at least four years after the first dose.

In some embodiments, the method includes administering a first dose of the composition to the human at about 11 years old and administering at least two doses of the composition to the human at least four years after the first dose. In some embodiments, the method includes administering the second and subsequent doses of the composition about five years after the first dose.

In some embodiments, the human is seronegative against *N. meningitidis* serogroup A. In some embodiments, the human is seronegative against *N. meningitidis* serogroup C. In some embodiments, the human is seronegative against *N. meningitidis* serogroup W. In some embodiments, the human is seronegative against *N. meningitidis* serogroup Y. In some embodiments, the human is seronegative against *N. meningitidis* serogroup A, C, W-135 and Y capsular polysaccharides.

In some embodiments, the human is seropositive against *N. meningitidis* serogroup A. In some embodiments, the human is seropositive against *N. meningitidis* serogroup C. In some embodiments, the human is seropositive against *N. meningitidis* serogroup W. In some embodiments, the human is seropositive against *N. meningitidis* serogroup Y. In some embodiments, the human is seropositive against *N. meningitidis* serogroup A, C, W-135 and Y capsular polysaccharides.

In one embodiment, the method includes administering to the human at least one dose of the composition described above. In a preferred embodiment, the method includes administering to the human at most one dose of the composition described above. In another embodiment, the method includes administering to the human at least a first dose and a second dose of the composition described above.

In one embodiment, the second dose is administered at least 20, 30, 50, 60, 100, 120, 160, 170, or 180 days after the first dose, and at most 250, 210, 200, or 190 days after the first dose. Any minimum value may be combined with any maximum value described herein to define a range.

In another embodiment, the second dose is administered about 30 days after the first dose. In another embodiment, the second dose is administered about 60 days after the first dose, such as, for example, in a 0, 2 month immunization schedule. In another embodiment, the second dose is administered about 180 days after the first dose, such as, for example, in a 0, 6 month immunization schedule. In yet another embodiment, the second dose is administered about 120 days after the first dose, such as, for example, in a 2, 6 month immunization schedule.

In one embodiment, the method includes administering to the human two doses of the composition and at most two doses. In one embodiment, the two doses are administered within a period of about 6 months after the first dose. In one embodiment, the method does not include further administration of a booster to the human. A "booster" as used herein refers to an additional administration of the composition to the human. Administering to the human at most two doses of the composition may be advantageous. Such advantages include, for example, facilitating a human to comply with a complete administration schedule and facilitating cost-effectiveness of the schedule.

In one embodiment, the first dose and the second dose are administered to the human over a period of about 25, 30, 40, 50, 60, 70, 80, 90, 100, 110, 120, 130, 140, 150, 160, 170, 180, 190, or 200 days, and most 400, 390, 380, 370, 365, 350, 340, 330, 320, 310, 300, 290, 280, 270, 260, 250, 240, 230, 220, 210, or 200 days after the first dose. Any minimum value may be combined with any maximum value described herein to define a range. Preferably, the first and second doses will be administered at least 4 weeks apart e.g. ≥8 weeks apart, ≥2 months apart, ≥3 months apart, ≥6 months apart, etc.

In one embodiment, the first dose and the second dose are administered to the human over a period of about 30 days. In another embodiment, the first dose and the second dose are administered to the human over a period of about 60 days. In another embodiment, the first dose and the second dose are administered to the human over a period of about 180 days.

Conveniently, the first dose can be administered at substantially the same time as (e.g. during the same medical consultation or visit to a healthcare professional or within 24 hours of the first dose of the meningococcal vaccine) another vaccine e.g. at substantially the same time as a hepatitis B virus vaccine, a diphtheria vaccine, a tetanus vaccine, a pertussis vaccine (either cellular or, preferably, acellular), a *Haemophilus influenzae* type b vaccine, a *Streptococcus pneumoniae* vaccine, and/or a polio vaccine (preferably in inactivated poliovirus vaccine). Each of these optionally co-administered vaccines may be a monovalent vaccine or may be part of a combination vaccine (e.g. as part of a DTP vaccine).

Conveniently, the second dose can be administered at substantially the same time as (e.g. during the same medical consultation or visit to a healthcare professional or within 24 hours of the second dose of the meningococcal vaccine) another vaccine e.g. at substantially the same time as a hepatitis B virus vaccine, a diphtheria vaccine, a tetanus vaccine, a pertussis vaccine (either cellular or acellular), a *Haemophilus influenzae* type b vaccine, a *Streptococcus pneumoniae* vaccine, a polio vaccine (preferably in inactivated poliovirus vaccine), an influenza vaccine, a chickenpox vaccine, a measles vaccine, a mumps vaccine, and/or a rubella vaccine. Each of these optionally co-administered vaccines may be a monovalent vaccine or may be part of a combination vaccine (e.g. as part of an MMR vaccine).

Conveniently, the third dose can be administered at substantially the same time as (e.g. during the same medical consultation or visit to a healthcare professional or within 24 hours of the third dose of the meningococcal vaccine) another vaccine e.g. at substantially the same time as a hepatitis B virus vaccine, a diphtheria vaccine, a tetanus vaccine, a pertussis vaccine (either cellular or acellular), a Haemophilus influenzae type b vaccine, a *Streptococcus pneumoniae* vaccine, a polio vaccine (preferably in inactivated poliovirus vaccine), an influenza vaccine, a chickenpox vaccine, a measles vaccine, a mumps vaccine, and/or a rubella vaccine. Each of these optionally co-administered vaccines may be a monovalent vaccine or may be part of a combination vaccine (e.g. as part of an MMR vaccine).

In one embodiment, a three-dose schedule of the composition induces a bactericidal titer against multiple strains expressing LP2086 (fHBP) heterologous to the first and/or second polypeptide in a greater percentage of humans than a two-dose schedule.

In one embodiment, the method includes administering to the human three doses of the composition. In another embodiment, the method includes administering at most three doses of the composition. In one embodiment, the three doses are administered within a period of about 6 months after the first dose. In one embodiment, the method includes an administration of a booster dose to the human after the third dose. In another embodiment, the method does not include administration of a booster dose to the human after the third dose. In another embodiment, the method does not further include administering a fourth or booster dose of the composition to the human. In a further embodiment, at most three doses within a period of about 6 months are administered to the human.

In an exemplary embodiment, the second dose is administered about 30 days after the first dose, and the third dose is administered about 150 days after the second dose, such as, for example, in a 0, 1, 6 month immunization schedule. In another exemplary embodiment, the second dose is administered about 60 days after the first dose, and the third dose is administered about 120 days after the second dose, such as, for example, in a 0, 2, 6 month immunization schedule.

In one embodiment, the first dose, second dose, and third dose are administered to the human over a period of about 150, 160, 170, or 180 days, and at most 240, 210 200, or 190 days. Any minimum value may be combined with any maximum value described herein to define a range. Preferably, the first dose, second dose, and third dose is administered to the human over a period of about 180 days or 6 months. For example, the second dose may be administered to the human about 60 days after the first dose, and the third dose may be administered to the human about 120 days after the second dose. Accordingly, an exemplary schedule of administration includes administering a dose to the human at about months 0, 2, and 6.

As described above, multiple doses of the immunogenic composition may be administered to the human, and the number of days between each dose may vary. An advantage of the method includes, for example, flexibility for a human to comply with the administration schedules.

In one embodiment, the method includes administering to the human at most three doses of the identical immunogenic composition. For example, in a preferred embodiment, the method does not include administering to the human a first dose of a first composition, administering to the human a second dose of a second composition, and administering to the human a third dose of a third composition, wherein the first, second, and third compositions are not identical. In another embodiment, the method includes administering to the human at most four doses of the identical immunogenic composition.

EXAMPLES

The following Examples illustrate embodiments of the disclosure. Unless noted otherwise herein, reference is made in the following Examples to a MnB bivalent rLP2086 composition, at the 120-μg bivalent rLP2086 dose level, which is a preferred exemplary embodiment of a composition including: 60 μg of a first lipidated polypeptide including the amino acid sequence set forth in SEQ ID NO: 1 per 0.5 mL dose, 60 μg of a second lipidated polypeptide including the amino acid sequence set forth in SEQ ID NO: 2 per 0.5 mL dose, 2.8 molar ratio polysorbate-80 to the first polypeptide, 2.8 molar ratio polysorbate-80 to the second polypeptide, 0.5 mg $Al^{3+}$/ml of the composition, 10 mM histidine, and 150 mM sodium chloride.

More specifically, the investigational bivalent recombinant rLP2086 vaccine at the 120-μg bivalent rLP2086 dose level includes (a) 60 μg of a first lipidated polypeptide including the amino acid sequence set forth in SEQ ID NO: 1; (b) 60 μg of a second lipidated polypeptide including the amino acid sequence set forth in SEQ ID NO: 2; (c) 18 μg polysorbate-80; (d) 250 μg aluminum; (e) 780 μg histidine, and (f) 4380 μg sodium chloride. Each dose is 0.5 mL.

Unless noted otherwise herein, reference is made in the following Examples to a MenACWY-TT composition, which is a preferred exemplary embodiment of a tetravalent meningococcal polysaccharide conjugated composition that includes *Neisseria meningitidis* capsular polysaccharides A, C, W-135 and Y each coupled to tetanus toxoid as a carrier protein. The *Neisseria meningitidis* serogroups A and C polysaccharides are conjugated with an adipic dihydrazide (AH) spacer and indirectly conjugated to the tetanus toxoid whereas the W-135 and Y polysaccharides are conjugated directly to tetanus toxoid. The composition does not contain any preservatives or adjuvants.

More specifically, the lyophilized MenACWY-TT composition described in the examples below includes 5 micrograms of *Neisseria meningitidis* serogroup A polysaccharide conjugated to tetanus toxoid carrier protein; 5 micrograms of *Neisseria meningitidis* serogroup C polysaccharide conjugated to tetanus toxoid carrier protein; 5 micrograms of *Neisseria meningitidis* serogroup W-135 polysaccharide conjugated to tetanus toxoid carrier protein; 5 micrograms of *Neisseria meningitidis* serogroup Y polysaccharide conjugated to tetanus toxoid carrier protein; 28 mg sucrose; 97 μg trometamol, per dose (0.5 mL).

Example 1: The MenABCWY Composition

The final MenABCWY composition is prepared by reconstituting the lyophilized MenACWY-TT Drug Product (described in Example 2 below) vial with 0.67 mL of MnB Bivalent rLP2086 Drug Product (described in Example 3 below) in order to withdraw 0.5 mL dose of MenABCWY vaccine for intramuscular injection. All components used in the preparation of the MenABCWY vaccine and their functions are provided in Table 1 below.

TABLE 1

Composition of MenABCWY vaccine

| Ingredients | Amount/dose |
|---|---|
| MnB rLP2086 subfamily A (SEQ ID NO: 1) | 60 mcg |
| MnB rLP2086 subfamily B (SEQ ID NO: 2) | 60 mcg |
| MenA$_{AH}$-TT conjugate | 5 mcg MenA |
| (mean TT/polysaccharide ratio: ~3) | ~7.5 mcg TT |
| MenC$_{AH}$-TT conjugate | 5 mcg MenC |
| (mean TT/polysaccharide ratio: ~3) | ~7.5 mcg TT |
| MenW-TT conjugate | 5 mcg MenW |
| (mean TT/polysaccharide ratio: ~1.5) | ~3.75 mcg TT |

TABLE 1-continued

Composition of MenABCWY vaccine

| Ingredients | Amount/dose |
| --- | --- |
| MenY-TT conjugate | 5 mcg MenY |
| (mean TT/polysaccharide ratio: ~1.3) | ~3.25 mcg TT |
| Tris-HCl | 97 mcg |
| Sodium Chloride[a] | 4.69-4.71 mg |
| Sucrose | 28 mg |
| L-Histidine | 0.78 mg |
| Polysorbate 80 (PS80) | 0.02 mg |
| Aluminum phosphate | 0.25 mg aluminum |
| Water for injection | qs to 0.5 mL |

[a] Sodium chloride concentration in MenABCWY Vaccine may vary between 160.5-161.1 mM based on the composition of the clinical and commercial NIMENRIX Drug Product (DP) lots.

MenABCWY is a combination product comprising of a single-dose of lyophilized MenACWY-TT in a 2 mL Type 1 glass vial, a non-graduated 1 mL Type I glass standard pre-filled syringe (PFS) containing MnB Bivalent rLP2086 suspension for reconstitution, and a 13 mm vial adapter.

The lyophilized MenACWY-TT drug product will be reconstituted by affixing the supplied vial adapter to the lyophilized vial and attaching the MnB Bivalent rLP2086 PFS to the vial adapter. This process is intended to facilitate aseptic delivery of the MnB suspension from the PFS into the vial and subsequent transfer of the reconstituted vaccine from the vial into the PFS for administration. After reconstitution, the contents of the vial will be withdrawn into the same syringe via the vial adapter. The vial adapter will be detached from the syringe and a needle will be affixed to the PFS for intramuscular (IM) injection. MnB Bivalent rLP2086 PFS will be designed to have a higher fill volume than TRUMENBA (~0.67 mL as opposed to the current 0.57 mL) to ensure that target dose volume (0.5 mL) of the final vaccine (MenABCWY) can be delivered.

The final vaccine composition includes rLP2086 subfamily A and B proteins formulated at 120 μg/mL/subfamily, purified capsular polysaccharides of *Neisseria meningitidis* serogroups A, C, W and Y at concentration of 10 μg/mL/type conjugated to tetanus toxoid at ratios of ~1:3, ~1:3, 1:1.5, ~1:3, respectively, in 10 mM histidine, 1.2 mM Tris buffer, 160.5-161.1 mM sodium chloride, 0.5 mg/mL aluminum as aluminum phosphate (AlPO4), 1.35 mg/mL polysorbate 80 and 56 mg/mL sucrose

Example 2: Description and Composition of the MnB Bivalent rLP2086 Drug Product MnB bivalent rLP2086 drug product is a sterile liquid formulation composed of rLP2086 subfamily A and B proteins formulated at 120 μg/mL/subfamily in 10 mM histidine buffer, 150 mM sodium chloride (NaCl) at pH 6.0 with 0.5 mg/mL aluminum as aluminum phosphate (AlPO4). Polysorbate 80 (PS-80) is added to drug substance to obtain the target PS-80 to protein molar ratio. Therefore, PS-80 is not added during the drug product formulation but is present in the final drug product at the same ratio. The drug product is filled into 1 mL syringes. A single dose of vaccine is 0.5 mL with no preservatives.

TABLE 2

Composition of MnB Bivalent rLP2086 Drug Product

| Ingredients | Quantity/dose |
| --- | --- |
| MnB rLP2086 subfamily A (SEQ ID NO: 1) | 120 μg/mL |
| MnB rLP2086 subfamily B (SEQ ID NO: 2) | 120 μg/mL |
| Sodium chloride | 150 mM |
| L-Histidine | 10 mM |
| Aluminum phosphate | 0.50 mg Aluminum phosphate/mL |
| Water for injection | qs to 1 mL |

[a] Polysorbate 80 (PS-80) is part of drug substance. PS-80 functions as a surfactant in the drug product.
[b] Equivalent to 0.25 mg aluminum per dose The Effect of Polysorbate 80 Concentration Polysorbate 80 (PS-80) is a non-ionic surfactant. It is used to stabilize and solubilize MnB rLP2086 subfamily A and B proteins in the formulation by preventing aggregation and adsorption that may be caused by temperature, filter, tubing, container/closure contact and process mixing. Stability studies using an in vitro monoclonal antibody based potency assay demonstrated instability of the subfamily B protein at higher molar ratios of PS-80 to MnB rLP2086 protein in the final formulation. Experiments with varying molar ratios of PS-80 to protein have demonstrated that the optimal molar ratio of PS-80 to MnB rLP2086 protein is approximately between 1.4 to 4.2 to retain potency.

Example 3: Description and Composition of the MenACWY-TT Composition

MenACWY-TT drug product is composed of the purified polysaccharides of *Neisseria meningitidis* serogroups A, C, W and Y, each conjugated to Tetanus Toxoid (TT) at ratios to polysaccharide of ~3, ~3, ~1.5 and ~1.3, respectively.

The MenACWY-TT drug product is presented as a lyophilized powder, supplied in a 3 mL glass vial with bromobutyl rubber closures suitable for lyophilization and aluminum flip-off caps. All components used in the manufacture of the MenACWY-TT Drug product and their functions are provided in Table 3.

TABLE 3

Composition of MenACWY-TT Drug product

| Ingredients | Quantity/dose |
| --- | --- |
| MenA$_{AH}$-TT conjugate | 5 mcg MenA |
| (mean TT/polysaccharide ratio: ~3) | ~15 mcg TT |

TABLE 3-continued

Composition of MenACWY-TT Drug product

| Ingredients | Quantity/dose |
| --- | --- |
| MenC$_{AH}$-TT conjugate | 5 mcg MenC |
| (mean TT/polysaccharide ratio: ~3) | ~15 mcg TT |
| MenW-TT conjugate | 5 mcg MenW |
| (mean TT/polysaccharide ratio: ~1.5) | ~7.5 mcg TT |
| MenY-TT conjugate | 5 mcg MenY |
| (mean TT/polysaccharide ratio: ~1.3) | ~6.5 mcg TT |
| Tris-HCl | 97 mcg |
| Sucrose | 28 mg |
| Sodium Chloride[a] | 306.0-325.0 mg |

[a]Lyophilized cake also contains sodium chloride resulting from the salt present in each of the bulk purified TT conjugates. Sodium chloride concentration varies between 10.5-11.1 mM based on the composition of the clinical and commercial lots.

Example 4: Preparation of the MenABCWY Composition

The final MenABCWY composition is prepared in the clinic by reconstituting the lyophilized MenACWY-TT drug product vial with 0.67 mL of MnB Bivalent rLP2086. The resulting MenABCWY composition (a vaccine liquid drug product) contains rLP2086 subfamily A and B proteins at 120 mcg/mL/subfamily, purified polysaccharides of *Neisseria meningitis* types A, C, W and Y at concentration of 10 mcg/mL/type conjugated to Tetanus Toxoid at ratios of ~3, ~3, ~1.5, and ~3 respectively in 10 mM histidine and 1.6 mM tris buffer containing 160.5-161.1 mM sodium chloride, 0.5 mg/mL aluminum as aluminum phosphate (AlPO4), 0.035 mg/mL polysorbate 80 and 56 mg/mL sucrose at pH of 6.05 for intramuscular injection.

The MenABCWY vaccine is prepared by mixing of two drug products, MenACWY-TT and MnB Bivalent rLP2086. Buffering components and excipients were chosen based on the individual development of each component and are shown to provide the necessary stability profile for extended shelf life.

Dosage verification studies were performed to demonstrate that MenACWY-TT drug product and MnB Bivalent rLP2086 drug product are compatible when mixed together for administration of MenABCWY vaccine and that all drug product and dosing solutions are compatible with the administration components and that dosing solutions are stable in the administration components for a period of time adequate to perform the dose preparation and administration operations. The stability of MenABCWY vaccine prepared by reconstitution of MenACWY-TT drug product with 0.67 mL of MnB Bivalent rLP2086 drug product over the hold time at ambient temperature and light conditions was confirmed in reconstituted vials and in dosing syringes.

Samples representing the dosing solutions of MenABCWY vaccine were tested using stability indicating methods such as RP-HPLC for antigen binding and purity, bioplex activity assay, ELISA, and ICP-MS with predefined acceptance criteria. The results of this study show acceptable stability of MenABCWY vaccine for 24 hours at room temperature and light conditions.

Example 5: Evaluation of the MenABCWY Vaccine

A study was carried out to assess whether there is acceptable physical compatibility and short-term stability when a lyophilized MenACWY-TT composition is reconstituted with the MnB bivalent rLP2086 composition. The lyophilized MenACWY-TT composition and the liquid MnB bivalent rLP2086 composition were combined and stored for up to 24 hours in an uncontrolled room temperature environment to approximate real life conditions. It was demonstrated that lyophilized MenACWY-TT composition could be reconstituted with the liquid MnB bivalent rLP2086 composition with gentle hand mixing and the combined pH and osmolality were within typical range for an injectable. All key attributes for the conjugates and proteins were similar to those of a control for up to 24 hours in the uncontrolled room temperature environment.

The physical compatibility was evaluated through assessing pH, appearance, ease of reconstitution, and osmolality of the combined drug product. The stability of the antigens was evaluated through assessing concentration, purity and the in-vitro relative antigenicity (IVRA) of the rLP2086 subfamily A and subfamily B proteins as well as the concentrations of the conjugated Meningococcal A, C, Y, and W-135 polysaccharides by ELISA.

Example 5 through Example 15 demonstrate that the combination of the lyophilized MenACWY-TT composition and the liquid MnB bivalent rLP2086 composition, i.e., the MenABCWY composition, was found to be compatible and stable for at least 24 hours at room temperature.

ELISAs for Determining Mening A, C, Y, and W-135 Polysaccharide Concentrations in the MenABCWY Composition-Development of the Mening A, C, Y and W-135 ELISA & Screening of the pAb for Detection Six antibodies were selected for screening for use in the ELISA assays. Each of four groups of ten rabbits was immunized with either Men A, C, Y or W-135 polysaccharide TT conjugates with rabbits subsequently exsanguinated after antibody development. Each rabbit was individually screened using Men A, C, Y or W-135 polysaccharides conjugated to a carrier protein CRM$_{197}$ for binding and specificity. Rabbit sera was screened for a positive binding signal, which is equivalent to an absorbance reading greater than three-fold above the background absorbance. Additionally, rabbit sera was screened for low non-specific binding, which was any absorbance readings for sera combinations without antigen, secondary or detection above the absorbance reading for the blank, as well as low cross-reactivity, which was any absorbance readings for heterologous serotypes that was above the background absorbance. Rabbits that met the screening criteria were pooled. The standard curve range was established using CRM conjugates and confirmed with reconstituted the lyophilized MenACWY-TT composition. The standard curve range was established using CRM conjugates and confirmed with reconstituted lyophilized MenACWY-TT composition.

The feasibility of quantitating the A, C, Y and W conjugates in the combined drug product (MenABCWY composition) was established. It was determined that the MnB Bivalent rLP2086 composition alone was not detected in the assay. Additionally, when aluminum phosphate in the MenABCWY composition samples was solubilized, full recovery of conjugates was obtained. Therefore, it was determined that the MnB bivalent rLP2086 composition does not interfere with the quantitation of the MenACWY-TT conjugates by ELISA.

Example 6: Evaluation of Suitability of Methods to Assess the MnB Bivalent rLP2086 Composition in the Presence of the MenACWY-TT Composition IEX-HPLC was evaluated for its suitability to determine the strength of the MnB bivalent rLP2086 composition subfamily A and B proteins in the presence of the Men-ACWY-TT composition. The total protein and bound protein results for the MnB bivalent rLP2086 composition in the presence of the MenACWY-TT composition and in the absence of the MenACWY-TT composition were accessed.

TABLE 4

| Sample | Subfamily | Bound Protein, % |
|---|---|---|
| the MnB bivalent rLP2086 composition no the MenACWY-TT composition | Protein A (SEQ ID NO: 1) | 107 |
| | Protein B (SEQ ID NO: 2) | 104 |
| the MnB bivalent rLP2086 composition with the MenACWY-TT composition | Protein A (SEQ ID NO: 1) | 108 |
| | Protein B (SEQ ID NO: 2) | 103 |

Figure 2A:
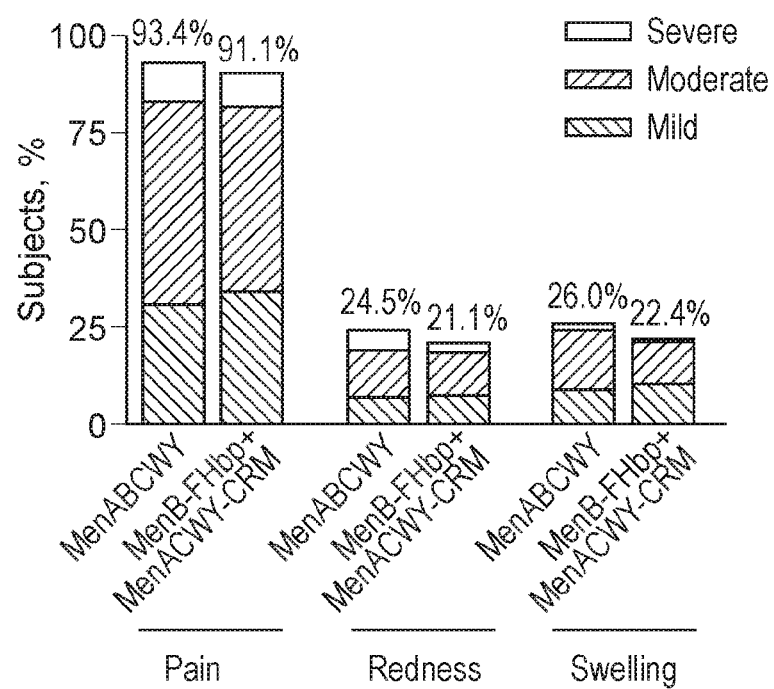
Figure 2B:
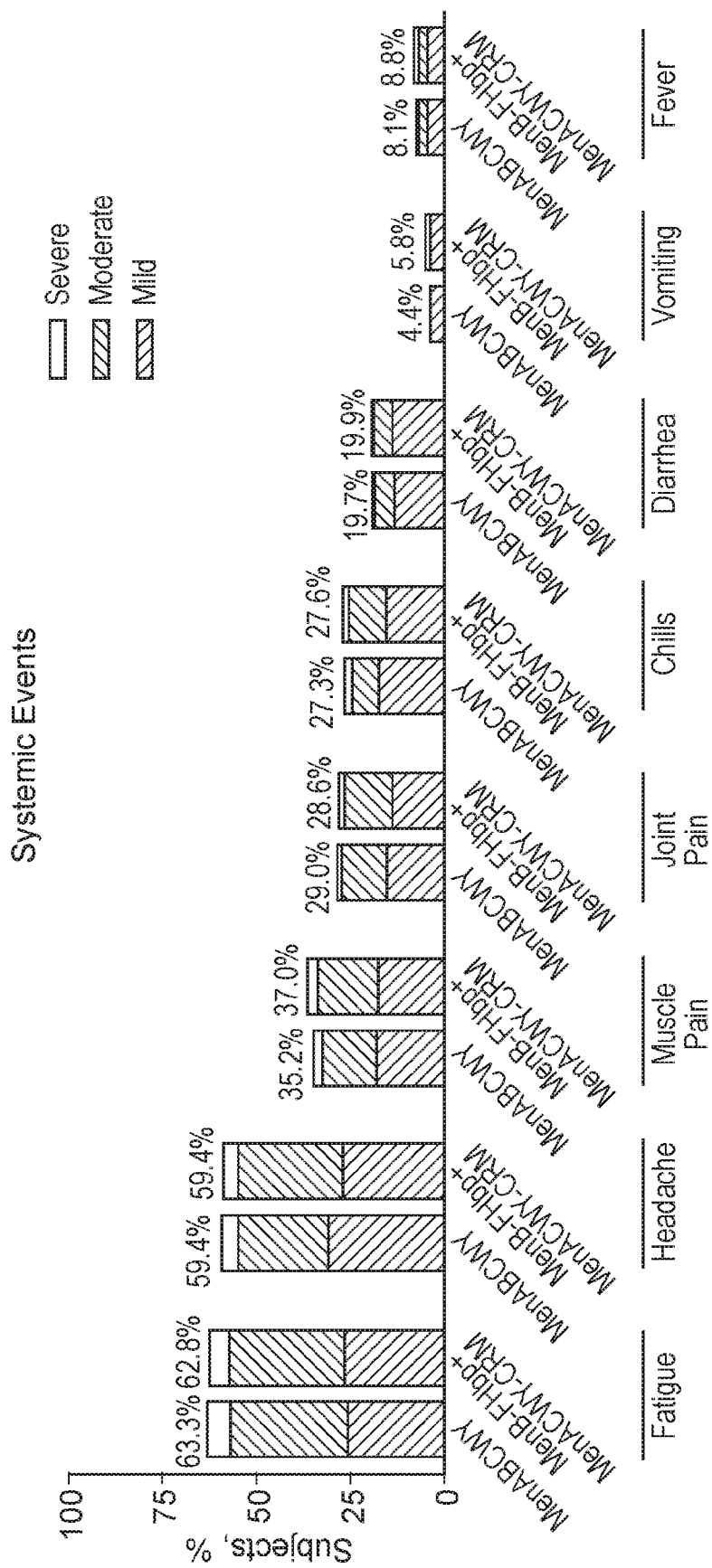

Example 7: Evaluation of the MnB Bivalent rLP2086 Composition Purity and Peak Ratio in the Presence of the MenACWY-TT Composition RP-HPLC was evaluated for its suitability to determine the purity of the MnB bivalent rLP2086 composition in the presence of the MenACWY-TT composition. The purity results for the MnB bivalent rLP2086 composition in the presence of the MenACWY-TT composition and in the absence of the MenACWY-TT composition were compared. The overlaid chromatograms are shown in FIG. 2 of U.S. Pat. No. 10,183,070. An example of the integration of the impurity peak is shown as an insert in FIG. 2 of U.S. Pat. No. 10,183,070. The evaluation results show that the presence of the MenACWY-TT composition does not interfere with evaluation of the MnB bivalent rLP2086 composition purity using the RP-HPLC method.

Example 8: Evaluation of the MnB Bivalent rLP2086 Composition IVRA in the Presence of the MenACWY-TT Composition The IVRA method was evaluated for its suitability for determination of in-vitro relative antigenicity of the MnB bivalent rLP2086 composition Subfamily A (SEQ ID NO: 1) and Subfamily B (SEQ ID NO: 2) proteins in the presence of the MenACWY-TT composition.

The IVRA results for the MnB bivalent rLP2086 composition Subfamily A and Subfamily B proteins in the presence and in the absence of the MenACWY-TT composition were compared. The feasibility evaluation results show that, within the assay variability the results are comparable and that the presence of the MenACWY-TT composition does not interfere with determination of in-vitro relative antigenicity.

Example 9: Reconstitution of the MenACWY-TT Composition Vials with the MnB Bivalent rLP2086 Composition The MenACWY-TT composition and the MnB bivalent rLP2086 composition drug products were performed using the MenACWY-TT composition vials reconstituted with the MnB bivalent rLP2086 composition drug product. The MenACWY-TT composition vials reconstituted with either saline or the MenACWY-TT composition matrix placebo were used as controls depending on the method.

TABLE 5

| Product | Component | Composition |
|---|---|---|
| The MenACWY-TT composition | Neisseria meningitidis Group A polysaccharide | 10 µg/mL |
| | Group C polysaccharide | 10 µg/mL |
| | Group W-135 polysaccharide | 10 µg/mL |
| | Group Y polysaccharide | 10 µg/mL |
| | Tetanus toxoid carrier protein | 88 µg/mL |
| | Sucrose | 164 mM |
| | Trometanol | 1.6 mM |
| the MnB bivalent rLP2086 composition | Sub-family A rLP2086 protein (SEQ ID NO: 1) | 120 µg/mL |
| | Sub-family B rLP2086 protein (SEQ ID NO: 2) | 120 µg/mL |
| | AlPO4 | 0.5 mg/mL |
| | Histidine | 10 mM |
| | NaCl | 150 mM |
| | | pH 6.0 |
| the MnB bivalent rLP2086 composition Placebo | AlPO4 | 0.5 mg/mL |
| | Histidine | 10 mM |
| | NaCl | 150 mM |
| | | pH 6.01 |
| Bulk MnB bivalent rLP2086 composition DP | Sub-family A rLP2086 protein (SEQ ID NO: 1) | 120 µg/mL |
| | Sub-family B rLP2086 protein (SEQ ID NO: 2) | 120 µg/mL |
| | AlPO4 | 0.5 mg/mL |
| | Histidine | 10 mM |
| | NaCl | 150 mM |
| | | pH 6.0 |

Determination of Saline Reconstitution Volume for the MenACWY-TT Composition

The NIMENRIX® commercial product package contains both a vial containing the lyophilized MenACWY-TT composition and a syringe containing 0.9% saline used for reconstitution. In order to reproduce the final NIMENRIX® concentration in the commercial vaccine upon reconstitution with the MnB bivalent rLP2086 composition, the amount of saline dispensed using the syringe from the commercial product had to be determined. This same volume of the MnB bivalent rLP2086 composition would then be used for all reconstitution studies.

Reconstitution of the MenACWY-TT Composition Vials with the MnB Bivalent rLP2086 Composition The MnB bivalent rLP2086 composition was pooled in a 10 mL glass vial. Approximately 800 µL of the solution was withdrawn into a 1 mL syringe. The adjusted contents of the syringe were injected into a vial containing the MenACWY-TT composition. The vial was swirled to dissolve the contents.

The pH and appearance were determined on duplicate samples on the MenABCWY composition. Osmolality was measured in triplicate on the MenACWY-TT composition reconstituted with saline and on the MenACWY-TT composition reconstituted with the MnB bivalent rLP2086 composition.

Example 10: SEC-MALLS to Evaluate Mening A, C, Y, and W-135 Polysaccharide Stability in DP Matrix Mening A, C, Y, and W-135 Polysaccharides were used as surrogates to assess if any instability of the conjugated Meningococcal A, C, Y, and W-135 polysaccharides in the combined drug product (the MenABCWY composition) could be expected.

Treatment of Mening A, C, Y, and W-135 Polysaccharides Reagent Preparation ("Full MenABCWY Composition Buffer Matrix")

2.24 g of sucrose and 7.8 mg of Tris (Tromethamine) was added to 20 ml of 2×MnB bivalent rLP2086 composition buffer matrix with MnB rLP2086 proteins (Histidine 20 mM pH 6.0, NaCl 300 mM, PS 80 0.07 mg/ml, AlPO4 1 mg/ml (8 mM), rLP2086 subfamily A (SEQ ID NO: 1) and subfamily B (SEQ ID NO: 2) proteins 240 μg/mL each).

Sample Preparation

Each Mening Polysaccharide was diluted 1:1 with Full MenABCWY composition Buffer Matrix and incubated for 0, 6 and 24 hours at 5° C., 25° C. and 37° C. After incubation the sample suspension was spun for 1 minute at 14,000 r.p.m. The supernatant was analyzed by SEC-MALLS.

Example 11: Stability of the MenABCWY Composition—Evaluation of pH, Appearance, and Osmolality of the Combined MnB Bivalent rLP2086 and MenACWY-TT Compositions The pH and appearance of the combined MnB bivalent rLP2086 composition and the MenACWY-TT composition, i.e., the MenABCWY composition, were evaluated immediately after reconstitution and again after 24 hours.

All results were as expected (Table 6).

TABLE 6

Appearance and pH of the MenABCWY composition

| Sample # | Sample | Time Point, hours | Appearance | pH |
|---|---|---|---|---|
| 1 | MenABCWY composition, Rep1 | 0 | Homogeneous white suspension | 5.8 |
| 2 | MenABCWY composition, Rep2 | 0 | Homogeneous white suspension | 5.8 |
| 3 | MenABCWY composition, Rep 1 | 24 | Homogeneous white suspension | 5.8 |
| 4 | MenABCWY composition, Rep 2 | 24 | Homogeneous white suspension | 5.8 |
| 5 | MenACWY-TT composition w/Saline | 0 | Clear, Colorless | 6.3 |
| 6 | MenACWY-TT composition w/Saline | 24 | Clear, Colorless | 6.4 |

The average osmolality of the MenACWY-TT composition reconstituted with the MnB bivalent rLP2086 composition was within 3% of the average osmolality of the MenACWY-TT composition reconstituted with saline.

TABLE 7

| Vial | Reconstituting Agent | Reading 1 mOsm | Reading 2 mOsm | Reading 3 mOsm | Average mOsm |
|---|---|---|---|---|---|
| MenACWY-TT composition | Saline | 471 | 473 | 478 | 474 |
| MenACWY-TT composition | MnB bivalent rLP2086 composition | 487 | 487 | 489 | 488 |

Example 12: Mening A, C, Y, and W-135 Polysaccharide Conjugate Concentrations in the Combined Drug Product The concentration of the Mening A, C, Y and W-135-TT conjugates in the MenABCWY composition was assessed initially and again after 24 hours. The concentrations of the four conjugates were stable over the twenty four hour time period (Table 8).

TABLE 8

Short Term Stability Results of the MnA, C, Y and W Conjugates in the MenABCWY composition by ELISA

| | MenACWY-TT composition + MnB bivalent rLP2086 composition | | | The MenACWY-TT composition + Saline | | |
|---|---|---|---|---|---|---|
| Serotype | Initial, μg/mL | After 24 hrs, μg/mL | Stability Ratio | Initial, μg/mL | After 24 hrs, μg/mL | Stability Ratio |
| A | 6.7 | 6.8 | 1.0 | 6.4 | 6.7 | 1.1 |
| C | 6.9 | 6.6 | 1.0 | 6.5 | 6.7 | 1.0 |
| Y | 8.1 | 8.7 | 1.1 | 9.6 | 9.8 | 1.0 |
| W | 8.5 | 8.8 | 1.0 | 8.8 | 9.0 | 1.0 |

Example 13: Evaluation of the Stability of the MnB Bivalent rLP2086 Proteins in the MenABCWY Composition Total and Bound rLP2086 Subfamily A (SEQ ID NO: 1) and Subfamily B (SEQ ID NO: 2) Protein Concentrations in the Combined Drug Product The MenABCWY composition samples were analyzed by IEX-HPLC to determine the protein concentrations. As shown in Table 9, the total protein, bound protein (to aluminum), and % bound of both MnB bivalent rLP2086 Subfamily A (SEQ ID NO: 1) and Subfamily B (SEQ ID NO: 2) proteins (bound to aluminum) did not change within 24 hours indicating that the rLP2086 Subfamily A and Subfamily B proteins were stable over the twenty four hour time period.

TABLE 9

Total and Bound Protein Stability

| Time Point, hours | Subfamily | Total Protein, μg/mL | Bound Protein, μg/mL | Bound Protein, % |
|---|---|---|---|---|
| 0 | A | 83 | 85 | 102 |
| | B | 88 | 87 | 99 |
| 24 | A | 87 | 88 | 101 |
| | B | 92 | 91 | 99 |

Example 14: rLP2086 Protein Purity and Peak Ratio in the Combined MenABCWY Composition The MenABCWY composition samples were analyzed by RP-HPLC to determine purity and peak ratios for the rLP2086 proteins. See FIG. 3 of U.S. Pat. No. 10,183,070. The peak at 11.9 min is excluded from the purity calculation.

rLP2086 Subfamily A and Subfamily B Protein IVRA in the Combined Drug Product

The IVRA of the MenABCWY composition samples was assessed for up to 24 hours after mixing. It was determined that the relative antigenicity of the rLP2086 Subfamily A (SEQ ID NO: 1) and Subfamily B (SEQ ID NO: 2) proteins in the MenABCWY composition was stable over the twenty four hour time period.

Example 15: Mening A, C, Y, and W-135 Polysaccharide Stability in Full MenABCWY Composition Buffer Matrix by SEC-MALS Stability of Mening A PS in Full MenABCWY Composition Buffer Matrix by SEC-MALLS after 6 and 24 Hours Incubation at Various Temperatures Mening A, C, W, and Y polysaccharides were mixed with the Full MenABCWY Composition Buffer Matrix and evaluated for stability by SEC-MALS after incubation at 5° C., 25° C. and 37° C. for up to 24 hours. All four polysaccharides appear to be stable for up to 24 hours at 5° C. and 25° C. Some degradation was observed at 37° C. for Mening A and Y. The degree of degradation could not be determined for Mening Y Polysaccharides due to formation of high Mw aggregates under all tested conditions except initial.

TABLE 10

| Sample | Incubation Time, hours | Incubation Temperature | Mw (kDa) | Δ Mw (%) |
|---|---|---|---|---|
| Mening A PS | 0 | NA | 169 | N/A |
|  | 24 | 5° C. | 171 | 1 |
|  |  | 25° C. | 157 | −7 |
|  |  | 37° C. | 126 | −26 |
| Mening C PS | 0 | NA | 213 | N/A |
|  | 24 | 5° C. | 216 | 1 |
|  |  | 25° C. | 215 | 1 |
|  |  | 37° C. | 220 | 3 |
| Mening Y PS* | 0 | NA | 294 | N/A |
|  | 24 | 5° C. | 734 | 149 |
|  |  | 25° C. | 756 | 157 |
|  |  | 37° C. | 696 | 136 |
| Mening W-135 PS | 0 | NA | 205 | N/A |
|  | 24 | 5° C. | 230 | 12 |
|  |  | 25° C. | 211 | 3 |
|  |  | 37° C. | 219 | 7 |

Example 16: Assessment of the *Neisseria meningitidis* Serogroup B Immunogenicity of Mn Pentavalent and Trumenba® Vaccines in CBA/J Mice The immune response to *Neisseria meningitidis* serogroup B fHBP following vaccination with either bivalent Mn B fHBP vaccine, Trumenba, or the bivalent Mn B fHBP vaccine formulated with quadrivalent ACWY polysaccharide conjugate vaccine (Mn Pentavalent ABCWY) was evaluated in CBA/J mice. Groups of CBA/J mice were immunized with 3 different vaccines: Pentavalent (ABCYW), Trumenba® (MnB) and Nimenrix® (ACYW) (Table 11).

TABLE 11

Study Design: Dose Levels for each Vaccine

Dose Levels, μg/0.25 mL Dose

| Dilution Factor | Mn Pentavalent (ABCWY) | TRUMENBA® (B) | NIMENRIX® (ACWY) | AlPO$_4$ (diluent) |
|---|---|---|---|---|
| 1 | 8 + 1.33 | 8 | 1.33 | 125 |
| 2 | 4 + 0.67 | 4 | 0.67 | 125 |
| 4 | 2 + 0.33 | 2 | 0.33 | 125 |
| 8 | 1 + 0.17 | 1 | 0.17 | 125 |

For each arm, CBA/J mice (25/group) were subcutaneously immunized in the scruff of the neck using 2-fold dilution dose levels of the respective vaccine (Table 11). Mice were primed with the vaccine at time 0 and boosted at week 2. Sera were collected PD2 at week 3 for testing using two different serum bactericidal assays that utilized human complement (hSBA). One hSBA used an fHBP subfamily A expressing strain (M98250771) and the other an fHBP subfamily B expressing strain (CDC1127).

The hSBA measures antibody-dependent, complement mediated bactericidal activity against *N. meningitidis* serogroup B strains. Briefly, test sera at the appropriate dilution were mixed in 96-well microtiter assay plates with freshly prepared bacterial cultures of the *N. meningitidis* B strains (subfamily A or B) and human complement. Assay plates were placed on an orbital shaker and mixed for 30 min in a humidified incubator (37° C./5% $CO_2$). Subsequently, aliquots of the assay reaction from each well were transferred to 96-well filter plates for enumeration of surviving bacteria.

Response rates to vaccination were calculated as the percentage of mice in each dosing group (n=25) that respond in hSBAs. When tested at a predetermined dilution level, mouse serum samples that kill ≥50% of the $T_{30}$ control meningococcal bacteria are considered responders. The $T_{30}$ control wells contain bacteria and complement but no test serum and are counted at the end of the 30 minute assay incubation.

Table 12 and Table 11

Table 13 show comparable dose-dependent response rates induced by either TRUMENBA® or Mn Pentavalent for both subfamily A and subfamily B of the *N. meningitidis* serotype B strains. As expected, NIMENRIX™ did not induce a functional immune response to Mn B strains.

TABLE 12

Subfamily A hSBA responses (% responders)

| Dilution Factor [a] | TRUMENBA | NIMENRIX | Penta |
|---|---|---|---|
| 8 | 24% | 0% | 8% |
| 4 | 40% | 0% | 16% |
| 2 | 52% | 0% | 56% |
| 1 | 80% | 0% | 92% |

[a] See corresponding dose levels in Table 11

TABLE 13

Subfamily B hSBA responses (% responders)

| Dilution Factor [a] | TRUMENBA | NIMENRIX | Penta |
|---|---|---|---|
| 8 | 28% | 0% | 36% |
| 4 | 56% | 0% | 60% |
| 2 | 60% | 0% | 76% |
| 1 | 72% | 0% | 76% |

[a] See corresponding dose levels in Table 11

Example 16: A Study to Describe the Immunogenicity, Safety, and Tolerability of a Bivalent rLP2086-Containing Pentavalent Vaccine (MenABCWY) in Healthy Subjects 10 to <26 Years of Age (B1971057)

B1971057 is a Phase 2 proof-of concept (POC) study to assess the safety and immunogenicity of Penta in healthy subjects 10 to <26 years of age. The study was initiated in April 2017 with approximately 530 subjects received Penta.

Meningococcal vaccines are licensed by an immunological surrogate, the serum bactericidal assay using human complement (hSBA) that demonstrates the ability of immune sera to kill meningococcal strains that represent the serogroups included in the vaccine. For MenACWY responses, one strain from each serogroup were evaluated in hSBAs and Penta responses were compared to the licensed ACWY vaccine MENVEO. For the MenB evaluation; 4 serogroup B strains were tested that were also used during the TRUMENBA licensure studies.

The study data showed Penta to be non-inferior to Menveo after 1 vaccination for the ACWY evaluation and for Penta to be non-inferior to Trumenba after 2 vaccinations for the B evaluation.

Investigational Penta Vaccine

For this study, the investigational products are bivalent rLP2086 (TRUMENBA), (Penta; described in Example 1 and Example 4 above), MenACWY-CRM (MENVEO), and placebo.

Study Design

B1971057 is a Phase 3, randomized, active-controlled, observer-blinded multicenter trial in which approximately 1590 subjects were randomly assigned to receive either Penta and placebo (saline), or Trumenba (Pfizer), and Menveo (GSK). All subjects were naive to any meningococcal group B vaccine prior to enrollment. Randomization was stratified by prior vaccination history; ~50% ACWY-naive subjects and ~50%. ACWY-experienced (having received 1 prior dose of a vaccine containing 1 or more ACWY Groups ≥4 years prior to the date of randomization). This ACWY experienced group was included because in the US 86% of teenagers receive a dose of an ACWY vaccine at approximately 11 years of age and should receive a booster dose at 16 years of age. Randomization was also stratified by geographic region. Approximately 80% subjects from US investigative sites and approximately 20% subjects from Europe. Regional stratification ensured sufficient population representation. The study was conducted in 2 stages. Stage 1, now completed, comprised the vaccination phase of a primary series. The visit schedule for Stage 1 is noted in Table 14 below. Stage 2 will evaluate persistence of immunity and a booster dose administered approximately 4 years after completion of the primary series of Penta.

TABLE 14

B1971057 Stage 1 Study Design

| | | Vaccination 1 | Post Vaccination 1 Blood Draw | Vaccination 2 | Post Vaccination 2 Blood Draw | Safety Telephone Call | Stage 2 Progression Telephone call |
|---|---|---|---|---|---|---|---|
| | | | | Month | | | |
| | | 0 | 1 | 6 | 7 | 12 | 12-18 |
| | | | | Visit | | | |
| | | 1 | 2 | 3 | 4 | 5 | 6 |
| ACWY Naïve Subjects | Group 1 (n~265) | Penta + Saline | | Penta | | | |
| | Group 2 (n~530) | Trumenba + Menveo | | Trumenba | | | |
| ACWY Naïve Subjects | Group 3 (n~265) | Penta + Saline | | Penta | | | |
| | Group 4 (n~530) | Trumenba + Menveo | | Trumenba | | | |

For assessment of the immune response, functional antibodies were analysed in hSBAs with meningococcal group A, B, C, W, and Y strains. The hSBA measures antibodies in human sera that result in complement-dependent killing of the target meningococcal strain. For assessment of the immune response to Trumenba and the B component of Penta, 4 primary MnB test strains, PMB80 (A22), PMB2001 (A56), PMB2948 (B24), and PMB2707 (B44), were used in the hSBAs for determination of the immunogenicity endpoints in this study. For assessment of the immune response to MENVEO and the ACWY components of Penta, test strains specific for each of the ACWY groups were identified and qualified in hSBAs prior to the commencement of testing. The validated assays used to evaluate MenB were the same as the ones used to license TRUMENBA.

Objectives

This study was designed to describe the safety, tolerability, and immunogenicity of Penta, and describe the immune response to groups A, B, C, W, and Y following administration of Penta, or Trumenba and Menveo a US licensed meningococcal group A, C, W-135, and Y conjugate vaccine. Nimenrix was not used as the ACWY comparator; it is not licensed in the US.

The immunogenicity of the MenACWY component of Penta was based on the hSBA geometric mean titers (GMTs) of Penta after a single dose when compared to hSBA GMTs observed for Trumenba+Menveo after 1 dose.

We conducted this assessment for individuals who had not previously received a dose of a MenACWY vaccine (ACWY naïve individuals) in addition to individuals who would be receiving their second MenACYW booster dose (ACWY experienced individuals). The POC criteria for the MenACWY component of Penta needed to be met for ACWY naïve individuals.

The criteria for immunogenicity of the MenB component of Penta was based on achieving point estimates of the 4-fold rise and composite hSBA responses after 2 doses of Penta administered on a 0-, 6-month schedule that predict meeting the Phase 3 LCI criteria established for the 0, 6-month schedule.

Secondary endpoints for the study included the standard noninferiority evaluations of the ratio of 2 GMTs being with a 2.0-fold margin and percent responders for B component of Penta. The percent responder analysis was conducted by defining a responder as achieving a ≥4-Fold Rise in hSBA Titer and Composite Response 1 Month After Vaccination 2 for Primary MenB Strains and then calculating the difference between Penta and Trumenba. A difference no larger than 10% was required to achieve success.

Immune Response to Penta and POC Immunogenicity Results

Study B1971057 shows in the following, with respect to the bactericidal responses against MenACWY between Penta and Menveo: similar hSBA GMTs for the ACWY components were observed for subjects who received Penta compared to Menveo after a single dose. A 1.5-fold GMT ratio non-inferiority (NI) margin was achieved in ACWY naïve subjects (Table 15) and a 2.0-fold GMT ratio NI margin was achieved in ACWY experienced (Table 16) subjects.

POC GMR point estimates for Penta vs Menveo ≥0.612 for MenA; ≥0.67 for MenC; ≥0.635 for MenW and ≥0.626 for MenY. All achieved.

Penta Non-inferiority to Menveo is established in ACWY naïve subjects at the 1.5-fold GMR margin as GMR LCIs for all serogroups are >0.67

Penta statistically greater to Menveo for Serogroups C, W and Y

TABLE 15

Penta ACWY hSBA GMTs compared to Menveo were within the 1.5-fold GMR NI margin after a single dose in ACWY Naïve Subjects

| Strain (Variant) Timepoint | Group 1 (Penta) | | | Group 2 (Trumenba + Menveo) | | | Ratio (Gr 1 vs Gr 2) |
|---|---|---|---|---|---|---|---|
| | N | GMT | (95% CI) | N | GMT | (95% CI) | (95% GMR CI) |
| Men A | | | | | | | |
| 1 Month after Vaccination 1 | 264 | 215.8 | (184.6, 252.4) | 510 | 203.2 | (178.7, 231.0) | 1.06 (0.86, 1.31) |
| MenC | | | | | | | |
| 1 Month after Vaccination 1 | 262 | 111.5 | (87.2, 142.6) | 509 | 81.4 | (68.1, 97.4) | 1.37 (1-01, 1.86) |
| MenW | | | | | | | |
| 1 Month after Vaccination 1 | 264 | 98.4 | (80.7, 120.0) | 512 | 71.2 | (61.5, 82.4) | 1.38 (1.08, 1.77) |
| MenY | | | | | | | |
| 1 Month after Vaccination 1 | 263 | 141.9 | (118.8, 169.4) | 510 | 96.6 | (83.9, 111.2) | 1.47 (1.16, 1.85) |

TABLE 16

Penta ACWY hSBA GMTs compared to Menveo were within the 1.5-fold GMR NI margin after a single dose in ACWY Experienced Subjects

| Strain (Variant) Timepoint | Group 3 (Penta) | | | Group 4 (Trumenba + Menveo) | | | Difference (Gr 3 vs Gr 4) |
|---|---|---|---|---|---|---|---|
| | N | GMT | (95% CI) | N | GMT | (95% CI) | (95% GMR CI) |
| MenA | | | | | | | |
| 1 Month after Vaccination 1 | 218 | 568.6 | (492.9, 656.0) | 411 | 916.1 | (809.1, 1037.3) | 0.62 (0.51, 0.76) |
| MenC | | | | | | | |
| 1 Month after Vaccination 1 | 264 | 814.9 | (689.4, 963.2) | 506 | 827.0 | (722.5, 946.6) | 0.99 (0.79, 1.23) |
| MenW | | | | | | | |
| 1 Month after Vaccination 1 | 219 | 1214.9 | (1032.0, 1430.1) | 414 | 1176.7 | (1017.9, 1360.2) | 1.03 (0.82, 1.30) |
| MenY | | | | | | | |
| 1 Month after Vaccination 1 | 218 | 1174.0 | (990.3, 1391.9) | 413 | 1000.2 | (872.1, 1147.1) | 1.17 (0.94, 1.47) |

Penta Non-inferiority to Menveo is established in this study at the 2.0 fold GMR margin as GMR LCIs for all serogroups are >0.5 in subjects with ACWY background Trumenba was licensed based on the proportion of subjects achieving 4-fold rise (and composite response) in antibody titers that met a prespecified Lower Limit 95% Confidence Interval (LCI) threshold. When 4-fold antibody responses are assessed they can be influenced by background titers in the population which may independently influence the proportion of subjects that have a 4-fold response to the vaccine. In addition, the hSBA assays used are comprised of biological components that even though tightly controlled, may affect absolute response criteria from study to study. Taking into consideration that the licensure LCI thresholds were calculated based on point estimates achieved in a different population and using different complement sources, we also compared Penta serogroup B responses to those from the Trumenba+Menveo arms. The results are provided in Table 17.

TABLE 17

4-Fold Rise and Composite Response All Ages (10 to <26) 1 Month Post Dose 2.

| Endpoint Strain (Variant) | Group 1 + 3 Combined (Penta) | | | Group 2 + 4 Combined (Trumenba) | | | POC Criteria Point Estimate |
|---|---|---|---|---|---|---|---|
| | N | % (n) | (95% CI) | N | % (n) | (95% CI) | 0, 6 Month |
| 4-fold Rise from Baseline | | | | | | | |
| PMB80 (A22) | 422 | 75.8 (320) | (71.5, 79.8) | 827 | 73.8 (610) | (70.6, 76.7) | 78.1 |

TABLE 17-continued

4-Fold Rise and Composite Response All Ages
(10 to <26) 1 Month Post Dose 2.

| Endpoint Strain (Variant) | Group 1 + 3 Combined (Penta) | | | Group 2 + 4 Combined (Trumenba) | | | POC Criteria Point Estimate 0, 6 Month |
|---|---|---|---|---|---|---|---|
| | N | % (n) | (95% CI) | N | % (n) | (95% CI) | |
| PMB2001 (A56) | 418 | 94.7 (396) | (92.1, 96.7) | 823 | 95.0 (782) | (93.3, 96.4) | 87.5 |
| PMB2948 (B24) | 430 | 69.3 (298) | (64.7, 73.6) | — | — | — | 58.6 |
| PMB2707 (B44) | 432 | 91.7 (396) | (88.6, 94.1) | 850 | 86.4 (734) | (83.9, 88.6) | 63.6 |
| Composite response (hSBA titer ≥LLOQ for all 4 strains) | 424 | 76.7 (325) | (72.3, 80.6) | — | — | — | 68.5 |

B24 data pending

For three of the 4 serogroup B test strains SBA 4-fold rise and composite responses considerably exceeded the pre-specified point estimates. For one strain, PMB80(A22), 75.8% of subjects achieved a 4-fold rise in titers (for the Trumenba group the point estimate (PE) was 73.8), compared to the POC criteria PE of 78.1%; however, as stated above, the 95% LCI criteria are more difficult to control in different populations and over time. The phase 2 study used to create LCI for this POC study enrolled a European population where the baseline hSBA rate for A22 was 22.1%. Since the PE of Penta was higher than that of Trumenba, it suggested that there was no immune interference of the MenB component of Penta. To confirm this point, the secondary endpoint analysis showed that Trumenba+Menveo was noninferior to Penta in 2 noninferiority analyses. Indeed, they met the stringent 1.5 GMR noninferiority margin (Table 18) and the percent responder analysis at the 5% margin (Table 19).

TABLE 18

GMTs and GMT ratio of Penta Compared to Trumenba 1 Month Post Dose 2.

| Strain (Variant) | Groups 1 + 3 Combined (Penta) | | | Groups 2 + 4 Combined (Trumenba) | | | Ratio (Gr 1 + 3 vs Gr 2 + 4) | |
|---|---|---|---|---|---|---|---|---|
| | N | % (n) | (95% CI) | N | % (n) | (95% CI) | % | (95% CI) |
| PMB80 (A22) | 433 | 51.0 | (46.7, 55.7) | 852 | 49.3 | (46.2, 52.6) | 1.03 | (0.93, 1.16) |
| PMB2001 (A56) | 435 | 152.3 | (138.5, 167.5) | 854 | 139.5 | (130.6, 149.1) | 1.09 | (0.97, 1.22) |
| PMB2948 (B24) | 431 | 20.2 | (18.3, 22.3) | — | — | — | — | — |
| PMB2707 (B44) | 436 | 43.3 | (39.1, 47.9) | 853 | 37.8 | (35.1, 40.8) | 1.14 | (1.01, 1.30) |

Penta Non-inferiority to Trumenba is established in this study at the 1.5-fold GMR margin for A22, A56 and B44 as GMR LCIs are >0.67. No interference

TABLE 19

Difference in % Responders Who Achieved 4-fold response

| Endpoint Strain (Variant) | Group 1 + 3 Combined (Penta) | | | Group 2 + 4 Combined (Trumenba) | | | Difference (Gr 1 + 3 − Gr 2 + 4) | |
|---|---|---|---|---|---|---|---|---|
| | N | % (n) | (95% CI) | N | % (n) | (95% CI) | % | (95% CI) |
| 4-fold Rise from Baseline | | | | | | | | |
| PMB80 (A22) | 422 | 75.8 (320) | (71.5, 79.8) | 827 | 73.8 (610) | (70.6, 76.7) | 2.1 | (−3.1, 7.0) |
| PMB2001 (A56) | 418 | 94.7 (396) | (92.1, 96.7) | 823 | 95.0 (782) | (93.3, 96.4) | −0.3 | (−3.2, 2.2) |

TABLE 19-continued

| | Difference in % Responders Who Achieved 4-fold response | | | | | | | |
|---|---|---|---|---|---|---|---|---|
| | Group 1 + 3 Combined (Penta) | | | Group 2 + 4 Combined (Trumenba) | | | Difference (Gr 1 + 3 − Gr 2 + 4) | |
| Endpoint Strain | | | | | | | | |
| (Variant) | N | % (n) | (95% CI) | N | % (n) | (95% CI) | % | (95% CI) |
| PMB2948 (B24) | 430 | 69.3 (298) | (64.7, 73.6) | — | — | — | — | — |
| PMB2707 (B44) | 432 | 91.7 (396) | (88.6, 94.1) | 850 | 86.4 (734) | (83.9, 88.6) | 5.3 | (1.7, 8.7) |
| Composite response (hSBA titer ≥LLOQ for all 4 strains) | 424 | 76.7 (325) | (72.3, 80.6) | | | | | |

Penta Non-inferiority to Trumenba is established in this study at the 5% margin for A22, A56 and B44
No interference between Trumenba and Penta Example 17: Potential Public Health Impact in the US of a Pentavalent Vaccine Targeting *Neisseria meningitidis* Serogroups A, B, C, W and Y Objective: To evaluate the potential for additional reductions of IMD cases among the US population under various assumptions of vaccination schedules and compliance rates with Pentavalent vaccine.

Vaccination Scenarios

Four primary vaccination scenarios were analyzed and compared to estimated cases averted with current recommendations and compliance levels (FIG. 1)
1. Replacing MenACWY/MenB vaccines at age 16 years with Penta, and retaining MenACWY at age 11 years
2. Replacing MenACWY/MenB vaccines at age 11 years and 16 years with Penta
3. Replacing MenACWY/MenB at age 16 years with Penta, and no MenACWY vaccination at age 11 years
4. Replacing MenACWY at age 11 years with 2 doses of Penta and MenACWY/MenB at age 16 years with 1 dose of Penta Vaccine coverage with each of the schedules was varied to estimate the impact of different recommendations on the overall levels of IMD reduction Disease reduction estimates were based on published 2018 estimates of adolescent immunization coverage in the United States
- 86.6% received ≥1 dose of MenACWY
- 68.1% of all adolescents received ≥1 dose of HPV
- 50.8% received ≥2 doses of MenACWY
- 17.2% received ≥1 dose of MenB
- Coverage for 2nd dose in a 2-dose series at age 16 years assumed to be 50% of that of the 1st dose 3 and 70% at age 11 years.

Results

Figure 3:
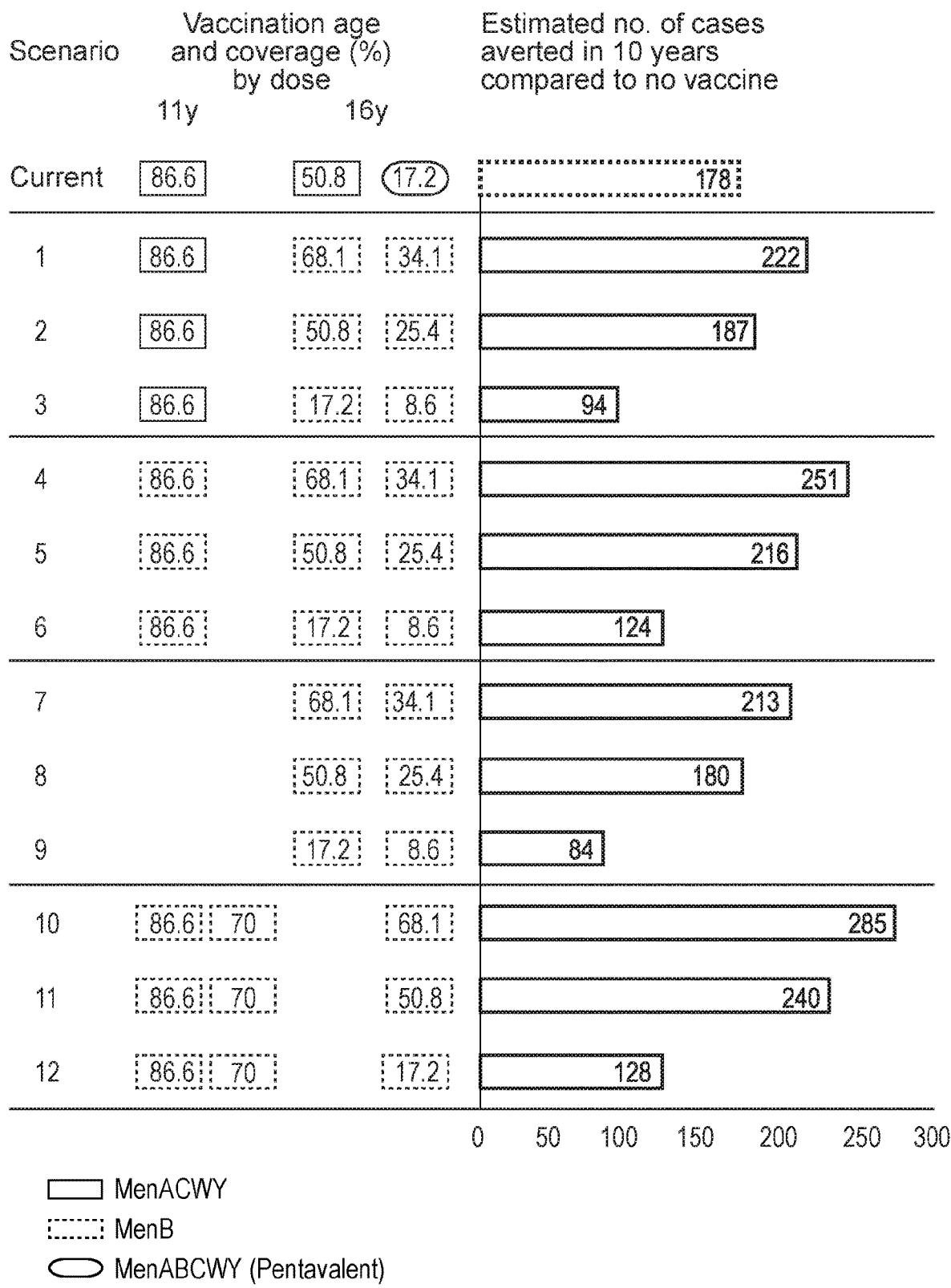

With the current coverage levels and a vaccination schedule that requires a total of 4 injections, the MenACWY and MenB vaccines are estimated to avert 178 IMD cases over 10 years, compared to the hypothetical of no vaccination at all. Replacing MenACWY or/and MenB vaccinations with Penta eliminates at least 1 injection; assuming the immunization coverage at age 16 years remains similar to the current MenACWY vaccine coverage, the Penta vaccine was estimated to avert a similar or higher number of IMD cases (FIG. 3).

Two doses of Penta at age 11 years and 1 dose of Penta at age 16 years (scenarios 10-12) could prevent the most cases (up to 282), compared with other vaccination schedule with comparable coverage rate.

One dose of Penta at age 11 years and 2 doses of Penta at age 16 years (scenarios 4-6) could prevent up to 251 cases.

With a slightly higher coverage of the 2nd dose of Penta than the current MenB coverage rate at age 16 years, a similar number of IMD cases could be prevented with one dose of MenACWY vaccine at age 11 years and 2 doses of Penta at age 16 years (scenario 3) or 2 doses of Penta at age 16 (scenario 8, see FIG. 1).

Conclusion

The disease impact of a vaccination strategy is directly related to the level of coverage obtained.
Replacing one or more MenACWY or MenB vaccine doses with Penta could further reduce IMD caused by all 5 meningococcal serogroups;
Reduce number of vaccine administrations for adolescents;
Potentially improve compliance with ACIP recommendations, reduce medical visits and the costs of public health responses to individual IMD cases.

Invasive meningococcal disease (IMD) caused by *Neisseria meningitidis* is an uncommon, rapidly progressing, and potentially deadly infection with highest incidence observed in infant and adolescent age groups. Serogroups A, B, C, W, and Y account for 94% of disease globally; in the United States, most disease is caused by serogroups B, C, and Y. According to 2018 surveillance data from the United States, the incidence of IMD was 0.10 cases per 100,000 population. Serogroup B was predominant among US adolescents and young adults (62% of cases among 16- to 23-year-olds) and also across all age groups (36% of cases).

The US Advisory Committee on Immunization Practices (ACIP) currently recommends 2 types of meningococcal vaccines to help protect healthy adolescents against IMD. The quadrivalent meningococcal serogroups A, C, W, and Y (MenACWY) vaccine is routinely recommended as a primary dose at age 11 to 12 years and a booster dose at age 16 years. Meningococcal serogroup B (MenB) vaccination is recommended for adolescents and young adults aged 16 to 23 years (16-18 years preferred) based on shared clinical decision-making. In 2018, the estimated MenACWY vaccination coverage for adolescents aged 13 to 17 years was 86.6% for ≥1 dose and 50.8% for ≥2 doses. In contrast, only 17.2% of 17-year-olds received ≥1 dose of a MenB vaccine, and fewer than 50% of these individuals completed the multidose vaccination series. These data suggest that many adolescents in the United States are not fully protected against meningococcal disease.

A single vaccine that can help protect against meningococcal disease caused by all 5 serogroups (ie, a MenABCWY pentavalent vaccine) instead of 2 separate MenB and MenACWY vaccines with different vaccination schedules could simplify immunization, reduce the number of injections required, and potentially improve vaccination coverage. We developed a model to evaluate the public health impact of assorted meningococcal immunization programs using a pentavalent MenABCWY vaccine.

2.0 Methods 2.1 Model Description

A population-based dynamic model was developed to estimate the expected number of IMD cases averted over a 10-year period in the United States. The model structure is similar to what has been previously described in full elsewhere. The population was stratified into 101 single-year age bands, and individuals in each age band transitioned to the next age band in the following year. Meningococcal carriage was the principal source of infectious disease transmission and was the primary consideration in the model calculations. Meningococcal carriage and transmission were modeled by stratifying the population into 10 mutually exclusive age groups (0-5 months, 6-12 months, 1 year, 2-4 years, 5-9 years, 10-14 years, 15-19 years, 20-24 years, 25-59 years, and 60 years). Each age group was characterized by a proportion of individuals who were carriers of meningococcal serogroups A, B, C, W, and Y and had age-specific probabilities of developing IMD and transmitting the bacteria within their age group or to other age groups. The proportion of meningococcal carriers in each of the 10 age groups for each year was calculated based on (1) carriage prevalence in the prior year; (2) bacterial transmission and mixing patterns within and among the age groups; (3) number of vaccinated individuals (vaccination coverage); and (4) vaccine efficacy against carriage acquisition. During each year of the 10-year time horizon within the model, proportions of individuals in targeted age groups were estimated to receive MenACWY, MenB, and/or MenABCWY vaccines under 4 different scheduling scenarios. For all vaccination scenarios, the model estimated that individuals who developed IMD either recovered with or without complications, or died.

2.2 Model Inputs

Average age-group-based IMD incidence rates for each serogroup were derived from the Centers for Disease Control and Prevention (CDC) Enhanced Meningococcal Disease Surveillance reports from 2015-2017. The MenABCWY vaccine was assumed to provide direct protection against serogroups A, B, C, W, and Y.

Vaccine efficacy assumptions against serogroup B in adolescents receiving 1 or 2 doses of the MenABCWY vaccine were based on a published clinical study for the MenB-FHbp vaccine (Trumenba®, bivalent rLP2086; Pfizer Inc, Philadelphia, PA). In this study, the percentage of subjects with serum bactericidal activity in assays using human complement (hSBA) titers ≥1:8 (standard correlate of protection is ≥1:4) at 1 month postvaccination ranged from 23.8% to 67.6% and 69.1% to 100% after 1 or 2 doses of MenB-FHbp, respectively. Based on these data, estimates of 30% and 85% vaccine efficacy against serogroup B were assumed for adolescents receiving 1 or 2 doses of MenABCWY vaccine, respectively.

Vaccine efficacy assumptions against serogroups A, C, W, and Y were based on a review of published immunogenicity and efficacy data from clinical studies of the MenACWY-TT vaccine (Nimenrix®, Pfizer Ltd, Sandwich, UK) in which the percentage of subjects with serum bactericidal activity in assays using rabbit complement (rSBA) or hSBA titers ≥1:8 at 1 month postvaccination ranged from 81.9% to 97.4% after 1 dose of MenACWY-TT. Based on these data, an estimate of 95% vaccine efficacy was assumed against serogroups A, C, W, and Y.

Indirect protection of nonvaccinated individuals due to reduction of carriage prevalence and transmission was assumed to be 0% for serogroup B and 36.2% for serogroups A, C, W, and Y, both derived from the published literature on MenB and MenACWY vaccines.

The 5-year duration of protection and a fixed 10% annual waning rate for the MenABCWY vaccine against serogroup B shown in were assumed based on considerations of (1) previous published health economic models and (2) clinical data from a phase 3 extension study in adolescents that evaluated persistence of the immune response elicited by the MenB-FHbp vaccine. Results from the clinical study indicated that response rates peaked after primary vaccination, declined over the subsequent 12 months, and then remained stable above baseline through 48 months. At 48 months after primary vaccination, 18.0% to 61.3% of subjects had hSBA titers greater than or equal to the lower limit of quantification (ie, 1:16 or 1:8 depending on strain) across the 4 diverse serogroup B test stains used to assess breadth of protection.

For assessment of the protection of the MenABCWY vaccine against serogroups A, C, W and Y (Table 2), the 5-year duration of direct protection and 10% annual waning rate were conservative assumptions based on clinical data from studies that evaluated persistence of the immune response elicited by MenACWY-TT in adolescents and adults aged 11 to 55 years through 10 years after primary vaccination. At year 10, 70.2% to 90.7% of vaccinated subjects had rSBA titers 1:8 across serogroups A, C, W and Y compared with 99.7% to 100% at 1 month postvaccination. Currently no data are available regarding the duration of indirect protection and waning rates for licensed MenACWY vaccines; the model therefore assumed waning rates for MenACWY were equal to MenABCWY.

2.3 Vaccination Scenarios and Sensitivity Analyses

The vaccination scenarios were built based on the existing adolescent meningococcal vaccination platform (ie, at age 11 and 16 years) in the United States. Four primary vaccination schedules were examined and compared with the current schedule: (1) 1 dose of MenACWY vaccine at age 11 years and 2 doses of MenABCWY vaccine at age 16 years; (2) 1 dose of MenABCWY vaccine at age 11 years and 2 doses of MenABCWY vaccine at age 16 years; (3) 2 doses of MenABCWY vaccine at age 16 years only; and (4) 2 doses of MenABCWY vaccine at age 11 years and 1 dose at age 16 years.

The assumptions of vaccination coverage for each primary schedule were taken from observed adolescent vaccination coverage, vaccination age, and number of doses required as reported in the 2018 National Immunization Survey-Teen (NIS-Teen). In line with the trends observed in the NIS-Teen survey, vaccination coverage among adolescents aged 11 years was assumed to be higher than at age 16 years, and the compliance (ie completion of the recommended dosing series) with a 2-dose series at age 11 years was assumed to be higher than compliance with a 2-dose series at age 16 years.

For the base case analysis, vaccination coverage for the first dose at age 11 years was assumed to be the same as the overall coverage of the primary dose of MenACWY vaccine reported in 2018 (86.6%), and vaccination coverage for the first dose at age 16 years was assumed to be the same as the coverage of the MenACWY booster dose (50.8%). It was assumed based on these data that 80% of adolescents aged 11 years who received the first dose of MenABCWY would complete the 2-dose series, whereas compliance with a 2-dose series at age 16 years was assumed to be 50% based on available information on MenB vaccine series completion. Sensitivity analyses were performed for each of the 4 meningococcal vaccine administration schedules using levels of adolescent vaccine coverage at age 16 years reported in 2018. The highest coverage assumed was the same as that for ≥1 dose of human papillomavirus (HPV) vaccine (68.1%) at age 11-12 years, and the lowest coverage assumed was the same as that for ≥1 dose of MenB vaccine (17.2%) at age 16 years. After considering the primary dosing schedules and vaccination coverage estimates, a total of 13 different scenarios were assessed.

3.0 Results

With the current vaccination schedule and reported vaccination coverage in 2018 (MenACWY, 86.6% at age 11 years and 50.8% at age 16 years; MenB, 17.2% at age 16 years), vaccination with 2 doses each of MenACWY and MenB vaccines, for a total of 4 injections between 11 and 16 years of age, could potentially avert 165 cases of IMD over the next 10 years compared with no meningococcal vaccination (current scenario). Under this scenario, 19 serogroup B cases (11.5% of the total preventable IMD cases) are estimated to be prevented over the next 10 years. Replacing either MenACWY and/or MenB vaccines with a pentavalent MenABCWY vaccine would eliminate 1 or 2 injections, depending on the vaccination schedule, and potentially avert a higher number of IMD cases (scenarios 1, 2, 4, 5, 7, 8, 10, and 11). This is assuming that MenABCWY vaccination coverage at 16 years of age remains similar to 2018 MenACWY vaccination coverage (50.8%; scenarios 1, 4, 7, and 10) or perhaps rises to the slightly higher HPV vaccination coverage observed at age 11 to 12 years (68.1%; scenarios 2, 5, 8, and 11).

However, assuming MenABCWY vaccination coverage at age 16 years is the same as for the current 2-dose MenB vaccination schedule at age 16 years (17.2%), a MenABCWY regimen of 1 dose at age 11 years and 2 doses at age 16 years (ie, similar to the current schedule) would prevent fewer IMD cases (n=137) compared with the current vaccination schedule (FIG. 2, scenario 6). These results are mainly driven by the assumption of lower MenACWY vaccination coverage than is currently reported at age 16 years, leading to a lower estimated number of serogroups A, C, W, and Y cases averted (n=89; 65.0%) compared with the current schedule.

3.1 Base Case Vaccination Coverage Assumptions

In all base case vaccination scenarios (scenarios 1, 4, 7, and 10), assuming MenABCWY vaccination coverage is the same as current coverage for the MenACWY vaccine at age 11 years (86.6%) or age 16 years (50.8%), replacing either the MenACWY and/or MenB vaccine with a pentavalent MenABCWY vaccine would avert a greater number of IMD cases than the current schedule (range, 189-256 IMD cases averted, depending on schedule). The higher number of total IMD cases averted compared with the current vaccination schedule is mainly driven by the greater number of serogroup B cases prevented (range, 55-111 serogroup B cases). Among all base case vaccination scenarios assessed, disease prevention would be maximized by administering 2 doses of MenABCWY vaccine at age 11 years and 1 dose at age 16 years (scenario 10; 256 cases averted [111 serogroup B; 146 serogroups A, C, W, and Y]).

3.2 Sensitivity Analysis Based on Alternative Vaccination Coverages

If MenABCWY vaccination coverage at age 16 years rises to the levels observed for the HPV vaccine at 11 to 12 years of age (68.1%), the greatest impact on meningococcal disease prevention would be provided by 2 doses of MenABCWY vaccine at age 11 and 1 dose at age 16 (scenario 11; 299 total cases averted). This schedule would also prevent the greatest number and percentage of serogroup B cases out of the total preventable cases over a 10-year period (140 serogroup B cases averted [46.8%]). The next best regimen was 1 dose of MenABCWY vaccine at age 11 and 2 doses of MenABCWY vaccine at age 16 (scenario 5; 263 cases averted; 103 serogroup B; 159 serogroups A, C, W, and Y). Additionally, a similar number of cases would be averted with or without including the currently recommended MenACWY dose at age 11 years (scenarios 2 [234 cases averted; 74 serogroup B; 159 serogroups A, C, W, and Y] and 8 [220 cases averted; 74 serogroup B; 146 serogroups A, C, W, and Y]). In contrast, regimens where MenABCWY vaccination coverage was assumed to be the same as for the current 2-dose MenB vaccination schedule at age 16 (17.2% for dose) led to far fewer estimated IMD cases prevented, mainly due to fewer serogroup B cases averted (scenarios 3, 6, 9, and 12). Under this vaccination coverage assumption, the lowest number of total IMD cases prevented would be through a regimen of 2 MenABCWY vaccines at age 16 (scenario 9, 93 total cases averted [19 serogroup B; 74 serogroups A, C, W, and Y]).

4.0 Discussion

This is the first study to our knowledge that models the impact of a pentavalent MenABCWY vaccine to protect against meningococcal disease caused by the 5 most prevalent disease-causing serogroups (ie, serogroups A, B, C, W, and Y) in the context of the US adolescent meningococcal immunization platform. Globally, various monovalent, bivalent, or quadrivalent meningococcal vaccine formulations that target different combinations of these 5 serogroups are used to help protect against meningococcal disease. In several countries, ongoing surveillance efforts have detected changes in circulating disease-causing meningococcal serogroups; these epidemiological shifts prompted changes to some national vaccination strategies to include MenACWY vaccines for comprehensive protection against IMD. Deploying a MenABCWY vaccine would potentially protect against the 94% of IMD cases worldwide estimated to be caused by these 5 serogroups.

In the United States, MenACWY vaccination for adolescents has been recommended since 2005, and MenB vaccination recommendations were put into effect in 2015. A single pentavalent MenABCWY vaccine could simplify immunization schedules by eliminating the need for multiple injections using 2 different vaccines at different ages, potentially improving vaccination coverage and enhancing protection against most prevalent disease-causing serogroups. Based on the current schedule and vaccination coverage for MenACWY and MenB vaccines in the United States, our model estimates that vaccination with both MenACWY and MenB vaccines could potentially avert 165 cases of IMD over 10 years compared with no vaccination. Assuming MenABCWY vaccination coverage is similar to current MenACWY vaccination coverage noted by the CDC NIS-Teen survey from 2018, our model estimates that replacing one or more MenACWY or MenB vaccine doses with a MenABCWY vaccine would lead to as many as 256 IMD cases averted among US adolescents while simultaneously reducing the recommended number of vaccine injections. In fact, most of the scenarios examined in this study demonstrate added benefit of a single MenABCWY vaccine in terms of greater number of cases averted compared with the current schedule.

Adolescent immunization delivery is challenging, in part because rates of preventative well-visits—when immunizations typically occur—decline steadily after 16 years of age, and when combined with the transition from pediatricians to medical providers who are typically less involved in adolescent immunizations, may contribute to suboptimal protection against disease in this age-group. An age-based platform for MenABCWY vaccination would support and catalyze adolescent immunization by enabling vaccine administration at ages where adolescents are more likely to receive and comply with multidose regimens and reduce the number of injections and visits. Importantly, immunization of adolescents with MenACWY conjugate vaccines and recombinant protein MenB vaccines both elicit protective immune responses following primary vaccination and robust responses following a booster dose. Together, these data not only support to the existing US adolescent MenACWY and MenB immunization platform, but also lend support to a flexible MenABCWY vaccination schedule where adolescents can start the vaccination series anywhere between the ages of 11 and 16 years and maintain protection throughout the period of highest risk.

Studies have shown that socioeconomic status, education, and race also play a role in vaccination awareness, access, and utilization, and series-completion rates. As such, a MenABCWY vaccine could help reduce these disparities by simplifying meningococcal vaccination recommendations, thereby reducing vaccine access issues, and eliminating confusion surrounding existing MenB and MenACWY vaccine recommendations. Moreover, combination vaccines in general have been shown to improve vaccination coverage among a variety of age groups.

Example 18: Breadth of the Human Immune Response to TRUMENBA: Summary of fHBP Variants Expressed by MenB Strains that are Susceptible in the hSBA Introduction & Aims: TRUMENBA (bivalent rLP2086), a vaccine for the prevention of Neisseria meningitis serogroup B (Men B) disease, includes two protein antigens, variants of meningococcal factor H binding protein (fHBP). fHBP exists as two subfamilies, A and B. Within each subfamily several hundred unique fHBP variants have been identified. Despite this sequence diversity, a vaccine containing one protein from each subfamily was demonstrated to induce broad coverage across MenB strains that represent the diversity of fHBP variants. Licensure was based on the ability of the vaccine to elicit antibodies that initiate complement-mediated killing of invasive MenB strains in a serum bactericidal assay using human complement (hSBA). Due to the endemic nature of meningococcal disease, it is not possible to predict which fHBP variants individuals may be exposed to. For this reason we have continued to explore the coverage conferred by TRUMENBA and present here additional evidence to illustrate the breadth of immune coverage.

Materials & Methods: MenB invasive strains (n=109) were selected to confirm TRUMENBA breadth of coverage. The strains encoded 22 and 16 unique subfamily A and subfamily B fHBP variants, respectively. The expression of fHBP at the bacterial surface was determined using the flow cytometric MEningococcal Antigen SURface Expression (MEASURE) assay. Exploratory hSBAs were performed using pre- and post-vaccination sera (subject-matched) from young adults. A strain was considered susceptible to TRUMENBA immune sera if a 4-fold rise in the hSBA titer was achieved between the pre- and post-vaccination serum samples.

Results: Of the 109 strains, 87 (nearly 80%) were susceptible to TRUMENBA immune serum in hSBAs. This included strains expressing fHBP variants A02, A28, A42, A63, A76, B05, B07, B08, B13, B52 and B107, in addition to variants that had been reported previously. The majority of strains that could not be killed had fHBP expression levels that were below the level considered sufficient to initiate bactericidal killing in an hSBA. See FIG. 3, Table 1, Table 2, and Table 3.

TABLE 20

| Strain ID | fHBP Variant | fHBP Expression (MFI) | Susceptible in hSBA[1] |
|---|---|---|---|
| PMB3693 | A02 | 13157 | + |
| PMB876 | A28 | 4193 | + |
| PMB3106 | A42 | 1614 | + |
| PMB2871 | A63 | 10818 | + |
| PMB1606 | A76 | 11331 | + |
| PMB2627 | B05 | 2916 | + |
| PMB2219 | B07 | 1350 | + |
| PMB1610 | B08 | 1561 | + |
| PMB1486 | B13 | 1850 | + |
| PMB2466 | B52 | 8734 | + |
| PMB891 | B107 | 11125 | + |

TABLE 21 fHBP variants expressed by MenB strains that were killed with TRUMENBA immune sera in hSBAs (% amino acid sequence identity with A05 (SEQ ID NO: 1) and B01 (SEQ ID NO: 2))

| Subfamily A | Subfamily B |
|---|---|
| A02 (94.3) | B02 (92.0) |
| A04 (96.6) | B03 (90.8) |
| A05 (vaccine antigen) | B05 (87.7) |
| A06 (96.2) | B07 (87.3) |
| A07 (85.4) | B08 (87.7) |
| A12 (85.4) | B09 (88.1) |
| A15 (85.1) | B107 (89.7) |
| A17 (88.1) | B13 (86.9) |
| A19 (88.1) | B15 (86.5) |
| A22 (88.9) | B16 (86.2) |
| A26 (85.8) | B24 (86.2) |
| A28 (96.9) | B44 (91.6) |
| A42 (91.6) | B52 (91.9) |
| A56 (98.1) | |
| A63 (96.6) | |
| A76 (95.0) | |

TABLE 22 fHBP variants* expressed by strains at <1000 MFI and were not killed with TRUMENBA immune sera in hSBAs (% amino acid sequence identity with vaccine antigens A05 (SEQ ID NO: 1) and B01 (SEQ ID NO: 2))

| Subfamily A | Subfamily B |
|---|---|
| A08 (85.9) | B10 (88.1) |
| A10 (85.4) | B91 (90.4) |
| A20 (87.7) | |
| A40 (85.1) | |
| A52 (96.6) | |

Conclusion: The hSBA is recognized as the surrogate of efficacy for meningococcal vaccines. Assay complexity prevents demonstration of the bactericidal activity of TRUMENBA immune sera against MenB strains that express each of the hundreds of unique fHBP sequence variants. To illustrate the breadth of immune coverage conferred by TRUMENBA, we show that MenB strains expressing additional diverse fHBP variants can be killed in hSBAs despite being heterologous to the vaccine antigens.

Example 19: Selection of Diverse Strains to Assess Broad Coverage of the Bivalent FHbp Meningococcal B Vaccine Although transmission of *Neisseria meningitidis* usually results in asymptomatic colonization of the upper respiratory tract, in some individuals, bacteremia and invasive meningococcal disease (IMD) occur. IMD commonly presents as meningitis and/or septicemia; pneumonia, septic arthritis, epiglottitis, and otitis media are less frequently observed. A high case fatality rate is associated with IMD (10%-15%), and approximately 20% of survivors have serious life-long sequelae such as limb amputation, hearing loss, and neurologic impairment.

Nearly all meningococcal disease worldwide is caused by 6 of the 12 characterized meningococcal serogroups (ie, A, B, C, W, X, and Y). Effective vaccines based on capsular polysaccharides have been developed for serogroups A, C, W, and Y. However, immunogenicity of the MenB polysaccharide is poor because of similarity to polysialic acid structures present on human neuronal cells. During recent years, meningococcal serogroup B (MenB) in particular has been associated with a large proportion of IMD in Europe, the United States, Canada, Australia, and New Zealand. Although vaccines based on outer membrane vesicles (OMVs) have been successfully used to control epidemics caused by a single MenB outbreak strain, the generated immune response is predominantly against the highly variable porin A protein (PorA). Therefore, effectiveness is generally limited to the target strain. Consequently, surface-exposed proteins capable of inducing protective bactericidal antibodies across diverse MenB strains have been sought for the development of a broadly effective MenB vaccine.

Factor H binding protein (FHbp; also known as LP2086 and GNA1870), a conserved surface-exposed lipoprotein expressed on nearly all strains of MenB, was identified as such a target. Based on amino acid sequence, FHbp variants segregate into 2 immunologically distinct subfamilies (termed subfamily A and subfamily B); each MenB strain expresses a single subfamily variant (see FIG. 1A).

MenB-FHbp (TRUMENBA®, bivalent rLP2086; Pfizer Inc, Philadelphia, PA, USA) is a bivalent, recombinant protein MenB vaccine composed of equal amounts of 2 recombinant lipidated FHbp antigens, one from subfamily A (variant A05) and the other from subfamily B (variant B01). Importantly, it is predicted that this combination of FHbp variants is capable of providing protection against diverse MenB strains. MenB-FHbp has been approved for the prevention of IMD in several countries and regions, including the United States, Canada, Europe, and Australia. Another MenB vaccine, MenB-4C (Bexsero®, 4CMenB; GlaxoSmithKline Vaccines, Srl, Siena, Italy), also has a recombinant FHbp component (nonlipidated variant 1.1 from subfamily B) as well as 2 other recombinant protein antigens and an OMV. Thus, MenB-4C is different from MenB-FHbp, which contains two variants of a single antigen to afford broad coverage.

The serum bactericidal assay using human complement (hSBA) measures complement-dependent, antibody-mediated lysis of meningococcal bacteria. An hSBA titer is defined as the highest serum dilution killing ≥50% of assay bacteria; an hSBA titer ≥1:4 is the accepted correlate of protection against meningococcal disease, and hSBA response rates based on this correlate have been used as surrogates for meningococcal vaccine efficacy. The SBA response rate has been specifically correlated with natural protection for the serogroup C and A polysaccharide vaccines. Because serogroup-specific polysaccharides are not variable, a single strain from each serogroup was sufficient to infer broad vaccine coverage. MenB OMV vaccines are also efficacious and vaccine-elicited hSBA titers correlated with protection against the target strain causing the epidemic. Accurately predicting strain coverage of protein-based vaccines is more complex using hSBA than for vaccines targeting capsular polysaccharides, given that protein sequence diversity and variability in expression levels differ among the different meningococcal disease strains. For example, (PorA is the predominant target for serum bactericidal antibodies conferring protection after OMV vaccine immunization. PorA is a cell surface porin whose small cell surface exposed region has a high degree of sequence diversity. It has been estimated that protective immunity would need to be demonstrated with strains expressing 20 different PorA serosubtypes to protect against approximately 80% of sporadic MenB disease-causing strains in the United States. Historically, OMV vaccines have contained 1 PorA and have not demonstrated protection against strains with PorA sequences that are heterologous in amino acid sequence compared with the vaccine antigen. Therefore, selection of representative test strains to demonstrate that vaccine-elicited antibodies can be effective against a meningococcal disease strain is of paramount importance for protein-based vaccines.

Immune sera elicited by MenB-FHbp in preclinical and early clinical studies demonstrated broad bactericidal antibodies that could kill diverse MenB strains containing FHbp subfamily A and B variants heterologous to the vaccine FHbp variants A05 and B01. In an early assessment of the potential breadth of MenB-FHbp coverage, 100 MenB isolates with diverse FHbp variants, geographic origins, and genetic backgrounds were tested in hSBAs using MenB-FHbp immune rabbit serum. Of the 100 strains tested, 87 were killed in these hSBAs. Analysis of the 13 strains that were not killed suggested that the threshold FHbp surface expression level on a given MenB strain affected the hSBA response. A threshold FHbp surface expression level was subsequently determined, above which isolates were predictably killed in hSBA. Additional investigations of potential factors determining strain susceptibility found that killing was largely independent of FHbp sequence variant, multilocus sequence type, or PorA subtype.

To select strains with broad antigenic and epidemiologic diversity for clinical testing, over 1200 invasive MenB disease isolates were collected from laboratories and health agencies in the United States and Europe to represent the prevalence of MenB isolates that were contemporary at the time of collection; all strains contained the FHbp gene. An unbiased approach was used to select 4 antigenically and epidemiologically diverse representative test strains for use in MenB-FHbp immunogenicity studies. Selection criteria included expression of FHbp variants heterologous to the vaccine antigens and adequately reflecting the diversity of FHbp in MenB disease isolates, low to medium FHbp surface expression levels, and low baseline hSBA seropositivity rates. These 4 primary MenB test strains express FHbp variants from both FHbp subfamilies (strain [variant]: PMB2001 [A22], PMB80 [A56], PMB2707 [B24], and PMB2948 [B44]; see FIG. 1A).

To supplement immunogenicity data generated using the 4 primary MenB test strains and to demonstrate that immune responses against the 4 primary MenB test strains are predictive of immune responses against the diversity of FHbp variants expressed by MenB disease-causing isolates, hSBAs using 10 additional test strains were developed. The 10 additional test strains were selected to include prevalent FHbp variants found in MenB disease-causing strains in the United States and Europe. Here, we (i) describe the strategy and criteria used to select the 10 additional test strains, and (ii) present data demonstrating that the immune responses measured by hSBA using the 4 primary MenB strains are predictive of the responses obtained using 10 additional test strains, which further demonstrate and support the broad coverage of the immune response elicited by MenB-FHbp.

Results

Sources and Selection Criteria for the Additional MenB Test Strains

Nine of the 10 additional MenB test strains were obtained from a collection of 1263 invasive disease-causing MenB strains (the MenB isolate collection). For the MenB isolate collection, US strains were from the Active Bacterial Core Surveillance sites (2000-2005), covering approximately 13% of the population. European isolates (2001-2006) were from the public health laboratories of Norway, France, Czech Republic and the Health Protection Agency in Manchester (which covers England, Wales, and Northern Ireland) and were collected systematically (every seventh or eighth isolate was included by order received at the country's reference laboratory) and represented approximately 13% of invasive MenB isolates during the period. The strains expressing FHbp variant A07 were obtained from an extension of the MenB isolate collection that included an additional 551 disease-causing MenB strains from Spain and Germany (n=1814). The extended MenB isolate collection was used as A07-expressing strains in the MenB isolate collection were not suitable because of the low surface expression of FHbp on these strains, high baseline seropositivity, and lack of readily available source of complement.

The criteria used to select the additional MenB test strains were (i) FHbp variant prevalence among MenB disease-causing strains in the United States and/or Europe, (ii) the FHbp variant needed to be different from those expressed by MenB primary test strains, (iii) in vitro FHbp expression levels at or below median levels for the respective FHbp variant group to ensure that the strain was representative of the variant group it belonged to, (iv) technical compatibility in the hSBA, and (v) being considered a predominant clonal complex for the variant group (if a predominant complex existed). Strains meeting these criteria also needed to be technically compatible in the hSBA, including adequate availability of suitable human complement lots (FIG. 2). Strains in each FHbp variant group with expression levels below the cutoff level (ie, at or below median levels for the respective FHbp variant group) were randomly selected, with the first strains within an FHbp variant group meeting the required genetic, phenotypic, and hSBA development criteria becoming the additional MenB test strains. An exception to this methodology was made for the strain expressing FHbp variant B03, which was selected in collaboration with and using guidance provided by the US FDA based on its previous use in a phase 2 study.

Characteristics of the Additional MenB Test Strains

Figure 1B:
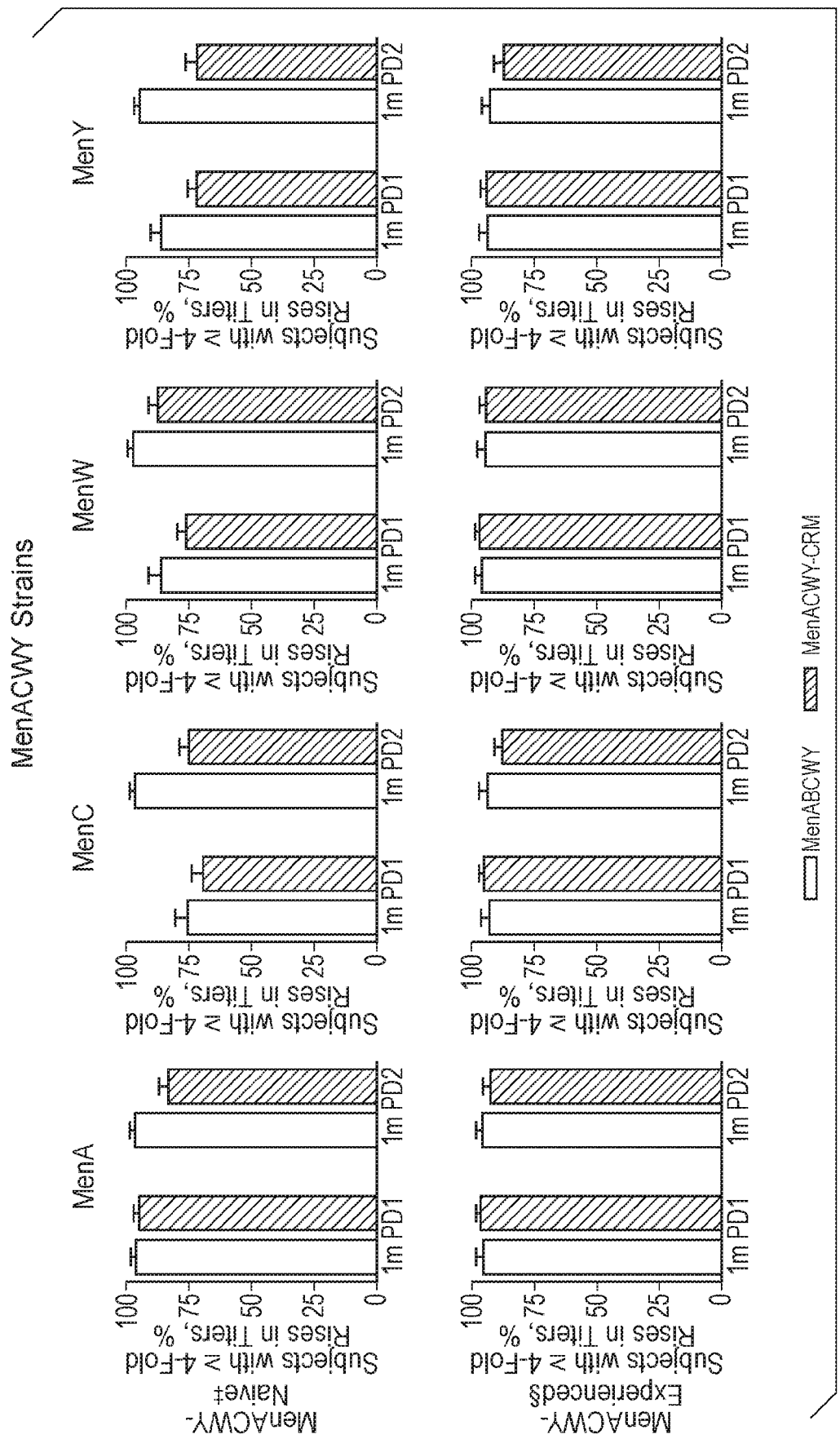

The 10 additional selected MenB test strains express FHbp variants A06, A07, A12, A15, A19, A29, B03, B09, B15, and B16 which differ from the ones in the 4 primary test strains (A22, A56, B24, B44) and have different sequences compared to the vaccine antigens (Table 23). The specific variants expressed by the 4 primary test strains are present in 42.0% (530/1263) of disease-causing isolates in the MenB isolate collection, and the specific variants expressed by the 10 additional test strains are present in an additional, non-overlapping 38.8% (490/1263) of disease-causing isolates in the MenB isolate collection (FIG. 1B).

TABLE 23

Characteristics of the 4 Primary and 10 Additional MenB Test Strains

| Strain | FHbp Variant | Percentage Identity to Vaccine Component | Strain MEASURE MFI$^a$ (±1 SD) | FHbp Variant Group MEASURE MFI Median$^b$ (±1 SD) | Clonal Complex | Country of Isolation |
|---|---|---|---|---|---|---|
| Primary Strains | | | | | | |
| PMB80 | A22 | 88.9 | 3127 (2440, 4007) | 2502 (1952, 3207) | CC41/44 | United States |
| PMB2001 | A56 | 98.1 | 5002 (3903, 6410) | 5002$^c$ | CC213 | France |
| PMB2948 | B24 | 86.2 | 6967 (5436, 8929) | 8457 (6599, 10,839) | CC32 | France |
| PMB2707 | B44 | 91.6 | 11,283 (8804, 14,461) | 14,753 (11,511, 18,907) | CC269 | United Kingdom |
| Additional Strains | | | | | | |
| PMB3010 | A06 | 96.2 | 3370 (2629, 4319) | 3088 (2410, 3958) | CC461 | United Kingdom |
| PMB3040 | A07 | 85.4 | 1379 (1076, 1767) | 1100 (858, 1409) | CC162 | Germany |
| PMB824 | A12 | 85.4 | 2540 (1982, 3255) | 2467 (1925, 3161) | CC35 | United States |
| PMB1672 | A15 | 85.1 | 2995 (2337, 3838) | 2904 (2266, 3721) | CC103 | France |
| PMB1989 | A19 | 88.1 | 1934 (1509, 2479) | 1759 (1372, 2254) | CC8 | United Kingdom |

TABLE 23-continued

Characteristics of the 4 Primary and 10 Additional MenB Test Strains

| Strain | FHbp Variant | Percentage Identity to Vaccine Component | Strain MEASURE MFI$^a$ (±1 SD) | FHbp Variant Group MEASURE MFI Median$^b$ (±1 SD) | Clonal Complex | Country of Isolation |
|---|---|---|---|---|---|---|
| PMB3175 | A29 | 93.1 | 3839 (2995, 4920) | 5994 (4677, 7682) | CC32 | United States |
| PMB1256 | B03 | 90.8 | 3976 (3102, 5096) | 2935 (2290, 3762) | CC41/44 | United Kingdom |
| PMB866 | B09 | 88.1 | 2089 (1630, 2677) | 2275 (1775, 2916) | CC269 | United Kingdom |
| PMB431 | B15 | 86.5 | 3785 (2953, 4851) | 4822 (3763, 6180) | CC41/44 | United States |
| PMB648 | B16 | 86.2 | 2347 (1831, 3008) | 1996 (1557, 2558) | CC41/44 | United Kingdom |

FHbp = factor H binding protein; MenB = *Neisseria meningitidis* serogroup B; MFI = mean fluorescence intensity; SBA = serum bactericidal assay.
$^a$MFI ± 1 SD from MEASURE assay.
$^b$Based on the MenB SBA isolate collection (n = 1263), except for variant group A07, which was calculated from the extended MenB SBA isolate collection (n = 1814). Strains in each FHbp variant group with expression levels at or below median levels for the respective FHbp variant group were randomly selected. The cutoff level adopted for each FHbp variant group was the observed median MFI plus 1 SD, using the precision estimate of 25.2% relative SD.
$^c$There is only one strain expressing A56; thus, no SD values are included.

Immunogenicity Analysis: Subjects With hSBA Titer ≥LLOQ for the 10 Additional Strains The 4 primary strains were used to assess serological responses after 2 or 3 doses of MenB-FHbp in subjects participating in 2 pivotal phase 3 studies in adolescents and young adults. Serological responses to the 10 additional hSBA strains were assessed in a subgroup of the study subjects. The majority of subjects had hSBAs lower limit of quantitation (LLOQ; ie, hSBA titer equal to 1:8 or 1:16, depending on strain) 1 month after dose 2 and 1 month after dose 3 for each of the primary (64.0%-99.1% and 87.1%-99.5%, respectively) and the 10 additional MenB test strains (51.6%-100.0% and 71.3%-99.3%, respectively) (Table 24). For the primary and additional MenB test strains, a substantial increase from baseline in the proportion of subjects achieving an hSBA titer ≥LLOQ was observed among MenB-FHbp recipients (0, 2, 6 month schedule) after the second MenB-FHbp dose, with additional increases after the third dose.

TABLE 24

Subjects With hSBA Titers ≥LLOQ (1:8 or 1:16) for Primary and Additional MenB Test Strains

| | % (95% CI) [n] | | | | | |
|---|---|---|---|---|---|---|
| | Adolescents$^a$ | | | Young Adults$^a$ | | |
| FHbp Variant | Prevaccination | 1 Month After Dose 2 | 1 Month After Dose 3 | Prevaccination | 1 Month After Dose 2 | 1 Month After Dose 3 |
| Primary strain | | | | | | |
| A22 | 33.2 (30.6, 35.9) [1238] | 94.3 (92.9, 95.5) [1263] | 97.8 (96.8, 98.5) [1266] | 33.6 (31.3, 35.9) [1704] | 84.7 (82.9, 86.4) [1697] | 93.5 (92.2, 94.6) [1714] |
| A56 | 27.5 (24.9, 30.2) [1135] | 99.1 (98.4, 99.5) [1222] | 99.5 (98.9, 99.8) [1229] | 32.2 (29.9, 34.5) [1657] | 97.4 (96.5, 98.1) [1701] | 99.4 (98.9, 9 9.7) [1708] |
| B24 | 6.4 (5.1, 7.9) [1264] | 66.4 (63.6, 69.0) [1216] | 87.1 (85.1, 88.9) [1250] | 33.1 (30.9, 35.4) [1696] | 86.5 (84.7, 88.1) [1685] | 95.1 (93.9, 96.0) [1702] |
| B44 | 3.6 (2.6, 4.8) [1230] | 64.0 (61.3, 66.8) [1204] | 89.3 (87.4, 90.9) [1210] | 11.0 (9.6, 12.6) [1716] | 68.3 (66.1, 70.6) [1693] | 87.4 (85.8, 89.0) [1703] |
| Additional strain | | | | | | |
| A06 | 9.4 (6.2, 13.5) [277] | 84.0 (75.0, 90.8) [79] | 95.7 (92.6, 97.8) [280] | 16.0 (11.9, 20.9) [275] | 77.8 (67.8, 85.9) [90] | 92.0 (88.1, 94.9) [275] |
| A07 | 43.1 (37.1, 49.3) [269] | 93.8 (86.9, 97.7) [90] | 96.4 (93.5, 98.3) [280] | 55.8 (49.7, 61.8) [274] | 97.9 (92.6, 99.7) [95] | 95.7 (92.6, 97.7) [277] |
| A12 | 3.9 (2.0, 6.9) [280] | 67.4 (57.0, 76.6) [64] | 75.1 (69.6, 80.1) [277] | 5.0 (2.8, 8.3) [278] | 57.6 (46.9, 67.9) [92] | 71.3 (65.5, 76.5) [275] |
| A15 | 20.7 (16.1, 26.1) [270] | 65.6 (55.0, 75.1) [61] | 87.2 (82.6, 91.0) [266] | 37.3 (31.6, 43.2) [279] | 83.2 (74.1, 90.1) [95] | 91.8 (87.9, 94.7) [279] |

TABLE 24-continued

Subjects With hSBA Titers ≥LLOQ (1:8 or 1:16) for Primary and Additional MenB Test Strains

| | % (95% CI) [n] | | | | | |
|---|---|---|---|---|---|---|
| | Adolescents[a] | | | Young Adults[a] | | |
| FHbp Variant | Prevaccination | 1 Month After Dose 2 | 1 Month After Dose 3 | Prevaccination | 1 Month After Dose 2 | 1 Month After Dose 3 |
| A19 | 11.3 (7.8, 15.7) [274] | 84.5 (75.8, 91.1) [82] | 92.7 (89.0, 95.5) [275] | 28.8 (23.5, 34.5) [278] | 87.4 (79.0, 93.3) [95] | 95.8 (92.7, 97.8) [284] |
| A29 | 17.5 (13.1, 22.5) [269] | 100.0 (96.3, 100.0) [97] | 98.6 (96.4, 99.6) [278] | 31.1 (25.7, 36.9) [280] | 96.8 (91.0, 99.3) [95] | 99.3 (97.5, 99.9) [283] |
| B03 | 4.3 (2.2, 7.4) [280] | 61.1 (50.3, 71.2) [55] | 92.5 (88.7, 95.3) [279] | 11.2 (7.7, 15.5) [277] | 57.9 (47.3, 68.0) [95] | 86.4 (81.8, 90.3) [273] |
| B09 | 15.2 (11.2, 19.9) [277] | 76.3 (66.4, 84.5) [71] | 86.2 (81.6, 90.1) [276] | 23.5 (18.6, 28.9) [277] | 65.3 (54.8, 74.7) [95] | 77.0 (71.6, 81.9) [274] |
| B15 | 28.7 (23.5, 34.5) [275] | 96.8 (90.9, 99.3) [90] | 98.2 (95.9, 99.4) [281] | 43.8 (37.8, 49.9) [274] | 86.5 (78.0, 92.6) [96] | 96.7 (93.9, 98.5) [276] |
| B16 | 7.6 (4.8, 11.4) [276] | 61.6 (50.5, 71.9) [53] | 81.7 (76.6, 86.0) [278] | 21.9 (17.1, 27.3) [270] | 51.6 (41.1, 62.0) [95] | 78.0 (72.6, 82.8) [273] |

FHbp = factor H binding protein; hSBA = serum bactericidal assay using human complement; LLOQ = lower limit of quantitation; MenB = *Neisseria meningitidis* serogroup B.
Observed proportions of subjects were summarized with exact 2-sided 95% CIs using the Clopper-Pearson method.
LLOQ = 1:16 for A06, A12, A19 and A22; LLOQ = 1:8 for A07, A15, A29, A56, B03, B09, B15, B16, B24, and B44.
[a]Evaluable immunogenicity population Positive Predictive Values for the Primary and Additional Strains The relationship between vaccine-induced hSBA responses for the primary MenB test strains and the 10 additional MenB test strains was assessed (Table 25). Within an FHbp subfamily, positive predictive values (PPVs) were greater than 80% for most primary/additional strain pairs 1 month after dose 3. Thus, the immune responses measured in hSBAs using the primary test strains were highly predictive of immune responses for the additional strains within the same subfamily. The PPVs 1 month after dose 2 usually were slightly lower than those observed 1 month after dose 3 and ranged from 61.6% to 100% and 70.0% to 100% for subfamily A and B strain pairs, respectively, across studies. In summary, all PPVs showed high predictability for protective responses when comparing the primary and additional strain hSBA responses.

TABLE 25

Positive Predictive Value of Immune Response to Primary Strain for Immune Response to Additional Strain following MenB-FHbp Vaccination

| | | % (95% CI)[a] [n/N][b] | | | |
|---|---|---|---|---|---|
| FHbp Variant | | Adolescents | | Young Adults | |
| Primary Test Strain | Additional Test Strain | 1 Month After Dose 2 | 1 Month After Dose 3 | 1 Month After Dose 2 | 1 Month After Dose 3 |
| A22 | A06 | 89.7 (81.27, 95.16) [78/87] | 96.0 (92.90, 97.97) [262/273] | 87.5 (77.59, 94.12) [63/72] | 94.0 (90.26, 96.59) [234/249] |
| | A07 | 98.9 (93.83, 99.97) [87/88] | 96.3 (93.37, 98.23) [263/273] | 100.0 (95.20, 100.00) [75/75] | 99.2 (97.15, 99.90) [249/251] |
| | A12 | 72.7 (62.19, 81.68) [64/88] | 75.9 (70.37, 80.90) [205/270] | 67.6 (55.68, 78.00) [50/74] | 77.9 (72.24, 82.91) [194/249] |
| | A15 | 70.9 (60.14, 80.22) [61/86] | 89.7 (85.31, 93.18) [227/253] | 92.4 (84.20, 97.16) [73/79] | 93.9 (90.27, 96.47) [246/262] |
| | A19 | 87.8 (79.18, 93.74) [79/90] | 95.4 (92.11, 97.60) [249/261] | 97.5 (91.15, 99.69) [77/79] | 98.9 (96.76, 99.77) [265/268] |

TABLE 25-continued

Positive Predictive Value of Immune Response to Primary Strain for Immune Response to Additional Strain following MenB-FHbp Vaccination

| FHbp Variant | | % (95% CI)[a] [n/N][b] | | | |
|---|---|---|---|---|---|
| | | Adolescents | | Young Adults | |
| Primary Test Strain | Additional Test Strain | 1 Month After Dose 2 | 1 Month After Dose 3 | 1 Month After Dose 2 | 1 Month After Dose 3 |
| | A29 | 100.0 (95.98, 100.00) [90/90] | 99.6 (97.91, 99.99) [263/264] | 98.7 (93.15, 99.97) [78/79] | 100.0 (98.62, 100.00) [266/266] |
| A56 | A06 | 84.3 (75.02, 91.12) [75/89] | 96.3 (93.29, 98.21) [260/270] | 83.3 (73.62, 90.58) [70/84] | 93.0 (89.23, 95.71) [251/270] |
| | A07 | 94.4 (87.37, 98.15) [84/89] | 97.0 (94.22, 98.71) [261/269] | 98.9 (93.90, 99.97) [88/89] | 96.0 (92.88, 97.96) [261/272] |
| | A12 | 68.2 (57.39, 77.71) [60/88] | 75.6 (69.94, 80.61) [201/266] | 61.6 (50.51, 71.92) [53/86] | 72.2 (66.47, 77.48) [195/270] |
| | A15 | 64.4 (53.38, 74.35) [56/87] | 89.2 (84.68, 92.76) [223/250] | 84.6 (75.54, 91.33) [77/91] | 92.0 (88.10, 94.90) [252/274] |
| | A19 | 83.5 (74.27, 90.47) [76/91] | 93.8 (90.12, 96.41) [242/258] | 90.1 (82.05, 95.38) [82/91] | 96.4 (93.48, 98.26) [268/278] |
| | A29 | 100.0 (96.03, 100.00) [91/91] | 98.9 (96.68, 99.76) [258/261] | 97.8 (92.29, 99.73) [89/91] | 99.6 (98.01, 99.99) [276/277] |
| B24 | B03 | 80.3 (68.16, 89.40) [49/61] | 97.1 (94.16, 98.83) [236/243] | 75.7 (63.99, 85.17) [53/70] | 89.9 (85.53, 93.28) [231/257] |
| | B09 | 88.7 (78.11, 95.34) [55/62] | 92.1 (87.96, 95.19) [222/241] | 82.9 (71.97, 90.82) [58/70] | 80.5 (75.17, 85.20) [207/257] |
| | B15 | 100.0 (94.22, 100.00) [62/62] | 99.6 (97.75, 99.99) [244/245] | 100.0 (94.87, 100.00) [70/70] | 98.8 (96.67, 99.76) [257/260] |
| | B16 | 82.1 (69.60, 91.09) [46/56] | 86.4 (81.46, 90.46) [210/243] | 70.0 (57.87, 80.38) [49/70] | 81.3 (76.01, 85.90) [209/257] |
| B44 | B03 | 78.9 (66.11, 88.62) [45/57] | 96.6 (93.40, 98.52) [227/235] | 88.9 (77.37, 95.81) [48/54] | 95.8 (92.38, 97.96) [227/237] |
| | B09 | 88.3 (77.43, 95.18) [53/60] | 90.1 (85.50, 93.61) [209/232] | 96.4 (87.47, 99.56) [53/55] | 85.9 (80.77, 90.09) [201/234] |
| | B15 | 100.0 (94.04, 100.00) [60/60] | 99.2 (96.99, 99.90) [235/237] | 100.0 (93.51, 100.00) [55/55] | 98.3 (95.74, 99.54) [233/237] |
| | B16 | 84.9 (72.41, 93.25) [45/53] | 85.5 (80.37, 89.77) [201/235] | 79.6 (66.47, 89.37) [43/54] | 83.8 (78.40, 88.24) [196/234] | hSBA = serum bactericidal assay using human complement; LLOQ = lower limit of quantitation; MenB = *Neisseria meningitidis* serogroup B.
LLOQ = 1:8 for strains expressing variants A07, A15, A29, A56, B03, B09, B15, B16, B24, and B44; LLOQ = 1:16 for strains expressing variants A06, A12, A19, and A22.
[a]Exact 2-sided CI based on the observed proportion of subjects using the Clopper-Pearson method.
[b]N = number of subjects with valid and determinate assay results for both the primary and additional strains with observed hSBA titer ≥LLOQ for the primary strain at 1 month after vaccination 2 and at 1 month after vaccination 3; n = number of subjects with observed hSBA titer ≥LLOQ for the given additional strain at 1 month after vaccination 2 and at 1 month after vaccination 3.

Discussion

A critical component of the clinical evaluation of the MenB-FHbp vaccine to determine the breadth of protection was the development of hSBAs using test strains with surface protein antigens whose sequence and expression variability are representative of the diversity of MenB disease-causing strains that were contemporary at the time of collection. As described in phase 3 studies in adolescents and young adults, hSBA response data for the 4 primary MenB test strains, all of which express FHbp variants heterologous to the vaccine antigens, strongly suggest that the bivalent MenB-FHbp vaccine provides broad coverage across diverse, disease-causing meningococcal strains. The 10 additional MenB test strains described here provide supportive immunologic data for MenB-FHbp and further confirm the validity of the use of the 4 primary test strains to measure the immune response to MenB-FHbp. As the responses obtained for the 4 primary test strains are predictive of the responses obtained for the additional 10 test strains, the immunological responses obtained by assessing the primary strains in hSBAs are representative of the diversity of strains causing invasive MenB disease.

For the hypothesis test-driven immunogenicity evaluations in licensure studies for MenB-FHbp, an unbiased approach was used to select the 4 primary MenB test strains from panels of disease-causing MenB collected in the United States and Europe. A similar method was used to select the 10 additional MenB hSBA test strains, taking into consideration specific selection criteria to ensure that test strains were representative of the antigenic diversity of MenB isolates. Collectively, the 14 MenB test strains represent the majority of the prevalent meningococcal FHbp, with FHbp variants corresponding to approximately 80% of circulating invasive disease-causing isolates in the United States and Europe.

Positive predictive value analyses were used to determine the association of immune responses, measured by hSBA, among primary and additional test strains expressing FHbps within the same subfamily. All of the PPV analyses showed the high predictability of the protective responses against the primary strain for the protective responses observed against the additional strains. These PPV analyses indicate that the responses observed against the 4 primary MenB test strains are representative of responses to other disease-causing MenB strains that express additional sequence-diverse FHbp variants different from the vaccine antigen variants.

The MenB-FHbp-elicited responses measured by hSBA to the 4 primary and 10 additional MenB test strains were evaluated using sera from individual vaccine recipients. By determining the proportion of vaccinated subjects with functional bactericidal antibodies, assessment of the breadth of MenB-FHbp coverage at the individual level was determined, which is not possible using pooled sera. The 4 primary MenB test strains were selected to represent the diversity of MenB disease-causing IMD and thus support the potential breadth of coverage for MenB-FHbp using hSBA. Responses of individuals with hSBA titers 1:4 are the accepted correlate of protection and a surrogate of meningococcal vaccine efficacy. Thus, the responses provide a comprehensive and biologically predictive assessment of breadth of vaccine coverage. The relevance of the hSBA responses to the 4 primary MenB test strains to describe breadth of vaccine coverage is supported by the demonstration of protective bactericidal responses by MenB-FHbp also observed against diverse and contemporary MenB outbreak strains from Europe and the United States and against non-MenB disease-causing strains (ie, meningococcal serogroups C, Y, W, and X).

Another methodology, the enzyme-linked immunosorbent assay-based Meningococcal Antigen Typing System (MATS), has been used to predict vaccine coverage of MenB-4C. However, MATS only predicts coverage of antigens specific to MenB-4C and is not useful for assessing coverage of other vaccines with different antigen compositions. Specifically, MATS measures antigen expression rather than bactericidal activity and is reported as a relative potency compared with a reference strain for each antigen. If the relative potency for any one of the component antigens is commensurate with bactericidal activity for MenB-4C immune sera (ie, achieves a positive bactericidal threshold), the strain is considered susceptible to killing. However, because sera from vaccinated individuals are not used in MATS, the assay is unable to predict the proportion of a population achieving hSBA titers ≥1:4 (ie, the correlate of protection) in response to immunization.

Of note, limitations in performing hSBAs exist. For example, hSBAs are labor intensive and can require large quantities of sera and assay-compatible complement, particularly when larger numbers of strains and/or sera are to be assessed. In addition, interlaboratory differences in the performance of the assay reagents and strains used in hSBAs limit comparison of responses and assessments of breadth of coverage between vaccines. A known limitation of PPV analysis is the dependence of the magnitude of the response on prevalence (ie, in this setting, the proportion of subjects achieving hSBA ≥LLOQ for the additional strains). However, it is notable in this analysis that although there was a range of postvaccination responses to the additional strains (at 1 month postdose 2 and postdose 3), PPVs were uniformly high.

Taken together, the immunogenicity data obtained from the 10 additional MenB hSBA test strains support the response data obtained from the 4 primary MenB hSBA test strains and confirm the broad coverage of MenB isolates conferred by MenB-FHbp. This is the first work that has applied a rigorous assessment of a MenB vaccine's elicited immune response using the epidemiology of MenB strains with regard to the vaccine antigen sequence and expression, in conjunction with the recognized surrogate of protection (hSBA), and, using this knowledge, led to vaccine licensure.

Methods

Quantitation of FHbp Surface Expression

For all strains, FHbp surface expression was quantified by the MEASURE assay, a flow cytometric assay using monoclonal antibody (MN86-994-11) recognition of a conserved FHbp epitope common to both FHbp subfamilies. Details of the MEASURE assay have been described previously. The cutoff level adopted for each FHbp variant group was the observed median mean fluorescence intensity plus 1 standard deviation, using the precision estimate of 25.2% relative standard deviation.

Immunogenicity Analysis

Each of the 10 additional MenB test strains were used in hSBAs to test sera from subjects participating in 2 pivotal phase 3 studies of MenB-FHbp. A total of 900 subjects from each study were to be divided into 3 subsets (n=300 each); the 10 additional test strains were allocated across these subsets so that 2 subsets each included 3 test strains and 1 subset included 4 test strains. The subsets included samples from 300 subjects to ensure that 150 evaluable hSBA results from each study would be obtained. Immune responses measured by hSBA using phase 3 clinical study sera were based on the assay LLOQ, which was an hSBA titer equal to 1:8 or 1:16 depending on the strain.

Positive Predictive Value Analyses

The PPV for each primary/additional strain pair within an FHbp subfamily was defined as the proportion of subjects responding to the additional strain (hSBA titer ALDO for the additional strain) among the total number of primary strain responders (hSBA titer LLOQ for the primary strain). PPV analyses assessed whether observed hSBA responses to the 4 primary strains predicted immune responses to additional strains expressing FHbps from the same subfamily.

Example 20: Pentavalent Meningococcal (MenABCWY) Vaccine is Safe and Well Tolerated With Immunogenicity Noninferior to Coadministered MenB-FHbp and MenACWY-CRM in a Phase 2 Study of Healthy Adolescents and Young Adults Background: Meningococcal serogroup A, B, C, W and Y cause nearly all meningococcal disease globally. Vaccination is complicated by different dosing recommendations for serogroup B (MenB) and quadrivalent (MenACWY) vaccines, which could be solved with a single pentavalent vaccine. This study in adolescents and young adults evaluated a new pentavalent MenABCWY vaccine that combines 2 licensed vaccines, MenB-FHbp (TRUMENBA®; bivalent rLP2086) and MenACWY-TT (NIMENRIX®), into a single vaccine.

Methods: In this ongoing, randomized, controlled, observer-blinded, multicenter study (NCT03135834), MenB vaccine-naive and MenACWY-naive or -experienced healthy 10-25-year-olds were randomized 1:2 to MenABCWY (Month 0, 6) or MenB-FHbp (Month 0, 6) and MenACWY-CRM (Month 0). Immune responses were measured by serum bactericidal activity assays with human complement (hSBA) against serogroup A, C, W and Y strains and 4 diverse, vaccine-heterologous MenB strains. Endpoints included percentages of subjects achieving 4-fold rises in titers from baseline. Noninferiority of immune responses were assessed a priori at the 10% margin (95% CI lower limit>−10%). Safety was assessed.

Results: Following dose 2, high percentages of MenABCWY (n=543) and MenB-FHbp (n=1057) recipients achieved ≥4-fold rises against each of the 4 MenB strains (75.8-94.7% vs 67.4-95.0%) and titers at least the lower limit of quantification against all 4 strains combined (79.9% vs 74.3%; FIG. 1A). MenABCWY was noninferior to MenB-FHbp for all 5 endpoints. MenABCWY was also noninferior to a single MenACWY-CRM dose with 75.5-96.9% and 93.0-97.4% of MenABCWY recipients after dose 1 or 2, respectively, achieving ≥4-fold rises against serogroup A, C, W and Y depending on prior MenACWY experience (FIG. 1B). Local reactions and systemic events after MenABCWY or MenB-FHbp were similarly frequent, mostly mild/moderate in severity (FIG. 2), and unaffected by MenACWY experience.

6.2.2.3 Immunogenicity Results from MenABCWY Clinical Development Program (Study B1971057) This portion of the study was the Phase 2 component of the overall study. For the MenB component of MenABCWY, the proportions of MenABCWY and bivalent rLP2086+MenACWY-CRM recipients achieving a 4-fold rise from baseline in hSBA titer at 1 month after Vaccination 2 were 75.8% and 73.8%, respectively, for PMB80 (A22); 94.7% and 95.0%, respectively, for PMB2001 (A56); 76.1% and 67.4%, respectively, for PMB2948 (B24); and 91.7% and 86.4%, respectively, for PMB2707 (B44). The proportions of MenABCWY and bivalent rLP2086+MenACWY-CRM recipients achieving a composite response (hSBA titers ≥LLOQ for all 4 MenB test strains) at 1 month after Vaccination 2 were 79.9% and 74.3%, respectively.

Conclusion: These results indicate that MenABCWY, whether given as a single dose or as a 2-dose series separated by 6 months, provides a high degree of protective immunity against MenB after 2 doses and MenACWY after 1 or 2 doses similar to that achieved when administering bivalent rLP2086 (0, 6-month) and MenACWY-CRM (0-month) separately, regardless of prior ACWY experience. MenABCWY 4-fold immune responses from baseline were robust and noninferior to MenB-FHbp and MenACWY-CRM administered separately. Vaccination on a 0-, 6-month schedule was safe and well tolerated. The favorable benefit-risk profile supports further MenABCWY development as a simplified alternative to current meningococcal vaccination practices.

Data generated from study B1971057 (MenABCWY [FIH]) demonstrated responses to MenABCWY to be non-inferior to TRUMENBA (meningococcal group B bivalent recombinant lipoprotein 2086 Vaccine) (MenB evaluation) and MENVEO (meningococcal (groups A, C, Y, and W-135) oligosaccharide CRM197 conjugate vaccine) (MenACWYCRM evaluation) when administered to healthy individuals 10 to 25 years of age (see Section 5.2). There was no immune interference between the component parts of MenABCWY observed in this FIH study.

Example 21: Effect of Shipping Stresses on Suspension Vaccines

This example illustrates the effect of shipping stresses (shock/drop, vibration, low-pressure/high altitude, and temperature) on the suspension vaccine. Re-dispersion of the vaccine suspension is an important consideration. Understanding the factors that can affect re-dispersion times to minimize re-dispersion time for end-users is the key product development goal. We present the systematic way of assessing the parameters that affect the re-dispersion time for a suspension vaccine and associated control strategy.

Suspension vaccines are thermodynamically unstable systems that constitute significant challenges in maintaining physical properties during storage and shipping in comparison to liquid or lyophilized powder. Although shipping stresses could impact product quality as well as the physical properties of a vaccine product, this example focuses on the impact of shipping stresses on the physical properties of suspension vaccines. Implications for product quality is out of scope since product quality is molecule dependent and can be evaluated by product-specific analytical and biological methods.

Aluminum-containing adjuvants have been included in vaccines to enhance or modify the immune response to antigens for over seven decades. Aluminum-containing vaccine is a suspension in which the internal phase consists of insoluble aluminum-containing salts (aluminum phosphate or aluminum hydroxide), and the external phase is a liquid vehicle. The addition of insoluble adjuvants to a vaccine drug product results in a suspension where the dispersed phase tends to settle with time. Ideally, a suspension should be uniform, and any sedimentation which occurs during storage can be easily re-dispersed on agitation. Compare a pre-filled syringe containing vaccine suspension before and after re-dispersion. Often enough, the re-dispersion issue is prevalent after the suspension is filled into pre-filled syringes and kept for long term storage. Countless research has focused on the addition of controlled flocculating agents or polymer additives to form a large loose and easily dispersible sediments 4. Several commercial aluminum-based vaccines clearly instruct in their package insert to “shake vigorously immediately before use.” On Apr. 26, 2010, WHO recommended recall and destruction of all lots of SHAN 5 vaccine as a precautionary measure following incidents of white sediment sticking to SHAN 5 vaccine vials that were difficult or impossible to re-suspend 5. Therefore, re-dispersion of vaccine suspension should be evaluated thoroughly to understand the factors affecting the re-dispersion time, and if needed, mitigation countermeasures can be placed.

INTERPLAY BETWEEN PARTICLE SIZE, CHARGE AND SETTLING RATE. It is essential to understand the factors that affect suspension stability as we seek to understand the cause for increased redispersion time. In this section, background on considerations for suspension stability is presented along with a case study of two suspensions to understand the interplay between particle size, charge, and settling of the suspension.

In an ideal suspension system, the dispersed phase is suspended for a prolonged time, and if settling of the sparse system happens, the dispersed system can be easily resuspended or dispersed. Suspension stability can be achieved through thermodynamic or kinetic means. Thermodynamic stability approaches include imparting charge on the suspension particle surface, thereby inducing steric hindrance due to particle-particle repulsion leading to suspension stabilization. On the other hand, a kinetic approach includes increasing viscosity of the suspension results in reduced settling of suspension and, hence providing the stability. Particle size plays an essential role in this interplay of thermodynamic and kinetic stability. For suspension systems which have particle size more than sub-micron, density differences between the clear phase and dispersed phase are significant factors and can lead to settling of the dispersed phase due to gravity. It is reported that particle size may affect the flocculation or coagulation of a suspension system. PEG, for example, is added to a lot of injectable solid/liquid suspensions to allow the solid active ingredient particles to form bigger flocculated sediment, thus making the sediment easier to resuspend. Whereas super-micron particles are ideally suited to slow down the dissolution kinetics, they are much more affected by gravity effects, which may lead to rather compact and hardly re-suspendable sediment.

Sedimentation or settling is a result of collective interactions in concentrated suspensions. Collective interactions include hydrodynamic and particle-particle interactions (determined through charge-charge interactions). Hydrodynamic effects account for the retardation of the backflow, which is the reverse flow of fluid to compensate for the movement of settling particles. Particle-particle interactions are due to the attractive self-depletion and repulsive structural forces in concentrated dispersions.

Two suspension systems are illustrated to describe the interplay between charge, settling rate, and particle size. Vaccine suspension drug product in the study is designated as suspension 1 and 2 for this illustration. Suspension 1 and suspension 2 depict comparable particle size (approximately 15 μm). These suspensions behave vastly differently when settling rates are compared. Suspension 1 settles significantly faster with settling rate of approximately 0.04 abs/min while suspension 2 takes weeks even to start settling. This difference is stark despite having comparable particle size distribution. As discussed earlier, an understanding charge on the particle surface becomes essential. Zeta potential for suspension 1 is approximately −5 mV, while suspension 2 has a zeta potential of −45 mV. Since suspension 1 has a little charge on the particle surface, thermodynamic suspension instability promotes particle-particle attraction and eventually settling of the dispersed phase.

On the other hand, high charge for suspension 2 system makes the systemic thermodynamically stable and particle-particle repulsion leads to significantly slow settling of the dispersed phase. Based on this, suspension 2 imparts maximum thermodynamic stability and is desirable. Although the biggest question is whether the thermodynamically stable suspension is easier to disperse after the dispersed system settles or vice versa, how does this translate into ease of suspension in syringes for vaccine suspensions? Our data with these two suspensions suggests that although suspension 1 is thermodynamically unstable due to lack of charge results in particle-particle interaction and possibly the formation of bigger flocculated sediment resulting in faster sedimentation and hence making the dispersed phase system easily resuspendable. On the other hand, suspension 2 takes a significantly longer time to settle due to charge-charge polarity, although once settled, the finer particles pack together to form significantly harder to resuspend settled dispersed phase.

Based on these observations and background, two key questions were tested in our studies to understand the increase in redispersion time for suspension 1 vaccine: Can shipping stress alter thermodynamic suspension stability resulting in increased redispersion time? What is the impact of individual shipping stress components during shipping, and if there is a correlation to increased redispersion time?

Effect of Shipping Stress on Thermodynamic Suspension Stability

In another study, vaccine drug product suspension was subjected to simulated shipping stresses including shipping tempereature, shock/drop and vibration. Thermodynamic suspension stability was determined through measurement of charge (zeta potential), particle size distribution, and settling rate before and after shipping.

Drug product suspension exhibited zeta potential values around −5 mV, suggesting that there is a little charge on suspension particles. This thermodynamic instability of the suspension promotes particle-particle attraction and eventually settling of the dispersed phase. Our data suggest that there were no apparent changes in zeta potential value, particle size distribution, and measured settling rate before and after the simulated shipping of syringes. These results suggest that shipping stress does not alter the thermodynamic suspension stability for drug product suspension. Since these properties are not changed after shipping, it can be concluded that thermodynamic stability is not the driving factor for observed increased redispersion time and necessitates the need to evaluate the effect of shipping stresses and understand if any specific physical mechanism is contributing to the observed redispersion time.

Impact of Individual Shipping Stresses on Redispersion Time

When a package is shipped, the product will distinctly experience various shipping stresses. These include shock/drop stress when the package is dropped from various heights, vibrations during either truck or aircraft transport, although the amplitude of vibration frequency is different between aircraft and truck. The impact of individual shipping stress on redispersion time was assessed when drug product syringes were subjected to simulated shipping[11]. The study design also included the assessment of the impact of shipping stress as a function of syringe orientation. Syringes were kept in three distinct orientations: tip cap down, tip cap up, and tip cap horizontal. The study aims to decipher individual stresses and understand the impact.

It was observed that shock/drop stress reduced re-dispersion time for tip cap down orientation, and there was little effect of shock/drop on the re-dispersion in tip cap horizontal and tip cap up orientations.

On the other hand, aircraft vibration increased re-dispersion time for tip cap down orientation. This was an interesting finding and can be related to the vibration frequencies encountered during aircraft transportation. Vibration frequency when syringes are in tip cap down orientation can further facilitate the particles of the suspension to go down the syringe bore. There was little effect of aircraft vibration on the syringes arranged tip cap up and horizontal. Similar to aircraft vibration, truck vibration increased re-dispersion time in tip cap down orientation. These findings are similar to aircraft vibration, although the extent of increase in redispersion time was more compared to aircraft vibration. Additionally, there was little effect of truck vibration on the syringes arranged tip cap up and horizontally consistent with aircraft vibration. Also, when the syringes were assessed for redispersion time for combination stress (shock/drop, aircraft vibration, truck vibrational shock/drop), the data was confounding, suggesting that in actual shipping, most likely one or more modes of shipping stress can dominate the results-producing utterly different outcome.

It was interesting to note that vibration frequency intensity is an important factor based on the differences seen in aircraft and truck vibration. The increase in re-dispersion time when the syringe is placed in tip cap down orientation can be because the downward movement of suspension particles originated from gravity and aggravated by vibration facilitates tight packing of larger particles with the smaller particles filling the void spaces. Particles at the bottom, especially the bore of the syringe, are gradually pressed together by the weight of the ones above.

When a drug product is shipped in tip cap up orientation, gravity effect still exists, but sedimentation happens in the broader surface of the plunger instead of the narrow bore. The packing of the mass is not apparent. When drug product is shipped in tip cap horizontal orientation, the lateral motion resulted from Brownian movement and convection current from vibration overcome gravity. Even when sedimentation does happen, it will occur on the large surface of the syringe wall with little chance of packing the particles. Therefore, re-suspension is not an issue for both tip cap up and tip cap horizontal orientations with tip cap horizontal orientation yielding slightly better results presumably due to larger surface area. When shipped, shipping vibration is the dominant force that results in the end state, where sedimentation is packed. Depending on the orientation of the syringe and different surface areas available, re-dispersion time corresponds to these open surface areas.

Mitigation Strategy to Reduce High Redispersion Time

Based on the simulated shipping study data, it is clear that either tip cap horizontal or tip cap up orientation can mitigate the higher re-dispersion times for the vaccine suspension.

Impact of Shipping Temperature on Suspension Vaccines

In addition to re-dispersion, product quality of vaccine suspensions could also be affected by temperature during shipping. After freezing, the bond between adjuvant and antigen could be broken. Separated adjuvant tends to form agglomerate that gets bigger in particle size and weight, then gradually settles to the bottom of the container. The size of the agglomerate may increase after repeated freezing and thawing cycles. The formation of agglomerate impacts both re-dispersion, physical and chemical properties of the product. WHO Guidelines on the International Packaging and Shipping of Vaccines have attached a shake test protocol to determine whether adsorbed vaccines have been affected by freezing. The guidelines also specify the shake test on a random sample of vaccines if there is an indication that temperatures have dropped below zero during transportation. Higher temperatures, on the other hand, could also impact product quality of vaccine suspension, resulting in particle formation and chemical property changes or both. Therefore, WHO specifies +8° C. as the maximum temperature allowed inside the insulated Class A packaging during international transport, for at least 48 hours. The maximum temperature allowed for Class B and C packaging is +30° C.

The following clauses describe additional embodiments of the invention:

C1. A composition comprising (a) a first polypeptide derived from a *Neisseria meningitidis* factor H binding protein (fHBP); (b) a second polypeptide derived from a *Neisseria meningitidis* factor H binding protein (fHBP); (c) a *Neisseria meningitidis* serogroup A capsular saccharide conjugate; (d) a *Neisseria meningitidis* serogroup C capsular saccharide conjugate; (e) a *Neisseria meningitidis* serogroup W capsular saccharide conjugate; and (f) a *Neisseria meningitidis* serogroup Y capsular saccharide conjugate; wherein the composition elicits an immune response to any one of the *N. meningitidis* serogroups A, C, W-135 and Y capsular polysaccharides, wherein said serum bactericidal antibody response is higher than that elicited by a licensed vaccine against the *N. meningitidis* serogroup.

C2. The method according to clause C1, wherein the polypeptide comprises an amino acid sequence having at least 70% identity to any one amino acid sequence selected from SEQ ID NO: 1 to SEQ ID NO: 62.

C3. The method according to clause C1, wherein the composition comprises (a) a first polypeptide comprising the amino acid sequence set forth in SEQ ID NO: 1; (b) a second polypeptide comprising the amino acid sequence set forth in SEQ ID NO: 2; (c) a *Neisseria meningitidis* serogroup A capsular saccharide conjugated to an adipic acid dihydrazide (ADH) linker by 1-cyano-4-dimethylamino pyridinium tetrafluoroborate, wherein the linker is conjugated to tetanus toxoid by carbodiimide chemistry; (d) a *Neisseria meningitidis* serogroup C capsular saccharide conjugated to an ADH linker by 1-cyano-4-dimethylamino pyridinium tetrafluoroborate, wherein the linker is conjugated to tetanus toxoid by carbodiimide chemistry; (e) a *Neisseria meningitidis* serogroup W capsular saccharide directly conjugated to tetanus toxoid by 1-cyano-4-dimethylamino pyridinium tetrafluoroborate, in the absence of a linker; and (f) a *Neisseria meningitidis* serogroup Y capsular saccharide directly conjugated to tetanus toxoid by 1-cyano-4-dimethylamino pyridinium tetrafluoroborate, in the absence of a linker.

C4. The method according to any one of clause C1 to clause C3, wherein the composition elicits an immune response to any one of *N. meningitidis* serogroups A, C, W-135 and Y, wherein said serum bactericidal antibody response is higher than that elicited by a licensed *N. meningitidis* serogroups A, C, W-135 and Y meningococcal capsular polysaccharide vaccine.

C5. The method according to any one of clause C1 to clause C3, wherein the composition elicits an immune response to *N. meningitidis* serogroup A, wherein said serum bactericidal antibody response is higher than that elicited by a licensed *N. meningitidis* serogroups A, C, W-135 and Y meningococcal capsular polysaccharide vaccine.

C6. The method according to any one of clause C1 to clause C3, wherein the composition elicits an immune response to *N. meningitidis* serogroup C, wherein said serum bactericidal antibody response is higher than that elicited by a licensed *N. meningitidis* serogroups A, C, W-135 and Y meningococcal capsular polysaccharide vaccine.

C7. The method according to any one of clause C1 to clause C3, wherein the composition elicits an immune response to *N. meningitidis* serogroup W, wherein said serum bactericidal antibody response is higher than that elicited by a licensed *N. meningitidis* serogroups A, C, W-135 and Y meningococcal capsular polysaccharide vaccine.

C8. The method according to any one of clause C1 to clause C3, wherein the composition elicits an immune response to *N. meningitidis* serogroup Y, wherein said serum bactericidal antibody response is higher than that elicited by a licensed *N. meningitidis* serogroups A, C, W-135 and Y meningococcal capsular polysaccharide vaccine.

C9. The method according to any one of clause C1 to clause C3, wherein the composition elicits an immune response to each of the *N. meningitidis* serogroups A, C, W-135 and Y, wherein said serum bactericidal antibody response is higher than that elicited by a licensed *N. meningitidis* serogroups A, C, W-135 and Y meningococcal capsular polysaccharide vaccine.

C10. The method according to any one of clause C1 to clause C3, wherein the composition elicits an immune response to *N. meningitidis* serogroup B, wherein said serum bactericidal antibody response is higher than that elicited by a licensed meningococcal serogroup B factor H binding vaccine.

C11. The method according to any one of clause C1 to clause C3, wherein the composition elicits an immune response to each of the *N. meningitidis* serogroups A, C, W-135 and Y, wherein said serum bactericidal antibody response to each of the *N. meningitidis* serogroups A, C, W-135 and Y capsular polysaccharides is higher than that elicited by a licensed *N. meningitidis* serogroups A, C, W-135 and Y meningococcal capsular polysaccharide vaccine; and the composition elicits an immune response to *N. meningitidis* serogroup B, wherein said serum bactericidal antibody response is higher than that elicited by a licensed meningococcal serogroup B factor H binding vaccine; wherein the licensed *N. meningitidis* serogroups A, C, W-135 and Y meningococcal capsular polysaccharide vaccine and the licensed meningococcal serogroup B factor H binding vaccine are administered sequentially and are not in a combined dose.

C12. The method according to any one of clause C1 to clause C3, wherein the composition comprises an adjuvant.

C13. The method according to any one of clause C1 to clause C3, wherein the composition comprises an aluminum adjuvant.

C14. The method according to any one of clause C1 to clause C3, wherein the composition comprises aluminum hydroxide.

C15. The method according to any one of clause C1 to clause C3, wherein the composition comprises aluminum phosphate.

C16. The method according to any one of clause C1 to clause C3, wherein the composition comprises comprising aluminum.

C17. The method according to any one of clause C1 to clause C3, wherein at least 90% of the first polypeptide is bound to aluminum in the composition.

C18. The method according to any one of clause C1 to clause C3, wherein at least 90% of the second polypeptide is bound to aluminum in the composition.

C19. The method according to any one of clause C1 to clause C3, wherein the composition is formulated as a sterile liquid.

C20. The method according to any one of clause C1 to clause C3, wherein the composition comprises a pharmaceutically acceptable preservative.

C21. The method according to any one of clause C1 to clause C3, wherein the composition comprises polysorbate-80.

C22. The method according to any one of clause C1 to clause C3, wherein the composition comprises Tris-HCl; sodium chloride; sucrose; histidine; polysorbate 80; and aluminum phosphate.

C23. The method according to any one of clause C1 to clause C3, wherein the composition comprises about 120 μg/ml of the first polypeptide; about 120 μg/ml of the second polypeptide; about 0.5 mg/ml aluminum as aluminum phosphate; about 0.02 mg polysorbate-80; about 10 mM histidine; and about 150 mM sodium chloride.

C24. The method according to any one of clause C1 to clause C3, wherein the composition comprises about 60 μg of the first polypeptide; about 60 μg of the second polypeptide; about 5 μg of the MenA capsular saccharide conjugated to about 7.5 μg TT; about 5 μg of the MenC capsular saccharide conjugated to about 7.5 μg TT; about 5 μg of the MenW capsular saccharide conjugated to about 3.75 μg TT; about 5 μg of the MenY capsular saccharide conjugated to about 3.25 μg TT; about 97 μg Tris-HCl, pH 6.8±0.3; 4.69-4.71 mg of sodium chloride; about 28 mg of sucrose; about 0.78 mg of L-Histidine; about 0.02 mg polysorbate-80; about 0.25 mg aluminum; and further comprising 0.5 mL water, per dose.

C25. The method according to any one of clause C1 to clause C3, wherein the immune response comprises a serum bactericidal antibody.

C26. The method according to any one of clause C1 to clause C3, wherein the composition is capable of eliciting a booster immune response to at least one of the *N. meningitidis* serogroups A, C, W-135 and Y.

C27. The method according to any one of clause C1 to clause C3, wherein the composition is capable of eliciting a booster immune response to *N. meningitidis* serogroup B.

C28. The method according to any one of clause C1 to clause C3, wherein the immune response is elicited in a human 10 to 26 years old.

C29. The method according to any one of clause C1 to clause C3, wherein the immune response is elicited in a human aged 12 to <18 Months or 18 to <24 Months.

C30. The method according to any one of clause C1 to clause C3, wherein the immune response is elicited in a human aged 18 to <24 Months.

C31. The method according to any one of clause C1 to clause C3, wherein the immune response is elicited in a human aged 24 Months to <10 Years.

C32. The method according to any one of clause C1 to clause C3, wherein the immune response is elicited in a human that is seronegative against *N. meningitidis* serogroups A, C, W-135 and Y.

C33. The method according to any one of clause C1 to clause C3, wherein the immune response is elicited in a human that is seropositive against *N. meningitidis* serogroups A, C, W-135 and Y.

C34. The method according to any one of clause C1 to clause C3, wherein the composition is administered to the human in at least two doses, wherein the second dose is about 6 months after the first dose.

C35. The method according to clause C34, wherein the human is at least 10 years of age and at most 17 years of age.

C36. The method according to clause C35, wherein a third dose of the composition is administered to the human, wherein the human is at least 16 years of age.

C37. The method according to any one of clause C1 to clause C3, wherein the composition is administered to the human in at most two doses, wherein the second dose is about 6 months after the first dose.

C38. The method according to any one of clause C1 to clause C3, wherein the composition elicits an immune response against A22.

C39. The method according to any one of clause C1 to clause C3, wherein the composition elicits an immune response against A56.

C40. The method according to any one of clause C1 to clause C3, wherein the composition elicits an immune response against B24.

C41. The method according to any one of clause C1 to clause C3, wherein the composition elicits an immune response against B44.

C42. The method according to any one of clause C1 to clause C3, wherein the composition comprises about 60 µg of the first polypeptide; about 60 µg of the second polypeptide; about 5 µg of the MenA capsular saccharide conjugated to about 7.5 µg TT; about 5 µg of the MenC capsular saccharide conjugated to about 7.5 µg TT; about 5 µg of the MenW capsular saccharide conjugated to about 3.75 µg TT; about 5 µg of the MenY capsular saccharide conjugated to about 3.25 µg TT; about 97 µg Tris-HCl, pH 6.8±0.3; 4.69-4.71 mg of sodium chloride; about 28 mg of sucrose; about 0.78 mg of L-Histidine; about 0.02 mg polysorbate-80; about 0.25 mg aluminum; and further comprising 0.5 mL water, per dose.

C43. A composition comprising (a) a first polypeptide derived from a *Neisseria meningitidis* factor H binding protein (fHBP); (b) a second polypeptide derived from a *Neisseria meningitidis* factor H binding protein (fHBP); (c) a *Neisseria meningitidis* serogroup A capsular saccharide conjugate; (d) a *Neisseria meningitidis* serogroup C capsular saccharide conjugate; (e) a *Neisseria meningitidis* serogroup W capsular saccharide conjugate; and (f) a *Neisseria meningitidis* serogroup Y capsular saccharide conjugate; wherein the composition elicits an immune response to at least one of *N. meningitidis* serogroups A, C, W-135 and Y, wherein said serum bactericidal antibody response is higher than that elicited by a licensed vaccine against the *N. meningitidis* serogroup.

C44. The composition according to clause C43, wherein the polypeptide comprises an amino acid sequence having at least 70% identity to any one amino acid sequence selected from SEQ ID NO: 1 to SEQ ID NO: 62.

C45. A composition comprising (a) a first polypeptide derived from a *Neisseria meningitidis* factor H binding protein (fHBP); (b) a second polypeptide derived from a *Neisseria meningitidis* factor H binding protein (fHBP); (c) a *Neisseria meningitidis* serogroup A capsular saccharide conjugated to an adipic acid dihydrazide (ADH) linker by 1-cyano-4-dimethylamino pyridinium tetrafluoroborate, wherein the linker is conjugated to tetanus toxoid by carbodiimide chemistry; (d) a *Neisseria meningitidis* serogroup C capsular saccharide conjugated to an ADH linker by 1-cyano-4-dimethylamino pyridinium tetrafluoroborate, wherein the linker is conjugated to tetanus toxoid by carbodiimide chemistry; (e) a *Neisseria meningitidis* serogroup W capsular saccharide directly conjugated to tetanus toxoid by 1-cyano-4-dimethylamino pyridinium tetrafluoroborate, in the absence of a linker; and (f) a *Neisseria meningitidis* serogroup Y capsular saccharide directly conjugated to tetanus toxoid by 1-cyano-4-dimethylamino pyridinium tetrafluoroborate, in the absence of a linker; wherein the composition elicits an immune response to each of the *N. meningitidis* serogroups A, C, W-135 and Y capsular polysaccharides, wherein said serum bactericidal antibody response is higher than that elicited by a licensed *N. meningitidis* serogroups A, C, W-135 and Y meningococcal capsular polysaccharide vaccine.

C46. A method for inducing an immune response against a *Neisseria meningitidis* serogroup B subfamily A strain and against a *Neisseria meningitidis* serogroup B subfamily B strain in human, comprising administering to the human an effective amount of the composition according to any one of clause C43 to clause C45.

C47. A method for inducing an immune response against a *Neisseria meningitidis* serogroup A, a *Neisseria meningitidis* serogroup C, a *Neisseria meningitidis* serogroup W, and/or a *Neisseria meningitidis* serogroup Y strain in a human, comprising administering to the human an effective amount of the composition according to any one of clause C43 to clause C45.

C48. A method for inducing an immune response against a *Neisseria meningitidis* serogroup A, *Neisseria meningitidis* serogroup B, a *Neisseria meningitidis* serogroup C, a *Neisseria meningitidis* serogroup W, and/or a *Neisseria meningitidis* serogroup Y strain in a human, comprising administering to the human an effective amount of the composition according to any one of clause C43 to clause C45.

C49. A method for inducing an immune response against a *Neisseria meningitidis* serogroup A, *Neisseria meningitidis* serogroup B, a *Neisseria meningitidis* serogroup C, a *Neisseria meningitidis* serogroup W, a *Neisseria meningitidis* serogroup Y strain, and/or a *Neisseria meningitidis* serogroup X strain in a human, comprising administering to the human an effective amount of the composition according to any one of clause C43 to clause C45.

C50. The method according to any one of clauses C46 to C49, wherein the patient has not previously received a multivalent meningococcal capsular saccharide-carrier protein conjugate vaccine prior to the first administration of the composition according to any one of clause C43 to clause C45.

C51. The method according to any one of clauses C46 to C49, wherein the patient previously received a multivalent meningococcal capsular saccharide-carrier protein conjugate vaccine prior to the first administration of the composition according to any one of clause C1 and clause 010.

C52. Use of an effective amount of a composition for inducing an immune response against *Neisseria meningitidis* serogroup B in a human, wherein said composition comprises a) a first lipidated polypeptide comprising the amino acid sequence set forth in SEQ ID NO: 1, and b) a second lipidated polypeptide comprising the amino acid sequence set forth in SEQ ID NO: 2, wherein the composition induces an immune response against at least one *N. meningitidis* serogroup B strain expressing a polypeptide selected from the group consisting of A02, A28, A42, A63, A76, B05, B07, B08, B13, B52 and B107.

C53. The use according to clause C52, wherein the immune response induced is bactericidal.

C54. The use according to clause C52, wherein the composition further comprises polysorbate-80.

C55. The use according to any one of clauses C52 to C54, wherein the composition further comprises aluminum.

C56. The use according to any one of clauses C52 to C55, wherein the composition further comprises histidine buffer.

C57. The use according to any one of clauses C52 to C56, wherein the composition further comprises sodium chloride.

C58. The use according to any one of clauses C52 to C57, wherein the composition comprises about 120 µg/ml of the first polypeptide; about 120 µg/ml of the second polypeptide; about 2.8 molar ratio of polysorbate-80; about 0.5 mg/ml aluminum; about 10 mM histidine; and about 150 mM sodium chloride.

C59. The use according to any one of clauses C52 to C58, wherein the composition comprises about 60 μg of the first polypeptide; about 60 μg of the second polypeptide; about 18 μg polysorbate-80; about 250 μg aluminum; about 780 μg histidine; and about 4380 μg sodium chloride.

C60. The use according to any one of clauses C52 to C59, wherein the composition further comprises at least one additional immunogenic composition comprising a mixture of four distinct and separately made protein-capsular polysaccharide conjugates, wherein the first conjugate comprises *N. meningitidis* capsular polysaccharide of serogroup W conjugated to a carrier protein, the second conjugate comprises *N. meningitidis* capsular polysaccharide of serogroup Y conjugated to a carrier protein, the third conjugate comprises *N. meningitidis* capsular polysaccharide of serogroup A conjugated to a carrier protein, and the fourth conjugate comprises *N. meningitidis* capsular polysaccharide of serogroup C conjugated to a carrier protein, wherein the carrier protein is selected from the group consisting of diphtheria toxoid, CRM197, and tetanus toxoid.

C61. The use according to clause C60, wherein the carrier protein is diphtheria toxoid.

C62. The use according to clause C60, wherein the carrier protein is tetanus toxoid.

C63. The use according to clause C60, wherein the at least one additional immunogenic composition is a liquid composition.

C64. The use according to clause C60, wherein the at least one additional immunogenic composition is not lyophilized.

C65. The use according to any one of clauses C60 to C64, wherein the composition induces an immune response against at least one *Neisseria meningitidis* serogroup A strain.

C66. The use according to any one of clauses C60 to C64, wherein the composition induces an immune response against at least one *Neisseria meningitidis* serogroup C strain.

C67. The use according to any one of clauses C60 to C64, wherein the composition induces an immune response against at least one *Neisseria meningitidis* serogroup W strain.

C68. The use according to any one of clauses C60 to C64, wherein the composition induces an immune response against at least one *Neisseria meningitidis* serogroup Y strain.

C69. The use according to any one of clauses C60 to C64, wherein the composition induces an immune response against at least one of a *Neisseria meningitidis* serogroup A strain, a *Neisseria meningitidis* serogroup C strain, a *Neisseria meningitidis* serogroup Y strain, a *Neisseria meningitidis* serogroup W strain, and any combination thereof.

C70. The use according to any one of clauses C52 to C69, wherein the effective amount of the composition comprises one dose.

C71. The use according to any one of clauses C52 to C70, wherein the effective amount of the composition comprises two doses.

C72. The use according to any one of clauses C52 to C70, wherein the effective amount of the composition further comprises a booster dose.

C73. The use according to any one of clauses C52 to C70, wherein the effective amount of the composition comprises at most two doses.

C74. The use according to any one of clauses C52 to C70, wherein the effective amount of the composition comprises at most three doses.

C75. The use according to clause C52, wherein the composition does not comprise a hybrid protein.

C76. The use according to clause C52, wherein the composition does not comprise a fusion protein.

C77. The use according to clause C52, wherein the composition is not lyophilized.

C78. The use according to clause C52, wherein the composition does not comprise formaldehyde.

C79. The use according to clause C60, wherein the composition does not comprise diphtheria toxoid or CRM.

C80. The use according to clause C60, wherein the *Neisseria meningitidis* serogroup A (MenA) capsular saccharide is conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate).

C81. The use according to clause C60, wherein the *Neisseria meningitidis* serogroup C (MenC) capsular saccharide is conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate).

C82. The use according to clause C60, wherein the *Neisseria meningitidis* serogroup W (MenW) capsular saccharide is directly conjugated to tetanus toxoid carrier protein (TT) by 1-cyano-4-dimethylamino pyridinium tetrafluoroborate chemistry, in the absence of a linker (MenW-TT conjugate).

C83. The use according to clause C60, wherein the *Neisseria meningitidis* serogroup Y (MenY) capsular saccharide is directly conjugated to tetanus toxoid carrier protein (TT) by 1-cyano-4-dimethylamino pyridinium tetrafluoroborate chemistry, in the absence of a linker (MenY-TT conjugate).

C84. The use according to clause C60, wherein the *Neisseria meningitidis* serogroup A (MenA) capsular saccharide is conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate); the *Neisseria meningitidis* serogroup C (MenC) capsular saccharide is conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate); the *Neisseria meningitidis* serogroup W (MenW) capsular saccharide is directly conjugated to tetanus toxoid carrier protein (TT) by 1-cyano-4-dimethylamino pyridinium tetrafluoroborate chemistry, in the absence of a linker (MenW-TT conjugate); and the *Neisseria meningitidis* serogroup Y (MenY) capsular saccharide is directly conjugated to tetanus toxoid carrier protein (TT) by 1-cyano-4-dimethylamino pyridinium tetrafluoroborate chemistry, in the absence of a linker (MenY-TT conjugate).

C85. The use according to clause C60, wherein the composition does not comprise a MenA capsular saccharide in the absence of an adipic acid dihydrazide (ADH) linker.

C86. The use according to any one of clauses C52 to C85, wherein the patient is aged 12 to <18 Months or 18 to <24 Months.

C87. The use according to any one of clauses C52 to C85, wherein the patient is aged 18 to <24 Months.

C88. The use according to any one of clauses C52 to C85, wherein the patient is aged 24 Months to <10 Years.

C89. The use according to any one of clauses C52 to C88, wherein the composition induces a bactericidal titer of serum immunoglobulin that is at least 2-fold higher in the human after receiving the first dose than a bactericidal titer of serum immunoglobulin in the human prior to receiving the first dose, when measured under identical conditions in a serum bactericidal assay using human complement.

C90. The use according to any one of clauses C52 to C89, wherein the composition induces a bactericidal titer of serum immunoglobulin that is at least 4-fold higher in the human after receiving the first dose than a bactericidal titer of serum immunoglobulin in the human prior to receiving the first dose, when measured under identical conditions in a serum bactericidal assay using human complement.

C91. The use according to any one of clauses C52 to C90, wherein the composition induces a bactericidal titer of serum immunoglobulin that is at least 8-fold higher in the human after receiving the first dose than a bactericidal titer of serum immunoglobulin in the human prior to receiving the first dose, when measured under identical conditions in a serum bactericidal assay using human complement.

C92. A method of inducing an immune response in a human, comprising administering to the human a composition comprising
a) a first polypeptide comprising the amino acid sequence set forth in SEQ ID NO: 1; (b) a second polypeptide comprising the amino acid sequence set forth in SEQ ID NO: 2; (c) a *Neisseria meningitidis* serogroup A capsular saccharide conjugated to an adipic acid dihydrazide (ADH) linker by 1-cyano-4-dimethylamino pyridinium tetrafluoroborate, wherein the linker is conjugated to tetanus toxoid by carbodiimide chemistry; (d) a *Neisseria meningitidis* serogroup C capsular saccharide conjugated to an ADH linker by 1-cyano-4-dimethylamino pyridinium tetrafluoroborate, wherein the linker is conjugated to tetanus toxoid by carbodiimide chemistry; (e) a *Neisseria meningitidis* serogroup W capsular saccharide directly conjugated to tetanus toxoid by 1-cyano-4-dimethylamino pyridinium tetrafluoroborate, in the absence of a linker; and (f) a *Neisseria meningitidis* serogroup Y capsular saccharide directly conjugated to tetanus toxoid by 1-cyano-4-dimethylamino pyridinium tetrafluoroborate, in the absence of a linker, wherein the composition induces an immune response to at least one of *N. meningitidis* serogroups A, C, W-135 and Y, wherein the immune response comprises a titer of serum bactericidal antibodies, and wherein the titer is higher than that induced by a licensed vaccine against *N. meningitidis* serogroups A, C, W-135 and Y meningococcal capsular polysaccharides.

C93. The method according to claim 1, wherein the licensed vaccine against *N. meningitidis* serogroups A, C, W-135 and Y meningococcal capsular polysaccharides is MENVEO.

C94. A method of inducing an immune response in a human, comprising administering to the human a composition comprising a) a first polypeptide comprising the amino acid sequence set forth in SEQ ID NO: 1; (b) a second polypeptide comprising the amino acid sequence set forth in SEQ ID NO: 2; (c) a *Neisseria meningitidis* serogroup A capsular saccharide conjugated to an adipic acid dihydrazide (ADH) linker by 1-cyano-4-dimethylamino pyridinium tetrafluoroborate, wherein the linker is conjugated to tetanus toxoid by carbodiimide chemistry; (d) a *Neisseria meningitidis* serogroup C capsular saccharide conjugated to an ADH linker by 1-cyano-4-dimethylamino pyridinium tetrafluoroborate, wherein the linker is conjugated to tetanus toxoid by carbodiimide chemistry; (e) a *Neisseria meningitidis* serogroup W capsular saccharide directly conjugated to tetanus toxoid by 1-cyano-4-dimethylamino pyridinium tetrafluoroborate, in the absence of a linker; and (f) a *Neisseria meningitidis* serogroup Y capsular saccharide directly conjugated to tetanus toxoid by 1-cyano-4-dimethylamino pyridinium tetrafluoroborate, in the absence of a linker, wherein the composition induces an immune response to *N. meningitidis* serogroup B, wherein the immune response comprises a titer of serum bactericidal antibodies that is higher than a titer of serum bactericidal antibodies induced by a licensed vaccine against *N. meningitidis* serogroup B.

C95. The method according to clause C94, wherein the licensed vaccine against *N. meningitidis* serogroup B is TRUMENBA.

C96. A method of inducing an immune response in a human, comprising administering to the human a composition comprising a) a first polypeptide comprising the amino acid sequence set forth in SEQ ID NO: 1; (b) a second polypeptide comprising the amino acid sequence set forth in SEQ ID NO: 2; (c) a *Neisseria meningitidis* serogroup A capsular saccharide conjugated to an adipic acid dihydrazide (ADH) linker by 1-cyano-4-dimethylamino pyridinium tetrafluoroborate, wherein the linker is conjugated to tetanus toxoid by carbodiimide chemistry; (d) a *Neisseria meningitidis* serogroup C capsular saccharide conjugated to an ADH linker by 1-cyano-4-dimethylamino pyridinium tetrafluoroborate, wherein the linker is conjugated to tetanus toxoid by carbodiimide chemistry; (e) a *Neisseria meningitidis* serogroup W capsular saccharide directly conjugated to tetanus toxoid by 1-cyano-4-dimethylamino pyridinium tetrafluoroborate, in the absence of a linker; and (f) a *Neisseria meningitidis* serogroup Y capsular saccharide directly conjugated to tetanus toxoid by 1-cyano-4-dimethylamino pyridinium tetrafluoroborate, in the absence of a linker, wherein the composition induces an immune response to at least one of *N. meningitidis* serogroups A, C, W-135 and Y and *N. meningitidis* serogroup B, wherein the immune response comprises a titer of serum bactericidal antibodies to each of *N. meningitidis* serogroups A, C, W-135 and Y that is higher than a titer of serum bactericidal antibodies induced by a licensed vaccine against *N. meningitidis* serogroups A, C, W-135 and Y capsular polysaccharide, and wherein the immune response comprises a titer of serum bactericidal antibodies to *N. meningitidis* serogroup B that is higher than a titer of serum bactericidal antibodies induced by a licensed vaccine against *N. meningitidis* serogroup B.

C97. The method according to clause C96, wherein the licensed vaccine against *N. meningitidis* serogroups A, C, W-135 and Y meningococcal capsular polysaccharides is MENVEO.

C98. The method according to any one of clauses C94 to C97, wherein the composition further comprises an adjuvant.

C99. The method according to any one of clauses C94 to C97, wherein the composition further comprises aluminum.

C100. The method according to clause C99, wherein the adjuvant comprises aluminum hydroxide.

C101. The method according to clause C99, wherein the adjuvant comprises aluminum phosphate.

C102. The method according to clause C94, wherein at least 90% of the first polypeptide is bound to aluminum in the composition.

C103. The method according to clause C94, wherein at least 90% of the second polypeptide is bound to aluminum in the composition.

C104. The method according to any one of clauses C94 to C97, wherein the composition is formulated as a sterile liquid.

C105. The method according to any one of clauses C94 to C97, wherein the composition further comprises polysorbate-80.

C106. The method according to any one of clauses C94 to C97, wherein the composition further comprises Tris-HCl; sodium chloride; sucrose; histidine; polysorbate 80; and aluminum phosphate.

C107. The method according to any one of clauses C94 to C97, wherein the composition comprises about 120 µg/ml of the first polypeptide; about 120 µg/ml of the second polypeptide; about 0.5 mg/ml aluminum as aluminum phosphate; about 0.02 mg polysorbate-80; about 10 mM histidine; and about 150 mM sodium chloride.

C108. The method according to any one of clauses C94 to C97, wherein the composition comprises about 60 µg of the first polypeptide; about 60 µg of the second polypeptide; about 5 µg of the MenA capsular saccharide conjugated to about 7.5 µg TT; about 5 µg of the MenC capsular saccharide conjugated to about 7.5 µg TT; about 5 µg of the MenW capsular saccharide conjugated to about 3.75 µg TT; about 5 µg of the MenY capsular saccharide conjugated to about 3.25 µg TT; about 97 µg Tris-HCl, pH 6.8±0.3; 4.69-4.71 mg of sodium chloride; about 28 mg of sucrose; about 0.78 mg of L-Histidine; about 0.02 mg polysorbate-80; about 0.25 mg aluminum; and further comprising 0.5 mL water, per dose.

C109. The method according to any one of clauses C94 to C97, wherein the composition is capable of eliciting a booster immune response to each of the *N. meningitidis* serogroups A, C, W-135 and Y.

C110. The method according to any one of clauses C94 to C97, wherein the composition is capable of eliciting a booster immune response to *N. meningitidis* serogroup B.

C111. The method according to any one of clauses C94 to C97, wherein the human is aged between 10 to 26 years old.

C112. The method according to any one of clauses C94 to C97, wherein the human is aged between 12 to <18 Months or 18 to <24 Months.

C113. The method according to any one of clauses C94 to C97, wherein the human is aged between 18 to <24 Months.

C114. The method according to any one of clauses C94 to C97, wherein the human is aged between ≥24 Months to <10 Years.

C115. The method according to any one of clauses C94 to C97, wherein the human is at least 16 years old.

C116. The method according to clause C115, comprising administering one dose to the human.

C117. The method according to any one of clauses C94 to C97, wherein the human is 10 to 12 years old.

C118. The method according to clause C113, comprising administering to the human at least two doses.

C119. The method according to clause C113, wherein the human is at most 16 years old.

C120. The method according to any one of clauses C94 to C97, comprising administering at least one dose of the composition to the human at about 11 years old and administering a further dose of the composition to the human at least four years after the first dose.

C121. The method according to any one of clauses C94 to C97, comprising administering at least one dose of the composition to the human at about 11 years old and administering a further dose of the composition to the human at least four years after the last dose.

C122. The method according to clause C116, wherein the further dose of the composition is administered about five years after the last dose.

C123. The method according to any one of clauses C94 to C97, comprising administering one dose of the composition to the human at about 11 years old and administering at least two doses of the composition to the human about five years after the first dose.

C124. The method according to any one of clauses C94 to C97, wherein the human is seronegative against *N. meningitidis* serogroups A, C, W-135 and Y capsular polysaccharides.

C125. The method according to any one of clauses C94 to C97, wherein the human is seropositive against *N. meningitidis* serogroups A, C, W-135 and Y capsular polysaccharides.

C126. The method according to any one of clauses C94 to C97, comprising administering a first dose and a second dose of the composition, wherein the second dose is about 6 months after the first dose.

C127. The method according to clause C122, wherein the human is at most 17 years of age.

C128. The method according to clause C122, comprising administering a third dose of the composition to the human at 16 years of age.

C129. The method according to any one of clauses C94 to C97, comprising administering at most two doses of the composition, wherein the second dose is about 6 months after the first dose.

C130. The method according to any one of clauses C94 to C97, wherein the composition elicits an immune response against a *N. meningitidis* serogroup B strain expressing A22.

C131. The method according to any one of clauses C94 to C97, wherein the composition elicits an immune response against a *N. meningitidis* serogroup B strain expressing A56.

C132. The method according to any one of clauses C94 to C97, wherein the composition elicits an immune response against a *N. meningitidis* serogroup B strain expressing B24.

C133. The method according to any one of clauses C94 to C97, wherein the composition elicits an immune response against a *N. meningitidis* serogroup B strain expressing B44.

C134. The method according to any one of clauses C94 to C97, wherein the composition induces a bactericidal immune response against any one of *N. meningitidis* serogroup B A22, A56, B24, B44 strains, or any combination thereof.

C135. The method according to any one of clauses C94 to C97, wherein the composition induces a bactericidal immune response against any one of *N. meningitidis* serogroup B B24, B16, B44, A22, B03, B09, A12, A19, A05, A07, B153 strains, or any combination thereof.

What is claimed is:

1. A method of inducing an immune response against *Neisseria meningitidis* in a human subject aged between 10 to 26 years old, the method comprising administering to the human subject an effective amount of an immunogenic composition comprising a) a licensed bivalent liquid composition comprising a first purified polypeptide comprising the amino acid sequence set forth in SEQ ID NO: 1; and a second purified polypeptide comprising the amino acid sequence set forth in SEQ ID NO: 2; and b) a lyophilized quadrivalent conjugate composition comprising:

(i) a purified *Neisseria meningitidis* serogroup A capsular polysaccharide (MenA) individually conjugated to an adipic acid dihydrazide (ADH) linker by 1-cyano-4-dimethylamino pyridinium tetrafluoroborate, wherein the linker is conjugated to tetanus toxoid (TT) by carbodiimide chemistry;

(ii) a purified *Neisseria meningitidis* serogroup C capsular polysaccharide (MenC) individually conjugated to an ADH linker by 1-cyano-4-dimethylamino pyridinium tetrafluoroborate, wherein the linker is conjugated to tetanus toxoid (TT) by carbodiimide chemistry;

(iii) a purified *Neisseria meningitidis* serogroup W capsular polysaccharide (MenW) individually conjugated directly to tetanus toxoid (TT) by 1-cyano-4-dimethylamino pyridinium tetrafluoroborate, in the absence of a linker; and (iv) a purified *Neisseria meningitidis* serogroup Y capsular polysaccharide (MenY) individually conjugated directly to tetanus toxoid (TT) by 1-cyano-4-dimethylamino pyridinium tetrafluoroborate, in the absence of a linker, wherein the composition induces an immune response to *N. meningitidis* serogroups A, B, C, W-135 and Y;

wherein the lyophilized conjugate composition is reconstituted with the bivalent liquid composition; and wherein the immune response comprises a titer of serum bactericidal antibodies that is higher than that induced by a composition selected from any one of (a) a licensed quadrivalent conjugate vaccine comprising conjugates of capsular oligosaccharides of *N. meningitidis* serogroups A, C, W-135 and Y, wherein the capsular oligosaccharides of *N. meningitidis* serogroups A, C, W-135 and Y are conjugated to CRM197, wherein the licensed conjugate vaccine does not comprise a *N. meningitidis* polypeptide; and (b) a licensed bivalent vaccine composition comprising a serogroup B *N. meningitidis* polypeptide comprising SEQ ID NO: 1 and a serogroup B *N. meningitidis* polypeptide comprising SEQ ID NO: 2 which does not comprise capsular polysaccharide conjugates of *N. meningitidis* serogroups A, C, W-135 and Y;

wherein the human subject is naive to vaccination with *N. meningitidis* serogroups A, C, W-135 and Y capsular polysaccharides; and wherein the immunogenic composition is administered to the human subject in a first dose and a second dose, wherein the second dose is administered to the subject about 6 months after the first dose.

2. The method of claim 1, wherein the aluminum is aluminum hydroxide.

3. The method of claim 1, wherein the aluminum is aluminum phosphate.

4. The method of claim 1, wherein between 90% and 100% of the amount of the first polypeptide is bound to the aluminum in the composition for 24 hours.

5. The method of claim 1, wherein between 90% and 100% of the amount of the second polypeptide is bound to the aluminum in the composition for 24 hours.

6. The method of claim 1, wherein the immunogenic composition further comprises polysorbate 80.

7. The method of claim 1, wherein the immunogenic composition further comprises Tris-HCl, sodium chloride, sucrose, histidine, polysorbate 80, and water; and wherein the aluminum is aluminum phosphate.

8. The method of claim 1, wherein the method comprises administering no more than the first dose and the second dose of the immunogenic composition.

9. The method of claim 1, wherein the serum bactericidal antibodies are against a serogroup B *Neisseria meningitidis* strain expressing A22 fHBP polypeptide.

10. The method of claim 1, wherein the serum bactericidal antibodies are against a serogroup B *Neisseria meningitidis* strain expressing A56 fHBP polypeptide.

11. The method of claim 1, wherein the serum bactericidal antibodies are against a serogroup B *Neisseria meningitidis* strain expressing B24 fHBP polypeptide.

12. The method of claim 1, wherein the serum bactericidal antibodies are against a serogroup B *Neisseria meningitidis* strain expressing B44 fHBP polypeptide.

13. The method of claim 1, wherein the serum bactericidal antibodies are against any one of serogroup B *Neisseria meningitidis* A22, A56, B24 and B44 strains, or any combination thereof.

* * * * *

SEQUENCE LISTING

<160> NUMBER OF SEQ ID NOS: 74

<210> SEQ ID NO 1
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 1

Cys Gly Ser Ser Gly Gly Gly Val Ala Ala Asp Ile Gly Thr Gly
1               5                   10                  15

Leu Ala Asp Ala Leu Thr Ala Pro Leu Asp His Lys Asp Lys Gly Leu
                20                  25                  30

Lys Ser Leu Thr Leu Glu Asp Ser Ile Ser Gln Asn Gly Thr Leu Thr
            35                  40                  45

Leu Ser Ala Gln Gly Ala Glu Lys Thr Phe Lys Val Gly Asp Lys Asp
        50                  55                  60

Asn Ser Leu Asn Thr Gly Lys Leu Lys Asn Asp Lys Ile Ser Arg Phe
65                  70                  75                  80

Asp Phe Val Gln Lys Ile Glu Val Asp Gly Gln Thr Ile Thr Leu Ala
                85                  90                  95

Ser Gly Glu Phe Gln Ile Tyr Lys Gln Asp His Ser Ala Val Val Ala
                100                 105                 110

Leu Gln Ile Glu Lys Ile Asn Asn Pro Asp Lys Ile Asp Ser Leu Ile
            115                 120                 125

Asn Gln Arg Ser Phe Leu Val Ser Gly Leu Gly Gly Glu His Thr Ala
        130                 135                 140

Phe Asn Gln Leu Pro Ser Gly Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
            180                 185                 190

Asn Val Glu Leu Ala Ser Ala Glu Leu Lys Ala Asp Glu Lys Ser His
        195                 200                 205

Ala Val Ile Leu Gly Asp Thr Arg Tyr Gly Ser Glu Glu Lys Gly Thr
210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln

<210> SEQ ID NO 2
<211> LENGTH: 261
<212> TYPE: PRT
<213> ORGANISM: Artificial Sequence
<220> FEATURE:
<223> OTHER INFORMATION: Synthetic amino acid sequence

<400> SEQUENCE: 2

Cys Gly Ser Ser Gly Gly Gly Gly Ser Gly Gly Gly Gly Val Thr Ala
1               5                   10                  15

Asp Ile Gly Thr Gly Leu Ala Asp Ala Leu Thr Ala Pro Leu Asp His
                20                  25                  30

Lys Asp Lys Gly Leu Lys Ser Leu Thr Leu Glu Asp Ser Ile Ser Gln

```
                35                  40                  45
Asn Gly Thr Leu Thr Leu Ser Ala Gln Gly Ala Glu Lys Thr Tyr Gly
 50                  55                  60

Asn Gly Asp Ser Leu Asn Thr Gly Lys Leu Lys Asn Asp Lys Val Ser
 65                  70                  75                  80

Arg Phe Asp Phe Ile Arg Gln Ile Glu Val Asp Gly Gln Leu Ile Thr
                 85                  90                  95

Leu Glu Ser Gly Glu Phe Gln Val Tyr Lys Gln Ser His Ser Ala Leu
                100                 105                 110

Thr Ala Leu Gln Thr Glu Gln Glu Gln Asp Pro Glu His Ser Glu Lys
                115                 120                 125

Met Val Ala Lys Arg Arg Phe Arg Ile Gly Asp Ile Ala Gly Glu His
                130                 135                 140

Thr Ser Phe Asp Lys Leu Pro Lys Asp Val Met Ala Thr Tyr Arg Gly
145                 150                 155                 160

Thr Ala Phe Gly Ser Asp Asp Ala Gly Gly Lys Leu Thr Tyr Thr Ile
                165                 170                 175

Asp Phe Ala Ala Lys Gln Gly His Gly Lys Ile Glu His Leu Lys Ser
                180                 185                 190

Pro Glu Leu Asn Val Asp Leu Ala Val Ala Tyr Ile Lys Pro Asp Glu
                195                 200                 205

Lys His His Ala Val Ile Ser Gly Ser Val Leu Tyr Asn Gln Asp Glu
210                 215                 220

Lys Gly Ser Tyr Ser Leu Gly Ile Phe Gly Glu Lys Ala Gln Glu Val
225                 230                 235                 240

Ala Gly Ser Ala Glu Val Glu Thr Ala Asn Gly Ile His His Ile Gly
                245                 250                 255

Leu Ala Ala Lys Gln
                260

<210> SEQ ID NO 3
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 3

Cys Gly Ser Ser
1

<210> SEQ ID NO 4
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 4

Cys Gly Ser Ser Gly Gly Gly Gly Val Ala Ala Asp
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic amino acid sequence

<400> SEQUENCE: 5
```

```
Cys Ser Ser Gly Ser Gly Ser Gly Gly Gly Val Ala Ala Asp
1               5                   10                  15
```

<210> SEQ ID NO 6
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 6

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Lys Ala Glu Glu Val Ala Gly Ser Ala Glu Val
225                 230                 235                 240

Lys Thr Val Asn Gly Ile Arg His Ile Gly Leu Ala Ala Lys Gln
                245                 250                 255
```

<210> SEQ ID NO 7
<211> LENGTH: 259
<212> TYPE: PRT
<213> ORGANISM: Neisseria meningitidis (group B)

<400> SEQUENCE: 7

```
Cys Ser Ser Gly Gly Gly Gly Gly Val Ala Ala Asp Ile Gly Thr
1               5                   10                  15

Gly Leu Ala Asp Ala Leu Thr Ala Pro Leu Asp His Lys Asp Lys Gly
                20                  25                  30

Leu Lys Ser Leu Thr Leu Glu Asp Ser Ile Pro Gln Asn Gly Thr Leu
            35                  40                  45
```

```
Thr Leu Ser Ala Gln Gly Ala Glu Lys Thr Phe Lys Ala Gly Asp Lys
    50                  55                  60

Asp Asn Ser Leu Asn Thr Gly Lys Leu Lys Asn Asp Lys Ile Ser Arg
65                  70                  75                  80

Phe Asp Phe Val Gln Lys Ile Glu Val Asp Gly Gln Thr Ile Thr Leu
                85                  90                  95

Ala Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
130                 135                 140

Ala Phe Asn Gln Leu Pro Gly Asp Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln

<210> SEQ ID NO 8
<211> LENGTH: 261
<212> TYPE: PRT
<213> ORGANISM: Neisseria meningitidis (group B)

<400> SEQUENCE: 8

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
                20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Lys Thr Phe Lys Val Gly
        50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
130                 135                 140

His Thr Ala Phe Asn Gln Leu Pro Ser Gly Lys Ala Glu Tyr His Gly
145                 150                 155                 160
```

```
Lys Ala Phe Ser Ser Asp Asp Ala Gly Gly Lys Leu Thr Tyr Thr Ile
                165                 170                 175
Asp Phe Ala Ala Lys Gln Gly His Gly Lys Ile Glu His Leu Lys Thr
            180                 185                 190
Pro Glu Gln Asn Val Glu Leu Ala Ser Ala Glu Leu Lys Ala Asp Glu
        195                 200                 205
Lys Ser His Ala Val Ile Leu Gly Asp Thr Arg Tyr Gly Ser Glu Glu
    210                 215                 220
Lys Gly Thr Tyr His Leu Ala Leu Phe Gly Asp Arg Ala Gln Glu Ile
225                 230                 235                 240
Ala Gly Ser Ala Thr Val Lys Ile Arg Glu Lys Val His Glu Ile Gly
                245                 250                 255
Ile Ala Gly Lys Gln
            260

<210> SEQ ID NO 9
<211> LENGTH: 254
<212> TYPE: PRT
<213> ORGANISM: Neisseria meningitidis (group B)

<400> SEQUENCE: 9

Cys Ser Ser Gly Gly Gly Gly Val Ala Ala Asp Ile Gly Ala Gly Leu
1               5                   10                  15
Ala Asp Ala Leu Thr Ala Pro Leu Asp His Lys Asp Lys Ser Leu Gln
            20                  25                  30
Ser Leu Thr Leu Asp Gln Ser Val Arg Lys Asn Glu Lys Leu Lys Leu
        35                  40                  45
Ala Ala Gln Gly Ala Glu Lys Thr Tyr Gly Asn Gly Asp Ser Leu Asn
    50                  55                  60
Thr Gly Lys Leu Lys Asn Asp Lys Val Ser Arg Phe Asp Phe Ile Arg
65                  70                  75                  80
Gln Ile Glu Val Asp Gly Gln Thr Ile Thr Leu Ala Ser Gly Glu Phe
                85                  90                  95
Gln Ile Tyr Lys Gln Asn His Ser Ala Val Val Ala Leu Gln Ile Glu
            100                 105                 110
Lys Ile Asn Asn Pro Asp Lys Ile Asp Ser Leu Ile Asn Gln Arg Ser
        115                 120                 125
Phe Leu Val Ser Gly Leu Gly Gly Glu His Thr Ala Phe Asn Gln Leu
    130                 135                 140
Pro Asp Gly Lys Ala Glu Tyr His Gly Lys Ala Phe Ser Ser Asp Asp
145                 150                 155                 160
Pro Asn Gly Arg Leu His Tyr Ser Ile Asp Phe Thr Lys Lys Gln Gly
                165                 170                 175
Tyr Gly Arg Ile Glu His Leu Lys Thr Pro Glu Gln Asn Val Glu Leu
            180                 185                 190
Ala Ser Ala Glu Leu Lys Ala Asp Glu Lys Ser His Ala Val Ile Leu
        195                 200                 205
Gly Asp Thr Arg Tyr Gly Gly Glu Glu Lys Gly Thr Tyr His Leu Ala
    210                 215                 220
Leu Phe Gly Asp Arg Ala Gln Glu Ile Ala Gly Ser Ala Thr Val Lys
225                 230                 235                 240
Ile Arg Glu Lys Val His Glu Ile Gly Ile Ala Gly Lys Gln
                245                 250

<210> SEQ ID NO 10
```

<211> LENGTH: 254
<212> TYPE: PRT
<213> ORGANISM: Neisseria meningitidis (group B)

<400> SEQUENCE: 10

```

```
Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
            115                 120                 125

Gly Lys Met Val Ala Lys Arg Gln Phe Arg Ile Gly Asp Ile Val Gly
130                 135                 140

Glu His Thr Ser Phe Asp Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
            195                 200                 205

Asp Glu Lys His His Ala Val Ile Ser Gly Ser Val Leu Tyr Asn Gln
210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260

<210> SEQ ID NO 12
<211> LENGTH: 255
<212> TYPE: PRT
<213> ORGANISM: Neisseria meningitidis (group B)

<400> SEQUENCE: 12

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
            115                 120                 125

Phe Lys Ile Gly Asp Ile Ala Gly Glu His Thr Ser Phe Asp Lys Leu
        130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
```

```
                  195                 200                 205
Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 13
<211> LENGTH: 255
<212> TYPE: PRT
<213> ORGANISM: Neisseria meningitidis (group B)

<400> SEQUENCE: 13

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 14
<211> LENGTH: 255
<212> TYPE: PRT
<213> ORGANISM: Neisseria meningitidis (group B)

<400> SEQUENCE: 14

Cys Ser Ser Gly Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
```

```
                    20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 15
<211> LENGTH: 255
<212> TYPE: PRT
<213> ORGANISM: Neisseria meningitidis (group B)

<400> SEQUENCE: 15

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140
```

```
Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 16
<211> LENGTH: 263
<212> TYPE: PRT
<213> ORGANISM: Neisseria meningitidis (group B)

<400> SEQUENCE: 16

Cys Ser Ser Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Arg Thr Phe Lys Ala
        50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Gly Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260
```

<210> SEQ ID NO 17
<211> LENGTH: 255
<212> TYPE: PRT
<213> ORGANISM: Neisseria meningitidis (group B)

<400> SEQUENCE: 17

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 18
<211> LENGTH: 254
<212> TYPE: PRT
<213> ORGANISM: Neisseria meningitidis (group B)

<400> SEQUENCE: 18

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

```
Gln Ile Glu Val Asp Gly Gln Leu Ile Thr Leu Ser Gly Glu Phe
                85                  90                  95

Gln Ile Tyr Lys Gln Asp His Ser Ala Val Val Ala Leu Gln Ile Glu
           100                 105                 110

Lys Ile Asn Asn Pro Asp Lys Ile Asp Ser Leu Ile Asn Gln Arg Ser
       115                 120                 125

Phe Leu Val Ser Gly Leu Gly Gly Glu His Thr Ala Phe Asn Gln Leu
130                 135                 140

Pro Gly Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 19

<400> SEQUENCE: 19

000

<210> SEQ ID NO 20
<211> LENGTH: 257
<212> TYPE: PRT
<213> ORGANISM: Neisseria meningitidis (group B)

<400> SEQUENCE: 20

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Lys
                20                  25                  30

Ser Leu Thr Leu Glu Asp Ser Ile Ser Gln Asn Gly Thr Leu Thr Leu
            35                  40                  45

Ser Ala Gln Gly Ala Glu Lys Thr Phe Lys Val Gly Asp Lys Asp Asn
        50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asn His Ser Ala Val Val Ala Leu
                100                 105                 110

Gln Ile Glu Lys Ile Asn Asn Pro Asp Lys Ile Asp Ser Leu Ile Asn
            115                 120                 125

Gln Arg Ser Phe Leu Val Ser Gly Leu Gly Gly Glu His Thr Ala Phe
        130                 135                 140

Asn Gln Leu Pro Gly Gly Lys Ala Glu Tyr His Gly Lys Ala Phe Ser
145                 150                 155                 160
```

```
Ser Asp Asp Ala Gly Gly Lys Leu Thr Tyr Thr Ile Asp Phe Ala Ala
            165                 170                 175

Lys Gln Gly His Gly Lys Ile Glu His Leu Lys Thr Pro Glu Gln Asn
        180                 185                 190

Val Glu Leu Ala Ala Glu Leu Lys Ala Asp Glu Lys Ser His Ala
        195                 200                 205

Val Ile Leu Gly Asp Thr Arg Tyr Gly Ser Glu Lys Gly Thr Tyr
    210                 215                 220

His Leu Ala Leu Phe Gly Asp Arg Ala Gln Glu Ile Ala Gly Ser Ala
225                 230                 235                 240

Thr Val Lys Ile Gly Glu Lys Val His Glu Ile Ser Ile Ala Gly Lys
                245                 250                 255

Gln

<210> SEQ ID NO 21
<211> LENGTH: 254
<212> TYPE: PRT
<213> ORGANISM: Neisseria meningitidis (group B)

<400> SEQUENCE: 21

Cys Ser Ser Gly Gly Gly Gly Val Ala Ala Asp Ile Gly Ala Gly Leu
1               5                   10                  15

Ala Asp Ala Leu Thr Thr Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 22
<211> LENGTH: 262
```

```
<212> TYPE: PRT
<213> ORGANISM: Neisseria meningitidis (group B)

<400> SEQUENCE: 22
```

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
        50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Asp Lys Ala Glu Tyr His
145                 150                 155                 160

Gly Lys Ala Phe Ser Ser Asp Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Leu Asn Val Asp Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

```
<210> SEQ ID NO 23
<211> LENGTH: 255
<212> TYPE: PRT
<213> ORGANISM: Neisseria meningitidis (group B)

<400> SEQUENCE: 23
```

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Ile Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

```
Gln Ile Glu Val Asp Gly Gln Leu Ile Thr Leu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
            130                 135                 140

Pro Glu Gly Gly Arg Ala Thr Tyr Arg Gly Thr Ala Phe Ser Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Asp Ile Lys Pro Asp Glu Lys His His Ala Val Ile
            195                 200                 205

Ser Gly Ser Val Leu Tyr Asn Gln Ala Glu Lys Gly Ser Tyr Ser Leu
        210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 24
<211> LENGTH: 17
<212> TYPE: PRT
<213> ORGANISM: Artificial Sequence
<220> FEATURE:
<223> OTHER INFORMATION: Synthetic amino acid sequence

<400> SEQUENCE: 24

Cys Gly Ser Ser Gly Gly Gly Ser Gly Gly Gly Gly Val Thr Ala
1               5                   10                  15

Asp

<210> SEQ ID NO 25
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 25

Cys Ser Ser Gly Gly Gly Gly Ser Gly Gly Gly Gly Val Thr Ala Asp
1               5                   10                  15

<210> SEQ ID NO 26
<211> LENGTH: 255
<212> TYPE: PRT
<213> ORGANISM: Neisseria meningitidis

<400> SEQUENCE: 26

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
```

```
                  50                  55                  60
Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Arg His Ala Val Ile
            195                 200                 205

Ser Gly Ser Val Leu Tyr Asn Gln Ala Glu Lys Gly Ser Tyr Ser Leu
210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 27
<211> LENGTH: 254
<212> TYPE: PRT
<213> ORGANISM: Neisseria meningitidis

<400> SEQUENCE: 27

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175
```

-continued

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 28
<211> LENGTH: 254
<212> TYPE: PRT
<213> ORGANISM: Neisseria meningitidis

<400> SEQUENCE: 28

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 29
<211> LENGTH: 260
<212> TYPE: PRT
<213> ORGANISM: Neisseria meningitidis

<400> SEQUENCE: 29

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Gln Ser Leu Met Leu Asp Gln Ser Val Arg Lys Asn
        35                  40                  45

Glu Lys Leu Lys Leu Ser Ala Gln Gly Ala Glu Lys Thr Tyr Gly Asn
50                  55                  60

Gly Asp Ser Leu Asn Thr Gly Lys Leu Lys Asn Asp Lys Ile Ser Arg
65                  70                  75                  80

Phe Asp Phe Ile His Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Val Gln Asp Ser Glu His Ser Glu Lys Met
        115                 120                 125

Val Ala Lys Arg Arg Phe Lys Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Ala Gly Gly Lys Leu Thr Tyr Thr Ile Asp
                165                 170                 175

Phe Ala Ala Lys Gln Gly His Gly Lys Ile Glu His Leu Lys Ser Pro
                180                 185                 190

Glu Leu Asn Val Glu Leu Ala Ala Tyr Ile Lys Pro Asp Glu Lys
            195                 200                 205

Arg His Ala Val Ile Ser Gly Ser Val Leu Tyr Asn Gln Asp Glu Lys
210                 215                 220

Gly Ser Tyr Ser Leu Gly Ile Phe Gly Gly Gln Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
        260

<210> SEQ ID NO 30
<211> LENGTH: 255
<212> TYPE: PRT
<213> ORGANISM: Neisseria meningitidis

<400> SEQUENCE: 30

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
            115                 120                 125

Phe Lys Ile Gly Asp Ile Ala Gly Glu His Thr Ser Phe Asp Lys Leu
            130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Val Ala Tyr Ile Lys Pro Asp Glu Lys His His Ala Val Ile
            195                 200                 205

Ser Gly Ser Val Leu Tyr Asn Gln Asp Glu Lys Gly Ser Tyr Ser Leu
            210                 215                 220

Gly Ile Phe Gly Glu Lys Ala Gln Glu Val Ala Gly Ser Ala Glu Val
225                 230                 235                 240

Lys Thr Ala Asn Gly Ile His His Ile Gly Leu Ala Ala Lys Gln
                245                 250                 255

<210> SEQ ID NO 31
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 31

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu His Ser Gly Lys Met Val Ala Lys Arg Gln Phe
            115                 120                 125

Arg Ile Gly Asp Ile Ala Gly Glu His Thr Ser Phe Asp Lys Leu Pro
            130                 135                 140

Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ser Asp Ile Lys Pro Asp Lys Lys Arg His Ala Val Ile Ser
            195                 200                 205

Gly Ser Val Leu Tyr Asn Gln Ala Glu Lys Gly Ser Tyr Ser Leu Gly
            210                 215                 220

```
Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250

<210> SEQ ID NO 32
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 32

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Asp His Ser Ala Val Val Ala Leu Gln Ile Glu Lys
            100                 105                 110

Ile Asn Asn Pro Asp Lys Ile Asp Ser Leu Ile Asn Gln Arg Ser Phe
        115                 120                 125

Leu Val Ser Gly Leu Gly Gly Glu His Thr Ala Phe Asn Gln Leu Pro
    130                 135                 140

Gly Gly Lys Ala Glu Tyr His Gly Lys Ala Phe Ser Ser Asp Pro
145                 150                 155                 160

Asn Gly Arg Leu His Tyr Ser Ile Asp Phe Thr Lys Lys Gln Gly Tyr
                165                 170                 175

Gly Arg Ile Glu His Leu Lys Thr Pro Glu Gln Asn Val Glu Leu Ala
            180                 185                 190

Ser Ala Glu Leu Lys Ala Asp Glu Lys Ser His Ala Val Ile Leu Gly
        195                 200                 205

Asp Thr Arg Tyr Gly Ser Glu Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250

<210> SEQ ID NO 33
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 33

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
```

```
                    20                  25                  30
Leu Thr Leu Asp Gln Ser Val Arg Lys Asn Glu Lys Leu Lys Leu Ala
                35                  40                  45

Ala Gln Gly Ala Glu Lys Thr Tyr Gly Asn Gly Asp Ser Leu Asn Thr
            50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                        85                  90                  95

Ile Tyr Lys Gln Asp His Ser Ala Val Val Ala Leu Gln Ile Glu Lys
                100                 105                 110

Ile Asn Asn Pro Asp Lys Ile Asp Ser Leu Ile Asn Gln Arg Ser Phe
            115                 120                 125

Leu Val Ser Gly Leu Gly Gly Glu His Thr Ala Phe Asn Gln Leu Pro
        130                 135                 140

Asp Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
                180                 185                 190

Ala Ala Glu Leu Lys Ala Asp Glu Lys Ser His Ala Val Ile Leu Gly
            195                 200                 205

Asp Thr Arg Tyr Gly Ser Glu Glu Lys Gly Thr Tyr His Leu Ala Leu
        210                 215                 220

Phe Gly Asp Arg Ala Gln Glu Ile Ala Gly Ser Ala Thr Val Lys Ile
225                 230                 235                 240

Gly Glu Lys Val His Glu Ile Gly Ile Ala Gly Lys Gln
                245                 250

<210> SEQ ID NO 34
<211> LENGTH: 256
<212> TYPE: PRT
<213> ORGANISM: Artificial Sequence
<220> FEATURE:
<223> OTHER INFORMATION: Synthetic amino acid sequence

<400> SEQUENCE: 34

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Lys Ser
            20                  25                  30

Leu Thr Leu Glu Asp Ser Ile Ser Gln Asn Gly Thr Leu Thr Leu Ser
        35                  40                  45

Ala Gln Gly Ala Glu Lys Thr Phe Lys Val Gly Asp Lys Asp Asn Ser
    50                  55                  60

Leu Asn Thr Gly Lys Leu Lys Asn Asp Lys Ile Ser Arg Phe Asp Phe
65                  70                  75                  80

Val Gln Lys Ile Glu Val Asp Gly Gln Thr Ile Thr Leu Ala Ser Gly
                85                  90                  95

Glu Phe Gln Ile Tyr Lys Gln Asn His Ser Ala Val Val Ala Leu Gln
                100                 105                 110

Ile Glu Lys Ile Asn Asn Pro Asp Lys Ile Asp Ser Leu Ile Asn Gln
            115                 120                 125

Arg Ser Phe Leu Val Ser Gly Leu Gly Gly Glu His Thr Ala Phe Asn
```

```
            130                 135                 140

Gln Leu Pro Gly Gly Lys Ala Glu Tyr His Gly Lys Ala Phe Ser Ser
145                 150                 155                 160

Asp Asp Ala Gly Gly Lys Leu Thr Tyr Thr Ile Asp Phe Ala Ala Lys
                165                 170                 175

Gln Gly His Gly Lys Ile Glu His Leu Lys Thr Pro Glu Gln Asn Val
            180                 185                 190

Glu Leu Ala Ala Ala Glu Leu Lys Ala Asp Glu Lys Ser His Ala Val
            195                 200                 205

Ile Leu Gly Asp Thr Arg Tyr Gly Ser Glu Glu Lys Gly Thr Tyr His
            210                 215                 220

Leu Ala Leu Phe Gly Asp Arg Ala Gln Glu Ile Ala Gly Ser Ala Thr
225                 230                 235                 240

Val Lys Ile Gly Glu Lys Val His Glu Ile Ser Ile Ala Gly Lys Gln
                245                 250                 255

<210> SEQ ID NO 35
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 35

Ser Ser Gly Gly Gly Val Ala Ala Asp Ile Gly Ala Gly Leu Ala
1               5                   10                  15

Asp Ala Leu Thr Thr Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Thr Ile Thr Leu Ala Ser Gly Glu Phe Gln
                85                  90                  95

Ile Tyr Lys Gln Asn His Ser Ala Val Val Ala Leu Gln Ile Glu Lys
                100                 105                 110

Ile Asn Asn Pro Asp Lys Ile Asp Ser Leu Ile Asn Gln Arg Ser Phe
            115                 120                 125

Leu Val Ser Gly Leu Gly Gly Glu His Thr Ala Phe Asn Gln Leu Pro
        130                 135                 140

Asp Gly Lys Ala Glu Tyr His Gly Lys Ala Phe Ser Ser Asp Pro
145                 150                 155                 160

Asn Gly Arg Leu His Tyr Ser Ile Asp Phe Thr Lys Lys Gln Gly Tyr
                165                 170                 175

Gly Arg Ile Glu His Leu Lys Thr Pro Glu Gln Asn Val Glu Leu Ala
            180                 185                 190

Ser Ala Glu Leu Lys Ala Asp Glu Lys Ser His Ala Val Ile Leu Gly
        195                 200                 205

Asp Thr Arg Tyr Gly Gly Glu Glu Lys Gly Thr Tyr His Leu Ala Leu
        210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250
```

245                 250

<210> SEQ ID NO 36
<211> LENGTH: 261
<212> TYPE: PRT
<213> ORGANISM: Artificial Sequence
<220> FEATURE:
<223> OTHER INFORMATION: Synthetic amino acid sequence

<400> SEQUENCE: 36

Ser Ser Gly Gly Gly Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Pro Gln Asn Gly
        35                  40                  45

Thr Leu Thr Leu Ser Ala Gln Gly Ala Glu Lys Thr Phe Lys Ala Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asn His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Gly Asp Lys Ala Glu Tyr His Gly
145                 150                 155                 160

Lys Ala Phe Ser Ser Asp Pro Asn Gly Arg Leu His Tyr Thr Ile
                165                 170                 175

Asp Phe Thr Asn Lys Gln Gly Tyr Gly Arg Ile Glu His Leu Lys Thr
            180                 185                 190

Pro Glu Leu Asn Val Asp Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Gly Glu Lys Val His Glu Ile Gly
                245                 250                 255

Ile Ala Gly Lys Gln
            260

<210> SEQ ID NO 37
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 37

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

```
Leu Ile Leu Asp Gln Ser Val Arg Lys Asn Glu Lys Leu Lys Leu Ala
             35                  40                  45

Ala Gln Gly Ala Glu Lys Thr Tyr Gly Asn Gly Asp Ser Leu Asn Thr
 50                  55                  60

Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Val Tyr Lys Gln Ser His Ser Ala Leu Thr Ala Leu Gln Thr Glu Gln
                100                 105                 110

Val Gln Asp Ser Glu His Ser Gly Lys Met Val Ala Lys Arg Gln Phe
            115                 120                 125

Arg Ile Gly Asp Ile Ala Gly Glu His Thr Ser Phe Asp Lys Leu Pro
130                 135                 140

Glu Gly Gly Arg Ala Thr Tyr Arg Gly Thr Ala Phe Ser Ser Asp Asp
145                 150                 155                 160

Ala Gly Gly Lys Leu Ile Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ala Asp Ile Lys Pro Asp Glu Lys His His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Lys Ala Gln Glu Val Ala Gly Ser Ala Glu Val Lys
225                 230                 235                 240

Thr Val Asn Gly Ile Arg His Ile Gly Leu Ala Ala Lys Gln
                245                 250

<210> SEQ ID NO 38
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 38

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
 50                  55                  60

Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Val Tyr Lys Gln Ser His Ser Ala Leu Thr Ala Leu Gln Thr Glu Gln
                100                 105                 110

Val Gln Asp Ser Glu His Ser Gly Lys Met Val Ala Lys Arg Gln Phe
            115                 120                 125

Arg Ile Gly Asp Ile Ala Gly Glu His Thr Ser Phe Asp Lys Leu Pro
130                 135                 140
```

```
Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ser Asp Ile Lys Pro Asp Lys Lys Arg His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250
```

<210> SEQ ID NO 39
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 39

```
Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Asp His Ser Ala Val Val Ala Leu Gln Ile Glu Lys
                100                 105                 110

Ile Asn Asn Pro Asp Lys Ile Asp Ser Leu Ile Asn Gln Arg Ser Phe
            115                 120                 125

Leu Val Ser Gly Leu Gly Gly Glu His Thr Ala Phe Asn Gln Leu Pro
        130                 135                 140

Ser Gly Lys Ala Glu Tyr His Gly Lys Ala Phe Ser Ser Asp Asp Pro
145                 150                 155                 160

Asn Gly Arg Leu His Tyr Ser Ile Asp Phe Thr Lys Lys Gln Gly Tyr
                165                 170                 175

Gly Arg Ile Glu His Leu Lys Thr Pro Glu Gln Asn Val Glu Leu Ala
                180                 185                 190

Ser Ala Glu Leu Lys Ala Asp Glu Lys Ser His Ala Val Ile Leu Gly
            195                 200                 205

Asp Thr Arg Tyr Gly Gly Glu Glu Lys Gly Thr Tyr His Leu Ala Leu
        210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250
```

```
<210> SEQ ID NO 40
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 40

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Asp His Ser Ala Val Val Ala Leu Gln Ile Glu Lys
            100                 105                 110

Ile Asn Asn Pro Asp Lys Ile Asp Ser Leu Ile Asn Gln Arg Ser Phe
        115                 120                 125

Leu Val Ser Gly Leu Gly Gly Glu His Thr Ala Phe Asn Gln Leu Pro
    130                 135                 140

Asp Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
            180                 185                 190

Ala Ala Glu Leu Lys Ala Asp Glu Lys Ser His Ala Val Ile Leu Gly
        195                 200                 205

Asp Thr Arg Tyr Gly Ser Glu Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Gly Glu Lys Val His Glu Ile Gly Ile Ala Gly Lys Gln
                245                 250

<210> SEQ ID NO 41
<211> LENGTH: 259
<212> TYPE: PRT
<213> ORGANISM: Artificial Sequence
<220> FEATURE:
<223> OTHER INFORMATION: Synthetic amino acid sequence

<400> SEQUENCE: 41

Ser Ser Gly Gly Gly Gly Ser Gly Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Gln Ser Leu Met Leu Asp Gln Ser Val Arg Lys Asn Glu
        35                  40                  45

Lys Leu Lys Leu Ser Ala Gln Gly Ala Glu Lys Thr Tyr Gly Asn Gly
    50                  55                  60
```

```
Asp Ser Leu Asn Thr Gly Lys Leu Lys Asn Asp Lys Ile Ser Arg Phe
 65                  70                  75                  80

Asp Phe Ile His Gln Ile Glu Val Asp Gly Gln Leu Ile Thr Leu Glu
                 85                  90                  95

Ser Gly Glu Phe Gln Val Tyr Lys Gln Ser His Ser Ala Leu Thr Ala
            100                 105                 110

Leu Gln Thr Glu Gln Val Gln Asp Ser Glu His Ser Glu Lys Met Val
            115                 120                 125

Ala Lys Arg Arg Phe Lys Ile Gly Asp Ile Ala Gly Glu His Thr Ser
130                 135                 140

Phe Asp Lys Leu Pro Lys Asp Val Met Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Glu Leu Ala Ala Ala Tyr Ile Lys Pro Asp Glu Lys Arg
            195                 200                 205

His Ala Val Ile Ser Gly Ser Val Leu Tyr Asn Gln Asp Glu Lys Gly
210                 215                 220

Ser Tyr Ser Leu Gly Ile Phe Gly Gly Gln Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln

<210> SEQ ID NO 42
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 42

Ser Ser Gly Gly Gly Val Ala Ala Asp Ile Gly Ala Gly Leu Ala
 1               5                  10                  15

Asp Ala Leu Thr Ala Pro Leu Asp His Lys Asp Lys Gly Leu Gln Ser
                 20                  25                  30

Leu Thr Leu Asp Gln Ser Val Arg Lys Asn Glu Lys Leu Lys Leu Ala
             35                  40                  45

Ala Gln Gly Ala Glu Lys Thr Tyr Gly Asn Gly Asp Ser Leu Asn Thr
 50                  55                  60

Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Val Tyr Lys Gln Ser His Ser Ala Leu Thr Ala Leu Gln Thr Glu Gln
            100                 105                 110

Glu Gln Asp Pro Glu His Ser Gly Lys Met Val Ala Lys Arg Arg Phe
            115                 120                 125

Lys Ile Gly Asp Ile Ala Gly Glu His Thr Ser Phe Asp Lys Leu Pro
130                 135                 140

Lys Asp Val Met Ala Thr Tyr Arg Gly Thr Ala Phe Gly Ser Asp Asp
145                 150                 155                 160
```

```
Ala Gly Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Val Ala Tyr Ile Lys Pro Asp Glu Lys His His Ala Val Ile Ser
        195                 200                 205

Gly Ser Val Leu Tyr Asn Gln Asp Glu Lys Gly Ser Tyr Ser Leu Gly
    210                 215                 220

Ile Phe Gly Glu Lys Ala Gln Glu Val Ala Gly Ser Ala Glu Val Lys
225                 230                 235                 240

Thr Ala Asn Gly Ile His His Ile Gly Leu Ala Ala Lys Gln
                245                 250

<210> SEQ ID NO 43
<211> LENGTH: 262
<212> TYPE: PRT
<213> ORGANISM: Artificial Sequence
<220> FEATURE:
<223> OTHER INFORMATION: Synthetic amino acid sequence

<400> SEQUENCE: 43

Ser Ser Gly Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Arg Thr Phe Lys Ala Gly
50                  55                  60

Asp Lys Asp Asn Ser Leu Asn Thr Gly Lys Leu Lys Asn Asp Lys Ile
65                  70                  75                  80

Ser Arg Phe Asp Phe Ile Arg Gln Ile Glu Val Asp Gly Gln Leu Ile
                85                  90                  95

Thr Leu Glu Ser Gly Glu Phe Gln Val Tyr Lys Gln Ser His Ser Ala
            100                 105                 110

Leu Thr Ala Leu Gln Thr Glu Gln Val Gln Asp Ser Glu His Ser Gly
        115                 120                 125

Lys Met Val Ala Lys Arg Gln Phe Arg Ile Gly Asp Ile Val Gly Glu
130                 135                 140

His Thr Ser Phe Gly Lys Leu Pro Lys Asp Val Met Ala Thr Tyr Arg
145                 150                 155                 160

Gly Thr Ala Phe Gly Ser Asp Asp Ala Gly Lys Leu Thr Tyr Thr
                165                 170                 175

Ile Asp Phe Ala Ala Lys Gln Gly His Gly Lys Ile Glu His Leu Lys
            180                 185                 190

Ser Pro Glu Leu Asn Val Asp Leu Ala Ala Asp Ile Lys Pro Asp
        195                 200                 205

Glu Lys His His Ala Val Ile Ser Gly Ser Val Leu Tyr Asn Gln Ala
225                 210                 215                 220

Glu Lys Gly Ser Tyr Ser Leu Gly Ile Phe Gly Gly Gln Ala Gln Glu
225                 230                 235                 240

Val Ala Gly Ser Ala Glu Val Glu Thr Ala Asn Gly Ile Arg His Ile
                245                 250                 255

Gly Leu Ala Ala Lys Gln
            260
```

<210> SEQ ID NO 44
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 44

```
Ser Ser Gly Gly Gly Val Ala Ala Asp Ile Gly Ala Gly Leu Ala
1               5                  10                 15

Asp Ala Leu Thr Ala Pro Leu Asp His Lys Asp Lys Gly Leu Gln Ser
                20                 25                 30

Leu Thr Leu Asp Gln Ser Val Arg Lys Asn Glu Lys Leu Lys Leu Ala
            35                 40                 45

Ala Gln Gly Ala Glu Lys Thr Tyr Gly Asn Gly Asp Ser Leu Asn Thr
        50                 55                 60

Gly Lys Leu Lys Asn Asp Lys Val Ser Arg Phe Asp Phe Ile Arg Gln
65                 70                 75                 80

Ile Glu Val Asp Gly Lys Leu Ile Thr Leu Glu Ser Gly Glu Phe Gln
                85                 90                 95

Val Tyr Lys Gln Ser His Ser Ala Leu Thr Ala Leu Gln Thr Glu Gln
            100                105                110

Val Gln Asp Ser Glu Asp Ser Gly Lys Met Val Ala Lys Arg Gln Phe
        115                120                125

Arg Ile Gly Asp Ile Ala Gly Glu His Thr Ser Phe Asp Lys Leu Pro
130                135                140

Lys Gly Gly Ser Ala Thr Tyr Arg Gly Thr Ala Phe Gly Ser Asp Asp
145                150                155                160

Ala Gly Gly Lys Leu Thr Tyr Thr Ile Asp Phe Ala Ala Lys Gln Gly
                165                170                175

His Gly Lys Ile Glu His Leu Lys Ser Pro Glu Leu Asn Val Glu Leu
            180                185                190

Ala Thr Ala Tyr Ile Lys Pro Asp Glu Lys Arg His Ala Val Ile Ser
        195                200                205

Gly Ser Val Leu Tyr Asn Gln Asp Glu Lys Gly Ser Tyr Ser Leu Gly
    210                215                220

Ile Phe Gly Gly Gln Ala Gln Glu Val Ala Gly Ser Ala Glu Val Glu
225                230                235                240

Thr Ala Asn Gly Ile His His Ile Gly Leu Ala Ala Lys Gln
                245                250
```

<210> SEQ ID NO 45
<211> LENGTH: 259
<212> TYPE: PRT
<213> ORGANISM: Artificial Sequence
<220> FEATURE:
<223> OTHER INFORMATION: Synthetic amino acid sequence

<400> SEQUENCE: 45

```
Ser Ser Gly Gly Gly Ser Gly Gly Gly Val Ala Ala Asp Ile
1               5                  10                 15

Gly Ala Gly Leu Ala Asp Ala Leu Thr Ala Pro Leu Asp His Lys Asp
                20                 25                 30

Lys Gly Leu Gln Ser Leu Thr Leu Asp Gln Ser Val Arg Lys Asn Glu
            35                 40                 45

Lys Leu Lys Leu Ala Ala Gln Gly Ala Glu Lys Thr Tyr Gly Asn Gly
        50                 55                 60
```

```
Asp Ser Leu Asn Thr Gly Lys Leu Lys Asn Asp Lys Val Ser Arg Phe
 65                  70                  75                  80

Asp Phe Ile Arg Gln Ile Glu Val Asp Gly Lys Leu Ile Thr Leu Glu
                 85                  90                  95

Ser Gly Glu Phe Gln Val Tyr Lys Gln Ser His Ser Ala Leu Thr Ala
            100                 105                 110

Leu Gln Thr Glu Gln Val Gln Asp Ser Glu Asp Ser Gly Lys Met Val
            115                 120                 125

Ala Lys Arg Gln Phe Arg Ile Gly Asp Ile Ala Gly Glu His Thr Ser
130                 135                 140

Phe Asp Lys Leu Pro Lys Gly Gly Ser Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Glu Leu Ala Thr Ala Tyr Ile Lys Pro Asp Glu Lys Arg
            195                 200                 205

His Ala Val Ile Ser Gly Ser Val Leu Tyr Asn Gln Asp Glu Lys Gly
210                 215                 220

Ser Tyr Ser Leu Gly Ile Phe Gly Gly Gln Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln

<210> SEQ ID NO 46
<211> LENGTH: 260
<212> TYPE: PRT
<213> ORGANISM: Artificial Sequence
<220> FEATURE:
<223> OTHER INFORMATION: Synthetic amino acid sequence

<400> SEQUENCE: 46

Ser Ser Gly Ser Gly Ser Gly Gly Gly Val Ala Ala Asp Ile Gly
 1               5                  10                  15

Thr Gly Leu Ala Asp Ala Leu Thr Ala Pro Leu Asp His Lys Asp Lys
                 20                  25                  30

Gly Leu Lys Ser Leu Thr Leu Glu Asp Ser Ile Ser Gln Asn Gly Thr
             35                  40                  45

Leu Thr Leu Ser Ala Gln Gly Ala Glu Lys Thr Phe Lys Val Gly Asp
 50                  55                  60

Lys Asp Asn Ser Leu Asn Thr Gly Lys Leu Lys Asn Asp Lys Ile Ser
 65                  70                  75                  80

Arg Phe Asp Phe Val Gln Lys Ile Glu Val Asp Gly Gln Thr Ile Thr
                 85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
            115                 120                 125

Leu Ile Asn Gln Arg Ser Phe Leu Val Ser Gly Leu Gly Gly Glu His
130                 135                 140

Thr Ala Phe Asn Gln Leu Pro Ser Gly Lys Ala Glu Tyr His Gly Lys
145                 150                 155                 160
```

```
Ala Phe Ser Ser Asp Asp Ala Gly Gly Lys Leu Thr Tyr Thr Ile Asp
            165                 170                 175

Phe Ala Ala Lys Gln Gly His Gly Lys Ile Glu His Leu Lys Thr Pro
        180                 185                 190

Glu Gln Asn Val Glu Leu Ala Ser Ala Glu Leu Lys Ala Asp Glu Lys
            195                 200                 205

Ser His Ala Val Ile Leu Gly Asp Thr Arg Tyr Gly Ser Glu Glu Lys
        210                 215                 220

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
            245                 250                 255

Ala Gly Lys Gln
            260

<210> SEQ ID NO 47
<211> LENGTH: 259
<212> TYPE: PRT
<213> ORGANISM: Artificial Sequence
<220> FEATURE:
<223> OTHER INFORMATION: Synthetic amino acid sequence

<400> SEQUENCE: 47

Ser Ser Gly Gly Gly Ser Gly Gly Gly Gly Val Thr Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Tyr Gly Asn Gly
    50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Gln Leu Ile Thr Leu Glu
                85                  90                  95

Ser Gly Glu Phe Gln Val Tyr Lys Gln Ser His Ser Ala Leu Thr Ala
            100                 105                 110

Leu Gln Thr Glu Gln Glu Gln Asp Pro Glu His Ser Glu Lys Met Val
        115                 120                 125

Ala Lys Arg Arg Phe Arg Ile Gly Asp Ile Ala Gly Glu His Thr Ser
    130                 135                 140

Phe Asp Lys Leu Pro Lys Asp Val Met Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Asp Leu Ala Val Ala Tyr Ile Lys Pro Asp Glu Lys His
        195                 200                 205

His Ala Val Ile Ser Gly Ser Val Leu Tyr Asn Gln Asp Glu Lys Gly
    210                 215                 220

Ser Tyr Ser Leu Gly Ile Phe Gly Glu Lys Ala Gln Glu Val Ala Gly
225                 230                 235                 240

Ser Ala Glu Val Glu Thr Ala Asn Gly Ile His His Ile Gly Leu Ala
                245                 250                 255
```

Ala Lys Gln

<210> SEQ ID NO 48
<211> LENGTH: 260
<212> TYPE: PRT
<213> ORGANISM: Artificial Sequence
<220> FEATURE:
<223> OTHER INFORMATION: Synthetic amino acid sequence

<400> SEQUENCE: 48

Cys Ser Ser Gly Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
    130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
        195                 200                 205

His His Ala Val Ile Ser Gly Ser Val Leu Tyr Asn Gln Asp Glu Lys
    210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260

<210> SEQ ID NO 49
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 49

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Ile Leu Asp Gln Ser Val Arg Lys Asn Glu Lys Leu Lys Leu
             35                  40                  45

Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
            130                 135                 140

Pro Glu Gly Gly Arg Ala Thr Tyr Arg Gly Thr Ala Phe Ser Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Asp Ile Lys Pro Asp Glu Lys His His Ala Val Ile
            195                 200                 205

Ser Gly Ser Val Leu Tyr Asn Gln Ala Glu Lys Gly Ser Tyr Ser Leu
            210                 215                 220

Gly Ile Phe Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 50
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 50

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
             20                  25                  30

Ser Leu Thr Leu Asp Gln Ser Val Arg Lys Asn Glu Lys Leu Lys Leu
             35                  40                  45

Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
            130                 135                 140

```
Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
            195                 200                 205

Ser Gly Ser Val Leu Tyr Asn Gln Ala Glu Lys Gly Ser Tyr Ser Leu
        210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 51
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 51

Gly Ser Ser Gly Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
            195                 200                 205

Ser Gly Ser Val Leu Tyr Asn Gln Ala Glu Lys Gly Ser Tyr Ser Leu
        210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255
```

<210> SEQ ID NO 52
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 52

```
Gly Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 53
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 53

```
Ser Ser Gly Gly Gly Gly Ser Gly Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Ser Leu Gln Ser Leu Thr Leu Asp Gln Ser Val Arg Lys Asn Glu
        35                  40                  45

Lys Leu Lys Leu Ala Ala Gln Gly Ala Glu Lys Thr Tyr Gly Asn Gly
    50                  55                  60
```

```
Asp Ser Leu Asn Thr Gly Lys Leu Lys Asn Asp Lys Val Ser Arg Phe
 65                  70                  75                  80

Asp Phe Ile Arg Gln Ile Glu Val Asp Gly Gln Thr Ile Thr Leu Ala
                 85                  90                  95

Ser Gly Glu Phe Gln Ile Tyr Lys Gln Asn His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
130                 135                 140

Phe Asn Gln Leu Pro Asp Gly Lys Ala Glu Tyr His Gly Lys Ala Phe
145                 150                 155                 160

Ser Ser Asp Asp Pro Asn Gly Arg Leu His Tyr Ser Ile Asp Phe Thr
                165                 170                 175

Lys Lys Gln Gly Tyr Gly Arg Ile Glu His Leu Lys Thr Pro Glu Gln
            180                 185                 190

Asn Val Glu Leu Ala Ser Ala Glu Leu Lys Ala Asp Glu Lys Ser His
        195                 200                 205

Ala Val Ile Leu Gly Asp Thr Arg Tyr Gly Gly Glu Glu Lys Gly Thr
    210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln

<210> SEQ ID NO 54
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 54

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Ile Tyr Lys Gln Asp His Ser Ala Val Val Ala Leu Gln Ile Glu Lys
            100                 105                 110

Ile Asn Asn Pro Asp Lys Ile Asp Ser Leu Ile Asn Gln Arg Ser Phe
        115                 120                 125

Leu Val Ser Gly Leu Gly Gly Glu His Thr Ala Phe Asn Gln Leu Pro
130                 135                 140

Ser Gly Lys Ala Glu Tyr His Gly Lys Ala Phe Ser Ser Asp Asp Ala
145                 150                 155                 160
```

```
Gly Gly Lys Leu Thr Tyr Thr Ile Asp Phe Ala Ala Lys Gln Gly His
                165                 170                 175
Gly Lys Ile Glu His Leu Lys Thr Pro Glu Gln Asn Val Glu Leu Ala
            180                 185                 190
Ser Ala Glu Leu Lys Ala Asp Glu Lys Ser His Ala Val Ile Leu Gly
        195                 200                 205
Asp Thr Arg Tyr Gly Gly Glu Lys Gly Thr Tyr His Leu Ala Leu
    210                 215                 220
Phe Gly Asp Arg Ala Gln Glu Ile Ala Gly Ser Ala Thr Val Lys Ile
225                 230                 235                 240
Arg Glu Lys Val His Glu Ile Gly Ile Ala Gly Lys Gln
                245                 250
```

<210> SEQ ID NO 55
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 55

```
Cys Ser Ser Gly Gly Gly Val Ala Ala Asp Ile Gly Ala Gly Leu
1               5                   10                  15
Ala Asp Ala Leu Thr Ala Pro Leu Asp His Lys Asp Lys Gly Leu Gln
                20                  25                  30
Ser Leu Thr Leu Asp Gln Ser Val Arg Lys Asn Glu Lys Leu Lys Leu
            35                  40                  45
Ala Ala Gln Gly Ala Glu Lys Thr Tyr Gly Asn Gly Asp Ser Leu Asn
        50                  55                  60
Thr Gly Lys Leu Lys Asn Asp Lys Val Ser Arg Phe Asp Phe Ile Arg
65                  70                  75                  80
Gln Ile Glu Val Asp Gly Lys Leu Ile Thr Leu Glu Ser Gly Glu Phe
                85                  90                  95
Gln Val Tyr Lys Gln Ser His Ser Ala Leu Thr Ala Leu Gln Thr Glu
                100                 105                 110
Gln Val Gln Asp Ser Glu Asp Ser Gly Lys Met Val Ala Lys Arg Gln
            115                 120                 125
Phe Arg Ile Gly Asp Ile Ala Gly Glu His Thr Ser Phe Asp Lys Leu
130                 135                 140
Pro Lys Gly Gly Ser Ala Thr Tyr Arg Gly Thr Ala Phe Gly Ser Asp
145                 150                 155                 160
Asp Ala Gly Gly Lys Leu Thr Tyr Thr Ile Asp Phe Ala Ala Lys Gln
                165                 170                 175
Gly His Gly Lys Ile Glu His Leu Lys Thr Pro Glu Gln Asn Val Glu
            180                 185                 190
Leu Ala Ser Ala Glu Leu Lys Ala Asp Glu Lys Ser His Ala Val Ile
        195                 200                 205
Leu Gly Asp Thr Arg Tyr Gly Gly Glu Lys Gly Thr Tyr His Leu
    210                 215                 220
Ala Leu Phe Gly Asp Arg Ala Gln Glu Ile Ala Gly Ser Ala Thr Val
225                 230                 235                 240
Lys Ile Arg Glu Lys Val His Glu Ile Gly Ile Ala Gly Lys Gln
                245                 250                 255
```

<210> SEQ ID NO 56
<211> LENGTH: 254

```
<212> TYPE: PRT
<213> ORGANISM: Artificial Sequence
<220> FEATURE:
<223> OTHER INFORMATION: Synthetic amino acid sequence

<400> SEQUENCE: 56

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Lys Leu Ile Thr Leu Glu Ser Gly Glu Phe Gln
                85                  90                  95

Val Tyr Lys Gln Ser His Ser Ala Leu Thr Ala Leu Gln Thr Glu Gln
                100                 105                 110

Val Gln Asp Ser Glu Asp Ser Gly Lys Met Val Ala Lys Arg Gln Phe
            115                 120                 125

Arg Ile Gly Asp Ile Ala Gly Glu His Thr Ser Phe Asp Lys Leu Pro
        130                 135                 140

Lys Gly Gly Ser Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
                180                 185                 190

Ala Ser Ala Glu Leu Lys Ala Asp Glu Lys Ser His Ala Val Ile Leu
            195                 200                 205

Gly Asp Thr Arg Tyr Gly Gly Glu Glu Lys Gly Thr Tyr His Leu Ala
        210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 57
<211> LENGTH: 262
<212> TYPE: PRT
<213> ORGANISM: Artificial Sequence
<220> FEATURE:
<223> OTHER INFORMATION: Synthetic amino acid sequence

<400> SEQUENCE: 57

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
        50                  55                  60

Gly Asp Lys Asp Asn Ser Leu Asn Thr Gly Lys Leu Lys Asn Asp Lys
65                  70                  75                  80
```

```
Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Asp Lys Ala Glu Tyr His
145                 150                 155                 160

Gly Lys Ala Phe Ser Asp Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Leu Asn Val Asp Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
                260

<210> SEQ ID NO 58
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 58

Ser Ser Gly Gly Gly Gly Val Ala Ala Asp Ile Gly Ala Val Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
    130                 135                 140

Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175
```

His Gly Lys Ile Glu His Leu Lys Ser Pro Glu Leu Asn Val Asp Leu
            180                 185                 190

Ala Ala Ser Asp Ile Lys Pro Asp Lys Arg His Ala Val Ile Ser
        195                 200                 205

Gly Ser Val Leu Tyr Asn Gln Ala Glu Lys Gly Ser Tyr Ser Leu Gly
210                 215                 220

Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250

<210> SEQ ID NO 59
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 59

Cys Gly Ser Ser Gly Gly Gly Val Ala Ala Asp Ile Gly Thr Gly
1               5                   10                  15

Leu Ala Asp Ala Leu Thr Ala Pro Leu Asp His Lys Asp Lys Gly Leu
            20                  25                  30

Lys Ser Leu Thr Leu Glu Asp Ser Ile Ser Gln Asn Gly Thr Leu Thr
        35                  40                  45

Leu Ser Ala Gln Gly Ala Glu Lys Thr Phe Lys Val Gly Asp Lys Asp
    50                  55                  60

Asn Ser Leu Asn Thr Gly Lys Leu Lys Asn Asp Lys Ile Ser Arg Phe
65                  70                  75                  80

Asp Phe Val Gln Lys Ile Glu Val Asp Gly Gln Thr Ile Thr Leu Ala
                85                  90                  95

Ser Gly Glu Phe Gln Ile Tyr Lys Gln Asp His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
    130                 135                 140

Phe Asn Gln Leu Pro Ser Gly Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
            180                 185                 190

Asn Val Glu Leu Ala Ser Ala Glu Leu Lys Ala Asp Glu Lys Ser His
        195                 200                 205

Ala Val Ile Leu Gly Asp Thr Arg Tyr Gly Ser Glu Glu Lys Gly Thr
    210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln

<210> SEQ ID NO 60
<211> LENGTH: 257

```
<212> TYPE: PRT
<213> ORGANISM: Artificial Sequence
<220> FEATURE:
<223> OTHER INFORMATION: Synthetic amino acid sequence

<400> SEQUENCE: 60

Gly Ser Ser Gly Gly Gly Val Ala Ala Asp Ile Gly Thr Gly Leu
1               5                   10                  15

Ala Asp Ala Leu Thr Ala Pro Leu Asp His Lys Asp Lys Gly Leu Lys
            20                  25                  30

Ser Leu Thr Leu Glu Asp Ser Ile Ser Gln Asn Gly Thr Leu Thr Leu
        35                  40                  45

Ser Ala Gln Gly Ala Glu Lys Thr Phe Lys Val Gly Asp Lys Asp Asn
    50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asp His Ser Ala Val Val Ala Leu
            100                 105                 110

Gln Ile Glu Lys Ile Asn Asn Pro Asp Lys Ile Asp Ser Leu Ile Asn
        115                 120                 125

Gln Arg Ser Phe Leu Val Ser Gly Leu Gly Gly Glu His Thr Ala Phe
    130                 135                 140

Asn Gln Leu Pro Ser Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
            180                 185                 190

Val Glu Leu Ala Ser Ala Glu Leu Lys Ala Asp Glu Lys Ser His Ala
        195                 200                 205

Val Ile Leu Gly Asp Thr Arg Tyr Gly Ser Glu Lys Gly Thr Tyr
    210                 215                 220

His Leu Ala Leu Phe Gly Asp Arg Ala Gln Glu Ile Ala Gly Ser Ala
225                 230                 235                 240

Thr Val Lys Ile Arg Glu Lys Val His Glu Ile Gly Ile Ala Gly Lys
                245                 250                 255

Gln

<210> SEQ ID NO 61
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 61

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60
```

```
Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Val Tyr Lys Gln Ser His Ser Ala Leu Thr Ala Phe Gln Thr Glu Gln
            100                 105                 110

Ile Gln Asp Ser Glu His Ser Gly Lys Met Val Ala Lys Arg Gln Phe
            115                 120                 125

Arg Ile Gly Asp Ile Ala Gly Glu His Thr Ser Phe Asp Lys Leu Pro
    130                 135                 140

Glu Gly Gly Arg Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

Asn Gly Lys Ile Glu His Leu Lys Ser Pro Glu Leu Asn Val Asp Leu
            180                 185                 190

Ala Ala Ala Asp Ile Lys Pro Asp Gly Lys Arg His Ala Val Ile Ser
            195                 200                 205

Gly Ser Val Leu Tyr Asn Gln Ala Glu Lys Gly Ser Tyr Ser Leu Gly
    210                 215                 220

Ile Phe Gly Gly Lys Ala Gln Glu Val Ala Gly Ser Ala Glu Val Lys
225                 230                 235                 240

Thr Val Asn Gly Ile Arg His Ile Gly Leu Ala Ala Lys Gln
                245                 250
```

<210> SEQ ID NO 62
<211> LENGTH: 252
<212> TYPE: PRT
<213> ORGANISM: Artificial Sequence
<220> FEATURE:
<223> OTHER INFORMATION: Synthetic amino acid sequence

<400> SEQUENCE: 62

```
Gly Gly Gly Gly Val Ala Ala Asp Ile Gly Ala Gly Leu Ala Asp Ala
  1               5                  10                  15

Leu Thr Ala Pro Leu Asp His Lys Asp Lys Gly Leu Gln Ser Leu Thr
                 20                  25                  30

Leu Asp Gln Ser Val Arg Lys Asn Glu Lys Leu Lys Leu Ala Ala Gln
             35                  40                  45

Gly Ala Glu Lys Thr Tyr Gly Asn Gly Asp Ser Leu Asn Thr Gly Lys
 50                  55                  60

Leu Lys Asn Asp Lys Val Ser Arg Phe Asp Phe Ile Arg Gln Ile Glu
 65                  70                  75                  80

Val Asp Gly Gln Leu Ile Thr Leu Glu Ser Gly Glu Phe Gln Val Tyr
                 85                  90                  95

Lys Gln Ser His Ser Ala Leu Thr Ala Phe Gln Thr Glu Gln Ile Gln
            100                 105                 110

Asp Ser Glu His Ser Gly Lys Met Val Ala Lys Arg Gln Phe Arg Ile
            115                 120                 125

Gly Asp Ile Ala Gly Glu His Thr Ser Phe Asp Lys Leu Pro Glu Gly
    130                 135                 140

Gly Arg Ala Thr Tyr Arg Gly Thr Ala Phe Gly Ser Asp Asp Ala Gly
145                 150                 155                 160

Gly Lys Leu Thr Tyr Thr Ile Asp Phe Ala Ala Lys Gln Gly Asn Gly
                165                 170                 175
```

Lys Ile Glu His Leu Lys Ser Pro Glu Leu Asn Val Asp Leu Ala Ala
                180                 185                 190

Ala Asp Ile Lys Pro Asp Gly Lys Arg His Ala Val Ile Ser Gly Ser
            195                 200                 205

Val Leu Tyr Asn Gln Ala Glu Lys Gly Ser Tyr Ser Leu Gly Ile Phe
        210                 215                 220

Gly Gly Lys Ala Gln Glu Val Ala Gly Ser Ala Glu Val Lys Thr Val
225                 230                 235                 240

Asn Gly Ile Arg His Ile Gly Leu Ala Ala Lys Gln
            245                 250

<210> SEQ ID NO 63
<211> LENGTH: 262
<212> TYPE: PRT
<213> ORGANISM: Neisseria meningitidis (group B)

<400> SEQUENCE: 63

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Gly Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 64
<211> LENGTH: 262
<212> TYPE: PRT
<213> ORGANISM: Neisseria meningitidis (group B)

<400> SEQUENCE: 64

```
Cys Ser Ser Gly Gly Gly Ser Gly Gly Gly Val Ala Ala Asp
 1               5                  10                  15

Ile Gly Thr Gly Leu Ala Asp Ala Leu Thr Ala Pro Leu Asp His Lys
             20                  25                  30

Asp Lys Gly Leu Lys Ser Leu Thr Leu Glu Asp Ser Ile Pro Gln Asn
         35                  40                  45

Gly Thr Leu Thr Leu Ser Ala Gln Gly Ala Glu Lys Thr Phe Lys Ala
 50                  55                  60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
            115                 120                 125

Asp Ser Leu Ile Asn Gln Arg Ser Phe Leu Val Ser Gly Leu Gly Gly
130                 135                 140

Glu His Thr Ala Phe Asn Gln Leu Pro Gly Gly Lys Ala Glu Tyr His
145                 150                 155                 160

Gly Lys Ala Phe Ser Ser Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ala Ala Glu Leu Lys Ala Asp
            195                 200                 205

Glu Lys Ser His Ala Val Ile Leu Gly Asp Thr Arg Tyr Gly Ser Glu
210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Ser Ile Ala Gly Lys Gln
            260
```

<210> SEQ ID NO 65
<211> LENGTH: 257
<212> TYPE: PRT
<213> ORGANISM: Neisseria meningitidis (group B)

<400> SEQUENCE: 65

```
Cys Ser Ser Gly Gly Gly Val Ala Ala Asp Ile Gly Ala Gly Leu
 1               5                  10                  15

Ala Asp Ala Leu Thr Ala Pro Leu Asp His Lys Asp Lys Gly Leu Lys
             20                  25                  30

Ser Leu Thr Leu Glu Asp Ser Ile Ser Gln Asn Gly Thr Leu Thr Leu
         35                  40                  45

Ser Ala Gln Gly Ala Glu Arg Thr Phe Lys Ala Gly Asn Lys Asp Asn
 50                  55                  60

Ser Leu Asn Thr Gly Lys Leu Lys Asn Asp Lys Ile Ser Arg Phe Asp
 65                  70                  75                  80

Phe Val Gln Lys Ile Glu Val Asp Gly Gln Thr Ile Thr Leu Ala Ser
                 85                  90                  95
```

```
Gly Glu Phe Gln Ile Tyr Lys Gln Asn His Ser Ala Val Val Ala Leu
                100                 105                 110

Gln Ile Glu Lys Ile Asn Asn Pro Asp Lys Ile Asp Ser Leu Ile Asn
            115                 120                 125

Gln Arg Ser Phe Leu Val Ser Ser Leu Gly Gly Glu His Thr Ala Phe
130                 135                 140

Asn Gln Leu Pro Gly Gly Lys Ala Glu Tyr His Gly Lys Ala Phe Ser
145                 150                 155                 160

Ser Asp Asp Pro Asn Gly Arg Leu His Tyr Ser Ile Asp Phe Thr Lys
                165                 170                 175

Lys Gln Gly Tyr Gly Arg Ile Glu His Leu Lys Thr Pro Glu Gln Asn
                180                 185                 190

Val Glu Leu Ala Ala Ala Glu Leu Lys Ala Asp Glu Lys Ser His Ala
            195                 200                 205

Val Ile Leu Gly Asp Thr Arg Tyr Gly Ser Glu Glu Lys Gly Thr Tyr
210                 215                 220

His Leu Ala Leu Phe Gly Asp Arg Ala Gln Glu Ile Ala Gly Ser Ala
225                 230                 235                 240

Thr Val Lys Ile Gly Glu Lys Val His Glu Ile Gly Ile Ala Gly Lys
                245                 250                 255

Gln

<210> SEQ ID NO 66
<211> LENGTH: 262
<212> TYPE: PRT
<213> ORGANISM: Neisseria meningitidis (group B)

<400> SEQUENCE: 66

Cys Ser Ser Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
                100                 105                 110

Ala Val Val Ala Leu Gln Ile Glu Lys Ile Asn Asn Pro Asp Lys Ile
            115                 120                 125

Asp Ser Leu Ile Asn Gln Arg Ser Phe Leu Val Ser Gly Leu Gly Gly
        130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ala Ala Glu Leu Lys Ala Asp
        195                 200                 205
```

Glu Lys Ser His Ala Val Ile Leu Gly Asp Thr Arg Tyr Asp Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Ser Ile Ala Gly Lys Gln
            260

<210> SEQ ID NO 67
<211> LENGTH: 262
<212> TYPE: PRT
<213> ORGANISM: Neisseria meningitidis (group B)

<400> SEQUENCE: 67

Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Thr Glu Lys Val Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Val Gly Lys Ser Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Ser Ile Ala Gly Lys Gln
            260

<210> SEQ ID NO 68
<211> LENGTH: 255
<212> TYPE: PRT
<213> ORGANISM: Neisseria meningitidis (group B)

<400> SEQUENCE: 68

```
Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu Asp Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
            195                 200                 205

Ser Gly Ser Val Leu Tyr Asn Gln Asp Glu Lys Gly Ser Tyr Ser Leu
210                 215                 220

Gly Ile Phe Gly Gly Gln Ala Gln Glu Val Ala Gly Ser Ala Glu Val
225                 230                 235                 240

Glu Thr Ala Asn Gly Ile Gln His Ile Gly Leu Ala Ala Lys Gln
                245                 250                 255
```

<210> SEQ ID NO 69
<211> LENGTH: 255
<212> TYPE: PRT
<213> ORGANISM: Neisseria meningitidis (group B)

<400> SEQUENCE: 69

```
Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu Asp Ser Gly Lys Met Val Ala Lys Arg Gln
```

```
              115                 120                 125
Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Leu Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
            195                 200                 205

Ser Gly Ser Val Leu Tyr Asn Gln Asp Glu Lys Gly Ser Tyr Ser Leu
        210                 215                 220

Gly Ile Phe Gly Gly Gln Ala Gln Glu Val Ala Gly Ser Ala Glu Val
225                 230                 235                 240

Glu Thr Val Asn Gly Ile His His Ile Gly Leu Ala Ala Lys Gln
                245                 250                 255

<210> SEQ ID NO 70
<211> LENGTH: 255
<212> TYPE: PRT
<213> ORGANISM: Neisseria meningitidis (group B)

<400> SEQUENCE: 70

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu Asp Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
            195                 200                 205

Ser Gly Ser Val Leu Tyr Asn Gln Asp Glu Lys Gly Ser Tyr Ser Leu
        210                 215                 220

Gly Ile Phe Gly Gly Gln Ala Gln Glu Val Ala Gly Ser Ala Glu Val
225                 230                 235                 240
```

-continued

```
Glu Thr Ala Asn Gly Ile His His Ile Gly Leu Ala Ala Lys Gln
            245                 250                 255

<210> SEQ ID NO 71
<211> LENGTH: 255
<212> TYPE: PRT
<213> ORGANISM: Neisseria meningitidis (group B)

<400> SEQUENCE: 71

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Arg Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Asp Ile Lys Pro Asp Glu Lys His His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 72
<211> LENGTH: 255
<212> TYPE: PRT
<213> ORGANISM: Neisseria meningitidis (group B)

<400> SEQUENCE: 72

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60
```

```
Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Leu Gln Thr Glu
            100                 105                 110

Gln Glu Gln Asp Leu Glu His Ser Gly Lys Met Val Ala Lys Arg Arg
        115                 120                 125

Phe Lys Ile Gly Asp Ile Ala Gly Glu His Thr Ser Phe Asp Lys Leu
    130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Val Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Glu Lys Ala Gln Glu Val Ala Gly Ser Ala Glu Val
225                 230                 235                 240

Lys Thr Ala Asn Gly Ile His His Ile Gly Leu Ala Ala Lys Gln
                245                 250                 255

<210> SEQ ID NO 73
<211> LENGTH: 258
<212> TYPE: PRT
<213> ORGANISM: Neisseria meningitidis (group B)

<400> SEQUENCE: 73

Cys Ser Ser Gly Gly Gly Gly Val Ala Ala Asp Ile Gly Ala Gly Leu
 1               5                  10                  15

Ala Asp Ala Leu Thr Ala Pro Leu Asp His Lys Asp Lys Gly Leu Lys
                 20                  25                  30

Ser Leu Thr Leu Glu Asp Ser Ile Ser Gln Asn Gly Thr Leu Thr Leu
             35                  40                  45

Ser Ala Gln Gly Ala Glu Arg Thr Phe Lys Ala Gly Asp Lys Asp Asn
     50                  55                  60

Ser Leu Asn Thr Gly Lys Leu Lys Asn Asp Lys Ile Ser Arg Phe Asp
 65                  70                  75                  80

Phe Ile Arg Gln Ile Glu Val Asp Gly Gln Leu Ile Thr Leu Glu Ser
                 85                  90                  95

Gly Glu Phe Gln Val Tyr Lys Gln Ser His Ser Ala Leu Thr Ala Leu
            100                 105                 110

Gln Thr Glu Gln Val Gln Asp Ser Glu His Ser Gly Lys Met Val Ala
        115                 120                 125

Lys Arg Gln Phe Arg Ile Gly Asp Ile Val Gly Glu His Thr Ser Phe
    130                 135                 140

Gly Lys Leu Pro Lys Asp Val Met Ala Thr Tyr Arg Gly Thr Ala Phe
145                 150                 155                 160

Gly Ser Asp Asp Ala Gly Gly Lys Leu Thr Tyr Thr Ile Asp Phe Ala
                165                 170                 175

Ala Lys Gln Gly His Gly Lys Ile Glu His Leu Lys Ser Pro Glu Leu
            180                 185                 190
```

```
Asn Val Asp Leu Ala Ala Asp Ile Lys Pro Asp Glu Lys His His
        195                 200                 205

Ala Val Ile Ser Gly Ser Val Leu Tyr Asn Gln Ala Glu Lys Gly Ser
        210                 215                 220

Tyr Ser Leu Gly Ile Phe Gly Gly Gln Ala Gln Glu Val Ala Gly Ser
225                 230                 235                 240

Ala Glu Val Glu Thr Ala Asn Gly Ile Arg His Ile Gly Leu Ala Ala
                245                 250                 255

Lys Gln

<210> SEQ ID NO 74
<211> LENGTH: 257
<212> TYPE: PRT
<213> ORGANISM: Neisseria meningitidis (group B)

<400> SEQUENCE: 74

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Lys
                20                  25                  30

Ser Leu Thr Leu Glu Asp Ser Ile Ser Gln Asn Gly Thr Leu Thr Leu
            35                  40                  45

Ser Ala Gln Gly Ala Glu Lys Thr Phe Lys Val Gly Asp Lys Asp Asn
        50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asp His Ser Ala Val Val Ala Leu
                100                 105                 110

Gln Ile Glu Lys Ile Asn Asn Pro Asp Lys Ile Asp Ser Leu Ile Asn
            115                 120                 125

Gln Arg Ser Phe Leu Val Ser Gly Leu Gly Gly Glu His Thr Ala Phe
        130                 135                 140

Asn Gln Leu Pro Ser Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
                180                 185                 190

Val Glu Leu Ala Ser Ala Glu Leu Lys Ala Asp Glu Lys Ser His Ala
            195                 200                 205

Val Ile Leu Gly Asp Thr Arg Tyr Gly Ser Glu Glu Lys Gly Thr Tyr
        210                 215                 220

His Leu Ala Leu Phe Gly Asp Arg Ala Gln Glu Ile Ala Gly Ser Ala
225                 230                 235                 240

Thr Val Lys Ile Arg Glu Lys Val His Glu Ile Gly Ile Ala Gly Lys
                245                 250                 255

Gln
```